US010253368B2

(12) United States Patent
Orsulic et al.

(10) Patent No.: US 10,253,368 B2
(45) Date of Patent: Apr. 9, 2019

(54) MOLECULAR SIGNATURES OF OVARIAN CANCER

(71) Applicant: Cedars-Sinai Medical Center, Los Angeles, CA (US)

(72) Inventors: Sandra Orsulic, Los Angeles, CA (US); Beth Y. Karlan, Los Angeles, CA (US); Xiaojiang Cui, Arcadia, CA (US); Mourad Tighiouart, Beverly Hills, CA (US); Dong-Joo Cheon, Los Angeles, CA (US); Zhenqiu Liu, Sherman Oaks, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 28 days.

(21) Appl. No.: 14/690,291

(22) Filed: Apr. 17, 2015

(65) Prior Publication Data
US 2015/0322530 A1 Nov. 12, 2015

Related U.S. Application Data

(63) Continuation-in-part of application No. PCT/US2013/065537, filed on Oct. 17, 2013.

(60) Provisional application No. 61/715,183, filed on Oct. 17, 2012.

(51) Int. Cl.
C12Q 1/68 (2018.01)
C12Q 1/6886 (2018.01)
G01N 33/574 (2006.01)
C12N 15/113 (2010.01)

(52) U.S. Cl.
CPC .......... C12Q 1/6886 (2013.01); C12N 15/113 (2013.01); G01N 33/57449 (2013.01); C12N 2310/14 (2013.01); C12N 2310/531 (2013.01); C12Q 2600/112 (2013.01); C12Q 2600/118 (2013.01); C12Q 2600/158 (2013.01); C12Q 2600/16 (2013.01)

(58) Field of Classification Search
None
See application file for complete search history.

(56) References Cited

U.S. PATENT DOCUMENTS

2010/0169990 A1 7/2010 Clarke et al.
2011/0105596 A1* 5/2011 Hosen .................. C12Q 1/6886 514/44 R

FOREIGN PATENT DOCUMENTS

| AU | 2013331154 A1 | 4/2015 |
| CA | 2886607 A1 | 4/2014 |
| EP | 2908913 | 8/2015 |
| WO | 2004022778 A1 | 3/2004 |
| WO | 2007100304 A1 | 9/2007 |
| WO | 2011130435 A1 | 10/2011 |
| WO | 2014062978 A1 | 4/2014 |

OTHER PUBLICATIONS

Yamaguchi et al (Oncogene, 2010, 29: 1741-1752).*
Voutilainen et al (Int J Cancer, 2003, 107: 359-364).*
Cole et al (The Yale Journal of Biology and Medicine, 1989, 62: 367-378).*
Bookman et al (Journal of Clinical Oncology, 2009, 27(9): 1419-1425).*
Helleman et al (Int J Cancer, 2006, 118: 1963-1971).*
Wannunyokoli et al (Clin Cancer Res, 2006, 12(3): 690-700).*
Bononne et al (Cancer Res, 2005, 65(22): 10602-10612).*
Tothill et al (Clin Cancer Res, 2008, 14(16): 5198-5208).*
Wong et al (The American Journal of Pathology, 2010, 177(4): 1611-1617).*
Berchuck et al (Clin Cancer Res, 2005, 11(10): 3686-3696).*
Amon et al (PLOS One, 2010, 5(6): 1-9).*
Vergote et al (NEJM, 2010, 363(10): 943-953).*
Teeling et al (Eur J Gynaecol, 1990, 11(3): Abstract).*
International Search Report and Written Opinion for PCT/US2013065537 dated Jan. 16, 2014, 9 pages.
International Preliminary Report on Patentability for PCT/US2013065537 dated Apr. 21, 2015, 8 pages.
EP 13848075.1 Partial European Search Report dated May 24, 2016, 10 pages.
EP 13848075.1 Extended European Search Report dated Sep. 9, 2016, 14 pages.
Alvero et al., Molecular Phenotyping of Human Ovarian Cancer Stem Cells Unravel the Mechanisms for Repair and Chemo-Resistance, Cell Cycle, 2009, vol. 8(1), pp. 158-166.
Baba et al., Epigenetic Regulation of CD133 and Tumorigenicity of CD133+ Ovarian Cancer Cells, Oncogene, 2009, vol. 28(2), pp. 209-218.
Burgos-Ojeda et al., Ovarian Cancer Stem Cell Markers: Prognostic and Therapeutic Implications, Cancer Letters, 2012, vol. 322, pp. 1-7.
Friel et al., Epigenetic Regulation of CD133 and Tumorigenicity of CD133 Positive and Negative Endometrial Cancer Cells, Reprod Biol Endocrinol., 2010, vol. 8, p. 147.
Ho et al., Isolation and Characterization of Stromal Progenitor Cells From Ascites of Patients with Epithelial Ovarian Adenocarcinoma, J Biomed Sci, 2012, vol. 19, p. 23.

(Continued)

Primary Examiner — Sean E Aeder
(74) Attorney, Agent, or Firm — Linda B. Huber; Nixon Peabody LLP

(57) ABSTRACT

Described herein are gene signatures providing prognostic, diagnostic, treatment and molecular subtype classifications of ovarian cancers through generation of ovarian cancer disease signatures (OCDSs) that account for molecular heterogeneity present in gynecological cancers. An ovarian cancer fixed signature (OCFS) is described which relates to the core programming of disease development, in addition to an ovarian cancer stem cell (OCSC) signature. Development various disease signature, suggests personalized treatment strategies focused on molecular subtypes of gynecological cancers, such as triage tests for patients.

6 Claims, 62 Drawing Sheets
Specification includes a Sequence Listing.

(56) References Cited

OTHER PUBLICATIONS

Kim et al., Multi-Cancer Computational Analysis Reveals Invasion-Associated Variant of Desmoplastic Reaction Involving INHBA, THBS2 and COL11A1, BMC Medical Genomics, Biomed Central LTD., 2010, vol. 3(1), pp. 1-11.

Kwon et al., Epigenetic Regulation of Cancer-Associated Genes in Ovarian Cancer, Int J Mol Sci., 2011, vol. 12(2), pp. 983-1008.

Mor et al., Ovarian Cancer Stem Cells and Inflammation, Cancer Biology and Therapy, 2011, vol. 11(8), pp. 708-713.

Silva et al., Aldehyde Dehydrogenase in Combination with CD133 Defines Angiogenic Ovarian Cancer Stem Cells that Portend Poor Patient Survival, Cancer Res., 2011, vol. 71(11), pp. 3991-4001.

Steffensen et al. Prevalence of Epithelial Ovarian Cancer Stem Cells Correlates with Recurrence in Early-Stage Ovarian Cancer, J Oncol, 2011, vol. 2011, p. 620523.

Vathipadiekal et al., Identification of a Potential Ovarian Cancer Stem Cell Gene Expression Profile From Advanced Stage Papillary Serous Ovarian Cancer, PLoS One, 2012, vol. 7(1), pp. e29079.

Wang et al., Isolation and Characterization of Stem-Like Cells from a Human Ovarian Cancer Cell Line, Molecular and Cellular Biochemistry, 2011, vol. 363(1-2), pp. 257-268.

Yan et al., Drug-Tolerant Cancer Cells Show Reduced Tumor-Initiating Capacity: Depletion of CD44 Cells and Evidence for Epigenetic Mechanisms, PLoS One, 2011, vol. 6(9), p. e24397.

\* cited by examiner

FIG. 2A
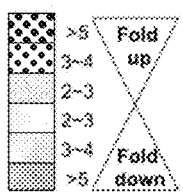
FIG. 2B
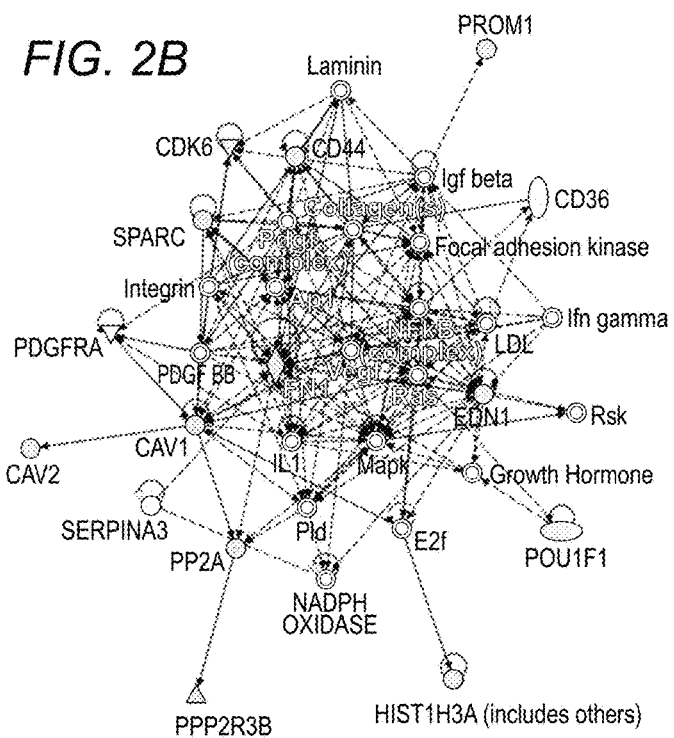
FIG. 2C

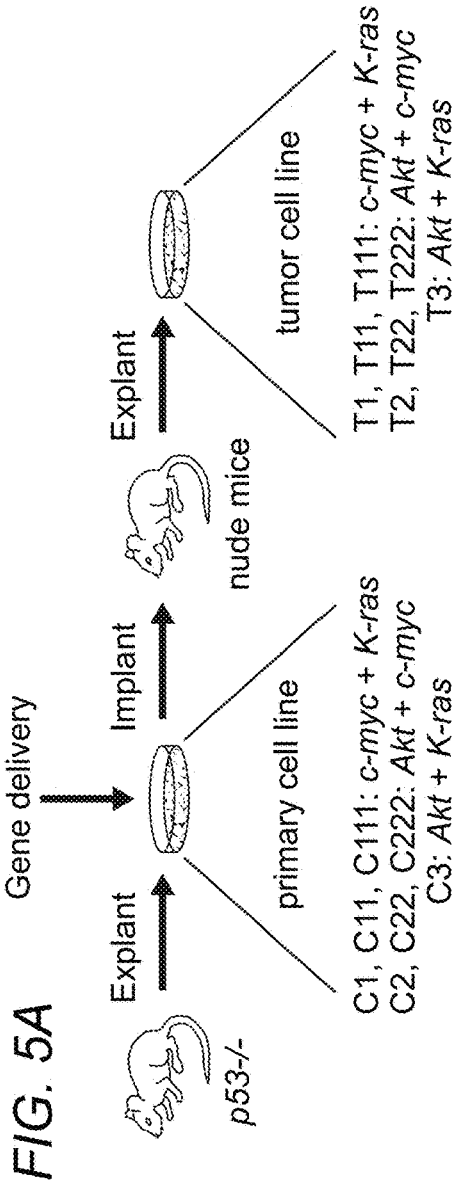
FIG. 5A
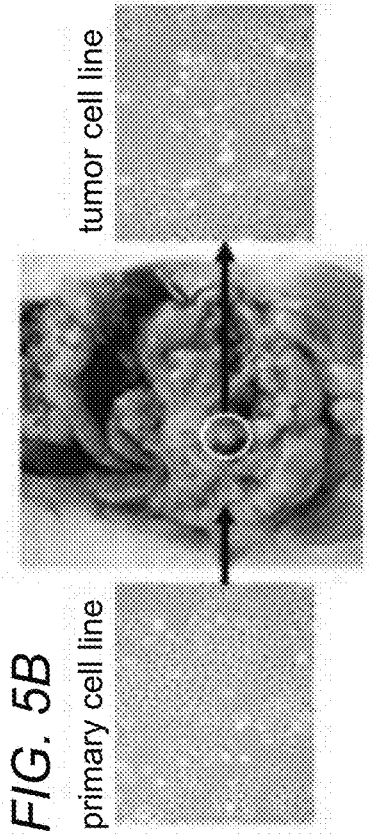
FIG. 5B
FIG. 5C
FIG. 5D

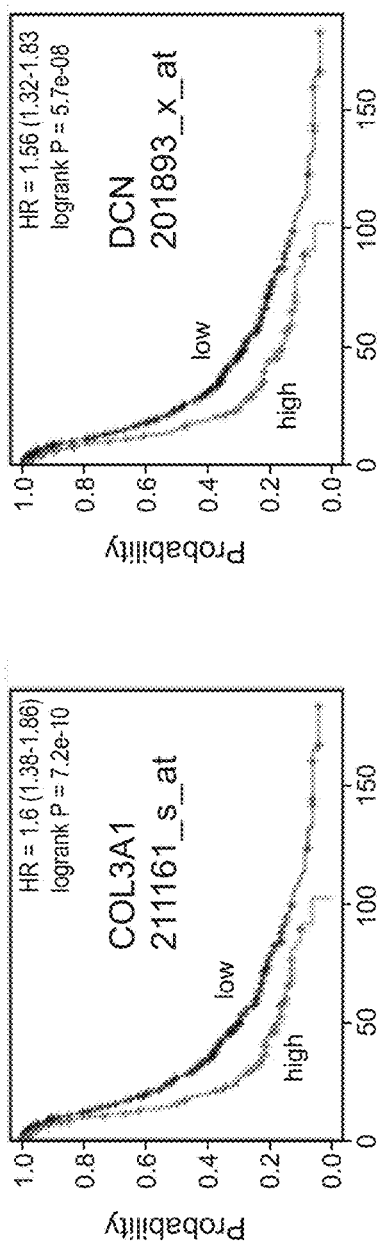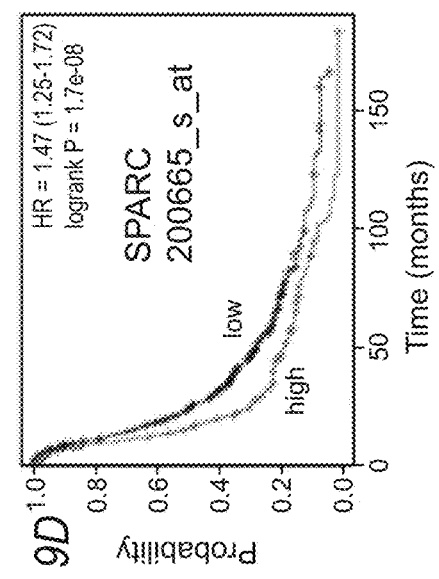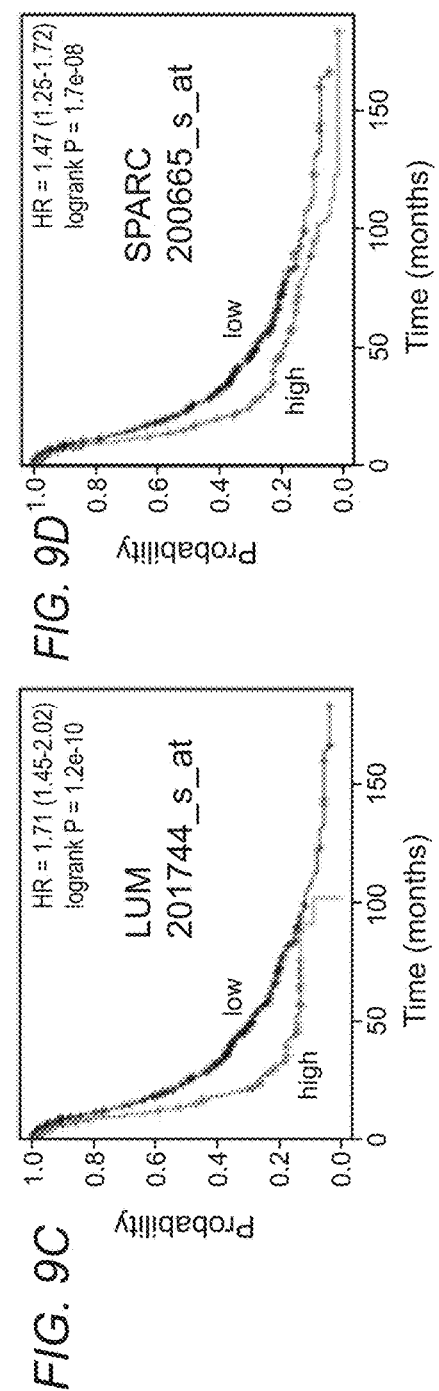

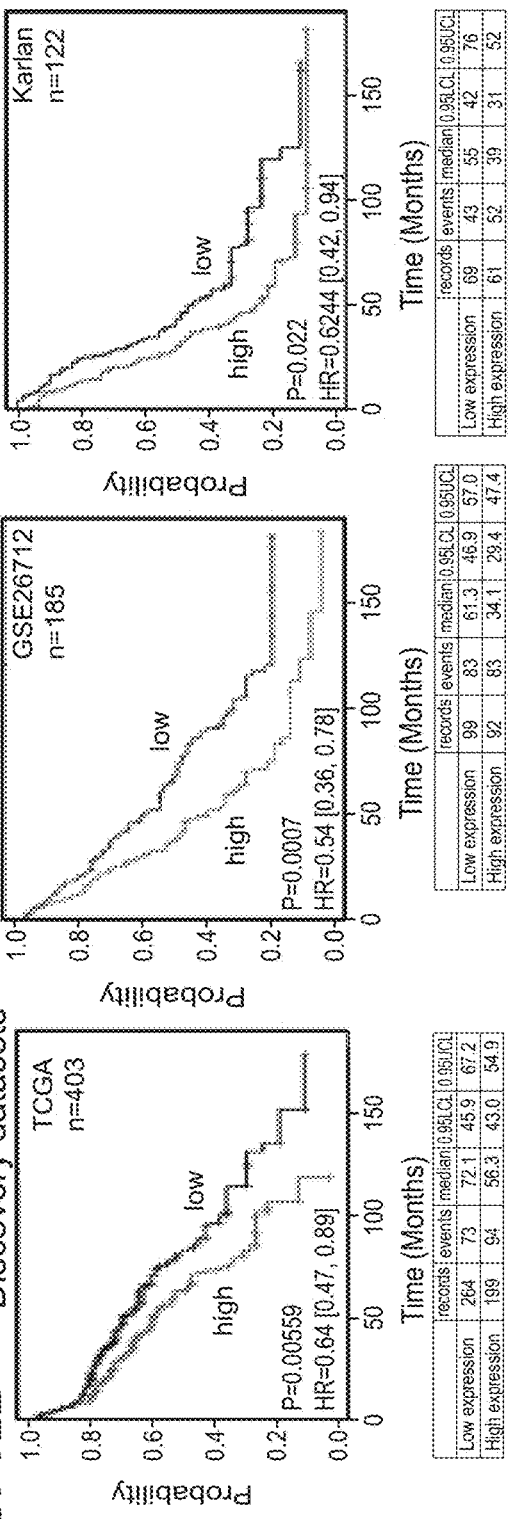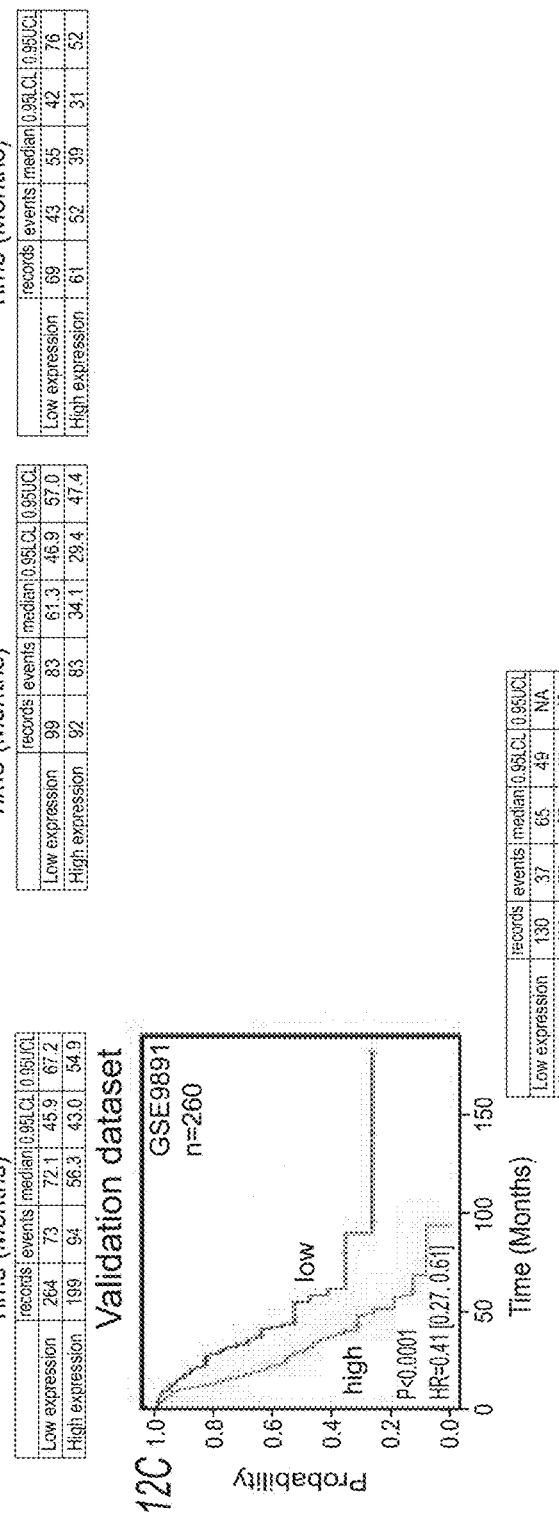

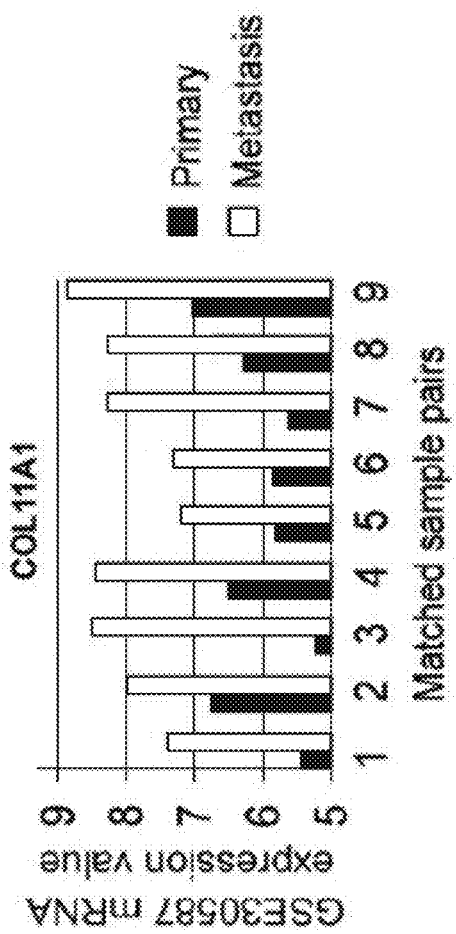

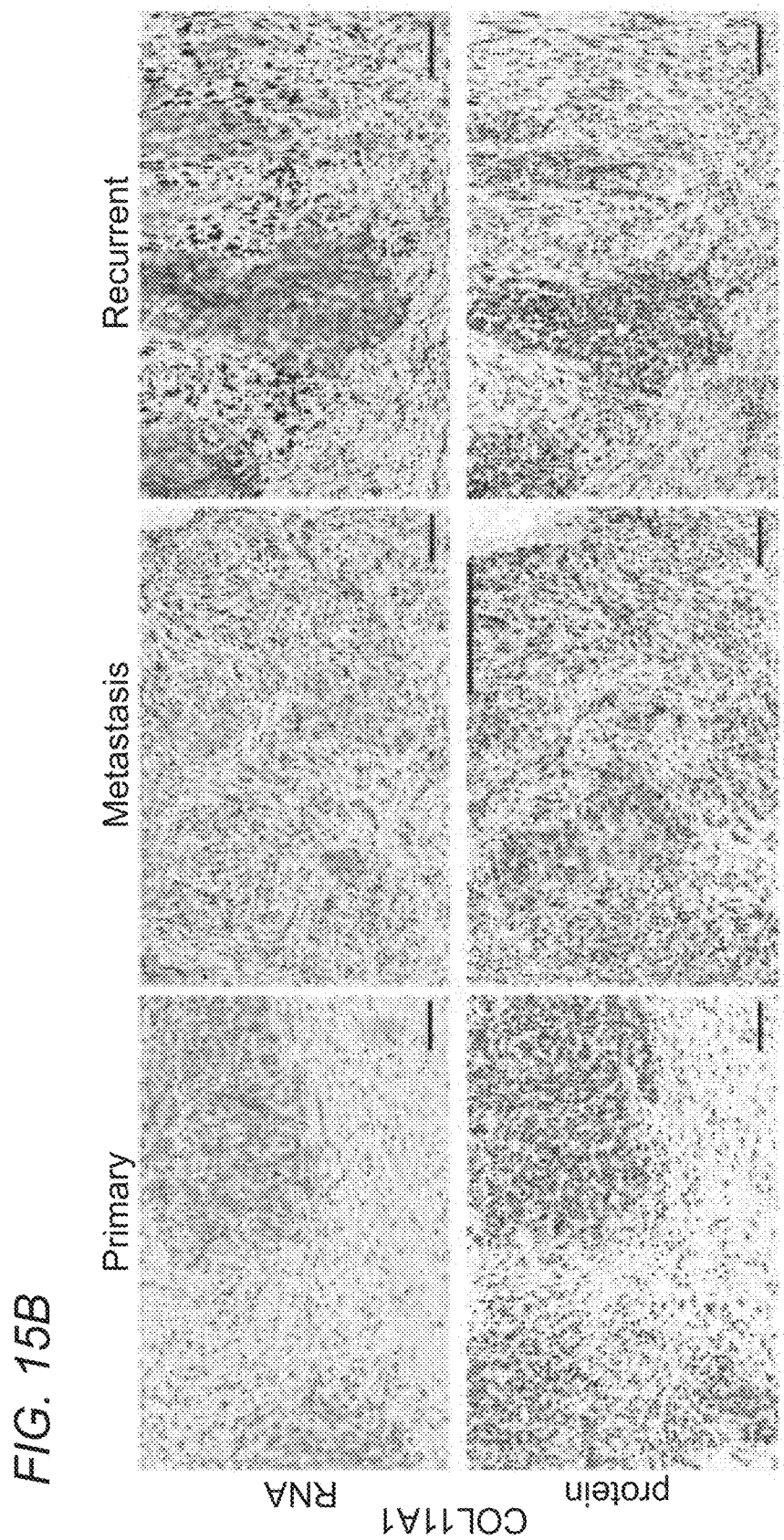

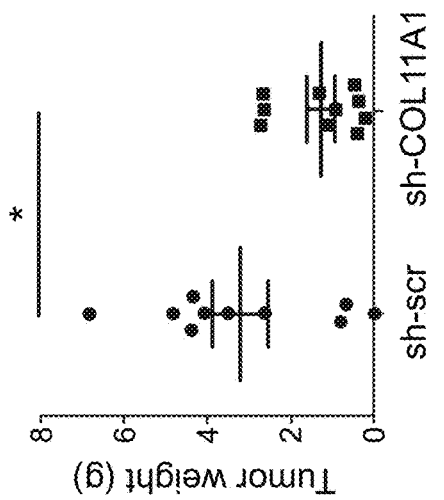
FIG. 16D
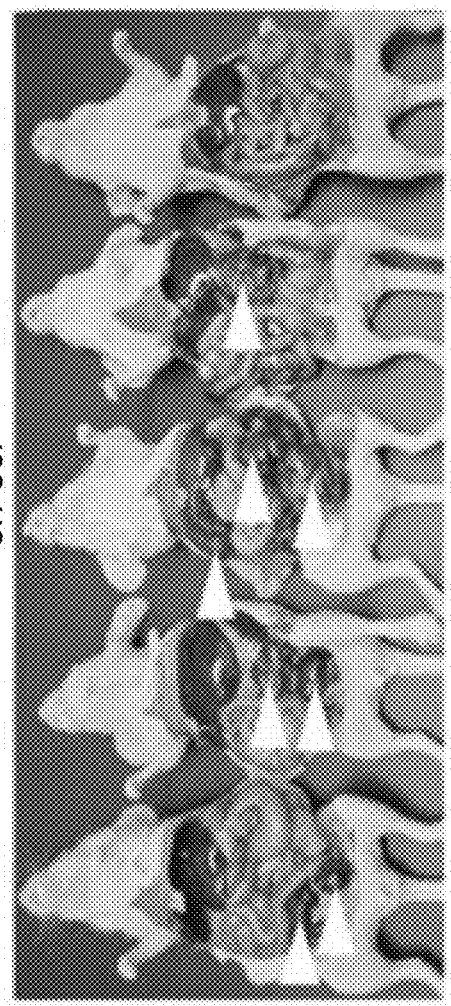
FIG. 16C

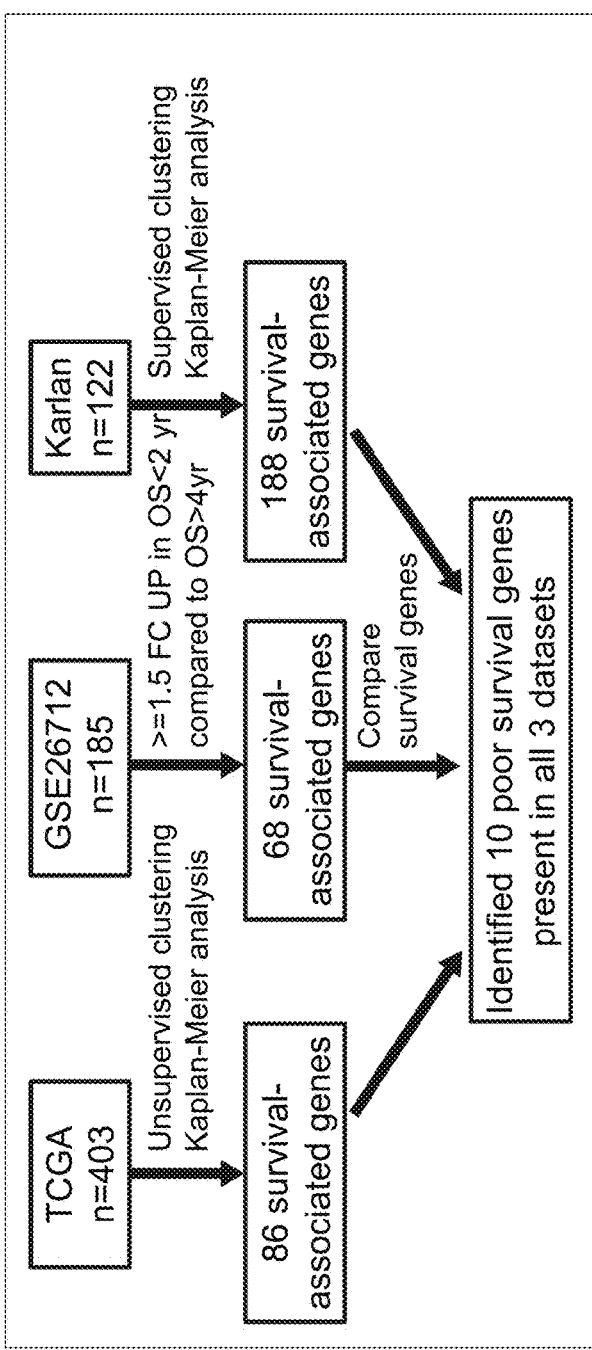
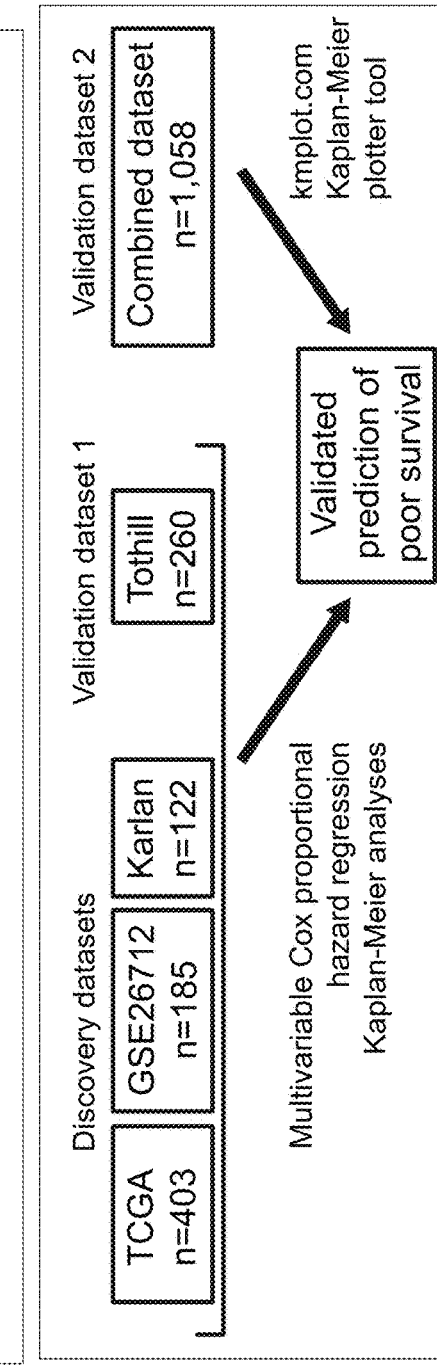
FIG. 17A
FIG. 17B

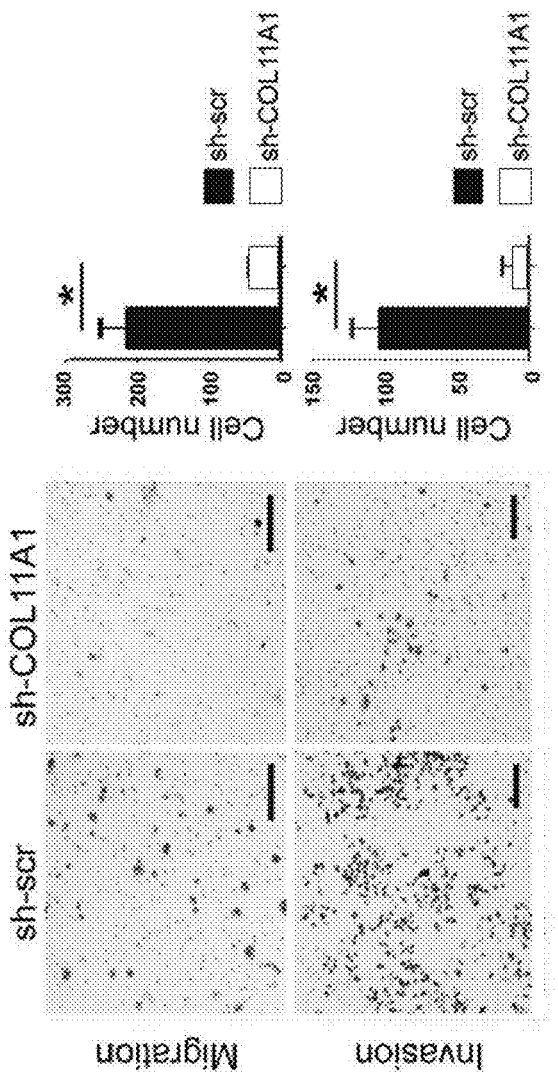
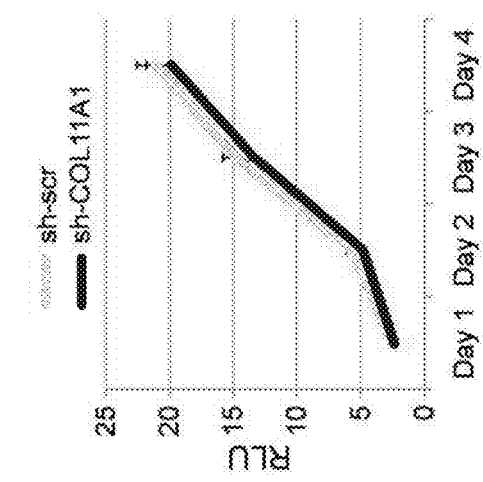
FIG. 25A
FIG. 25B

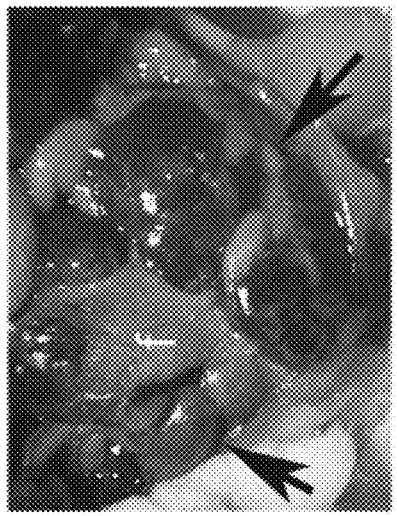
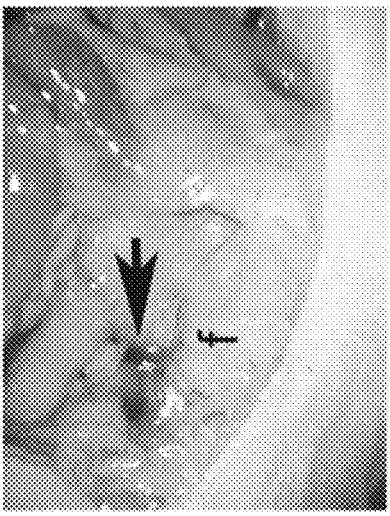
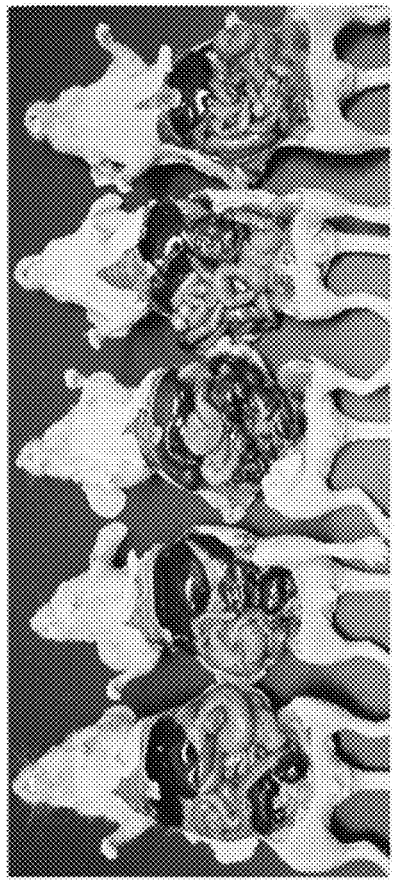
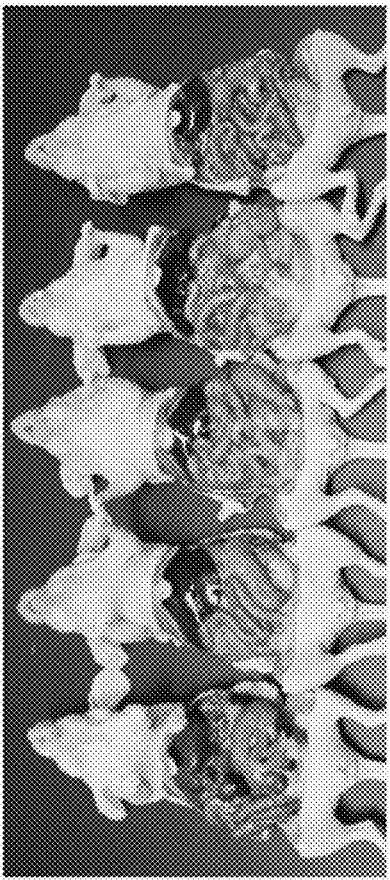
FIG. 25C
FIG. 25D

| C Gene ID | P-Values |
|---|---|
| COL11A1 | 2.98E-09 |
| TIMP3 | 8.29E-09 |
| FAP | 2.14E-08 |
| POSTN | 1.54E-07 |
| COLEC11 | 4.34E-07 |
| TNFAIP6 | 6.33E-07 |
| PDLIM3 | 1.53E-06 |
| SERPINE1 | 1.94E-06 |
| LOC100507472 | 5.49E-06 |
| LOX | 6.5E-06 |
| PRRX1 | 8.72E-06 |
| THBS2 | 1.31E-05 |
| COL5A2 | 1.9E-05 |
| CTSK | 6.73E-05 |
| PDGFRB | 8.85E-05 |
| MMP11 | 0.000202 |
| VCAN | 0.000323 |
| PLAU | 0.001262 |
| TAGLN | 0.002201 |
| PMP22 | 0.004771 |
| ACTG2 | 0.026409 |

D

SEQUENCE LISTING

<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
acaaagcaca tgctgcccag tg                                      22

<210> SEQ ID NO 2
<211> LENGTH: 22
<212> TYPE: DNA
<213> ORGANISM: Homo sapiens

<400> SEQUENCE: 2
ttccacgatg gctttgcggt tc                                      22

MOLECULAR SIGNATURES OF OVARIAN CANCER

CROSS REFERENCE TO OTHER APPLICATIONS

This application is a continuation-in-part of International Application No. PCT/US2013/065337, filed Oct. 17, 2013 and claims the benefit of U.S. Provisional Application No. 61/715,183, filed Oct. 17, 2012.

STATEMENT REGARDING FEDERALLY SPONSORED RESEARCH OR DEVELOPMENT

This invention was made with government support under Grant No. TR000124 awarded by the National Institutes of Health, and Grant No. W81XWH-14-1-0107 awarded by the Department of Defense. The government has certain rights in the invention.

FIELD OF THE INVENTION

This invention relates to genetic pathways involved in ovarian cancer growth; including, molecular signatures associated with identifying molecular subtypes of gynecological diseases and/or conditions, such as ovarian cancer. Such molecular signatures have wide application for classification of patent populations, prognosis, diagnosis and treatment of gynecological diseases and/or conditions, such as ovarian cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Ovarian cancer is the leading cause of gynecologic cancer deaths in the United States. Despite similarities in initial disease presentation, the existence of molecular subtypes of ovarian cancer is suggested by clinical outcomes displaying a broad range of survival end points. For example, some patients develop a chronic-type disease that can be maintained on chemotherapy for more than five years. Others are intrinsically resistant to chemotherapy or initially respond to chemotherapy, but then rapidly become resistant to the treatment and subsequently have low response rates to other second-line agents. Strategic approaches customized for treating these different patient groups is lacking, as ovarian cancer therapy is implemented on a watch-and-wait basis. No diagnostic tool exists that distinguishes among these patient groups, such as identifying those patients responsive to chemotherapy, others that develop preliminary or long-term chemoresistance, or those likely to experience relapse of disease. Consequently, there is a critical need for 1) prognostic and/or diagnostic classifiers that can reliably distinguish among molecular subtypes of gynecological cancer such as ovarian cancer; and 2) novel treatment therapies accounting for these differences in molecular subtypes.

The development of effective prognostic, diagnostic and treatment strategies must account for molecular abnormalities motivating the underlying pathophysiology of the disease. Thus, an initial step for developing such tools first requires identification and classification of specific molecular abnormalities associated with particular disease conditions. These biomarkers can be readily applied for early detection, and prognostication, which can guide development of personalized therapies. Reliable tests that identify patient molecular subtypes not only improves clinical management options, but also provides early warning indicators to enroll high risk patients in increasingly available clinical trials and the latest personalized treatment strategies.

Moreover, detection of disease subtypes at the molecular level allows one to take advantage of recent discoveries in cancer research, which would ordinarily fall outside the detection capabilities of traditional clinical assessments. For example, recent studies have highlighted the importance of cancer stem cells (CSCs) in tumor formation and chemoresistance. These CSCs possess the hallmark "stemness" capacity for self-renewal and the proliferative ability to drive continued expansion, along with the differentiation capacity for neoplastic formation. It is notable that CSCs could represent less than 1% of the overall cell population in a tumor, yet provide crucial biochemical machinery powering the rapid growth and development of malignant cells in tumors. The existence of such rare and transient cell populations thus requires development of detection and classification approaches at the molecular level.

Described herein are gene signatures providing prognostic, diagnostic, treatment and molecular subtype classifications of ovarian cancers. Biostatistical methods are applied across a variety of studies encompassing a wide array of laboratory and clinical variables, thereby leading to generation of ovarian cancer disease signatures (OCDSs) that account for molecular heterogeneity present in gynecological cancers. Statistical analysis across multiple independent data sets allows generation of a preliminary ovarian cancer fixed signature (OCFS), a comprehensive definition of the core programming of disease development. Also described herein is a specific biochemical definition of an ovarian cancer stem cell identified via an (OCSC) signature. Finally, the development of ovarian cancer cell lines, including ovarian cancer stem cell lines (OCSC), and selectively labeled animal models provides in vitro and in vivo models for applying the aforementioned signatures to develop clinical applications, such personalized treatment strategies focused on molecular subtypes of gynecological cancers.

SUMMARY OF THE INVENTION

Described herein is a method of determining a prognosis of cancer in an individual, including determining the presence or absence of a high level of expression in the individual relative to a normal baseline standard for a single prognostic panel of the following markers, ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM, and prognosing a case of cancer if the individual demonstrates the presence of a high level of expression relative to a normal baseline standard of at least one of the markers. In other embodiments, the individual demonstrates the presence of a high level of expression relative to a normal baseline standard of at least two, three, four, or five of the markers. In other embodiments, the individual demonstrates the presence of a high level of expression relative to a normal baseline standard of at least six, seven, eight, nine, ten or more of the markers. In other embodiments, the cancer is ovarian cancer. In other embodiments, the prognosis provides a therapeutic selection for the prognosed individual, selected from the group consisting of: chemotherapy, radiotherapy, surgery, and combinations thereof. In other embodiments, the markers are AEBP1, COL11A1, COL5A1, COL6A2, LOX, POSTN, SNAI2, THBS2, TIMP3, and VCAN Also described herein is a method of determining a diagnosis of cancer in an individual suspected of having cancer, including: obtaining sample from an individual suspected of having cancer; determining the presence or absence of a high level of expression in the individual relative to a normal baseline standard for a single diagnostic panel including the following markers ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM, and diagnosing a case of cancer if the individual demonstrates the presence of a high level of expression relative to a normal baseline standard of at least one of the markers. In other embodiments, the individual demonstrates the presence of a high level of expression relative to a normal baseline standard of at least two, three, four, or five of the markers. In other embodiments, the individual demonstrates the presence of a high level of expression relative to a normal baseline standard of at least six, seven, eight, nine, ten or more of the markers. In other embodiments, the cancer is ovarian cancer. In other embodiments, the diagnosis provides a molecular subtype classification for the diagnosed case of cancer in the individual. In other embodiments, the markers are AEBP1, COL11A1, COL5A1, COL6A2, LOX, POSTN, SNAI2, THBS2, TIMP3, and VCAN Further described herein is a method of modulating a tumor phenotype in an individual, including providing a quantity of an agent capable of modulating cancer stem cell (CSC) function, and administering the quantity of the agent to an individual, wherein modulation of CSC function results in modulation of a tumor phenotype in the individual. In other embodiments, the individual has cancer. In other embodiments, the cancer is ovarian cancer. In other embodiments, the agent is a small molecule, nucleic acid, anti-sense oligonucleotide, aptamer, protein, peptide and/or antibody. In other embodiments, the protein is collagenase. In other embodiments, the antibody is specific for CD24, CD44, CD117, CD133 or ALDH1. In other embodiments, the antibody modulates TGF-β pathway activity.

Also described herein is a composition including an isolated population of cancer stem cells (CSCs) obtained from an individual afflicted with cancer. In other embodiments, the cancer is ovarian cancer. In other embodiments, the composition is a cultured cell line.

Further described herein is a method, including providing isolated cells obtained from an individual afflicted with cancer, wherein the isolated cells include cancer stem cells (CSCs) and non-CSCs, adding a detectable reagent that preferentially binds to CSCs to the isolated cells, measuring a quantity of detectable reagent bound to the isolated cells and applying a ratio to the quantity, wherein application of the ratio to the quantity indicates the proportion of the isolated cells that are CSCs. In other embodiments, the detectable reagent is an antibody specific for CD24, CD44, CD117, CD133 or ALDH1. In other embodiments, the quantity of detectable reagent comprises flow cytometry, immunohistochemistry, immunocytochemistry, or enzyme-linked immunoassay (ELISA).

Further described herein is an assay for determining the subtype of a gynecological cancer, including determining the presence or absence of a high level of expression in the individual relative to a normal baseline standard for a single prognostic panel comprising the following markers, ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM, and determining the subtype of the gynecological cancer a case of cancer if the individual demonstrates the presence of a high level of expression relative to a normal baseline standard of at least one of the markers. In other embodiments, the gynecological cancer is ovarian cancer. In other embodiments, the ovarian cancer is characterized by elevated stromal or epithenlial-to-mesechymal transition activity. In other embodiments, the markers are AEBP1, COL11A1, COL5A1, COL6A2, LOX, POSTN, SNAI2, THBS2, TIMP3, and VCAN. In other embodiments, determining the subtype of the gynecological cancer indicates a therapeutic treatment. In other embodiments, therapeutic treatment is immunotherapy. In other embodiments, the therapeutic treatment is anti-fibrotic. In other embodiments, the therapeutic treatment modulates TGF-β pathway activity.

Further described herein is method for selecting treatment for a subject including: (a) measuring at least one biomarker selected from the group includes of: COL11A1, TIMP3, FAP, POSTN, COLEC11, TNFAIP6, PDLIM3, SERPINE1, LOC100503, LOX, PRRX1, THBS2, COL5A2, CTSK, PDGFRB, MMP11, VCAN, PLAU, TAGLN, PMP22 and ACTG2, in a tumor biopsy sample from a subject; (b) correlating the measurements of the presence, absence, or level of the measured biomarker with ovarian cancer status in the subject by comparison to a reference value; and (c) selecting treatment based on the status, wherein (i) expression of any of the at least one biomarker at a level higher than the reference value indicates treatment by neoadjuvant chemotherapy followed by interval cytoreduction, (ii) expression of any of the at least one biomarker at a level lower or equal than the reference values indicates treatment by primary debulking surgery followed by chemotherapy.

In other embodiments, the at least one biomarker at a level higher than the reference value indicating treatment by neoadjuvant chemotherapy followed by interval cytoreduction, includes one or more of COL11A1, TIMP3, FAP, POSTIN, THBS2, COL5A2, CTSK, PDGFRB, MMP11, VCAN and TAGLN. In other embodiments, the at least one biomarker at a level higher than the reference value indicating treatment by neoadjuvant chemotherapy followed by interval cytoreduction, includes one or more of COL11A1, TIMP3, FAP, POSTN, COLEC11, TNFAIP6. In other embodiments, the at least one biomarker at a level higher than the reference value indicating treatment by neoadjuvant chemotherapy followed by interval cytoreduction, includes one or more of COL11A1, TIMP3, FAP, and VCAN. In other embodiments, the at least one biomarker at a level lower or equal than the reference values indicates treatment by primary debulking surgery followed by chemotherapy includes 3 or more, 5 or more, 10 or more, 15 or more, 20 or more of the at least one biomarker. In other embodiments, the ovarian cancer is high grade serous ovarian carcinoma. In other embodiments, the chemotherapy includes paclitaxel, cisplatin and/or carboplatin. In other embodiments, the chemotherapy is administered in combination with bevacizumab. In other embodiments, the chemotherapy is followed by administration with bevacizumab. In other embodiments, the method further including measuring and correlating at least one additional biomarker selected from the group includes of: prealbumin, apolipoprotein A1, β2-microglobulin, transferring, HE4, and CA125. In other embodiments, the measuring includes quantitative real-time PCR. In other embodiments, the measuring includes immunoassay.

Further described herein is a method for qualifying ovarian cancer status in a subject including: (a) measuring at least one biomarker in a sample from a subject by an assay; and (b) correlating the measurements of the presence, absence, or level of the at least one biomarker with ovarian canc In other embodiments, the sample includes a tumor biopsy sample. In other embodiments, the assay includes quantitative real-time PCR. In other embodiments, the assay includes mass spectrometry or immunoassay. In other embodiments, the measuring at least one biomarker includes measuring and correlating at least one biomarker selected from the group includes of: ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and VIM. In other embodiments, the measuring at least one biomarker includes measuring and correlating at least one biomarker selected from the group includes of: COL11A1, TIMP3, FAP, POSTN, COLEC11, TNFAIP6, PDLIM3, SERPINE1, LOC100503, LOX, PRRX1, THBS2, COL5A2, CTSK, PDGFRB, MMP11, VCAN, PLAU, TAGLN, PMP22 and ACTG2.

In other embodiments, the measuring at least one biomarker includes measuring and correlating at least one biomarker selected from the group includes of: COL11A1, TIMP3, FAP, and VCAN. In other embodiments, the ovarian cancer status includes high grade serous carcinoma. In other embodiments, the ovarian cancer status includes low grade serous carcinoma. In other embodiments, the ovarian cancer status includes benign ovarian disease. In other embodiments, the (b) correlating the measurements of the presence, absence, or level of the measured biomarkers includes enrichment of the at least one biomarker compared to a normal baseline standard of subjects. In other embodiments, the normal baseline standard of subjects includes subjects without disease. In other embodiments, the normal baseline standard of subjects includes subjects without residual disease. In other embodiments, the method further including: (c) managing subject treatment based on the status. In other embodiments, the managing subject treatment includes primary debulking surgery (PDS) followed by chemotherapy. In other embodiments, the chemotherapy includes paclitaxel, cisplatin and/or carboplatin. In other embodiments, the managing subject treatment includes neoadjuvant chemotherapy followed by interval cytoreduction. In other embodiments, the chemotherapy includes paclitaxel, cisplatin and/or carboplatin. In other embodiments, the managing subject treatment results in optimal cytoreduction. In other embodiments, the managing subject treatment results in suboptimal cytoreduction. In other embodiments, the managing subject treatments results in no residual disease.

BRIEF DESCRIPTION OF THE FIGURES

FIG. 5(A) to FIG. 5(D). Derivation of primary and metastatic mouse ovarian cancer cell lines. (A) Diagram for the derivation of 7 primary and 7 metastatic cell lines that contain various combinations of genetic alterations in p53, c-myc, K-ras and Akt. (B) Implantation of primary transformed cell lines results in intraperitoneal carcinomatosis. Each metastatic tumor cell line was derived from a single tumor nodule. (C) H&E staining of an intraperitoneal tumor nodule. (D) Genes expressed more than 10-fold in metastatic vs. primary mouse ovarian cancer cell lines. biomarkers are highlighted in yellow.

FIG. 9(A) to FIG. 9(J). Individual genes that can effectively predict poor progression-free survival (PFS). Kaplan- Meier plots demonstrate that several biomarkers are associated with poor progression-free survival outcomes when highly expressed. These includes: (A) COL3A1 (B) DCN (C) LUM (D) SPARC (E) TIMP3 (F) VCAN (G) COL11A1 (H) COL5A1 and (I) POSTN. K-M Plotter was used to determine progression-free survival across 8 datasets listed in (J) for a total analysis across 1,107 patients. There were no restrictions based on stage, histology, grade, and treatment.

FIG. 12(A) to FIG. 12(C). Identification and validation of the 10-gene signature associated with poor overall survival. (A) Venn diagram of poor outcome gene signatures identified from three microarray datasets (TCGA, GSE26712, and Karlan). The number of overlapping genes is indicated and arrows point to the corresponding lists of overlapping genes. The 10 genes present in all three signatures are listed at the top. (B) Validation of the predictive value of the 10-gene signature from three discovery datasets (TCGA, GSE26712, and Karlan) and (C) one independent validation dataset (Tothill). Kaplan-Meier curves, log-rank P values and hazard ratios (HR) are shown to compare overall survival between two patient groups with 'high' (indicated by the red line) and 'low' (indicated by the black line) expression of the 10-gene signature. The cutoff for the risk index is the median of the continuous risk factor. 0.95 LCL, the 95% lower confidence limit interval for the median time; UCL, upper confidence limit.

FIG. 14(A) to FIG. 14(C). Enrichment of the 10-gene signature in metastatic ovarian cancer. (A) Oncomine mRNA expression analysis of the 10 poor outcome genes in three public ovarian cancer microarray datasets. Expression of the poor outcome genes are shown in primary (P) and metastatic (M) ovarian tumor samples using whisker plots with log 2 median-centered intensity. EPCAM and VIM were used as markers of the relative content of epithelial and stromal cells, respectively. (B) List of genes enriched in metastases compared to primary tumors in the GSE30587 microarray dataset, which consists of nine matched pairs of primary and metastatic tumors. Genes that overlap with the 10-gene signature are highlighted in yellow. Genes that are present in at least two of the three poor prognosis signatures are indicated in bold letters. (C) COL11A1 mRNA expression in nine matched primary and metastatic ovarian tumor samples in the GSE30587 microarray dataset.

FIG. 15(A) to FIG. 15(D). Increase in COL11A1 expression during ovarian cancer progression. (A) Quantification of COL11A1 in situ hybridization signal in matched triplets of primary ovarian cancer, concurrent metastasis, and recurrent/persistent metastasis from 10 patients. H score=% positive stromal cells×intensity (0, 1+, 2+, 3+) under 10× objective. Each point represents the H score in a single field. Nine intratumoral fields were scored in each sample except for two samples in which only three fields were scored due to a minimal amount of tumor tissue. Data are presented as the mean+/−SEM. *P<0.05; P<0.005; *P<0.0005; ****P<0.0001. (B) Representative COL11A1 in situ hybridization and COL11A1 immunohistochemistry in serial sections of samples from Patient 1. (C) Detection of a positive focal COL11A1 in situ hybridization signal in cells exhibiting stromal (S) and epithelial (E) morphology. (D) Representative image of COL11A1 distribution in intra- and peri-tumoral areas. tE, tumor epithelium; iS, intratumoral stroma; pS, peritumoral stroma; dS, distant stroma; F, fat. Hematoxylin counterstain. Size bar is 100 μm in all panels.

FIG. 16(A) to FIG. 16(D). COL11A1 knockdown results in decreased cell migration, invasion, and tumor progression. (A) Migration and (B) invasion assays of A2780 cells with scrambled shRNA (shscr) or shRNA specific to COL11A1 (sh-COL11A1). Shown are representative images of migrated cells after 24 hours and invasive cells after 48 hours. Size bar, 25 μm. The bar graph shows the quantification of migrated cells in four different fields at 10× magnification and invasive cells in four different fields at 4× magnification. Data are presented as the mean+/− standard deviation. *P<0.05. (C) Photograph of nude mice with tumors that formed 14 days after intraperitoneal injection of A2780 cells transduced with scrambled shRNA control (sh-scr; 5 mice) or shRNA specific to COL11A1 (sh-COL11A1; 5 mice). White arrowheads indicate large tumor nodules. (D) Quantification of wet tumor weight after resection of tumor nodules from 20 mice in the replication experiment of intraperitoneal injection of A2780 cells transduced with sh-scr (10 mice) or sh-COL11A1 (10 mice). Each dot indicate an individual mouse. Data are presented as the mean+/−SEM, *P=0.02.

FIG. 17(A) to FIG. 17(B). A schematic diagram of the methods, datasets and patient samples used to identify and characterize the 10 genes associated with poor survival in ovarian cancer. (A) Identification of the 10-gene signature. (B) Validation of the 10-gene signature in predicting poor overall survival.

FIG. 25(A) to FIG. 25(D). COL11A1 knockdown results in decreased in vitro cell migration and invasion and attenuated in vivo tumor progression. (A) Proliferation of A2780 cells transduced with scrambled shRNA control (sh-scr) or shRNA specific to COL11A1 (sh-COL11A1). Data are presented as average+/−SD. RLU, Relative Luminescent Units. (B) Migration and invasion assays of A2780 cells with sh-scr or sh-COL11A1. Shown are representative images of migrated cells after 24 hours and invasive cells after 48 hours. Size bar, 25 μm. The bar graph shows the quantification of migrated cells in 4 different fields at 10× magnification and invasive cells in 4 different fields at 4× magnification. Data are presented as the mean+/−SD. *P<0.0001. (C, D) Tumor formation in nude mice 14 days after intraperitoneal injection of A2780 cells with sh-scr or sh-COL11A1. The arrows points to tumor implants in the visceral fat (f).

FIG. 31(A) to FIG. 31(B). A consistent set of genes is coexpressed with COL11A1 in different cancer types. (A) Tumors with high levels of COL11A1 were investigated with identification of genes that most closely correlate with expression of COL11A1 in TCGA datasets representing 12 different cancer types. (B) Spearman's rank correlations between COL11A1 and coexpressed genes for each cancer type were calculated. The genes were then ranked based on the average correlation of each gene across the 12 cancer types. The top 196 highly correlated genes were selected based on the average correlation of greater than 0.4.

DETAILED DESCRIPTION

Figure 1:
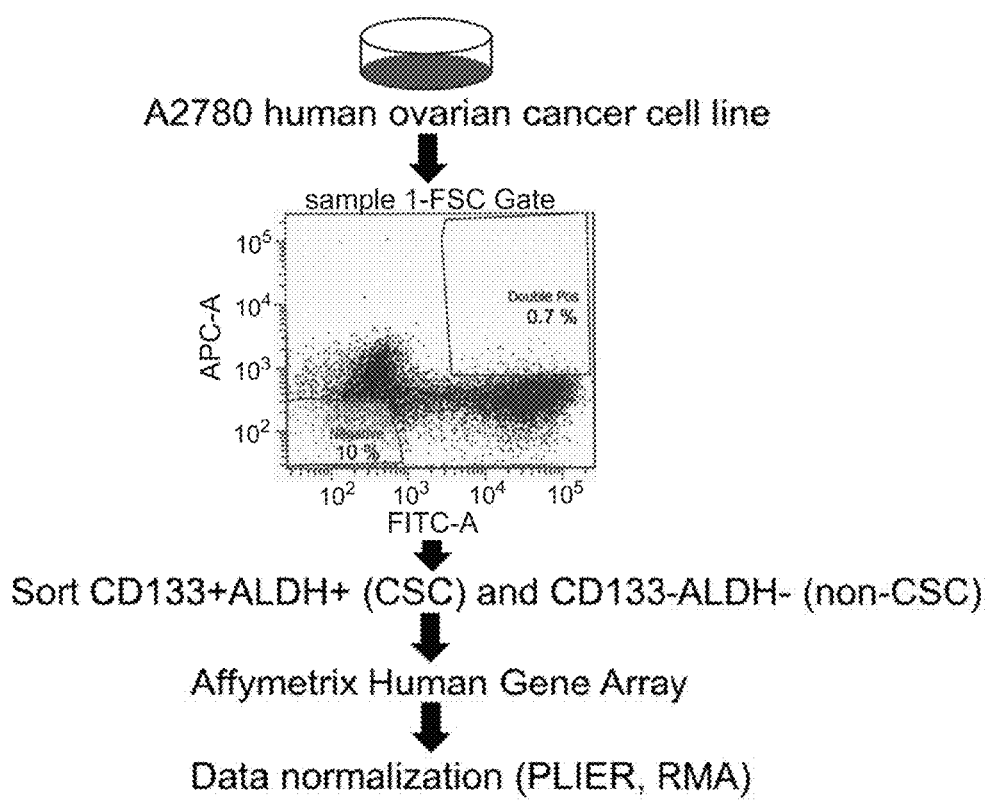
FIG. 1. Schematic diagram for the isolation and microarray analysis of human ovarian cancer stem cells FIG. 2 (A) to FIG. 2(E). Establishment of preliminary ovarian cancer stem cell (OCSC) signature. (A) Genes commonly expressed in OCSCs isolated from different markers. (B) Network analysis of OCSC biomarkers. (C) Example of a preliminary OCSC signature. (D) Annotated network analysis showing "hub" genes such as fibroblast growth factor (FGF1), fibronectin (FN1), tgf-beta 1 (TGFB1), tgf-beta 2 (TGFB2), thrombospondin 1 (THBS1), and filamin C (GLNC) as involved in "stemness" (E) Poor patient survival predicted by OCSC biomarkers (red) in The Cancer Genome Atlast (TCGA) dataset.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 4$^{th}$ ed., J. Wiley & Sons (New York, N.Y. 2012); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Most ovarian cancer patients are diagnosed at a late stage when the cancer has metastasized throughout the peritoneal cavity. Standard clinical management involves surgical tumor debulking followed by administration of platinum- and taxane-based chemotherapy. Patients with advanced ovarian cancer display a broad range of survival end points, despite the similarities in initial disease presentation (e.g., late-stage), histopathology (e.g., high-grade, serous ovarian cancer) and treatment (e.g., surgery followed by platinum- and taxane-based chemotherapy). For example, some patients develop a chronic-type disease and can live with ovarian cancer (despite intermittent chemotherapy treatments) for 5, 10 or more years. Others have tumors that are intrinsically resistant to chemotherapy or initially respond to chemotherapy but then rapidly recur due to regrowth of resistant disease and subsequently have low response rates to other second, third or Nth-line agents.

Currently, ovarian cancer surveillance and subsequent therapies are implemented on a "watch-and-wait" basis. Immunoassay detection of cancer-antigen CA125 can identify pre-clinical recurrence, but chemotherapy interventions prior to symptoms do not translate into improved overall survival. Moreover, CA125 has also been known to lead to a number of false positive in asymptomatic women, thereby highlighting the drawbacks of single biomarker detection via immunoassay. Thus, a quantitative, molecular-based approach incorporating several biomarkers is likely to provide more effective prognostic and diagnostic tools, with the further advantage of classifying patients with molecular subtypes of gynecological cancer. This includes the advantage of identifying those high-risk patients who have a greater likelihood of relapse at the completion of first line therapy. This would aid earlier inclusion into clinical trials or personalized treatment strategies that could improve overall survival rates. Consequently, there is a critical need for 1) prognostic and/or diagnostic classifiers that can reliably distinguish among molecular subtypes of gynecological cancer such as ovarian cancer; and 2) novel treatment therapies accounting for these differences in molecular subtypes.

In addition, the development of molecular-based approaches allows development of clinical strategies focused on totally new paradigms in cancer research. This includes focusing on cancer stem cells ("CSCs"), and "stroma" cells in tumor formation. Recent discoveries have highlighted the importance of CSCs in tumor formation and disease development. As described, most patients are diagnosed at a late stage, with standard clinical management initially focused on tumor debulking. While conventional therapies may provide effects via repression, modulation, or alteration of bulk tumor cell growth and development, therapeutic intervention focused on CSCs may provide a more effective two-pronged attack against cancer development. For example, identification of a CSC signature allows targeting of noxious CSCs, which may presently evade treatment strategies focused on tumor debulking. Further, modulation, repression, or alteration of the CSC signature or its related metabolic network, dismantles the biological machinery powering tumor formation and development. Although a variety of potential ovarian cancer stem cell (OCSC) candidates have been presented, the existence and role of CSCs in the ovarian cancer context is not well-understood. As tumors display morphological, phenotypical, and biochemical heterogeneity, different cells may possess only some or many hallmarks of a posited OCSC, yet fail to be a bona fide OCSC. Application of the described techniques can lead to positive identification of OCSCs and compilation of a precise, biochemical definition via an OCSC signature. Generation of such a signature contributes further in diagnostic and prognostic techniques would further benefit from early stage detection of OCSCs, as these cells are understood to be key actors in neoplastic tumor formation.

Further, solid tumors are now understood to be complex "organs" comprised of not only malignant cells, such as OCSCs, but also non-malignant cells, described under the umbrella term, "stroma". Most outcome-predicting gene signatures originate in cancer cells. However, it is becoming increasingly clear stromal cells are active contributors to tumor progression and that large amounts of tumor stroma are also associated with poor clinical outcome in multiple solid tumors. This dynamic bi-directional interaction between the malignant cells and "stroma" is not well understood, but recent studies have suggested "stroma" can modify the neoplastic properties of tumor cells and that tumor cells re-program the "stroma" to generate a unique microenvironment that is crucial for cancer survival, homeostasis, progression, and metastasis. Although many aspects of this complex microenvironment have been revealed in recent years, a better understanding of the molecular components that facilitate the communication in this complex microenvironment is aided by the earlier described signature-based approach for identifying the presence and absence of particular cell types. Identifying the cellular context of the poor prognosis signature will help focus on the correct cell type for the future development of assays to predict outcome in ovarian cancer patients and may provide a basis for future biologic or immune therapeutic targets.

Described herein is the development of gene signatures providing prognostic, diagnostic, treatment methods and molecular subtype classifications of ovarian cancers. Biostatistical methods are applied to link molecular, laboratory, and clinical data obtained from a variety of studies encompassing a wide array of laboratory and clinical variables. Each of these studies provides ovarian cancer disease signatures (OCDSs) that account for molecular heterogeneity present in gynecological cancers. Further, robust statistical analysis across these multiple independent data sets allows further optimization for generating an ovarian cancer fixed signature (OCFS). As OCFS is platform-independent, generation of an OCFS helps to define the core programming of disease development. Described further herein is a specific biochemical definition of an ovarian cancer stem cell via an (OCSC) signature. Finally, the development of ovarian cancer cell lines, including ovarian cancer stem cell lines (OCSC), and selectively labeled animal models provides in vitro and in vivo models for developing clinical applications, such as guided personalized treatment decisions. As further described herein, the various identified gene signatures, such as OCFS is correlated with ovarian cancer progression and poor outcome. The OCFS signature has strong predictive value, biological relevance, and translational potential. Future studies are warranted to optimize the gene signature for its predictive power and develop a quantitative assay that is appropriate for use in the clinical setting. Using the validated gene signature to identify patients who are unlikely to respond to standard treatment will provide opportunities to deliver individualized therapies that target the underlying mechanism of the poor outcome signature genes. Furthermore, a better understanding of how collagen remodeling contributes to ovarian cancer progression and metastasis could reveal the "Achilles heel" of these tumors and thus have a major impact on the development of improved therapies for advanced ovarian cancer.

Insights gained during these mechanistic studies provide specific guidance towards implementation of therapeutic approaches. Currently, standard primary treatment for ovarian cancer is surgery followed by chemotherapy. Specifically, current surgical outcomes among patients with advanced-stage ovarian cancer are defined by the amount of postoperative residual tumour. A complete gross resection (R0) is achieved if no macroscopic residual tumour remains. Following surgery, if any visible tumour remains it is classified according to the largest residual diameter. Operations resulting in residual tumour up to 1 or 2 cm in diameter have been classified as "optimal" whereas those resulting in any larger residual tumour being defined as "suboptimal". Several studies have firmly established the relationship between postoperative residual tumour and clinical outcomes, although some flexibility exists in regard to "optimal" resection criteria. Yet, the general indications support a rationale for surgery as the primary treatment to remove as much tumor as possible, and this has evolved to the standard clinical approach of primary cytoreduction followed by platinum-based chemotherapy as the standard management for patients with advanced-stage epithelial ovarian cancer. The definition of "optimal" cytoreduction, however, continues to evolve and remains a critical focus of ongoing investigation. For example, if tumor nodules have invaded vital organs, surgeons may not be able to remove them without compromising the patient's life. More recent data indicates that leaving tumor nodules larger than 1 cm (defined herein as "suboptimal debulking") is associated with reduced chemosensitivity and poor survival. Under such circumstances, if the tumor cannot be effectively removed by surgery, the patient is first treated with chemotherapy to partially shrink the tumor and then by surgery. But here, there is tremendous difficulty in that surgeons cannot predict whether surgery will be effective or not. Critically, the effect in individual patients is highly divergent depending on the biology of their disease. As such, biomarker is needed that may help physicians decide which patients should undergo surgery and which should be treated with chemotherapy first.

As described, surgical cytoreduction of advanced-stage ovarian cancer has long been considered a cornerstone for effective management of this disease. The sequence of chemotherapy and surgical intervention is debated, but there is broad consensus that integration of the two modalities represents the best initial strategy for women with metastatic disease based on a strong prognostic link between degree of postoperative residual disease and objective clinical and pathological complete response rates, progression-free survival (PFS) and overall survival. This relationship is most discriminative between patients with no detectable residual disease, so-called R0 resection, and those with any measure of residual disease. As described, conventional description of "optimal" involving residual disease volumes under 1 cm, but such reports show incremental survival benefits among even those patients with residual disease volumes under 1 cm. Reports of a limited benefit from a debulking effort if the residual disease cannot be reduced to less than 1 cm led to 1 cm being described as a metric for "optimal" surgical cytoreduction, but most recent indicates that optimal cytoreduction should instead be R0. With this adjusted classification in hand. Moreover, a personalized surgical approach is desirable to enable rational decision-making with regard to the timing of surgery.

Beyond surgical observations of disease state, understanding of ovarian cancer disease has benefited greatly from the use of biomarkers or imaging techniques to assess the state, probable future state of disease, and approaches for clinical management. Preoperative CA-125 levels is one of the most-studied parameters for predicting surgical outcome among patients with advanced-stage ovarian cancer, although this biomarker has significant limitations given that CA-125 levels are found to be elevated in more than 90% of patients. While initially serving as a useful surrogate marker for extent of tumour burden, the CA-125 cut point of 500 U/ml has been proposed as a critical value in the analysis of the ability to predict optimal cytoreduction. But varying degrees of success and reproducibility have shown the limitation of this biomarker, further obviated by evolving surgical practices wherein radical surgical procedures to achieve optimal cytoreduction now indicate levels of CA-125 as no longer able to correlate with surgical outcome. Similarly, CT imaging, the most commonly used modality for the preoperative assessment of patients with advanced-stage ovarian cancer, can be used for staging, and monitoring disease recurrence or persistent disease. Several studies have exploited disease characteristics from CT imaging and their predictive ability to estimate surgical success. However, several limitations of studies evaluating CT predictors of surgical outcome also exist, including variability in CT implementation and clinical judgment due radiologist skill, individual surgeons' views. Moreover, CT imaging is more likely to reveal disease that is clearly unresectable, such as the presence of extra abdominal metastases, making it less useful for predicting R0 resection for the afore mentioned reasons.

More recently techniques have been developed to exploit the specific tumor biology with a view towards clinical management. For example, it has been reported that approaches that incorporate tumour biology are better at predicting incomplete cyto reduction that results in macroscopic residual tumour (sensitivity 82% and positive predictive value 78%). One approach has relied on publicly available genomic datasets (The Cancer Genome Atlas (TCGA) and Tothill) to discover candidate genetic markers associated with a high likelihood of residual disease, including high levels of FABP4 and ADH1B expression in the tumour were increasing rates of R0 resection will result in a reciprocal improvement in both PFS and overall survival. In some instances, some propose laparoscopy (scored<8 with a modified Fagotti index) before attempting a debulking effort as a means to investigated as a complementary means of avoiding cytoreduction, and the potential morbidity associated with a laparotomy that results in sub optimal residual disease. But in such a context, and given the limitations of historical approaches using CA-125 and CT imaging, it is suggested that a pure genetic signature characterizing tumor biology of ovarian cancer disease would contribute as the objective determinate as part of an algorithm or independently. Here, a gene signature predicting suboptimal cytoreduction in high grade serious ovarian cancer patients is described, using statistical approaches incorporating not only expression levels, but gene networks pathway analysis, as associated with residual disease.

As described herein, the present invention includes a method of determining a prognosis of cancer in an individual includes, determining the presence or absence of a high level of expression in the individual relative to a normal baseline standard for a prognostic panel including one or more markers, and prognosing a case of cancer if the individual demonstrates the presence of a high level of expression relative to a normal baseline standard of at least one of the markers in the prognostic panel. In other embodiments, the individual demonstrates the presence of a high level of expression relative to a normal baseline standard of two, three, four, five, six, seven, eight, nine, ten, or at least ten of the markers in the prognostic panel. In other embodiments, the individual demonstrates the presence of a high level of expression relative to a normal baseline standard of at least ten, eleven, twelve, thirteen, fourteen, fifteen, sixteen, seventeen, eighteen, nineteen, twenty, or at least twenty of the markers in the prognostic panel. In another embodiment, the cancer is a gynecological cancer. In another embodiment, the cancer is ovarian cancer. In another embodiment, the prognosis provides a therapeutic selection for the prognosed individual, selected from the group consisting of: chemotherapy, radiotherapy, surgery, and/or combinations thereof.

In other embodiments, the markers are associated with the presence of ovarian cancer stem cells (OCSCs). In other embodiments, the markers are associated with co-expression of periostin. In other embodiments, the markers are associated with poor survival. In other embodiments, the markers are associated with poor prognosis. In other embodiments, the markers are associated with chemoresistance. In other embodiments, the markers are associated with late-stage ovarian cancer, high-grade, or serious ovarian cancer.

In certain embodiments, the prognostic panel includes one or more markers listed in Table 1.

TABLE 1

Representative Ovarian Cancer Stem Cell (OCSC) Genes

| | | | | | | |
|---|---|---|---|---|---|---|
| ABCD2 | CNN1 | FAM55C | IL7R | OGN | SPARC | YWHAB |
| ACTA2 | COL11A1 | FGF1 | KATNA1 | OLFML3 | SPOCK2 | ZFHX4 |
| ACTG2 | COL1A2 | FGFR2 | KSR1 | PCMT1 | SPP1 | ZNF804A |
| ADAM12 | COL3A1 | FLNC | LAMA4 | PDGFRA | SV2A | |
| ALDH1A1 | COL6A1 | FN1 | LAMB1 | PHLDB2 | TAGLN | |
| ALDH1A2 | COLEC12 | FNTA | LOX | PI3 | TFPI2 | |
| AMACR | CTGF | FXYD5 | LOXL1 | PIEZO2 | TGFB2 | |
| ANGPT1 | CYBRD1 | GADD45B | LRRC17 | PPIC | TGFBI | |
| ANGPTL2 | CYR61 | GAS1 | LUM | PPP3CA | THBS1 | |
| ANGPTL4 | DCLK1 | GPNMB | MAL | PRKCDBP | TIMP2 | |
| ANP32A | DCN | GREM1 | MMP2 | PXDN | TMEM47 | |
| APBA2 | DDX46 | GSTM3 | MMP1 | RAD52 | TNC | |
| AXL | DNAJC9 | HAND2 | MSLN | RIN2 | TPM1 | |
| BCHE | DOCK11 | HOXA7 | MSR1 | RND3 | TRHDE | |
| BIN1 | DSC2 | HOXA9 | MTSS1 | RNFT2 | TRO | |
| CALD1 | DSC3 | HOXA10 | NBL1 | S100A8 | TSHR | |
| CAV1 | ECM1 | HS3ST3A1 | NLK | SAR1B | TWIST1 | |
| CCL2 | EFEMP1 | HSPA2 | NNMT | SERPINE1 | TXNDC9 | |
| CD36 | ELL2 | IGFBP5 | NR2F2 | SFRP2 | VGLL3 | |
| CD302 | ELOVL4 | IGFBP6 | NR3C1 | SLC25A15 | VIM | |
| CDKN1A | EMP1 | IL6 | NUAK1 | SNX3 | XRCC4 | |

In various embodiments, the method of determining a prognosis of cancer in an individual includes, determining the presence or absence of a high level of expression in the individual relative to a normal baseline standard for a prognostic panel including one or more markers listed in Table 1, and prognosing a case of cancer if the individual demonstrates the presence of a high level of expression relative to a normal baseline standard of at least one of the markers listed in Table 1. In other embodiments, the individual demonstrates the presence of a high level of expression relative to a normal baseline standard of two, three, four, five, six, seven, eight, nine, ten, or at least ten of the markers listed in Table 1. In other embodiments, the individual demonstrates the presence of a high level of expression relative to a normal baseline standard of at least ten, eleven, twelve, thirteen, fourteen, fifteen, sixteen, seventeen, eighteen, nineteen, twenty, or at least twenty of the markers listed in Table 1. In another embodiment, the cancer is a gynecological cancer. In another embodiment, the cancer is ovarian cancer. In another embodiment, the prognosis provides a therapeutic selection for the prognosed individual, selected from the group consisting of: chemotherapy, radiotherapy, surgery, and/or combinations thereof. In another embodiment, the markers are associated with poor survival. In other embodiments, the markers associated with poor survival include ALDH1A2, ANGPTL4, COL1A2, COL3A1, COL6A1, EFEMP1, HOXA10, LUM, SPP1, TGFB2, THBS1, and/or TMEM47.

In certain embodiments, the single prognostic panel includes one or more markers listed in Table 2.

TABLE 2

Representative Periostin (POSTN)-Coexpressing Genes

| | | | | | | |
|---|---|---|---|---|---|---|
| ACTA2 | CNN1 | EPAS1 | IL6 | MMP11 | RAI14 | THBD |
| ACTC1 | COL10A1 | EPYC | IL7R | MMP19 | RASAL3 | THBS1 |
| ACTG2 | COL11A1 | ETV1 | INHBA | MMP1 | RASSF2 | THBS2 |
| ACTR2 | COL12A1 | FAM26E | ITGA1 | MOXD1 | RCAN1 | TIMP3 |
| ADAM12 | COL1A2 | FAP | ITGA5 | MPP1 | RGS16 | TMEM89 |
| AEBP1 | COL1A1 | FBLN1 | ITGA11 | MS4A4A | SCHIP1 | TMEM158 |
| AK5 | COL3A1 | FBLN2 | ITGB1 | MXRA5 | SDC1 | TMEM217 |
| ALDH1A3 | COL4A2 | FBN1 | ITGBL1 | NCF2 | SEC13 | TMEM45A |
| ANGPTL2 | COL5A1 | FCGR2B | KCNE4 | NNMT | SERPINF1 | TNC |
| AQP1 | COL5A2 | FGF7 | KIF26B | NTM | SERPINH1 | TNFAIP6 |
| ARHGAP30 | COL6A2 | FKBP14 | LAMA4 | NUAK1 | SFRP2 | TPM2 |
| ASPN | COL8A2 | FN1 | LAMB1 | P4HA2 | SFRP4 | TPM1 |
| BATF3 | COLEC12 | FSTL1 | LAPTM5 | PALLD | SH3PXD2A | TUBB6 |
| BATF | COMP | FTL | LCP1 | PDGFRB | SKAP2 | TUBB2A |
| BMP2 | COPZ2 | GALNT1 | LEPRE1 | PDLIM3 | SLC20A1 | UNC5B |
| C13orf33 | CRHR1 | GEM | LGI2 | PDPN | SNAI2 | VCAM1 |
| C1QTNF3 | CTHRC1 | GFPT2 | LILRB3 | PHLDB2 | SPARC | VCAN |
| C5orf62 | CTSB | GJB2 | LIMA1 | PLAU | SPHK1 | VIM |
| CALD1 | CTSK | GLRX | LOX | PLOD2 | SPON2 | VSIG4 |
| CCDC80 | CXCL14 | GPNMB | LOXL1 | PMP22 | SPP1 | WIPI1 |
| CCR7 | CYP1B1 | GPR32 | LOXL2 | POSTN | SRGN | |
| CD14 | CYR61 | GREM1 | LUM | PPAP2A | SUCNR1 | |
| CD53 | DCN | GUCY1A3 | MAFB | PPIC | SULF1 | |
| CD163 | DLC1 | HAAO | MARCKS | PTGIR | SYTL2 | |
| CD248 | DOCK11 | HCK | METRNL | PTPRC | TAGLN | |
| CD44 | DPYSL3 | HOXA7 | MICAL2 | PTRF | TDO2 | |

TABLE 2-continued

Representative Periostin (POSTN)-Coexpressing Genes

| | | | | | |
|---|---|---|---|---|---|
| CFD | EDIL3 | HSD17B6 | MIR22HG | RAB31 | TGFB3 |
| CHST11 | ELL2 | HTRA3 | MMP9 | RAB7L1 | TGFBI |

In various embodiments, the method of determining a prognosis of cancer in an individual includes, determining the presence or absence of a high level of expression in the individual relative to a normal baseline standard for a prognostic panel including one or more markers listed in Table 2, and prognosing a case of cancer if the individual demonstrates the presence of a high level of expression relative to a normal baseline standard of at least one of the markers listed in Table 2. In other embodiments, the individual demonstrates the presence of a high level of expression relative to a normal baseline standard of two, three, four, five, six, seven, eight, nine, ten, or at least ten of the markers listed in Table 2. In other embodiments, the individual demonstrates the presence of a high level of expression relative to a normal baseline standard of at least ten, eleven, twelve, thirteen, fourteen, fifteen, sixteen, seventeen, eighteen, nineteen, twenty, or at least twenty of the markers listed in Table 2. In another embodiment, the cancer is a gynecological cancer. In another embodiment, the cancer is ovarian cancer. In another embodiment, the prognosis provides a therapeutic selection for the prognosed individual, selected from the group consisting of: chemotherapy, radiotherapy, surgery, and/or combinations thereof. In another embodiment, the markers are co-expressed with periostin.

In certain embodiments, the single prognostic panel includes one or more markers listed in Table 3.

Table 3, and prognosing a case of cancer if the individual demonstrates the presence of a high level of expression relative to a normal baseline standard of at least one of the markers listed in Table 3. In other embodiments, the individual demonstrates the presence of a high level of expression relative to a normal baseline standard of two, three, four, five, six, seven, eight, nine, ten, or at least ten of the markers listed in Table 3. In other embodiments, the individual demonstrates the presence of a high level of expression relative to a normal baseline standard of at least ten, eleven, twelve, thirteen, fourteen, fifteen, sixteen, seventeen, eighteen, nineteen, twenty, or at least twenty of the markers listed in Table 3. In another embodiment, the cancer is a gynecological cancer. In another embodiment, the cancer is ovarian cancer. In another embodiment, the prognosis provides a therapeutic selection for the prognosed individual, selected from the group consisting of: chemotherapy, radiotherapy, surgery, and/or combinations thereof. In another embodiment, the markers are associated with poor survival. In other embodiments, the markers associated with poor survival include DCN, FN1, LOX, LUM, POSTN, SNAI2, SPARC, SPP1, THBS1, THBS2, TIMP3, and/or VCAN. In other embodiments, the markers associated with poor survival include COL3A1, DNC, LUM, SPARC, TIMP3, and/or VCAN. In other embodiments, the markers are associated with progression-free survival. In other embodiments, the

TABLE 3

Representative Genes Associated with Poor Survival

| | | | | | | |
|---|---|---|---|---|---|---|
| ADAM12 | CILP | CYR61 | FBLN2 | INHBA | PDLIM3 | SNAI2 |
| ADH1B | COL10A1 | DIO2 | FGF1 | ITGBL1 | PDPN | SPON2 |
| ADIPOQ | COL11A1 | DPT | FMO1 | LOX | PIEZO2 | SULF1 |
| AEBP1 | COL1A1 | DUSP1 | FOSB | LPPR4 | PLAU | TDO2 |
| ASPN | COL5A1 | DUSP5 | GLT8D2 | MATN3 | POSTN | THBS2 |
| ATF3 | COL5A2 | ECM1 | GREM1 | MFAP5 | PPBP | TIMP3 |
| C1QTNF3 | COL5A3 | EDNRA | GUCY1A3 | MMP11 | PRKG1 | VCAM1 |
| C7orf10 | COL6A2 | EGR1 | HAS2 | MN1 | PRRX1 | VCAN |
| CALB2 | COMP | EGR2 | HBA1/HBA2 | NR4A1 | PTGIS | |
| CCRL1 | CRISPLD2 | EGR3 | HBB | NR4A3 | PTPRD | |
| CD36 | CTSK | EPYC | HBG2 | NTM | RGS4 | |
| CD248 | CXCL14 | FABP4 | IGF1 | ODZ3 | SCG2 | |
| CH25H | CXCL12 | FAP | IGHG1 | OMD | SFRP4 | |

In various embodiments, the method of determining a prognosis of cancer in an individual includes, determining the presence or absence of a high level of expression in the individual relative to a normal baseline standard for a prognostic panel including one or more markers listed in markers associated with progression-free survival include COL3A1, DNC, LUM, SPARC, TIMP3, VCAN, COL11A1, AEBP1, COL5A1, POSTN, and/or THBS2.

In certain embodiments, the single prognostic panel includes one or more markers listed in Table 4 or 4a.

TABLE 4

Representative Genes Associated with Poor Prognosis

| | | | | | |
|---|---|---|---|---|---|
| ABCA8 | COL6A3 | FOSB | LMOD1 | POSTN | TIMP3 |
| ACTA2 | CXCL12 | HBA1/HBA2 | LOX | PTGIS | TMEM47 |
| ADH1B | CYP1B1 | HBB | LUM | RARRES1 | TMEM158 |
| AEBP1 | DCN | HEPH | MAL | RGS2 | TUBB2A |
| ALDH1A1 | DUSP1 | ID1 | NBL1 | RHOB | UBD |
| ALDH1A2 | EDNRA | IGF2 | NR2F2 | SEMA3C | VCAN |
| CAV1 | EFEMP1 | IGFBP3 | NR4A2 | SERPINE1 | VIM |
| CDH11 | EGR1 | IGFBP4 | OLFML3 | SERPINF1 | ZEB1 |

TABLE 4-continued

Representative Genes Associated with Poor Prognosis

| COL11A1 | FBLN1 | IGFBP5 | OSR2 | SNAI2 |
| COL3A1 | FBN1 | ISLR | PDGFRA | SPARC |
| COL5A1 | FN1 | ITM2A | PEG3 | TAGLN |
| COL6A2 | FOS | KLF2 | PLS3 | THBS2 |

TABLE 4a

Representative Genes in an Ovarian Cancer Fixed Signature

| AEBP1 | POSTN |
| COL11A1 | SNAI2 |
| COL5A1 | THBS2 |
| COL6A2 | TIMP3 |
| LOX | VCAN |

In various embodiments, the method of determining a prognosis of cancer in an individual includes, determining the presence or absence of a high level of expression in the individual relative to a normal baseline standard for a prognostic panel including one or more markers listed in Table 4 or 4a, and prognosing a case of cancer if the individual demonstrates the presence of a high level of expression relative to a normal baseline standard of at least one of the markers listed in Table 4. In other embodiments, the individual demonstrates the presence of a high level of expression relative to a normal baseline standard of two, three, four, five, six, seven, eight, nine, ten, or at least ten of the markers listed in Table 4. In other embodiments, the individual demonstrates the presence of a high level of expression relative to a normal baseline standard of two, three, four, five, six, seven, eight, nine, ten, or all ten of the markers listed in Table 4a. In other embodiments, the individual demonstrates the presence of a high level of expression relative to a normal baseline standard of at least ten, eleven, twelve, thirteen, fourteen, fifteen, sixteen, seventeen, eighteen, nineteen, twenty, or at least twenty of the markers listed in Table 4. In another embodiment, the cancer is a gynecological cancer. In another embodiment, the cancer is ovarian cancer. In another embodiment, the prognosis provides a therapeutic selection for the prognosed individual, selected from the group consisting of: chemotherapy, radiotherapy, surgery, and/or combinations thereof. In another embodiment, the markers are associated with poor prognosis.

In another aspect, described herein is a method of determining a diagnosis of cancer in an individual suspected of having cancer, including obtaining sample from an individual suspected of having cancer, determining the presence or absence of a high level of expression in the individual relative to a normal baseline standard for a single diagnostic panel, and diagnosing a case of cancer if the individual demonstrates the presence of a high level of expression relative to a normal baseline standard of at least one of the markers. In other embodiments, the single diagnostic panel includes one or more markers listed in Tables 1, 2, 3, 4 and/or 4a.

In different embodiments, the single prognostic panel includes one or more markers listed in at least two of Tables 1, 2, 3, 4 and 4a. For example, a single prognostic panel can include one or more of the following markers, which each appear in at least two of Tables 1, 2, 3, 4 and 4a: ACTA2, ACTG2, ADAM12, ADH1B, AEBP1, ALDH1A1, ALDH1A2, ANGPTL2, ASPN, C1QTNF3, CALD1, CAV1, CD36, CD248, CNN1, COL10A1, COL11A1, COL1A2, COL1A1, COL3A1, COL5A1, COL5A2, COL6A2, COLEC12, COMP, CTSK, CXCL14, CXCL12, CYP1B1, CYR61, DCN, DOCK11, DUSP1, ECM1, EDNRA, EFEMP1, EGR1, ELL2, EPYC, FAP, FBLN1, FBLN2, FBN1, FGF1, FN1, FOSB, GPNMB, GREM1, GUCY1A3, HBB, HOXA7, IGFBP5, IL6, IL7R, INHBA, ITGBL1, LAMA4, LAMB1, LOX, LOXL1, LUM, MAL, MMP11, MMP1, NBL1, NNMT, NR2F2, NTM, NUAK1, OLFML3, PDGFRA, PDLIM3, PDPN, PHLDB2, PIEZO2, PLAU, POSTN, PPIC, PTGIS, SERPINE1, SERPINF1, SFRP2, SFRP4, SNAI2, SPARC, SPON2, SPP1, SULF1, TAGLN, TDO2, TGFBI, THBS1, THBS2, TIMP3, TMEM47, TMEM158, TNC, TPM1, TUBB2A, VCAM1, VCAN, and/or VIM.

In different embodiments, the single prognostic panel includes one or more markers listed at in least three of Tables 1, 2, 3, 4 and 4a. For example, a single prognostic panel can include one or more of the following markers, which each appear in at least three of Tables 1, 2, 3, 4 and 4a: ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM. In another example, a single prognostic panel can include one or more of the following markers, which each appear in at least three of Tables 1, 2, 3, and 4: AEBP1, COL11A1, COL5A1, COL6A2, LOX, POSTN, SNAI2, THBS2, TIMP3, VCAN In different embodiments, the single prognostic panel includes one or more markers listed in all of Tables 1, 2, 3, 4 and 4a. For example, a single prognostic panel can include COL11A1, which appears in all of Tables 1, 2, 3, 4 and 4a. In certain embodiments, the single prognostic panels of Tables 1, 2, 3, 4 or 4a each provides one or more ovarian cancer disease signatures (OCSD). In other embodiments, one or more ovarian cancer disease signatures provides an ovarian cancer fixed signature (OCFS).

In different embodiments, the single diagnostic panel includes one or more markers listed in at least two of Tables 1, 2, 3, 4 and 4a. For example, a single diagnostic panel can include one or more of the following markers, which each appear in at least two of Tables 1, 2, 3, and 4: ACTA2, ACTG2, ADAM12, ADH1B, AEBP1, ALDH1A1, ALDH1A2, ANGPTL2, ASPN, C1QTNF3, CALD1, CAV1, CD36, CD248, CNN1, COL10A1, COL11A1, COL1A2, COL1A1, COL3A1, COL5A1, COL5A2, COL6A2, COLEC12, COMP, CTSK, CXCL14, CXCL12, CYP1B1, CYR61, DCN, DOCK11, DUSP1, ECM1, EDNRA, EFEMP1, EGR1, ELL2, EPYC, FAP, FBLN1, FBLN2, FBN1, FGF1, FN1, FOSB, GPNMB, GREM1, GUCY1A3, HBB, HOXA7, IGFBP5, IL6, IL7R, INHBA, ITGBL1, LAMA4, LAMB1, LOX, LOXL1, LUM, MAL, MMP11, MMP1, NBL1, NNMT, NR2F2, NTM, NUAK1, OLFML3, PDGFRA, PDLIM3, PDPN, PHLDB2, PIEZO2, PLAU, POSTN, PPIC, PTGIS, SERPINE1, SERPINF1, SFRP2, SFRP4, SNAI2, SPARC, SPON2, SPP1, SULF1, TAGLN, TDO2, TGFBI, THBS1, THBS2, TIMP3, TMEM47, TMEM158, TNC, TPM1, TUBB2A, VCAM1, VCAN, and/or VIM.

In different embodiments, the single diagnostic panel includes one or more markers listed at in least three of Tables 1, 2, 3, 4 and 4a. For example, a single diagnostic panel can include one or more of the following markers, which each appear in at least three of Tables 1, 2, 3, and 4: ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM. In another example, a single diagnostic panel can include one or more of the following markers, which each appear in at least three of Tables 1, 2, 3, and 4: AEBP1, COL11A1, COL5A1, COL6A2, LOX, POSTN, SNAI2, THBS2, TIMP3, VCAN In different embodiments, the single diagnostic panel includes one or more markers listed in all of Tables 1, 2, 3, 4 and 4a. For example, a single prognostic panel can include COL11A1, which appears in all of Tables 1, 2, 3, 4 and 4a. In certain embodiments, the single diagnostic panels of Tables 1, 2, 3, 4 or 4a each provides one or more ovarian cancer disease signatures (OCSD). In other embodiments, one or more ovarian cancer disease signatures provides an ovarian cancer fixed signature (OCFS).

In another aspect, described herein is a method, including providing isolated cells obtained from an individual afflicted with cancer, wherein the isolated cells include cancer stem cells (CSCs) and non-CSCs, adding a detectable reagent that preferentially binds to CSCs to the isolated cells, measuring a quantity of detectable reagent bound to the isolated cells, applying a ratio to the quantity, wherein application of the ratio to the quantity indicates the proportion of the isolated cells that are CSCs. In another embodiment, the detectable reagent is an antibody specific for CD24, CD44, CD117, CD133 or ALDH1. In another embodiment, the quantity of detectable reagent comprises flow cytometry, immunohistochemistry, immunocytochemistry, or enzyme-linked immunoassay (ELISA).

In another aspect, described herein is a composition including an enriched population of cancer stem cells (CSCs) obtained from an individual afflicted with cancer, wherein the CSCs express a higher level of at least one CSC marker when compared to non-CSCs, and wherein the CSCs are capable of self-renewal and differentiation. In another embodiment, the least one CSC marker includes one or more markers listed in Table 1. In another embodiment, the cancer is a gynecological cancer. In another embodiment, the cancer is ovarian cancer. In another embodiment, the composition is a cultured cell line. In another aspect, described herein is a composition including an isolated population of cancer stem cells (CSCs) obtained from an individual afflicted with cancer. In another embodiment, the cancer is ovarian cancer. In another embodiment, the composition is a cultured cell line.

In another aspect, described herein is a method of modulating a tumor phenotype in an individual, including providing a quantity of an agent capable of modulating cancer stem cell (CSC) function, and administering the quantity of the agent to an individual, wherein modulation of CSC function results in modulation of a tumor phenotype in the individual. In another embodiment, the individual has cancer. In another embodiment, the cancer is ovarian cancer. In another embodiment, the agent is a small molecule, nucleic acid, protein, peptide and/or antibody. In one embodiment, the protein is collagenase. In another embodiment, the small molecule is Salinomycin, Etoposide, Abamectin, Nigericin, Resveratrol, MS-275, Ciclopirox, Quinostatin, Alsterpaullone, Azacitidine, Bepridil, Fluspirilene, Cortisone, Etoposide, Loperamide, Ikarugamycin, Pyrvinium, Irinotecan, Phenoxybenzamine, Solanine Nicergoline, Monobenzone, Ellipticine, Norcyclobenzaprine, Tobramycin, Gossypol, Ethambutol, Daunorubicin, Methotrexate, Dextromethorphan, Thiostrepton, Propylthiouracil, Clotrimazole, Amiodarone, Thioguanosine, Rimexolone, Tranylcypromine, Ginkgolide A, GW-8510, Hycanthone, Rolitetracycline, Dipyridamole, Perphenazine, Beta-escin, Hexamethonium bromide, Vorinostat, Trifluoperazine, Prochlorperazine, 15-delta prostaglandin J2, Thioridazine, Trichostatin A, Fluphenazine, LY-294002, (Acetato)(2,3,5,6-tetramethylphenyl)mercury, beta.-D-arabinofuranosyl-5-fluorocytosine, beta.-D-ribofuranoside thymine-1 2-deoxy, -beta.-Pyrazomycin, 9-N(N0-bis-chloroethyl-N0-1,2-diamino ethyl) 2-methoxy acridine dihydrochloride, 9-N—(N0-chloroethyl-N0-1,6-diaminohexyl) 2-methoxyacridine, dihydrochloride, 9-N(N0-chloroethyl-N0-methyl-1,4-diaminobutyl) 2-methoxy acridine dihydrochloride, Aclarlubicin HCl, Acridine Orange, Albacarcin M, Albacarcin V, Anhydroarabinosyl-5-fluoro-cytosine hydrochloride, Arabinosyl cytosine palmitate, Combretastatin A4, Ellipticine, Ellipticine N-oxide, Ellipticine, 6-(3-aminopropyl)-, dihydrochloride, Ellipticine, 6-3-aminopropyl)-9-methoxy-, dihydrochloride, Ellipticine, 9-chloro-, Ellipticine, 9-dimethyl amino-ethoxy-, Ellipticine, 9-hydroxy-, hydrochloride, Ellipticine, 9-methyl-, Illudin M, Kidamycin, Labriformin, Landomycin A, Lycobetaine chloride, Megaphone acetate, N,N-Dibenzyldaunorubicin hydrochloride, Neriifolin, Nybomycin acetate, Predorine, Sanguilutine pseudobase, Scilliglaucosidin, Scutellaprostin D, or Metformin. In another embodiment, the nucleic acid is a small interefering RNA (siRNA) or short hairpin RNA (shRNA). In another embodiment, the siRNA or shRNA is cognate to fibroblast growth factor 1 (FGF1), fibronectin (FN1), or L1CAM. In another embodiment, the antibody is specific for ABCC5, CD24, CD44, CD117, CD133 or ALDH1. In another embodiment, the agent is capable of modulating the rate of epithelial-to-mesenchymal transition (EMT). In another embodiment, modulating a tumor phenotype includes treating an individual afflicted with cancer.

In another aspect, described herein is a method of modulating a tumor phenotype in an individual, including providing a quantity of an agent capable of modulating TGF-beta pathways, and administering the quantity of the agent to an individual, wherein modulation of TGF-beta pathways results in modulation of a tumor phenotype in the individual. In another embodiment, the individual has cancer. In another embodiment, the cancer is ovarian cancer. In another embodiment, the agent is a small molecule, nucleic acid, protein, peptide and/or antibody. In various embodiments, the agent is a ligand traps, antisense oligonucleotide (ASO), small molecule receptor kinase inhibitor, or peptide aptamer. In various embodiments, ligand traps can also include anti-ligand neutralizing antibodies and soluble decoy receptor proteins incorporating the ectodomains from either TβRII or βRIII/betaglycan protein, such as TGF-β monoclonal antibody, 1D11, or decoy receptor proteins such as recombinant Fc-fusion proteins with the soluble ectodomain of either TβRII (TβRII-Fc) or the type III receptor, betaglycan. In various embodiments, ASOs include nucleotides capable of reducing the bioavailability of active TGF-β ligands such as AP12009 (Trabedersen). In other embodiments, small molecule receptor kinase inhibitors include small molecule inhibitor of TβRI, SB-431542, TβRI/ALK5 kinase inhibitor, Ki26894, TβRI inhibitor SD-208, dual inhibitor of TβRI/II, LY2109761, or inhibitors selective for the kinase domain of the type 1 TGF-β receptor, LY2157299. In other embodiments, other therapeutics targeting related pathways such as EGFR (erlotinib), ABL/PDGFR/KIT (imatinib), and VEGFR/RAF/PDGFR (sorafenib), may be used in combination with a TGF-beta related therapeutic. In other embodiments, the agent targetings intracellular TGF-β signaling molecules, such as Smads. For example, aptamers are small peptide molecules containing a target-binding and a scaffolding domain that stabilizes and interferes with the function of the targets, and can be designed specifically against Smas such as Smad2 or Smad3, the Trx-SARA aptamer is one such example.

In various embodiments is capable of modulating the expression or function of ACTA2, ADAM12, COL11A1, COL3A1, COL5A1, COL6A2, CYR61, DCN, FN1, GREM1, LOX, POSTN, SNAI2, SPARC, TAGLN, TIMP3, VCAN, and/or VIM. In another embodiment, the nucleic acid is a small interefering RNA (siRNA) or short hairpin RNA (shRNA). In another embodiment, the siRNA or shRNA is cognate to ACTA2, ADAM12, COL11A1, COL3A1, COL5A1, COL6A2, CYR61, DCN, FN1, GREM1, LOX, POSTN, SNAI2, SPARC, TAGLN, TIMP3, VCAN or VIM. In another embodiment, the siRNA or shRNA is cognate to AEBP1, COL11A1, COL5A1, COL6A2, LOX, POSTN, SNAI2, THBS2, TIMP3, or VCAN. In another embodiment, the siRNA or shRNA is cognate to COL11A1, LOX, POSTN, THBS2, or VCAN.

In another aspect, described herein is a method, including providing isolated cells obtained from an individual afflicted with cancer, wherein the isolated cells include cancer stem cells (CSCs) and non-CSCs, adding a detectable reagent that preferentially binds to CSCs to the isolated cells, measuring a quantity of detectable reagent bound to the isolated cells, applying a ratio to the quantity, wherein application of the ratio to the quantity indicates the proportion of the isolated cells that are CSCs. In another embodiment, the detectable reagent is an antibody specific for ABCC5, CD24, CD44, CD117, CD133 or ALDH1. In another embodiment, the quantity of detectable reagent comprises flow cytometry, immunohistochemistry, immunocytochemistry, or enzyme-linked immunoassay (ELISA).

Further described herein is an assay for determining the subtype of a gynecological cancer, including determining the presence or absence of a high level of expression in the individual relative to a normal baseline standard for a single prognostic panel comprising the following markers, ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and/or VIM, and determining the subtype of the gynecological cancer a case of cancer if the individual demonstrates the presence of a high level of expression relative to a normal baseline standard of at least one of the markers. In other embodiments, the gynecological cancer is ovarian cancer. In other embodiments, the ovarian cancer is characterized by elevated stromal or epithnelial-to-mesechymal transition activity. In other embodiments, the markers are AEBP1, COL11A1, COL5A1, COL6A2, LOX, POSTN, SNAI2, THBS2, TIMP3, and VCAN. In other embodiments, determining the subtype of the gynecological cancer indicates a therapeutic treatment. In other embodiments, therapeutic treatment is immunotherapy. In other embodiments, the therapeutic treatment is anti-fibrotic. In other embodiments, the therapeutic treatment modulates TGF-β pathway activity.

Further described herein is method for selecting treatment for a subject including: (a) measuring at least one biomarker selected from the group includes of: COL11A1, TIMP3, FAP, POSTN, COLEC11, TNFAIP6, PDLIM3, SERPINE1, LOC100503, LOX, PRRX1, THBS2, COL5A2, CTSK, PDGFRB, MMP11, VCAN, PLAU, TAGLN, PMP22 and ACTG2, in a tumor biopsy sample from a subject; (b) correlating the measurements of the presence, absence, or level of the measured biomarker with ovarian cancer status in the subject by comparison to a reference value; and (c) selecting treatment based on the status, wherein (i) expression of any of the at least one biomarker at a level higher than the reference value indicates treatment by neoadjuvant chemotherapy followed by interval cytoreduction, (ii) expression of any of the at least one biomarker at a level lower or equal than the reference values indicates treatment by primary debulking surgery followed by chemotherapy.

In other embodiments, the at least one biomarker at a level higher than the reference value indicating treatment by neoadjuvant chemotherapy followed by interval cytoreduction, includes one or more of COL11A1, TIMP3, FAP, POSTN, THBS2, COL5A2, CTSK, PDGFRB, MMP11, VCAN and TAGLN. In other embodiments, the at least one biomarker at a level higher than the reference value indicating treatment by neoadjuvant chemotherapy followed by interval cytoreduction, includes one or more of COL11A1, TIMP3, FAP, POSTN, COLEC11, TNFAIP6. In other embodiments, the at least one biomarker at a level higher than the reference value indicating treatment by neoadjuvant chemotherapy followed by interval cytoreduction, includes one or more of COL11A1, TIMP3, FAP, and VCAN. In other embodiments, the at least one biomarker at a level lower or equal than the reference values indicates treatment by primary debulking surgery followed by chemotherapy includes 3 or more, 5 or more, 10 or more, 15 or more, 20 or more of the at least one biomarker. In other embodiments, the ovarian cancer is high grade serous ovarian carcinoma. In other embodiments, the chemotherapy includes paclitaxel, cisplatin and/or carboplatin. In other embodiments, the chemotherapy is administered in combination with bevacizumab. In other embodiments, the chemotherapy is followed by administration with bevacizumab. In other embodiments, the method further including measuring and correlating at least one additional biomarker selected from the group includes of: prealbumin, apolipoprotein A1, β2-microglobulin, transferring, HE4, and CA125. In other embodiments, the measuring includes quantitative real-time PCR. In other embodiments, the measuring includes immunoassay.

Further described herein is a method for qualifying ovarian cancer status in a subject including: (a) measuring at least one biomarker in a sample from a subject by an assay; and (b) correlating the measurements of the presence, absence, or level of the at least one biomarker with ovarian canc In other embodiments, the sample includes a tumor biopsy sample. In other embodiments, the assay includes quantitative real-time PCR. In other embodiments, the assay includes mass spectrometry or immunoassay. In other embodiments, the measuring at least one biomarker includes measuring and correlating at least one biomarker selected from the group includes of: ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, and VIM. In other embodiments, the measuring at least one biomarker includes measuring and correlating at least one biomarker selected from the group includes of: COL11A1, TIMP3, FAP, POSTN, COLEC11, TNFAIP6, PDLIM3, SERPINE1, LOC100503, LOX, PRRX1, THBS2, COL5A2, CTSK, PDGFRB, MMP11, VCAN, PLAU, TAGLN, PMP22 and ACTG2.

In other embodiments, the measuring at least one biomarker includes measuring and correlating at least one biomarker selected from the group includes of: COL11A1, TIMP3, FAP, and VCAN. In other embodiments, the ovarian cancer status includes high grade serous carcinoma. In other embodiments, the ovarian cancer status includes low grade serous carcinoma. In other embodiments, the ovarian cancer status includes benign ovarian disease. In other embodiments, the (b) correlating the measurements of the presence, absence, or level of the measured biomarkers includes enrichment of the at least one biomarker compared to a normal baseline standard of subjects. In other embodiments, the normal baseline standard of subjects includes subjects without disease. In other embodiments, the normal baseline standard of subjects includes subjects without residual disease. In other embodiments, the method further including: (c) managing subject treatment based on the status. In other embodiments, the managing subject treatment includes primary debulking surgery (PDS) followed by chemotherapy. In other embodiments, the chemotherapy includes paclitaxel, cisplatin and/or carboplatin. In other embodiments, the managing subject treatment includes neoadjuvant chemotherapy followed by interval cytoreduction. In other embodiments, the chemotherapy includes paclitaxel, cisplatin and/or carboplatin. In other embodiments, the managing subject treatment results in optimal cytoreduction. In other embodiments, the managing subject treatment results in suboptimal cytoreduction. In other embodiments, the managing subject treatments results in no residual disease.

EXAMPLES

The following examples are provided to better illustrate the claimed invention and are not to be interpreted as limiting the scope of the subject matter. To the extent that specific materials are mentioned, it is merely for purposes of illustration and is not intended to limit the invention. One skilled in the art may develop equivalent means, compositions or reactants without the exercise of inventive capacity and without departing from the scope of the present invention.

Example 1

Ovarian Cancer Stem Cells (OCSC), Generally

As described, preliminary studies of cancer stem cells ("CSCs) in the context of ovarian cancer have focused on certain types of cells that appear to be display some or all "stemness" characteristics of CSCs. These are good candidates for bona fide ovarian cancer stem cells ("OCSC"). However, as tumors display morphological, phenotypical, and biochemical heterogeneity, it is understood that different cells may possess only some or many hallmarks of a posited OCSC, yet fail to be a bona fide OCSC. Several leading OCSC candidates include, for example, cells expressing markers CD24, CD44, CD117, CD133 and ALDH1. Among them, CD133/ALDH1 double markers have been shown most reliable to enrich for OCSC candidates, as further described via morpholoogical and functional characteristics, such as spheroid formation, cisplatin resistance, clinical outcome, and perhaps most importantly, tumor formation with as few as 30 cells (i.e., high tumor seeding potential).

However, while OCSC candidates may display some or many characteristics of a bona fide OCSC, there is yet no positive determination of which particular cells drawn from heterogeneous populations within tumors display all of the "stemness" characteristics of a bona fide OCSC. Endpoint studies demonstrating capture of bona fide OCSC could be shown experimentally by isolation of a cell capable of recapitulating the generation of a continuously growing tumor. In another example, serial transplantation in animal models provides a functional assay for the two CSC hallmarks, self-renewal and differentiation. However, these endpoint functional studies fail to provide a molecular snapshot of the biochemical actors responsible for giving CSCs, including OCSCs, their unique properties. Therefore, an OCSC signature provides two important uses. The first is a specific, biochemical definition of a bona fide OCSC, which currently does not exist. The second includes applications for prognostic and diagnostic use, as a type of ovarian cancer disease signature (OCDS).

Example 2

Preliminary Identification of Ovarian Cancer Stem Cell (OCSC) Signature from Isolated OCSCs The lack of a specific definition for what constitutes a bona fide OCSC is readily understood when considering the lack of a comprehensive study characterizing a core transcriptional program as well as metabolic pathways which OCSCs rely for their survival. Identification of such a critical pathway(s) allows to selective identification and targeting of OCSCs, ultimately improving patients' clinical outcome, through effective prognosis and/or diagnosis of disease subtypes featuring varying populations of OCSC cell numbers, and focused therapy targeting the major culprit, OCSCs, responsible for rapid tumor formation and growth. Toward this goal, the inventors have established a preliminary OCSC signature, which upon validation as a comprehensive global OCSC signature, at the transcript and protein level, provides diagnostic, prognostic and therapeutic guidance to selectively target OCSCs.

Moreover, while an OCSC provides a precise biochemical definition of a specific cell type for identification, application of an OCSC in a prognostic or diagnostic context appears to find further utility as capable of classifying molecular subtypes of cancer. For example, ovarian cancer, like other cancers, is a multi-etiological disease, and variations in tumor cell origin, tissue compartment development, and/or other factors leads to the manifestation of disease subtypes. Tumor samples may include higher or lower numbers of OCSCs, as demonstrated by detection of an OCSC signature, and this variation may prove to be highly informative of clinical outcomes (e.g., chemoresistance, survival). In this regard, an OCSC may be considered as a type of OCDS, as capable of prognostic and diagnostic applications.

In order to identify an OCSC core transcriptional program (OCSC signature), the inventors isolated OCSC candidates and non-CSCs using ALDH1 and CD133/ALDH1 from A2780 human ovarian cancer cell line. As OCSCs are a rare and evanescent cell population, the A2780 cell line provides the greatest number OCSC candidates (1%) for analysis. The inventors then analyzed the CD133+ALDH1+ OCSC candidates using Affymetrix Human Gene Array, normalized the data with two independent algorithms, and compared their expression profiling to each other as well as to public array databases (OncoMine, Stanford Microarray database, Gene Expression Omnibus) (FIG. 1). List of OCSC genes constituting a preliminary signature are shown in Table 1.

In spite of the limited availability of OCSC candidate profiling data, the inventors' expression profiling data (FIG. 2A) indeed showed some overlapping genes with published array data of other OCSC candidates (FIG. 2C), isolated with CD44 and CD133 from patient samples and cell lines. Alvero et al. (2009) Molecular phenotyping of human ovarian cancer stem cells unravels the mechanisms for repair and chemoresistance. Cell Cycle. 8(1):158-66. Baba et al. (2009) Epigenetic regulation of CD133 and tumorigenicity of CD133+ ovarian cancer cells. Oncogene. 28(2):209-18.

These results support the notion that OCSC candidates (e.g., CD133+ALDH1+ or CD44+ and CD133+) might express a common set of genes to maintain pluripotency and survival, wherein these "stemness" genes could be used to identify bona fide OCSCs. Generally speaking, core transcriptional programming as tied to "stemness" characteristics relate to genes involved in pluripotency (e.g., transcription factors), self-renewal and differentiation (e.g., growth factors, epithelial-mesenchymal transition), surface antigens (e.g., adhesion markers, migration factors, matrix production), and metabolic regulators.

Further analysis, focus on expression level, patient survival, and implication in CSC biology. This integrative analysis resulted in a preliminary OCSC gene signature. Importantly, Gene Ontology analysis of this OCSC signature showed these genes to be mainly involved in the regulation of cell proliferation, cell adhesion, and metabolic processes (Table 5). Remarkably, the Ingenuity Pathway Analysis showed that OCSC genes were connected to each other and there were some highly connected nodes ("hubs") such as fibroblast growth factor 1 (FGF1) and fibronectin 1 (FN1) (FIG. 2B, 2D), which might be novel therapeutic targets for OCSCs.

Example 3

Figure 2D:
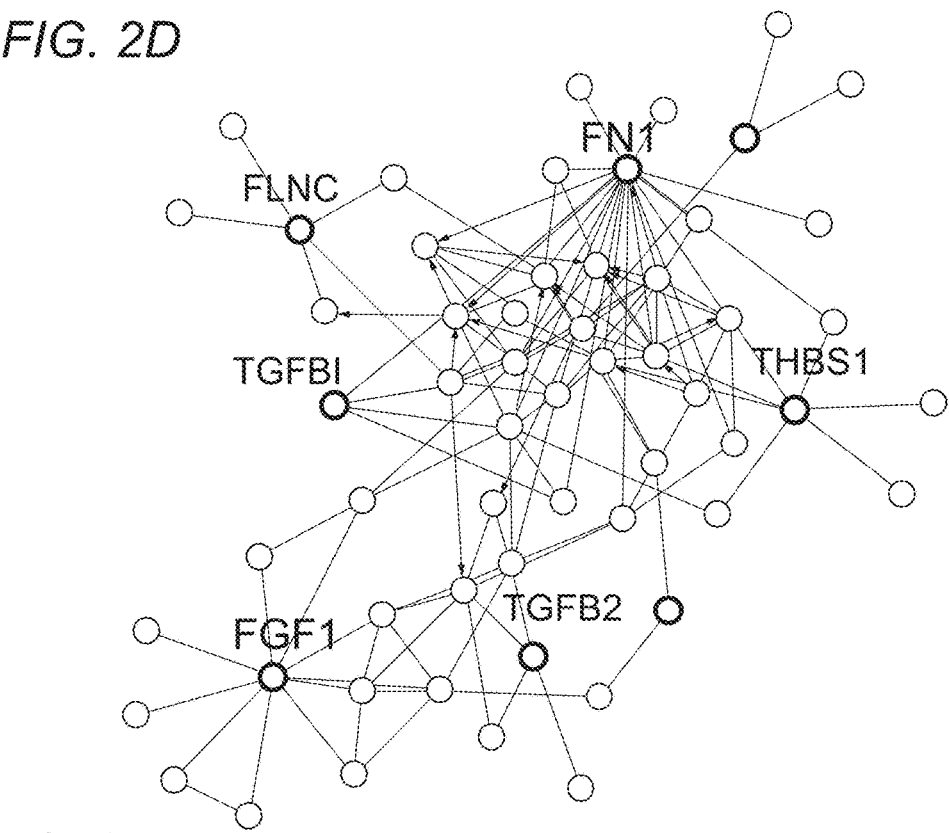
Figure 2E:
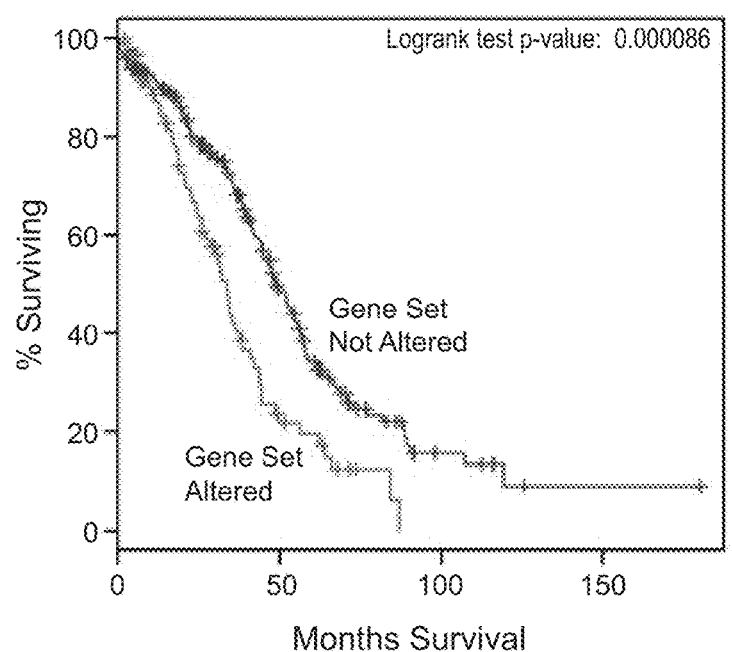
Figure 3B:
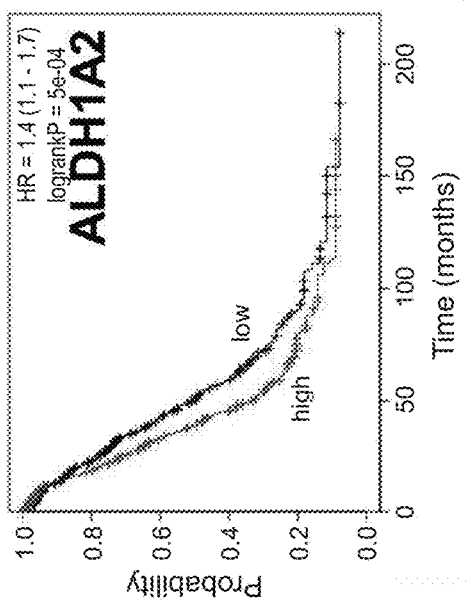
FIG. 3(A) to FIG. 3(C). Candidate ovarian cancer stem cell (OCSC) biomarkers to predict clinical outcome. In different examples, OCSC biomarkers, when highly expressed (red) are demonstrated to reduce overall survival in patients when compared to low expression (black) in patients. This includes examples such as OCSC biomarkers: (A) Secreted protein acidic and rich in cysteine (SPARC) (B) Aldehyde dehydrogenase 1 family member a2 (ALDH1A2) and (C) Desmocolin 2 (DSC2). Overall survival time (in months) is shown as drawn from 921 patient samples.
Figure 3A:
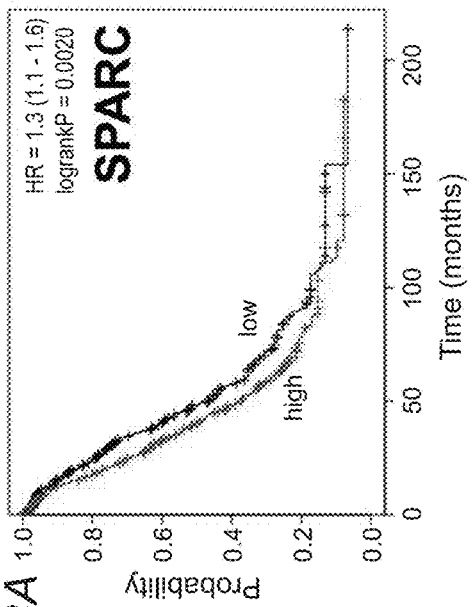
Figure 3C:
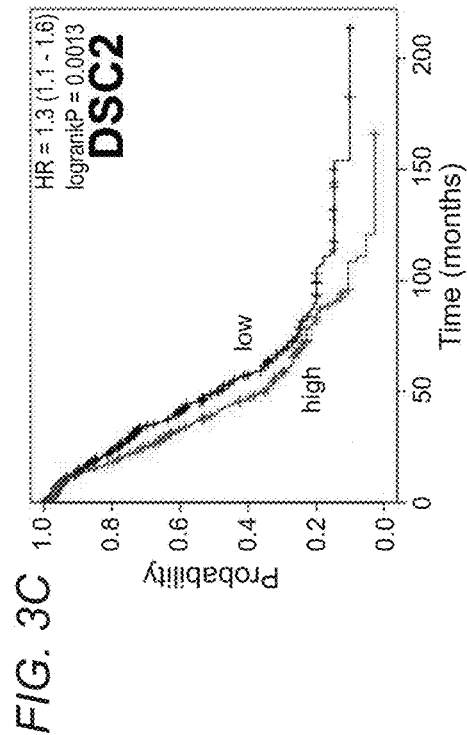

Application of OCSC Signature for Prognostic, Diagnostic, and Therapeutic Guidance Interestingly, application of the OCSC as a type of OCSD for prognostic applications indicates that, some biomarkers highly expressed in OCSCs predicted significantly poor patient survival (FIG. 2E), when used in a clinical study dataset (The Cancer Genome Atlas, TCGA dataset, FIG. 2). The inventors further confirmed that OCSC biomarkers, when highly expressed are demonstrated to reduce overall survival in patients when compared to low expression in patients. Specific examples shown include: secreted protein acidic and rich in cysteine (SPARC) (FIG. 3A), aldehyde dehydrogenase 1 family member a2 (ALDH1A2) (FIG. 3B), and desmocolin 2 (DSC2) (FIG. 3C). These results suggest that an OCSC can be applied for prognostic and/or diagnostic use as an OCDS, and demonstrate the advantages of a signature-based detection approach.

As proof-of-concept, the preliminary identification of an OCSC signature predicted candidate genes for potential therapeutic intervention and poor patient survival in public databases. Further validation of our preliminary OCSC signature using patient samples, in vitro cell culture, and statistical analysis are applied to determine prognostic and therapeutic power of an OCSC signature.

In one example, establishment of a comprehensive, global OCSC signature provides a series of biomarkers, wherein expression levels of one, some or all of the genetic markers, as a transcript or protein level, may be used to prognose a range of clinical outcomes for a patient, such as chemoresistance or survival. Further, an OCSC signature provides a definitive biochemical approach to positively identifying the proportion of cells in a tumor sample that can be confirmed as bona fide OCSCs. This focus on the percentage of cell

TABLE 5

Gene Ontology (GO) Analysis of Ovarian Cancer Stem Cells Biomarkers

| GO Term | % | P value | Genes |
| --- | --- | --- | --- |
| Regulation of cell proliferation | 31.42857 | 6.07E−06 | IGF1R, ALDH1A2, CAV1 PTRPM, SERPINE1, CDK6, SPARCH, GPNMB, FGF1, THBS1, TGFB2 |
| Response to organic substance | 25.71429 | 1.65E−04 | IF1R, ALDH1A2, CAV1, HSPA2, CD44, HSPB1, THBS1, SPP1, TGFB2 |
| Cell motion | 22.85714 | 7.95E−05 | PTPRM, NPY, CD44, MET, HSPB1, THBS1, TGFB2, FN1 |
| Cell adhesion | 22.85714 | 8.52E−04 | PTPRM, CD44, TGFB1, DSC2, GPNMB, THBS1, SPP1, FN1 |
| Response to extracellular stimulus | 20 | 9.06E−06 | ALDH1A2, CAV1, NPY, CD44, AXL, SPP1, MEST |
| Negative regulation of cell proliferation | 20 | 1.45E−04 | ALDH1A2, CAV1, PTPRM, CDK6, GPNMB, THBS1, TGFB2 |
| Phosphorous metabolic process | 20 | 0.021256 | IGS1R, PTPRM, MET, AXL, CDK6, THBS1, TGFB2 |
| Phosphate metabolic process | 20 | 0.021256 | IGS1R, PTPRM, MET, AXL, CDK6, THBS1, TGFB2 |
| Intracelluar signaling cascade | 20 | 0.062315 | IGF1R, ALDH1A2, CAV1, NPY, MET, FF1, THBS1 |
| Regulation of cell adhesion | 17.14286 | 17.14286 | TGFB1, CDK6, FGF1, THBS1, SPP1, TGFB2 | populations within a tumor samples, is critical as higher numbers are CSCs are generally understood to be indicators for poor prognostic outcomes (e.g., chemoresistance, increased tumor-sphere-forming ability, neoplastic regrowth). In another example, the genetic markers may serve as useful diagnostic tools to provide molecular subtype classifications of a gynecological cancer, such as ovarian cancer. This is of particular importance in the context of cancer, given the multi-etiological nature of these diseases.

Moreover, beyond prognostic and diagnostic applications, a comprehensive OCSC signature allows targeted therapeutic intervention focused on OCSC eradication and/or retardation. For example, current chemotherapeutic agents target the bulk population of cancer cells, and tumor regression may be observed. However, reducing bulk cancer cells that play a smaller role in tumor recurrence and chemoresistance may explain why tumor regression does not necessarily translate into increased patient survival. Worse yet, reduction of bulk cancer cell populations has been shown in certain contexts to enrich CSC populations, thereby positively the most noxious cells, OCSCs, that are responsible for poor clinical outcomes. In different examples, therapeutic approaches rely on chemical compounds (e.g., small molecule inhibitors) that selectively target OCSCs, thereby retarding CSC viability, spheroid formation, and/or limiting chemoresistance.

Example 4

Validation of OCSC Signature in Clinical Samples and Other Cell Lines

As described, a variety of OCSC candidates have been described, which may possess some or all of the features of bona fide OCSCs. As ovarian cancer, like other cancers, is a multi-etiological disease, variations in tumor cell origin, tissue compartment development, and/or other factors leads to the manifestation of disease subtypes, these subtypes exhibiting variations in clinical outcomes (e.g., chemoresistance, survival). Therefore, one may establish a preliminary OCSC signature, as obtained from cell lines, or clinical samples. Such preliminary OCSC signatures require further validation across a wider and more diverse array of cell lines and samples. This establishes those features consistently found across OCSC signatures from variable sources, thereby leading to establishment of a comprehensive, global OCSC signature. This comprehensive, global OCSC signature minimizes variation attributable to the cell source, thereby providing a biochemical definition of core transcriptional machinery responsible for providing the "stemness" characteristics of OCSCs, and one of that is agnostic to the originating source material.

Validation of a global OCSC signature is established by isolating OCSC candidates from surgical specimens and other ovarian cancer cell lines (Table 6). Further comparison with existing studies on OCSC candidates can also prove to be informative. An example of a meta-analysis conducted across existing studies is shown (Table 7). In either type of analytical sample, RNA can be extracted, and expression of OCSC biomarkers can be measured by Affymetrix Human Gene Array or quantitative real-time PCR. Non-CSCs isolated from each sample serve as controls to identify those genes uniquely upregulated in OCSCs.

TABLE 6

OCSC Markers to be Used to Isolate OCSC Candidates

| CSC marker | Sample | Expected CSC % |
| --- | --- | --- |
| CD133+*ALDH1+ | Solid tumors, ascites | 0.1% |
| CD133+ | Solid tumors, ascites | 1-20% |
| CD133+ | OVCAR8 cell line** | 40% |
| *ALDH1+ | OVCAR8 cell line | 1.9% |
| *ALDH1+ | HEY1 cell line** | 6.5% |

*ALDH1 activity is determined by ALDEFLUOR kit (Stem cell technologies, Inc).
**CD133+ALDH1+ population exists under <0.03% in these cell lines.

TABLE 7

Meta-Analysis of Cancer Stem Cell Microarray Data

| Comparison CSC v. non-CSC | Microarray Data Source | Microarray Platform | Ref |
| --- | --- | --- | --- |
| A2780 CD133+*ALDH1+ v. CD133-ALDH- | raw .CEL file | Afrymetrix GeneChip Human Gene 1.0 ST Array | Cheon |
| Patient CD44+ v. CD44- | Suppl. Table | | Alvero et al., 2009 |
| A2780CD133+ v. CD133- | Suppl. Table | Affiymetrix GeneChip Human U133A 2.0 Array | Baba et al., 2009 |
| Patient Side Population v. Major Population | GSE33874 | Affiymetrix GeneChip Human U133A Plus 2.0 Array | Vathipadiekal et al., 2012 |
| OVCAR3 spheroid-derived cells v. OVCAR3 | GSE28799 | Affiymetrix GeneChip Human U133A Plus 2.0 Array | Wang et al., 2012 |
| SKOV3 sphere v. SKOV3 | Suppl. Table | Agilent Whole Human Genome 4 x 44K microarray | Ma et al., 2010 |
| Cisplatin-resistant A2780 v. A2780 | GSE28648 | Affiymetrix GeneChip Human U133A Plus 2.0 Array | Zeller et al., 2012 |

TABLE 7-continued

Meta-Analysis of Cancer Stem Cell Microarray Data

| Comparison CSC v. non-CSC | Microarray Data Source | Microarray Platform | Ref |
|---|---|---|---|
| Cisplatin-resistant A2780 v. A2780 | GSE15709 | Affiymetrix GeneChip Human U133A Plus 2.0 Array | Li et al., 2009 |
| IGROV1 Side Population v. non-SP | GSE25191 | Affiymetrix GeneChip Human U133A Plus 2.0 Array | Rizzo et al., 2011 |

* Normalization was performed within individual study and across the studies.
* Genes which were differentially expressed in CSC were selected (top 200, bottom 200 genes) based on Significance Analysis of Microarray (SAM) method to determine fold change and statistical significance.
* CSC up genes that were common in > 2 studies were analyzed by the KM plot to identify individual gene that can predict poor OS and PFS.

Example 5

OCSC Signature as a Predictor of Clinical Outcome

As one example, establishing the predictive power of an OCSC signature can be determined by utilizing high-throughput qRT-PCR of the validated OCSC biomarkers in patient samples. One example includes the ABI Open Array® Real-time PCR system, wherein custom-designed array plates containing validated TaqMan® Real-time probes for 50 ovarian CSC identified biomarkers in duplicate are applied to patient samples. Various endogenous controls (ACTB, GAPDH, 18s rRNA, GUSB, PPIA, TBP, RPLP0, RPL4) are used for each plate for the normalization of all plates and samples.

Figure 4:
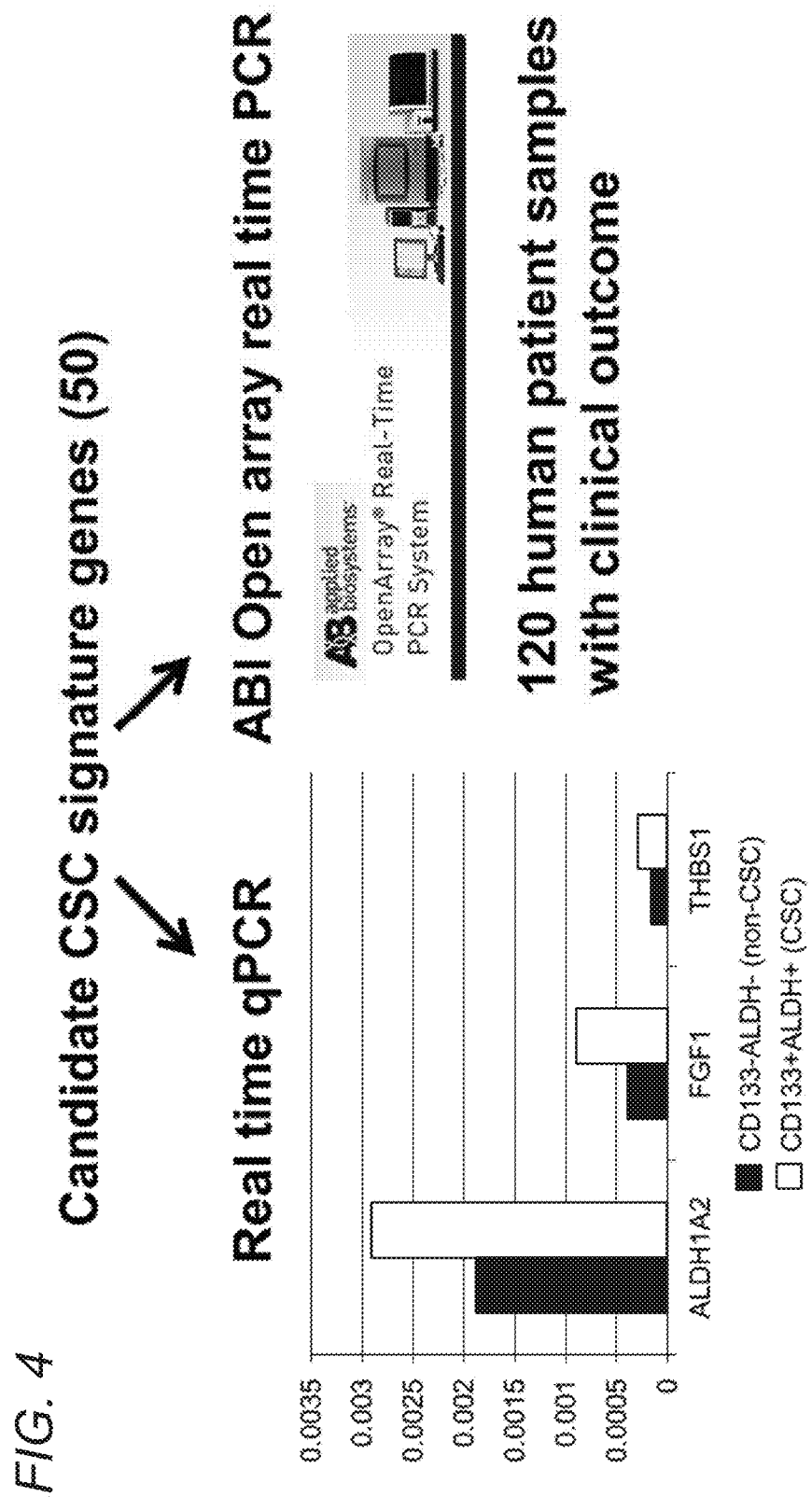
FIG. 4. Validation of preliminary ovarian cancer stem cell (OCSC) biomarkers to predict clinical outcome. Amongst 50 preliminary OCSC biomarkers, validation is performed using quantitative real-time PCR (qRT-PCR). Enhanced expression of OCSC biomarkers is confirmed, as drawn from CD133+ALDH+ OCSC candidates, and CD133− ALDH− non-OCSC cells. It is clearly observed that OCSC biomarkers are highly expressed in OCSC when compared to non-OCSC cells. This includes the example OCSC signature "hub" genes, ALDH1A2, FGF1, and THBS1. Additional confirmation is provided from clinical samples obtained from over 120 patients to establish a comprehensive OCSC signature.

Some examples of validation of preliminary OCSC biomarkers are shown in FIG. 4. Enhanced expression of OCSC biomarkers is confirmed, as drawn from CD133+ALDH+ ovarian cancer stem cells (OCSCs) candidates, and CD133−ALDH− non-OCSC cells. It is clearly observed that OCSC biomarkers are highly expressed in OCSC when compared to non-OCSC cells. This includes the example OCSC signature "hub" genes, aldehyde dehydrogenase 1 family member a2 (ALDH1A2), fibroblast growth factor 1 (FGF1), and thrombospondin (THBS1).

The expression data obtained from the qRT-PCR arrays are then matched to each patient clinical data. Examples of clinical features for analysis include FIGO stage, tumor grade, chemotherapy resistance, and survival. Two separate, but complementary statistical approaches allow one to determine the degree of association between features of an ovarian CSC signature, as tied to clinical features. Beer et al. (2002) Gene-expression profiles predict survival of patients with lung adenocarcinoma. Nat Med. 8(8):816-24. Under the first statistical approach, a number of patient samples (e.g., n=120) are randomly assigned to equivalent training and testing sets consisting of equal numbers of early stage (I+II) and late stage (III+IV) tumors to validate a novel risk-index function. The high number of patient samples allows for a robust determination of expression analysis as correlated with clinical features. Under the second statistical approach, a 'leave-one-out' cross-validation procedure can robustly confirm which genes are associated with survival, as assessed by Kaplan-Meier survival plots and log-rank tests. Beer et al. (2002). Application of these statistical approaches identifies the predictive power of a combined panel of genes. Examples of several OCSC biomarkers, such as ALDH1A2, ANGPTL4, COL1A2, COL3A1, COL6A1, EFEMP1, HOXA10, LUM, SPP1, TGFB2, THBS1, and TMEM47 also serve as effective predictors of poor overall survival outcomes as shown in FIG. 11. These results support the notion that OCSC signature provides not only a specific biochemical definition of OCSCs, but can also serve as a predictor of clinical outcome.

Example 6

Application of OCSC Signature for Identifying Key Therapeutic Targets

Establishing and validating an OCSC signature allows one to predict drugs that specifically target OCSCs and limit the noxious effects tied to their rapid proliferation and growth. In one example of this approach, an OCSC signature is analyzed using Connectivity Map (http://www.broadinstitute.org/cmap/) public database, which predicts candidate drugs modulating expression of a specific gene signature. Using Connectivity Map, pattern-matching of the query (e.g. OCSC gene signature) with a reference collection of gene expression profiles from cultured human cells treated with bioactive small molecules. Another example is the Ingenuity Pathway Analysis application described above. Application of Connectivity Map or Ingenuity Analysis with the ovarian CSC signature allows identification of compounds that repress, modulate, or alter targets associated with the OCSC signature. Commercially available chemical compounds, or existing compound libraries may be tested for efficacy in cell lines known to contain a population of OCSCs, such as A2780, HEY1, and OVCA8. In addition, the effect of those compounds on CSC viability (% of CD133+ALDH1+, CD133+, ALDH1+ cells by flow cytometry), spheroid formation, and chemoresistance (cisplatin IC50) is measured as parameters for identifying compound efficacy.

Figure 11A:
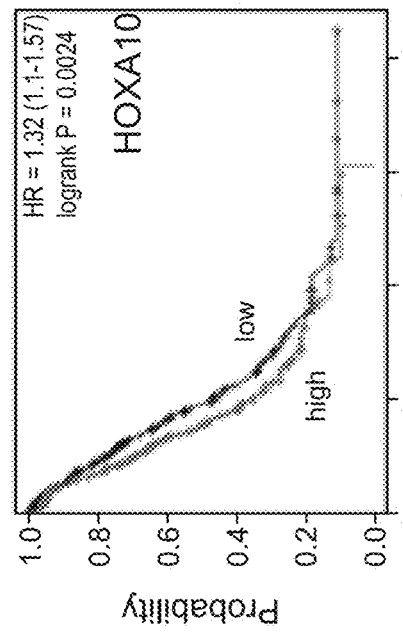
FIG. 11(A) to FIG. 11(L). Ovarian cancer stem cell (OCSC) genes predict poor overall survival. Kaplan-Meier plots demonstrate that biomarkers associated with ovarian cancer stem cells are also effective predictors of poor overall survival (OS). This includes (A) ALDH1A2 (B) HOXA10 (C) COL1A2 (D) COL3A1 (E) ANGPTL4 (F) THBS1 (G) COL6A1 (H) LUM (I) SPP1 (J) EFEMP1 (K) TGFB2 and (L) TGFB1.
Figure 11B:
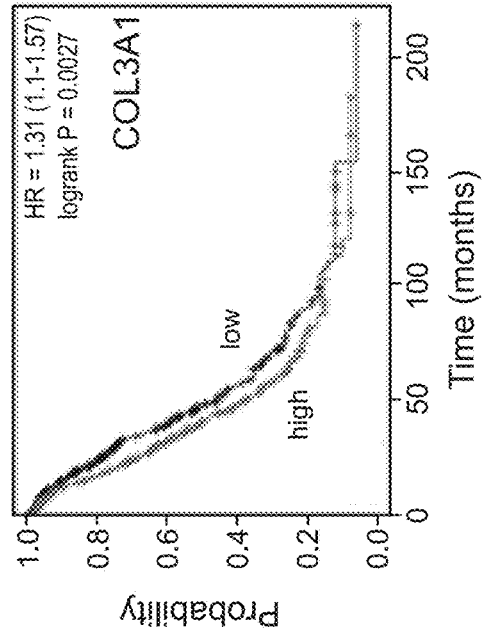
Figure 11C:
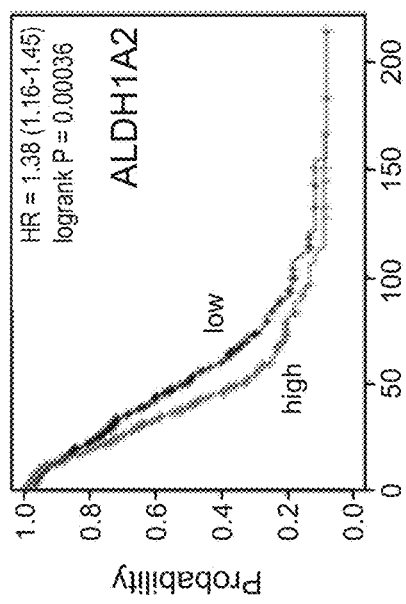
Figure 11D:
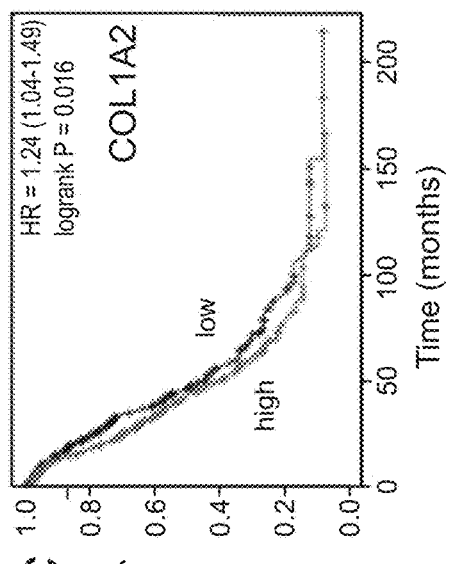
Figure 11F:
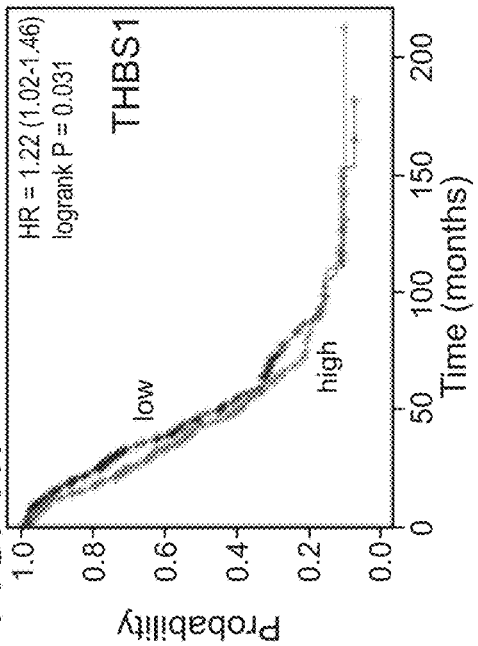
Figure 11H:
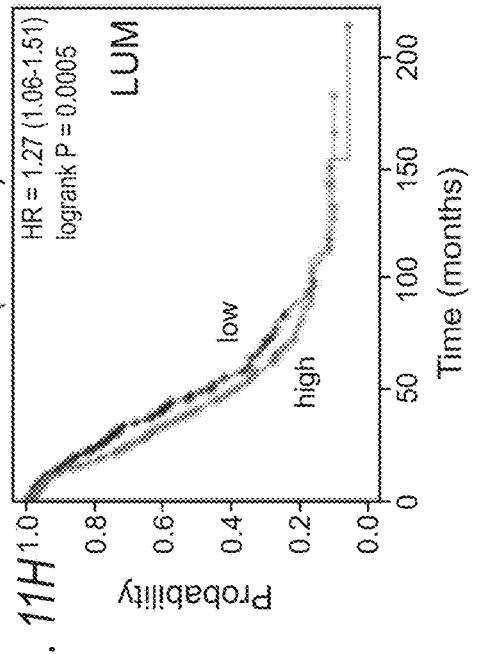
Figure 11E:
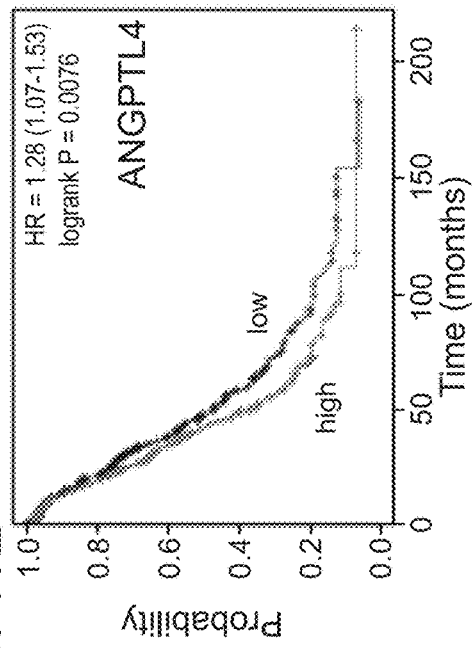
Figure 11G:
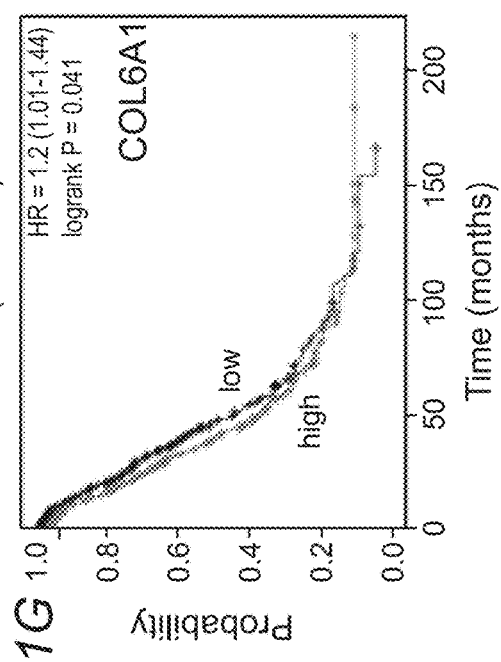
Figure 11J:
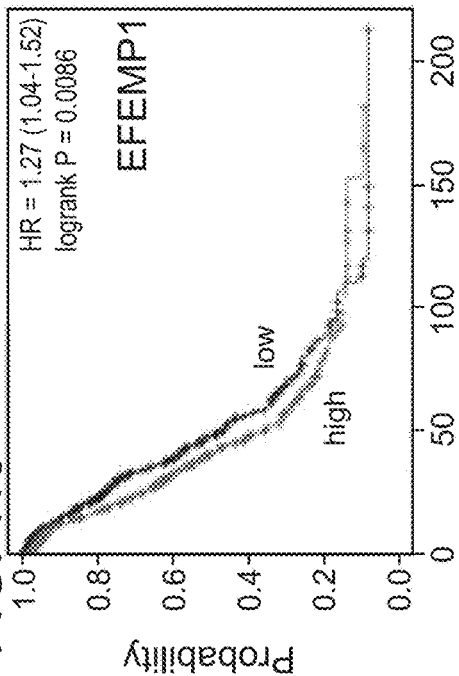
Figure 11L:
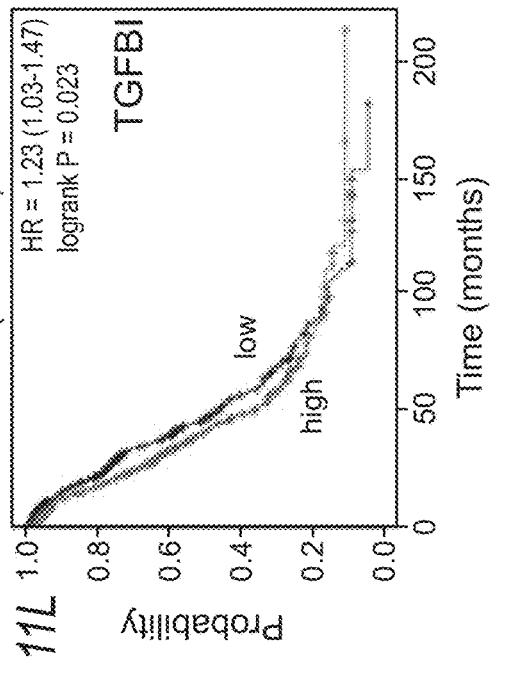
Figure 11I:
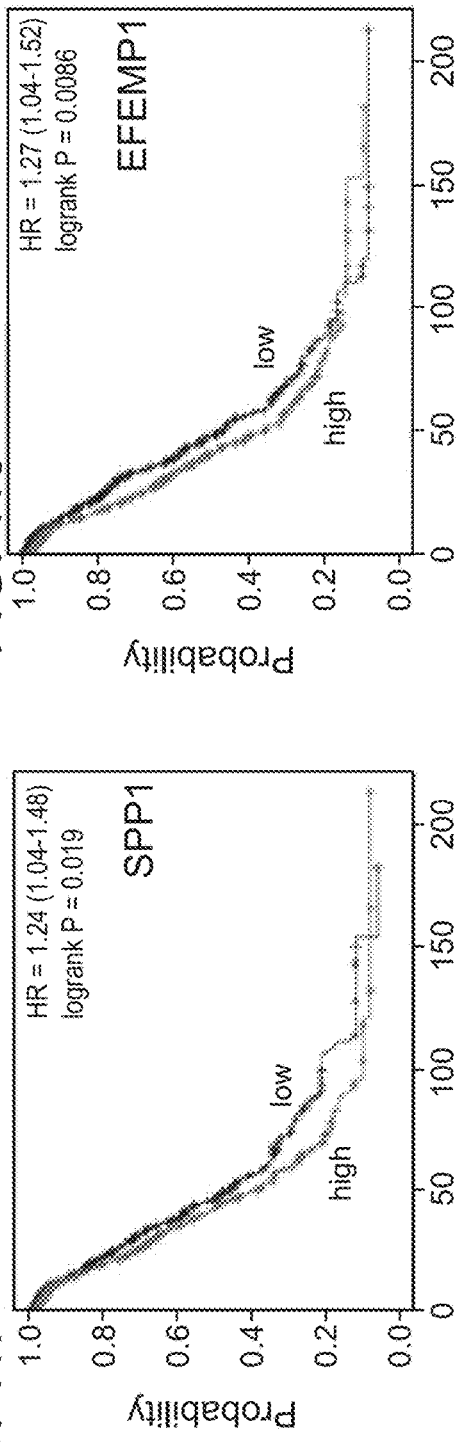
Figure 11K:
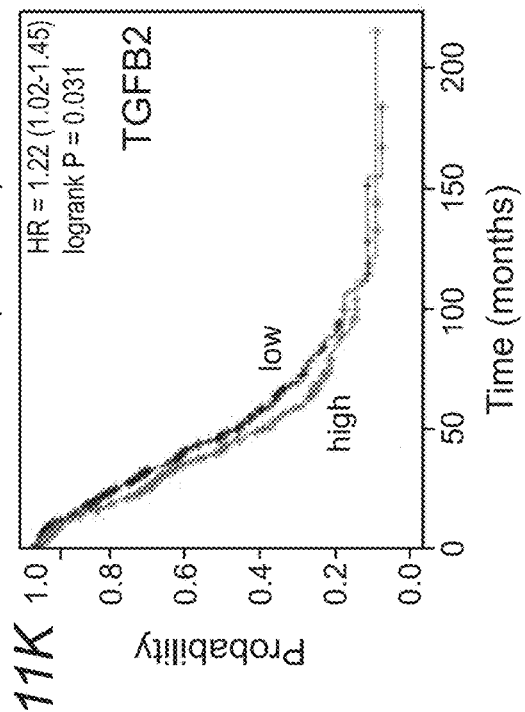

For example, as shown in FIGS. 11K and 11L, TGF-beta 1 and 2 are associated with OCSC signature and are effective predictors of poor survival. As TGF-beta is known to be an important signaling pathway involved in stem cell development, including regulation of epithelial to mesenchymal transition, aberrant TGF-beta regulation may be a key mechanism underlying the role of OCSC in tumor formation and disease progression. Interestingly, application of the Ingenuity Pathway Analysis demonstrates that several OCSC signature biomarkers are regulated by TGF-beta pathway proteins. These target OCSC biomarkers, include ACTA2, ADAM12, COL11A1, COL3A1, COL5A1, COL6A2, CYR61, DCN, FN1, GREM1, LOX, POSTN, SNAI2, SPARC, TAGLN, TIMP3, VCAN, and/or VIM. Upstream TGF-beta pathway regulators are listed in Table 8, along with their corresponding OCSC biomarkers. Each of these biomarkers could serve as targets of therapies that inhibit aberrant TGF pathway function, demonstrating the utility of a OCSC in developing personalized therapeutic strategies.

TABLE 8

OCSC Regulated by TGF-β pathway

| Upstream Regulator | Molecule Type | P-Value of Overlap | # of Signature Genes | Target Molecules in the Signature |
|---|---|---|---|---|
| TGFB1 | growth factor | 1.99E−18 | 18/21 | ACTA2, ADAM12, COL11A1, COLA3A1, COL5A1, COL6A2, CYR61, DCN, FN1, GREM1, LOX, POSTN, SNAI2, SPARCH, TAGLN, TIMP3, VCAN, VIM |
| ERBB2 | kinase | 5.60E−16 | 13/21 | ACTA2, ADAM12, COL3A1, COL5A1, COL6A2, FN1, TAGLN, TIMP3, VCAN, VIM |
| TGFB3 | growth factor | 3.45E−15 | 8/21 | ACTA2, ADAM12, COL11A1, COL5A1, CYR61, FN1, TAGLN, TIMP3 |
| EDN1 | cytokine | 1.24E−10 | 7/21 | ACTA2, ADAM12, COL5A1, FN1, TIMP3, VCAN, VIM |
| FGF2 | growth factor | 2.11E−10 | 8/21 | ACTA2, CYR61, DCN, FN1, GREM1, LOX, SPARC, VIM |
| RUNX2 | transcription regulator | 4.08E−10 | 6/21 | ACTA2, COLA11A1, FN1, LUM, SNAI2, TAGLN |
| LAMC1 | other | 9.71E−10 | 4/21 | ACTA2, FN1, SNAI2, VIM |
| SPARC | other | 1.32E−09 | 4/21 | FN1, SNAI2, SPARC, VIM |
| SMAD7 | transcription regulator | 1.39E−09 | 6/21 | ACTA2, COL3A1, DCN, FN1, TAGLN, TIMP3 |
| BMP4 | growth factor | 1.63E−09 | 6/21 | ACTA2, CYR61, GREM1, POSTN, SPARC, TAGLN |

Example 7

Repression, Modulation, or Alteration of OCSC Signature Targets

An important focus of the technology is that identification of an OCSC signature allows identification of not only individual targets that interact in a biochemical network, but specific "hub" genes that may amplify and enhance the role of many complementary targets involved OCSC survival. Without being bound by any particular theory, it is believed that repression, modulation, or alteration of these specific "hub" genes may prove to be more effective in dismantling the biochemical machinery underlying cancer pathogenesis, in contrast to disruption of individual targets involved in the growth and development of cancer.

Network analysis of ovarian CSC biomarkers indicates fibroblastic growth factor-1 (FGF1) and fibronectin (FN1) as preliminary candidates for "hub" genes (FIG. 2D). Confirmation of FGF1 and FN1 as essential factors for ovarian CSC survival can be shown by knockdown of FGF1 and FN1 in human ovarian cancer cell lines (A2780, HEY1, OVCAR8) using MISSION shRNA lentiviral particles (Sigma Aldrich). The impact of effective FGF1 and/or FN1 knockdown on CSC viability (% of CD133+ALDH1+, CD133+, ALDH+ cells by flow cytometry), spheroid formation, and chemoresistance (cisplatin IC50), demonstrates the importance of these "hub" genes in OCSC development, survival, and drug resistance. In complementary studies, knockdown of multiple genes may be used to display enhanced phenotypes OCSCs. These studies can be further supplemented by gain-of-function approaches, wherein the gene of interest is engineered into healthy cells of a relevant tissue type, thereby helping to reveal the phenotype of individual genes.

Example 8

Characterization of OCSCs, and Isolation from Various Sources

Ovarian cancer stem cells are rare cells, perhaps accounting for less than 1% of the total cell population in a clinical sample or cultured cell lines. Most ovarian cancer patients have bulky tumors and/or extensive metastatic spread at the time of diagnosis, and can provide a large volume of tumor and ascites from a single patient. Enriching for OCSC candidates can be performed by first pooling OCSC candidate using single markers (e.g., CD133 or ALDH1), to isolate more abundant populations for analysis. A second approach can be to induce greater numbers of ovarian CSC population by adding BMP2 to cell lines.

Example 9

Identify Key Metabolic Pathways in OCSCs

Initial data shaping a preliminary OCSC signature gene demonstrates enrichment in biochemical pathways related to regulation of cell proliferation, cell adhesion, and metabolic processes (Table 5). Study of the aforementioned "hub" genes, such as FGF1 and FN1, clearly suggest key factors as related to cell proliferation and cell adhesion.

In addition, no comprehensive study has focused on metabolites and metabolic pathways essential for ovarian CSC survival. A key focus of the present technology is establishing metabolic profiling of OCSCs, then integrating metabolome and transcriptome data for identification of key metabolic pathways in OCSCs. As metabolisis of a key feature of cancer growth and development, "hub" genes related to these processes provides therapeutic targets for repression, modulation, and/or alteration, thereby providing effective tools for targeting those biochemical targets unique to OCSCs and/or which may play a critical role in spurring cancer growth and/or pathogenesis. Disruption of OCSC growth, development and functional in the context of cancer pathogenesis is expected to be magnified by targeting "hub" genes.

For example, current chemotherapeutic agents have been largely selected for their ability to reduce the bulk population of cancer cells rather than the rare CSCs that may drive tumor recurrence and chemoresistance. This may explain why tumor regression does not necessarily translate into increased patient survival. Additionally, reduction of bulk cancer cell populations has been shown in certain contexts to enrich CSC populations, thereby enriching and selecting for these most noxious cells which may be responsible for rapid cancer disease progression. Furthermore, integrative studies using an OCSC signature model with metabolic profiling, as described further below, might reveal critical genes and pathways for ovarian CSC survival for the development of novel classes of therapeutics. More effective cancer therapies will emerge when CSC-targeted therapies are combined to conventional treatments directed at tumor bulk populations.

Example 10

Metabolic Profiling of OCSCs

Identifying metabolites specific to CSCs is accomplished through comprehensive, high-throughput metabolic profiling of OCSCs and non-CSCs. For this, ALDH1+CD133+ OCSC candidates and ALDH1-CD133- cell populations are isolated from both surgical specimens and A2780 human ovarian cancer cell line. After sorting, cells are harvested and frozen at −80° C. Metabolites are extracted from frozen cell pellets and analyzed by GC/MS and LC/MS platforms. Metabolites will be identified by comparison to library entries of purified standards or recurrent unknown entities. Welch's two-sample t-tests are used to identify metabolites that differ significantly between OCSCs and non-CSCs. Significantly altered metabolites will be put into the context of biochemical pathways after statistical analysis and data curation.

Example 11

Integration of Metabolome and Transcriptome Data for OCSCs

Initial integration of metabolome and transcriptome data is provided by first applying the preliminary expression profiling data establishing an OCSC signature via microarray, as well as qRT-PCR data obtained from the validated OCSC global signature to develop a mechanistic model of signaling in OCSCs. There is a particular focus on differentially expressed metabolic enzymes that display a clear connection with differential quantities of metabolites identified in the metabolic profiling. A significant emphasis is on those metabolomic pathways with high translational potential, such as those pathways already targeted by existing drugs capable of inhibiting the selected pathway.

A set of comprehensive metabolic characteristics of CSCs have not been described for any cancer type. Thus, these results provide the first and most comprehensive map of metabolic pathways in at least one types of cancer stem cell, OCSCs. If OCSCS share core transcriptional and metabolomics characteristics as other types of cancer stem cells from other cancers, it is likely that OCSCs will exhibit enhanced dependence on oxidative phosphorylation, aberrant glycine metabolism, altered fatty acid metabolism and glycolysis, and high PFKFB4 expression. In addition, OCSCs may uniquely utilization a subset of key metabolites and metabolic enzymes. Such features would provide novel therapeutic targets in ovarian cancer.

As described, enrichment of isolated OCSCs can be performed by pooling sorted cell populations from multiple surgical samples, inducing ovarian CSC population by adding BMP2 to cell lines, or using single markers (e.g., CD133 or ALDH1) to isolate more abundant populations of OCSC candidates including OCSCs.

As OCSC candidates may display some variation in metabolic properties, application of additional stem cell markers, such as CD44 to isolate OCSCs, allows further comparison of the levels of several key metabolites and transcripts to those in ALDH1+CD133+ cell populations.

Example 12

Cellular Context of OCSCs

Solid tumors are now understood to be complex "organs" comprised of not only malignant cells, such as OCSCs, but also non-malignant cells, thus, while OCSCs clearly play an important role in cancer disease progression, it is of paramount interest to identify the relative contribution of OCSCs in the overall context of tumor formation. For example, the relationship amongst OCSC and surrounding stromal cells is not totally understood. Better understanding processes would aid understanding of tumor formation events, as the roles for these cell types in tumor progression and metastasis are not well defined. Various non-malignant cell types are typically lumped together as tumor "stroma", and include fibroblasts, resident epithelial cells, immune cells, endothelial cells, pericytes, myofibroblasts and various mesenchymal stem cell types (MSCs) from recruited from bone marrow, fat, and connective tissues. Within this context, it is presently unknown if tumor formation is driven by: 1) recruitment of mesenchymal stem cells (MSCs) to the tumor from bone marrow or fat, or if 2) cancer cells induce de-differentiation of stromal cells into MSCs. Moreover, as the above described OCSC signature suggests aberrant expression of genes involved in epithelial-mesenchymal transitions (EMT) (Table 5), it is of further interest to understand the role of stromal cells in tumor formation, and the interrelation with appearance and generation of OCSC populations.

The above observations are extended to animal models to explore in vivo mechanisms of tumorigenesis and cancer development. In different approaches, the inventors generated primary and metastatic mouse ovarian cancer cell lines (FIG. 5). Primary cell lines (C lines) were generated by isolating ovarian surface epithelial cells from p53−/− mice and introducing various combinations of c-myc, K-ras, and Akt oncogenes in vitro (FIG. 5A). Primary cell lines were then intraperitoneally injected into nude mice. To establish corresponding metastatic cell lines (T lines), tumor nodules were then isolated from the intestinal lining (FIG. 5B, 5C).

Comparing the expression profiles of 7 metastatic vs. 7 primary cell lines shows that 510 genes are consistently expressed more than 2-fold in the metastatic cell lines in comparison to the primary cell lines (T lines vs. C lines in FIG. 5A). Importantly, this gene expression comparison highlight COL11A1, CXC112, POSTN as among the genes that are expressed more than 10-fold in the metastatic ovarian cancer cell lines (FIG. 5D).

Example 13

Selectively Labeled Stromal and Ovarian Cancer Cell Lines

Figure 6A:
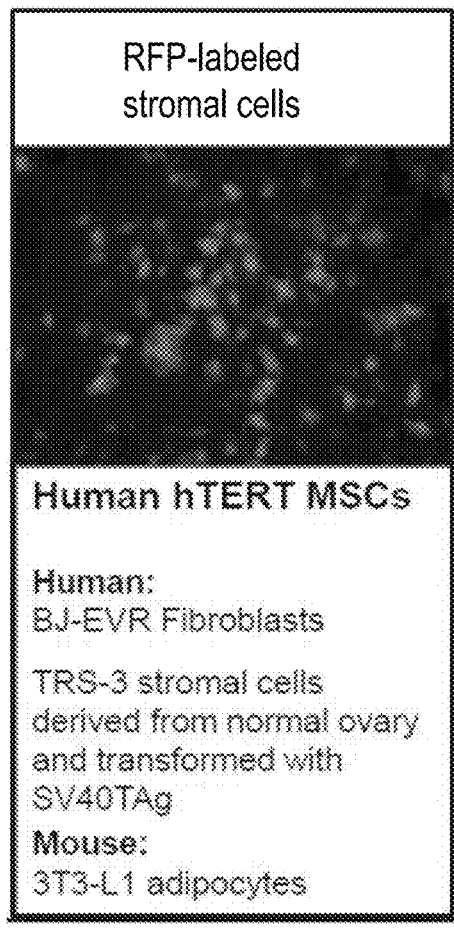
FIG. 6(A) to FIG. 6(B). Various cell lines can be specifically labeled to evaluate roles of cancer cells and stroma in tumor formation. Examples are shown, including (A) RFP-labeled stromal mesenchymal (MSCs), and (B) GFP-labeled ovarian cancer.
Figure 6B:
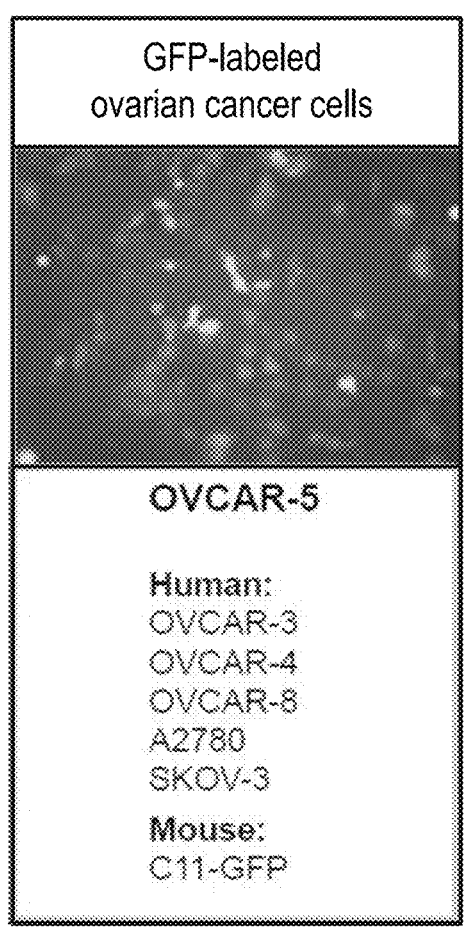

One approach for unraveling the contributing cell types in tumor formation relies on combining a mouse model of ovarian cancer with labeled stromal and ovarian cancer cell lines of human and mouse origin. Using stable gene expression, one can generate several red fluorescent protein (RFP)-labeled stromal cell lines of human and mouse origin, including human immortalized mesenchymal stem cells (MSCs), transformed foreskin fibroblasts, stromal cells derived from the normal ovary, and mouse adipocytes (FIG. 6). Additionally, several ovarian cancer cell lines of human and mouse origin were labeled with green fluorescent protein (GFP) (FIG. 6). Dual labeling of stromal cells via RFP and MSCs with GFP can therefore distinguish between the cell types, and provides a basis for identifying the cellular context of the signature genes.

For example, distinguishing between upregulated genes in malignant cells or instead, are the result of cells recruited by the tumor, such as fibroblasts, pericytes, immune cells, and bone marrow or fat MSCs, one can rely upon the above describe mouse model for generation of the mouse primary and metastatic ovarian cancer cell lines (FIG. 5) except that human ovarian cancer cell line SKOV3-GFP are used for intraperitoneal injection. Application of human- and mouse-specific PCR primers for selected genes that overlap between the human and mouse (i.e. COL11A1, CXCL12, and POSTN) allows determination of whether the signature in the tumor is of human or mouse origin. For example, those biomarkers originating from human cancer cells, would result in PCR products with human primers but not mouse primers. Conversely, biomarkers originating in mouse cells recruited to the tumor, would lead to an increase in PCR products with mouse primers, but not human primers.

Example 14

Contribution of Stromal Cells

Most outcome-predicting gene signatures originate in cancer cells, such as the described OCSC signature. However, as described, it is becoming increasingly clear stromal cells are active contributors to tumor progression and that large amounts of tumor stroma are also associated with poor clinical outcome in multiple solid tumors. However, as described, the interactions and signals between cancer cells and stromal cells are still poorly understood. Identifying the cellular context of the poor prognosis signature will help focus on the correct cell type for the future development of assays to predict outcome in ovarian cancer patients and may provide a basis for future biologic or immune therapeutic targets.

Another helpful insight on the contribution of stromal cells is provided by three different types of RFP-labeled stromal cell lines of human origin: human MSCs, fibroblasts, and stromal cells from the normal ovary (FIG. 6). Each of these cell lines can be co-injected with the C11-GFP mouse ovarian cancer cell line into mice for the development of carcinomatosis. The presence of RFP-labeled stromal cells within the tumors will be determined by immunofluorescent visualization of frozen tumor sections and by fluorescence cell sorting. The expression levels of the biomarkers will be determined using human- and mouse-specific PCR primers as described above. As it is known that stromal cells enhance tumor growth in xenografts, this approach identifies specific contributions of certain stromal cell types to tumor formation.

In addition to RNA analysis, fluorescence cell sorting (FACS) can be used to separate human and mouse cells before RNA isolation for expression profiling using qRT-PCR.or human- and mouse-specific microarrays. This approach identifies altered gene expression patterns that are involved in lineage-specific differentiation, and can further identify the specific contribution of differentiated adipocytes, osteocytes and chondrocytes to tumor formation. Further, co-injection with ovarian cancer cells further answers the question of whether the presence of cancer cells affects differentiation status (i.e. over-representation of genes involved in de-differentiation).

Example 15

Ovarian Cancer Disease Signature (OCDS): Molecular Subgroups, Patient Prognosis and Survival As described, the identification of a biochemical definition of OCSCs allows detection of the absence, presence, and population numbers of this cell type in patient samples. Aggressive tumors may contain cells of origin from a proliferative compartment and exhibit higher numbers of OCSC cells, whereas, a less aggressive tumor from more mature compartment may exhibit lower numbers of CSC cells. In this regard, the overall population numbers of OCSCs in the cancer tumors of an individual may ultimately prove to be suggestive of different cancer subtype classifications. As shown by preliminary data applying the OCSC as a predictor of clinical outcome, this demonstrates the OCSC signature is capable of serving as a prognostic and diagnostic tool (FIGS. 3 and 11). In this regard, OCSC serves as a type of ovarian cancer disease signature (OCDS) for classifying molecular subtypes of cancer disease.

Generation of OCDS along different experimental designs allows one to capture the breadth of molecular heterogeneity of gynecological cancers, particularly as cancer is a multi-etiological disease likely to arise from a variety of biological factors. As a different example, one can assess late-stage, high-grade, papillary serous ovarian adenocarcinomas classified into molecular subgroups that correlate with patient survival. An example of this data is provided by analysis of The Cancer Genome Atlast (TCGA) dataset, which includes ovarian serous cystadenocarcinoma. Analysis of this data by Orsulic et al. identified a 86 OCDS biomarker signature presented in Table 3, as associated with poor survival. A second example includes identification of individual genes that correlated with prognosis, such as the identification of genes associated with suboptimally debulked tumor, using the data set by Bonome et al. Bonome et al., (2008) A gene signature predicting for survival in suboptimally debulked patients with ovarian cancer. *Cancer Res,* 68:5478-86. Prognostic classification of this data, such as poor patient response to therapeutic treatment, identified a 68 OCDS biomarker signature, as analyzed by Cui et al. and shown in Table 4.

Further examples include studying genes co-expressed with periostin (POSTN) in in vitro ovarian cancer cells, as provided by Karlan et al. Periostin has been found to be overexpressed in a variety of human malignancies, and plays a critical role in both ovarian tumor angiogenesis and metastasis. This analysis yielded a 188 OCDS biomarker signature, as shown in Table 2.

In each case, in vivo samples, animal models and/or in vitro cell lines can identify those genes that can serve as predictive biomarkers of poor prognosis, such as suboptimal debulking, chemo resistance and poor survival rate, and potentially effective therapeutic targets. Each of these study approaches provides an OCDS, as shown in Tables 1-4, for further analysis and refinement.

Variation in experimental design is likely to best capture the molecular heterogeneity of the disease, and aid the understanding the cellular context of the poor-prognosis gene signature and disassembling the gene signature network. The OCDS provided by each study outperforms the predictive power of individual genes.

Example 16

Ovarian Cancer Fixed Signature (OCFS)

Four different approaches to OCDS identification were pursued, with examples of ovarian cancer disease signatures (OCDS) presented in Tables 2-4. In addition to the aforementioned OCSC signature (Table 1), three expression studies provided OCDS focused on gene clustering associated with: 1) poor survival (Orsulic et al.), 2) poor prognosis (Cui et al.), and 3) periostin (POSTN) co-expressing genes (Karlan et al.) As described, differences amongst the study designs allow one to encompass heterogeneity in ovarian cancer disease. These differences may provide vital clues in molecular subtyping of cancers, wherein clinical approaches may be adjusted to most effectively retard disease progression or render treatment.

Figures 7A, 7B:
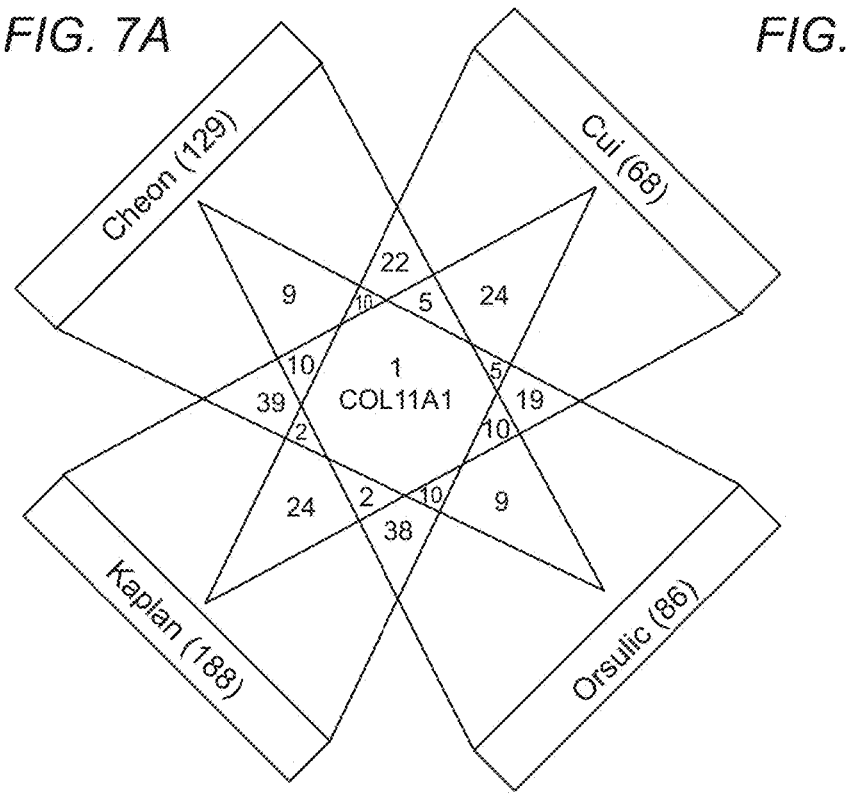
FIG. 7(A) to FIG. 7(C). Ovarian cancer disease signatures, ovarian cancer fixed signatures. (A) Gene overlap among 4 independently-derived ovarian cancer disease signatures (OCDS) that are associated with poor survival in patients with high-grade, late-stage, serous ovarian carcinoma. (B) List of genes that overlap between at least 3 of the 4 prognosis signatures—a preliminary ovarian cancer fixed signature (OCFS). (C) Overall survival based on periostin (POSTN)-correlated OCDS signature.

A composite of OCDS biomarkers helps identify the overlapping biomarkers which may identify core programming as associated with ovarian cancer, while eliminating outliers. In this regard, it is critical to establish ovarian cancer fixed signature (OCFS) as associated with core programming, and as a composite analysis of the various OCDS described herein. Importantly, the application of different data sets and different approaches to OCDS identification, revealed preliminary OCFS indicating poor-prognosis, as substantially overlapping between the four studies (FIG. 7A). It is notable that one gene (COL11A1) is present in all four signatures, while 21 genes listed in FIG. 7B are present in at least three of the four poor prognosis OCDS.

A 21-gene OCFS representing candidates present in three of four studies provides an preliminary "fixed signature" for further refinement. These 21 genes include ACTA2, ADAM12, AEBP1, COL11A1, COL3A1, COL5A1, COL6A2, CYR61, DCN, FN1, GREM1, LOX, LUM, POSTN, SNAI2, SPARC, TAGLN, THBS2, TIMP3, VCAN, VIM. As useful for characterizing molecular subtyping across cancers, a 101-gene OCFS represents candidates present in two of four studies, thereby allowing one to encompass heterogeneity of molecular subtypes. These 101-genes include ACTA2, ACTG2, ADAM12, ADH1B, AEBP1, ALDH1A1, ALDH1A2, ANGPTL2, ASPN, C1QTNF3, CALD1, CAV1, CD36, CD248, CNN1, COL10A1, COL11A1, COL1A2, COL1A1, COL3A1, COL5A1, COL5A2, COL6A2, COLEC12, COMP, CTSK, CXCL14, CXCL12, CYP1B1, CYR61, DCN, DOCK11, DUSP1, ECM1, EDNRA, EFEMP1, EGR1, ELL2, EPYC, FAP, FBLN1, FBLN2, FBN1, FGF1, FN1, FOSB, GPNMB, GREM1, GUCY1A3, HBB, HOXA7, IGFBP5, IL6, IL7R, INHBA, ITGBL1, LAMA4, LAMB1, LOX, LOXL1, LUM, MAL, MMP11, MMP1, NBL1, NNMT, NR2F2, NTM, NUAK1, OLFML3, PDGFRA, PDLIM3, PDPN, PHLDB2, PIEZO2, PLAU, POSTN, PPIC, PTGIS, SERPINE1, SERPINF1, SFRP2, SFRP4, SNAI2, SPARC, SPON2, SPP1, SULF1, TAGLN, TDO2, TGFBI, THBS1, THBS2, TIMP3, TMEM47, TMEM158, TNC, TPM1, TUBB2A, VCAM1, VCAN, and VIM.

The clinical utility of any new prognostic assay will depend on whether it provides therapeutically relevant information that is superior to the well-validated clinical variables. To date, four clinical variables, age, stage, residual tumor status after cytoreductive surgery, and levels of cancer-antigen CA125, have been validated as prognostic factors in ovarian cancer. The objective of our statistical analysis is to correlate progression-free survival (PFS) with gene expression to estimate if a gene expression signature can provide prognostic information beyond the existing standard in clinical practice. Optimization and validation of the 21-gene OCFS will be done in Three Phases as described below.

Example 17

Ovarian Cancer Fixed Signature (OCFS) Derivation

Genes identified across multiple OCDS identified a preliminary 2 genes forming a preliminary ovarian cancer fixed signature (OCFS), that most strongly correlated with overall survival. Refinement of a final OCFS relies upon iterative statistical approaches, which in further combination with additional clinical data sets, provides a robust signature composed of genes correlated with patient survival outcomes across different studies. In particular, as these 21 preliminary OCFS genes originate from 4 expression profile studies that used different platforms, a median rank score method for cross-platform normalization can be performed in order to make the expression values comparable.

One example of statistical methods for generating an OCFS, is the lasso method for the Cox model. This method is well-suited for preliminary analysis since this method cannot identify more than n genes, where n is the total number of patients. Further refinement can be provided by method of Supervised Principal Components regression (SPC), as a screening method to identifying a subset of genes strongly predictive of survival.

In addition, further stringency can be provided by application of Cox Univariate Shrinkage (CUS) approach, or Bayesian Model Average (BMA) algorithm. These methods are designed to identify genes that are highly correlated with the time to event of interest as they are entered in the Cox proportional hazards model. Bayesian Information Criteria (BIC) will be used to select the number of genes in the final model where the lowest point on the BIC curve corresponds to the best choice of covariates. Existing statistical R-packages will be used for these methods. In many instances, application of these various stringency tests is likely to result in signatures of 8 to 15 genes across the above described statistical methods, leading to establishment of a final OCFS.

Example 18

Ovarian Cancer Fixed Signature (OCFS) Validation

Figure 7C:
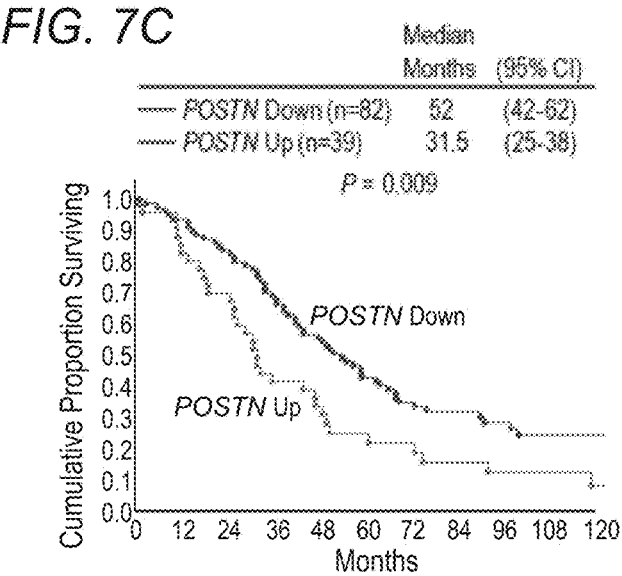

Further stringency and confirmation of the predictive power of the OCFS requires validation, with additional data sets. In particular, publicly-available data sets yet to be used for signature discovery. The Bild and Tothill data sets are selected as containing large number of samples from patients diagnosed with high-grade, late-stage, serous ovarian carcinoma. Bild, et al., (2006) Oncogenic pathway signatures in human cancers as a guide to targeted therapies. *Nature* 439:353-7. Tothill et al., (2008) Novel molecular subtypes of serous and endometrioid ovarian cancer linked to clinical outcome. *Clin Cancer Res,* 14:5198-208. Based on the excellent predictive power of some of the OCDS biomarkers (i.e. Kaplan-Meier plot for the POSTN gene signature is shown in FIG. 7C), a candidate OCFS can be optimized in satisfaction of the required performance criteria to identify patients who will relapse within a year after initial treatment.

Figure 10A:
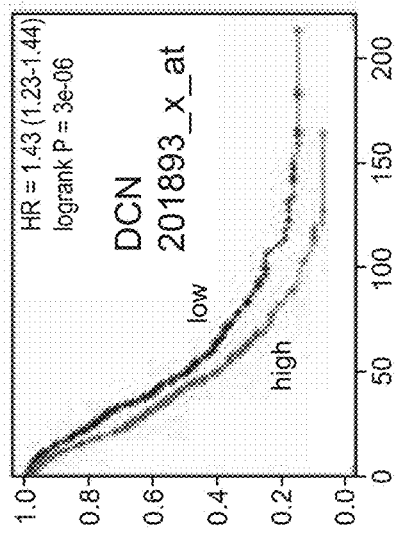
FIG. 10(A) to FIG. 10(I). Individual and combinations of genes can effectively predict poor overall survival (OS). Kaplan-Meier plots demonstrate that several biomarkers are associated with poor overall survival outcomes when highly expressed. This includes: (A) COL3A1 (B) DCN (C) LUM (D) SPARC (E) TIMP3 (F) VCAM. K-M Plotter was used to determine progression-free survival across 8 datasets listed in (G) for a total analysis across 1,339 patients. There were no restrictions based on stage, histology, grade, and treatment. Combinations of genes can also effectively predict poor overall survival, as shown in (H) using the combinations of genes listed in (I).
Figure 10B:
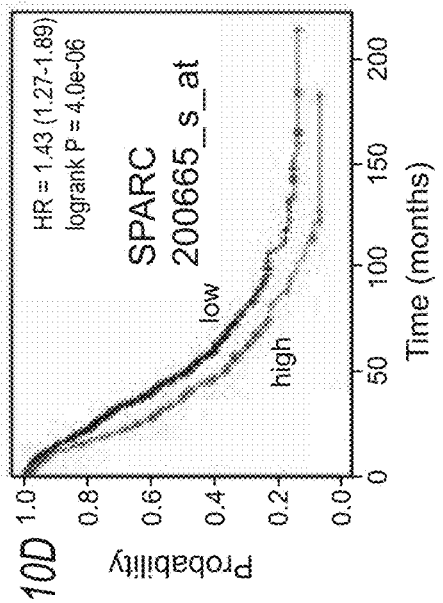
Figure 10C:
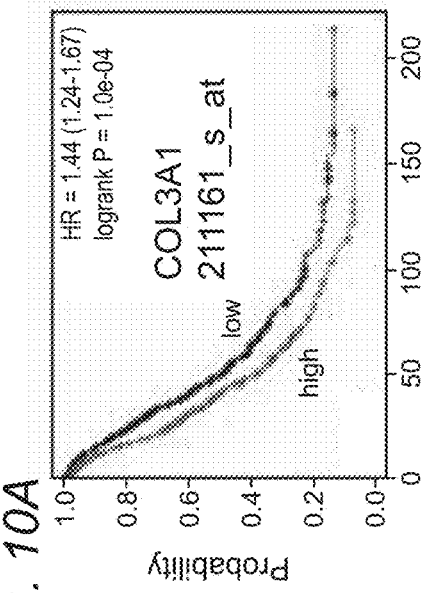
Figure 10D:
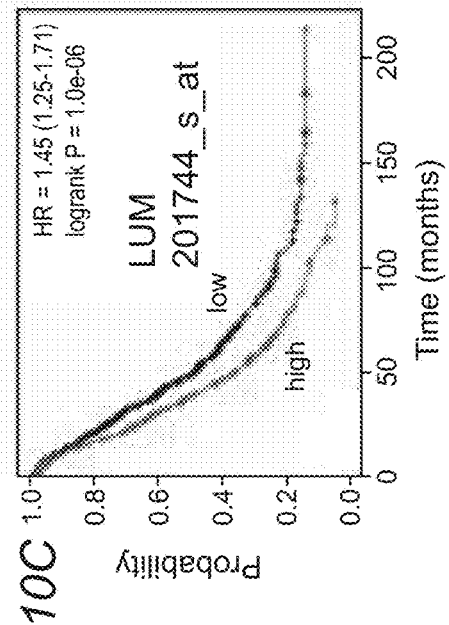
Figure 10E:
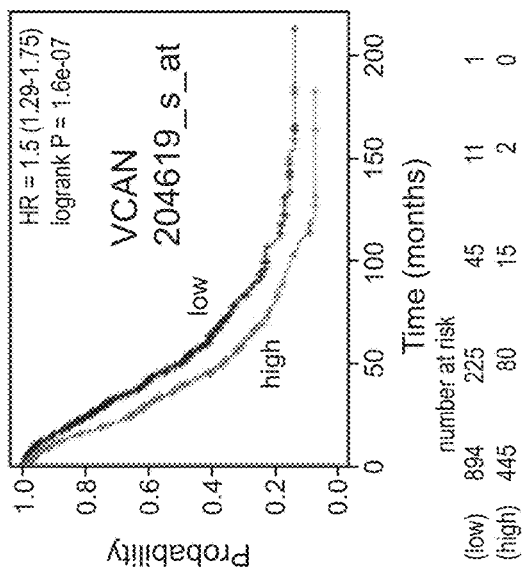
Figure 10F:
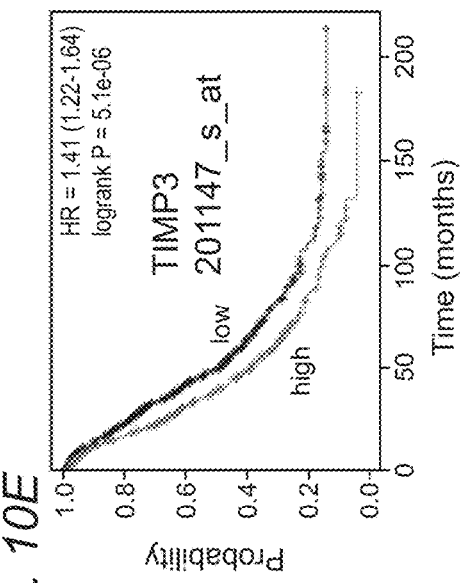
Figure 10G:
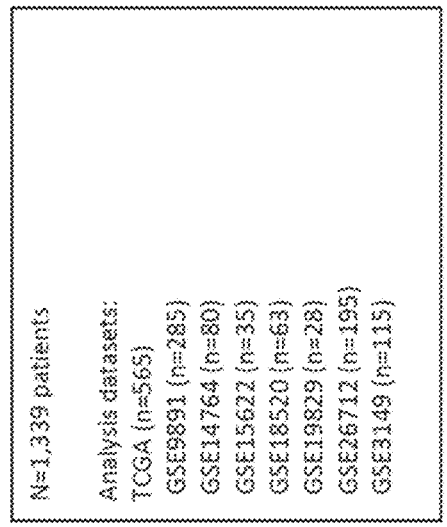
Figure 10I:
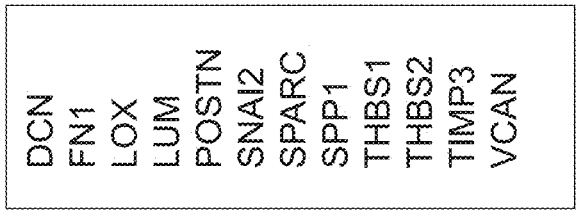
Figure 10H:
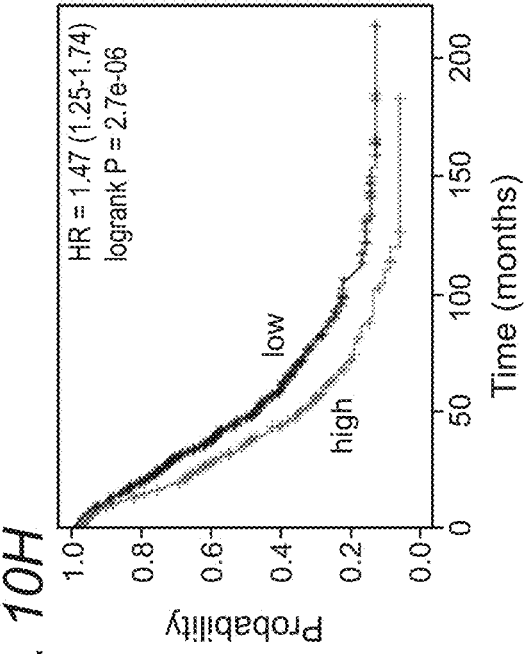

Additional examples of analyzing publicly available datasets for signature validation demonstrates the capability of individual biomarkers to predict specific clinical outcomes. For example, analysis across multiple data sets identified several biomarkers, that served as strong predictors of specific clinical outcomes. As shown in FIG. 9, high expression of COL3A1, DCN, LUM, SPARC, VCAN, COL11A1, COL5A1 and POSTN were individually predictive of poor progression-free survival when highly expressed, as shown by analysis across multiple data sets encompassing a total of 1,107 patients. Likewise, as shown in FIG. 10, other clinical parameters, such as poor overall survival, were effectively predicted by high expression of individual biomarkers, COL3A1, DCN, LUM, SPARC, TIMP3, and VCAM, as shown by analysis across multiple datasets encompassing 1,339 patients. Combination of biomarkers, as shown in FIGS. 10H and 10I, demonstrates the enhanced predictive power of using a panel of biomarkers, wherein high expression is highly predictive of overall survival.

Further validation can be provided by in vitro testing of the signature biomarkers, using the selectively labeled animal model, the 21-gene signature was not enriched when the primary cell lines were compared to the primary cell lines or when the metastatic cell lines were compared to the metastatic cell lines (i.e. comparison of 3 myc+Kras vs. 3 Akt+myc cell lines). The presence of the 21-gene signature in mouse primary vs. metastatic cell lines indicates that a process similar to human ovarian cancer progression occurs in the mouse model. Thus, this mouse model can be used to study the cellular context of the biomarkers.

Example 19

Figure 12A:
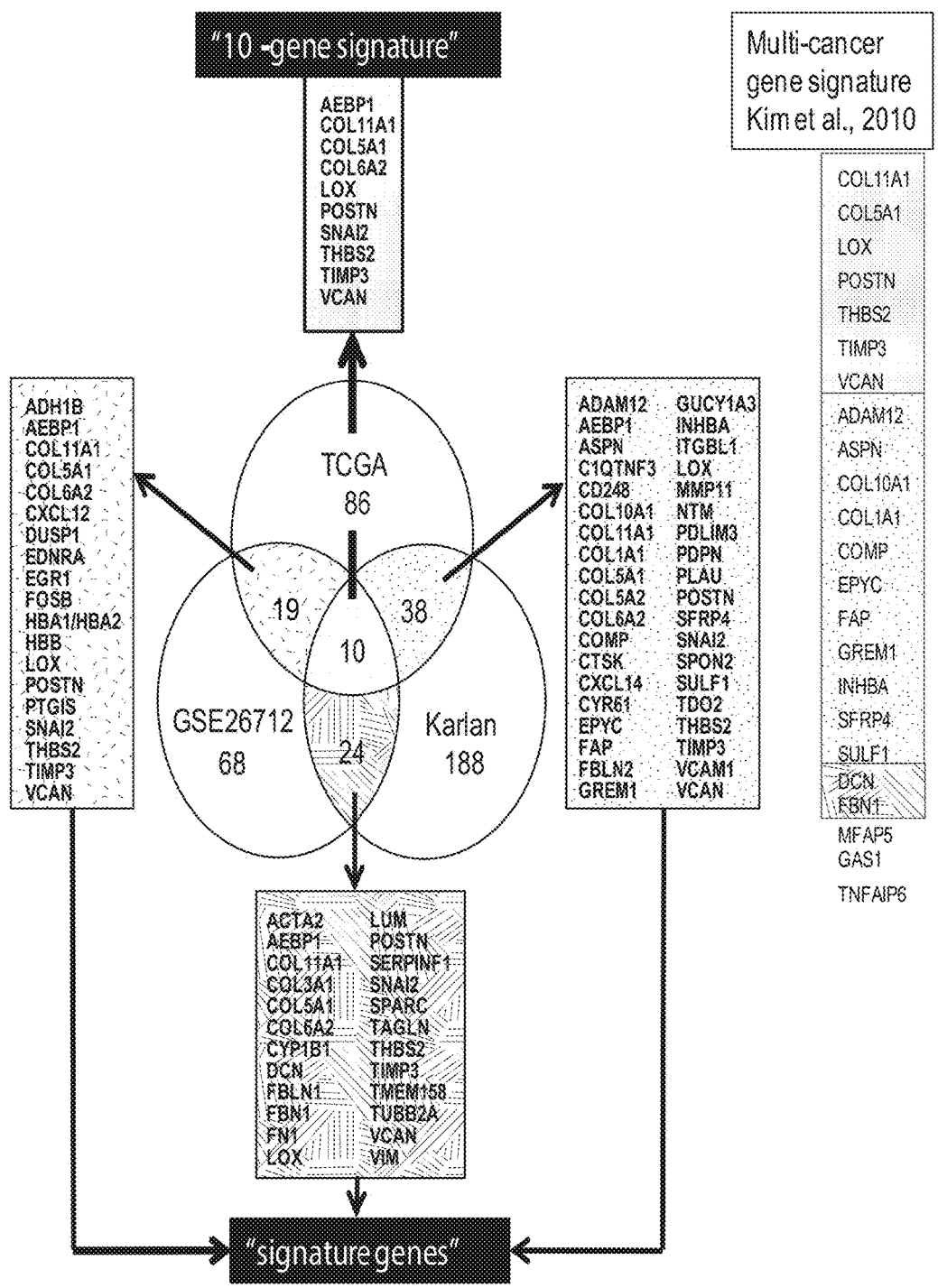

Identification of a 10-Gene Signature Associated with Poor Overall Survival in Patients with Serous Ovarian Cancer As described, the Inventors analyzed three large microarray datasets that primarily included high-grade, advanced-stage, primary serous ovarian carcinoma samples: TCGA (n=403) (5), the GSE26712 dataset (N=185) (6), and the Karlan dataset (n=122; GSE51088). Comparison of the three resultant gene signatures of poor survival identified 61 genes were present in at least two of the three signatures (19 genes in TCGA and GSE26712; 38 genes in TCGA and Karlan; and 24 genes in GSE26712 and Karlan) and that 10 of these 61 genes were present in all three datasets (FIG. 12A).

Figure 18:
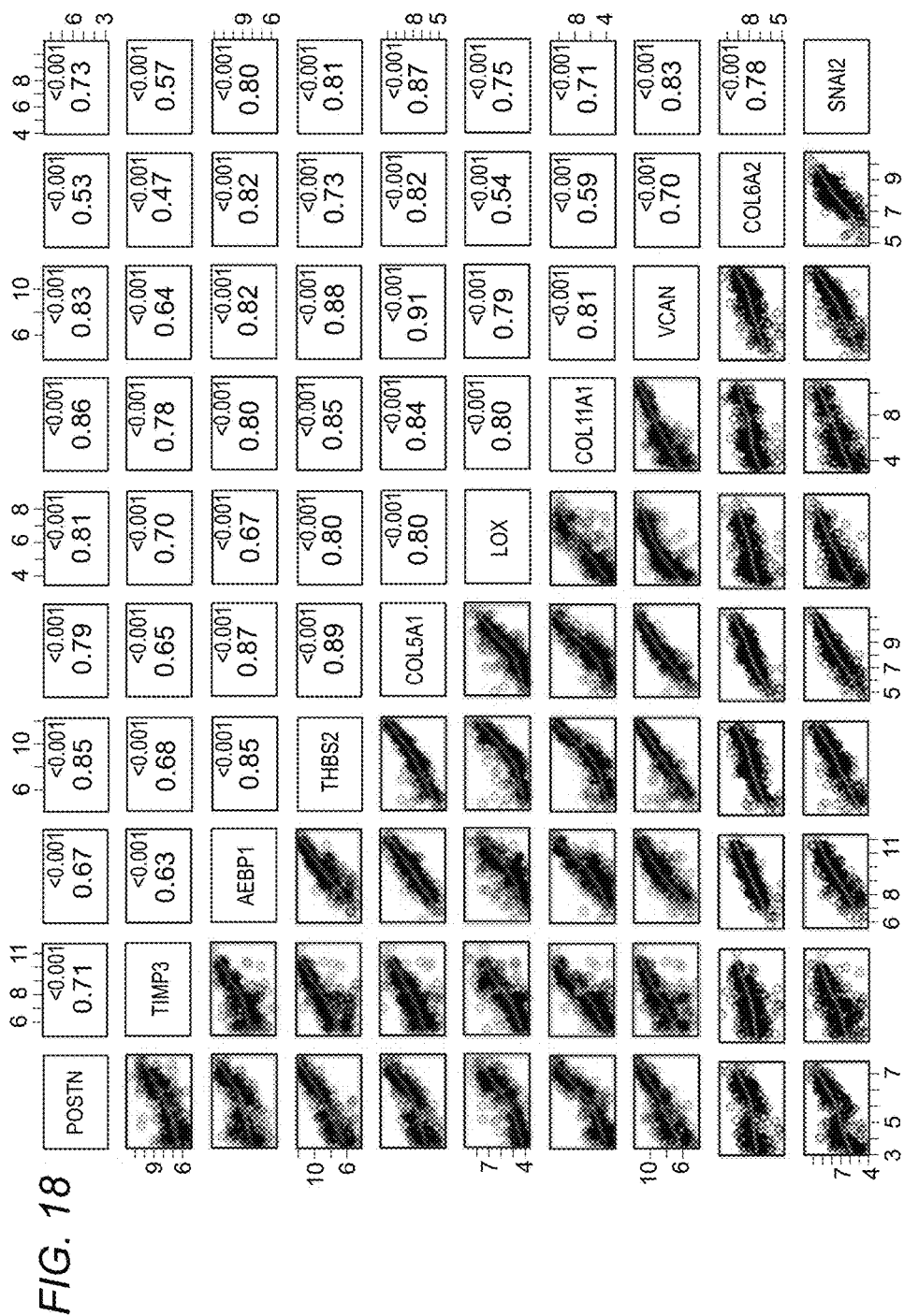
FIG. 18. Correlogram of the 10 poor outcome signature genes. The main diagonal shows the gene name. At the horizontal and vertical intersection of each gene, the Pearson correlation coefficient (center, in black) and the associated P value (top right corner, in red) are shown.

Interestingly, the 10 genes forming a candidate OCFS-AEBP1, COL11A1, COL5A1, COL6A2, LOX, POSTN, SNAI2, THBS2, TIMP3, VCAN (listed in Table 4a), are known to be localized in the extracellular matrix and are involved in cell adhesion and collagen remodeling. Pearson correlation showed that expression of the 10 genes is highly correlated (FIG. 18), suggesting their involvement in similar biological processes. The identification of 10 collagen-remodeling genes as a poor outcome gene OCFS suggests that collagen-remodeling might be a common biological process that contributes to poor overall survival among patients with serous ovarian carcinoma.

Example 20

Validation of the 10-Gene Signature in Predicting Poor Overall Survival

As the 10 signature genes were selected based on overlap among the three survival signatures rather than on predictive efficiency, the Inventors evaluated the potential predictive value of the 10-gene signature in the three discovery datasets and one independent validation dataset by comparing survival in patient groups with 'high' and 'low' expression of the 10 genes. In each of the 3 discovery datasets, the patient group with 'high' expression of the 10-gene signature had poor overall survival: TCGA (log-rank P=0.00559; HR=0.64 [0.47, 0.88]), GSE26712 (log-rank P=0.0007; HR=0.54 [0.38, 0.78]), and Karlan (log-rank P=0.022; HR=0.6244 [0.42, 0.94]) (FIG. 12B).

Figure 19:
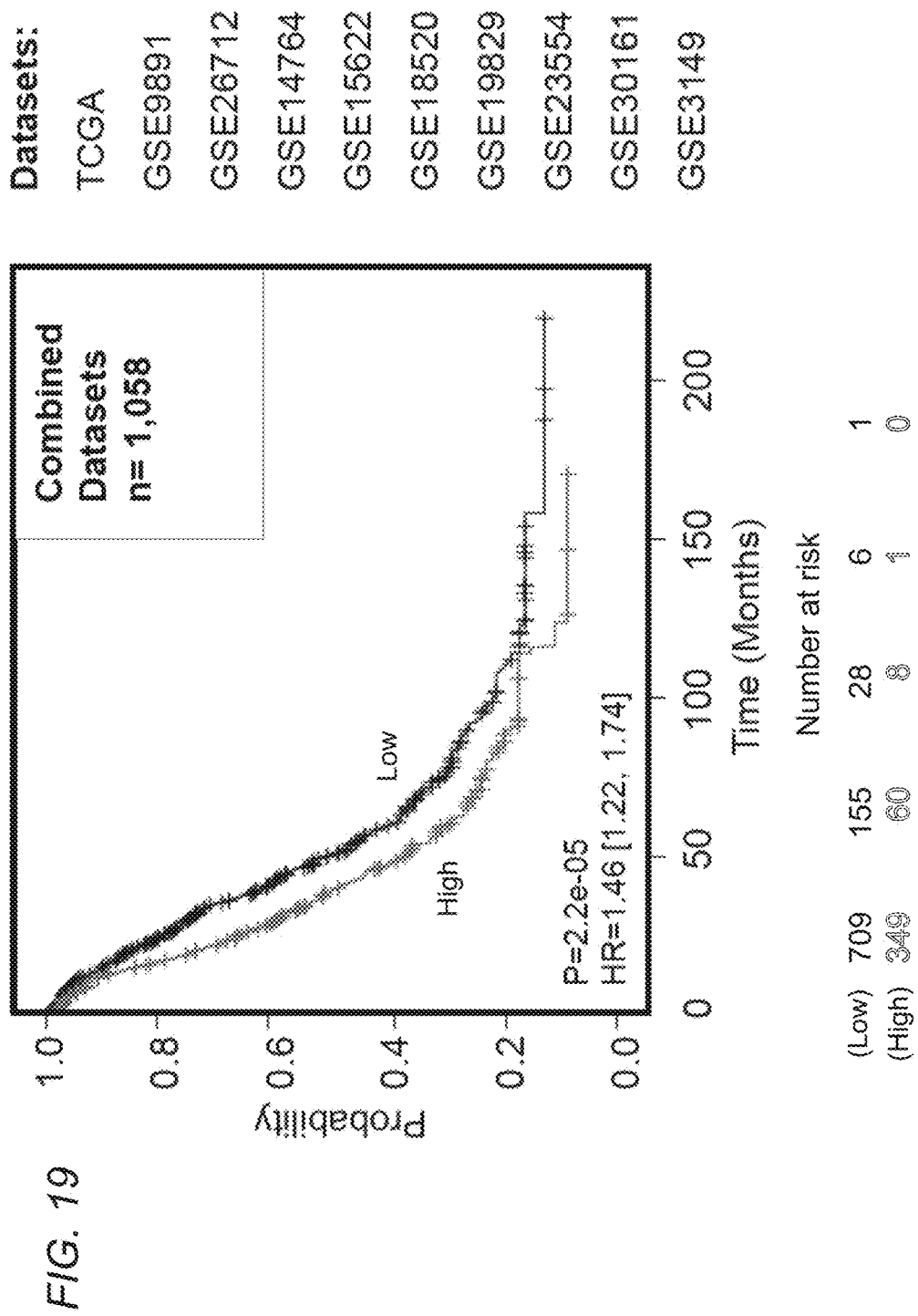
FIG. 19. Validation of the 10-gene signature in a dataset composed of 10 individual datasets. The Kaplan-Meier Plotter (http://kmplot.com/) was used to validate the predictive power of the 10-gene signature in a combined microarray of 10 datasets shown on the right. Affymetrix probe IDs of the 10 genes, including 201792_at (AEBP1), 204320_at (COL11A), 203325_s_at (COL5A1), 213290_at (COL6A2), 215446_s_at (LOX), 210809_s_at (POSTN), 213139_at (SNAI2), 203083_at (THBS2), 201147_s_at (TIMP3), 204619_s_at (VCAN), were uploaded to the website program. The mean expression of all 10 genes was analyzed for overall survival of patients with serous histology (n=1,058). Patient samples were randomly split by upper tertile. The Kaplan-Meier plot shows the overall survival in two patient groups with 'high' (red) and 'low' (black) expression of the 10-gene signature.
Figure 20:
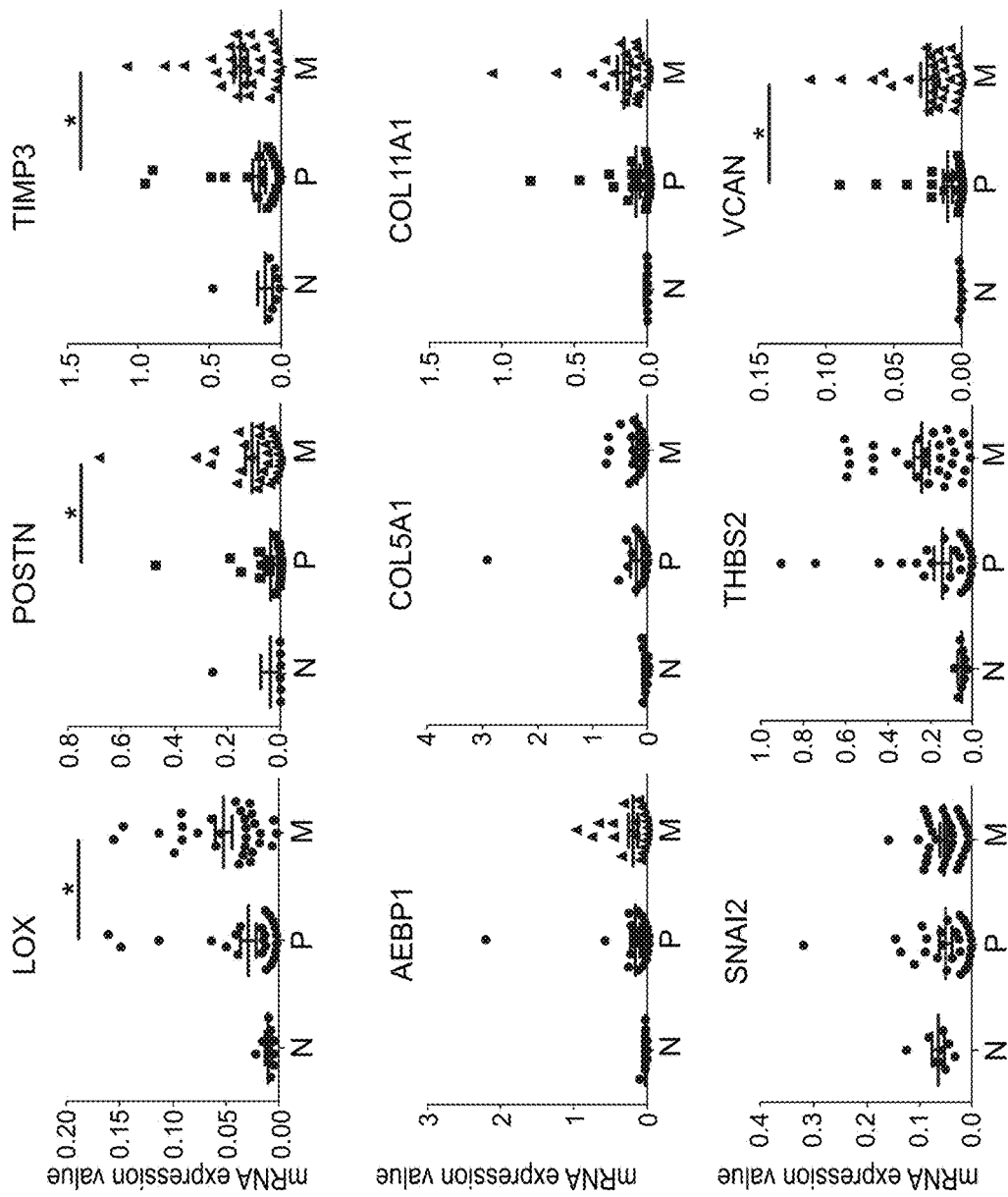
FIG. 20. ABI Open Array Real-time PCR of 9 poor outcome signature genes (COL6A2 was not available on the array) in normal (N, n=8), primary (P, n=30), and metastatic (M, n=29) ovarian cancer samples. Each dot represents an individual patient sample. Bars indicate the mean+/−SEM. * indicates statistical significance (P<0.05).

For validation, the Inventors used the Tothill dataset (GSE9891) since it comprised a large number of serous ovarian cancer samples (n=260) with well-defined clinical outcome data. In this validation dataset, the 10-gene signature predicted poor overall survival with statistical significance (log-rank P<0.0001; HR=0.41 [0.27, 0.61]) (FIG. 12C). Similar results were obtained after adjusting for cancer stage (not shown). The 10 gene-signature also predicted poor overall survival with statistical significance (log-rank P=2.2E-05; HR=1.46 [1.22, 1.74]) when applied to a large combined ovarian cancer dataset (n=1,058) consisting of 10 publicly available datasets (FIG. 19). These results validate the 10-gene OCFS as a predictor of poor overall survival.

Example 21

Regulation of Poor Outcome Gene Expression by the TGFβ Signaling Pathway

Figures 13A, 13B:
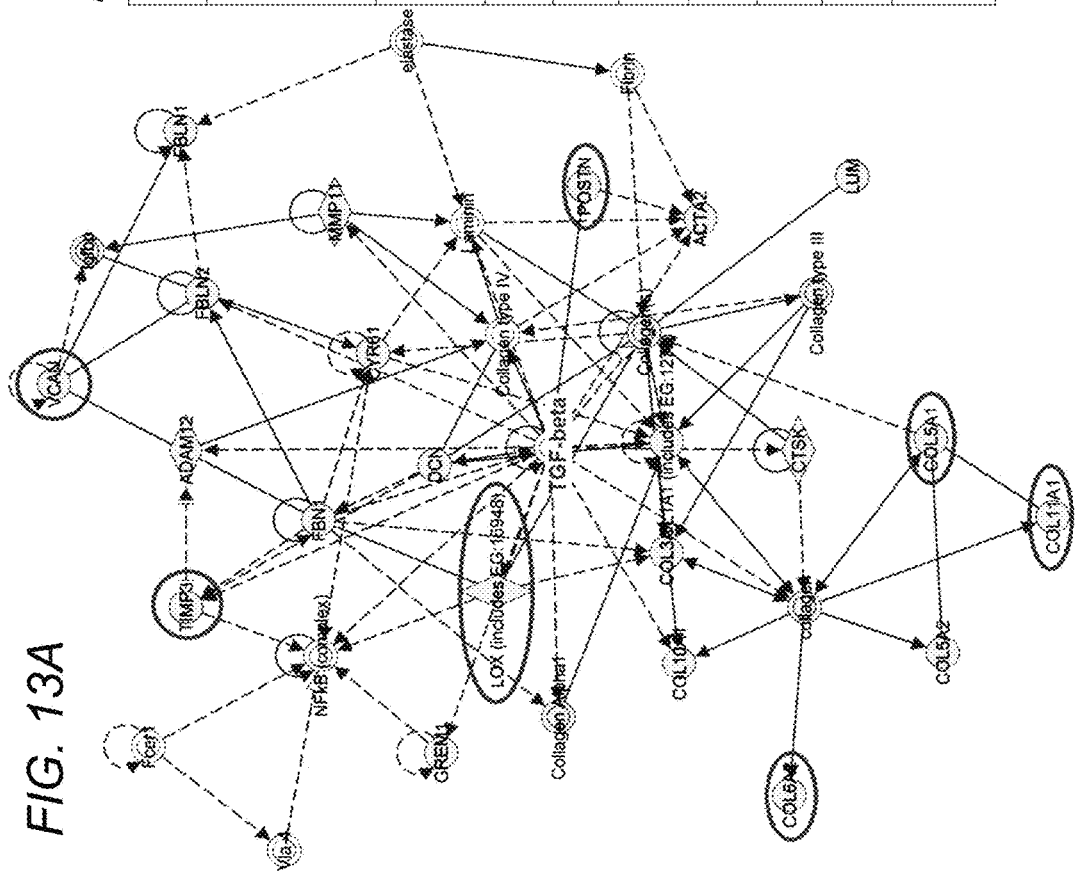
FIG. 13(A) to FIG. 13(C). Regulation of the poor outcome signature genes by TGFβ signaling. (A) Ingenuity Pathway Analysis of the 61 genes present in at least two of the three discovery signatures of poor outcome. Genes that are present in all three discovery signatures are circled in red. (B) Top upstream regulators of the 61 poor outcome genes. (C) Induction of the 10 poor outcome signature genes by TGFβ1 in the ovarian stromal cell line TRS3 and the ovarian cancer cell line OVCAR3. Cells were treated with TGFβ1 (10 ng/ml) for 48 hours (TRS3) or 1-3 hours (OVCAR3) with or without pre-treatment with the TGFβ1 receptor inhibitor, A83-01. Shown is the relative fold change of the mRNA levels compared to untreated control cells. Data are presented as the mean+/−SEM in triplicate samples. * indicates P<0.05. Data are representative of at least three independent experiments.

Ingenuity Pathway Analysis (IPA) using the 61 poor outcome signature genes that were present in at least two of the three initial discovery datasets (FIG. 12A) confirmed that many of these genes form a network centered around TGFβ and collagens (FIG. 13A). Identification of upstream regulators by IPA also indicated TGFβ1 as the top molecule regulating expression of the 61-gene poor outcome signature (FIG. 2B). In addition to TGFβ1, other members of the TGFβ signaling pathway (TGFβ2, TGFβ3, SMAD3, and SMAD7) were also identified as top transcription factors regulating expression of the 61 poor outcome genes (FIG.

13B). These results all suggest that the TGFβ signaling pathway may be the main upstream regulator of these genes.

To validate the predicted regulation of the poor outcome genes by TGFβ1, the Inventors treated the human ovarian stromal cell line TRS3 and the ovarian cancer cell line OVCAR3 with TGFβ1 and measured mRNA expression of the 10 poor outcome genes before and after TGFβ1 treatment.

Figure 13C:
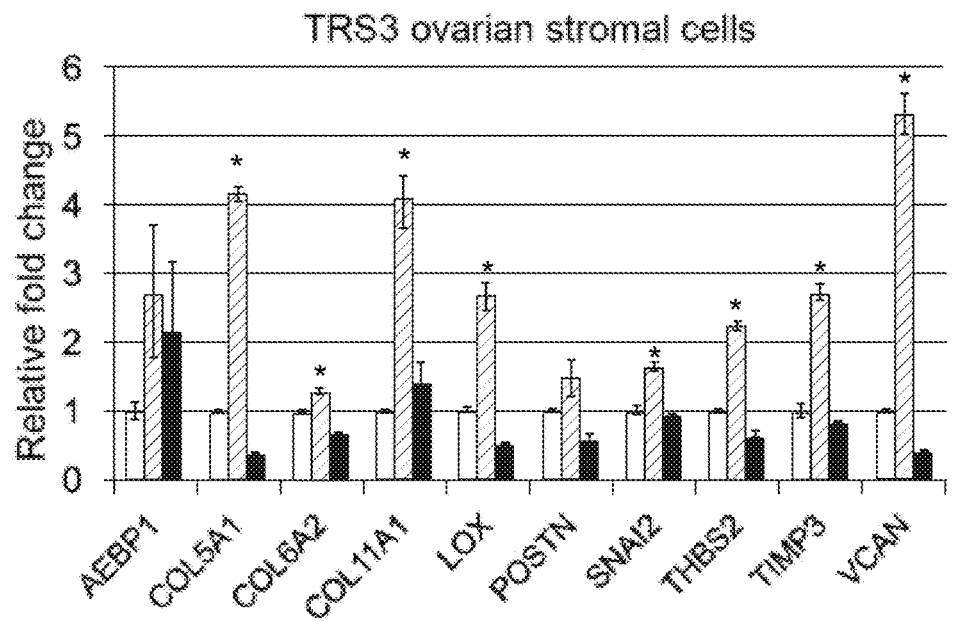
Figure 13C:
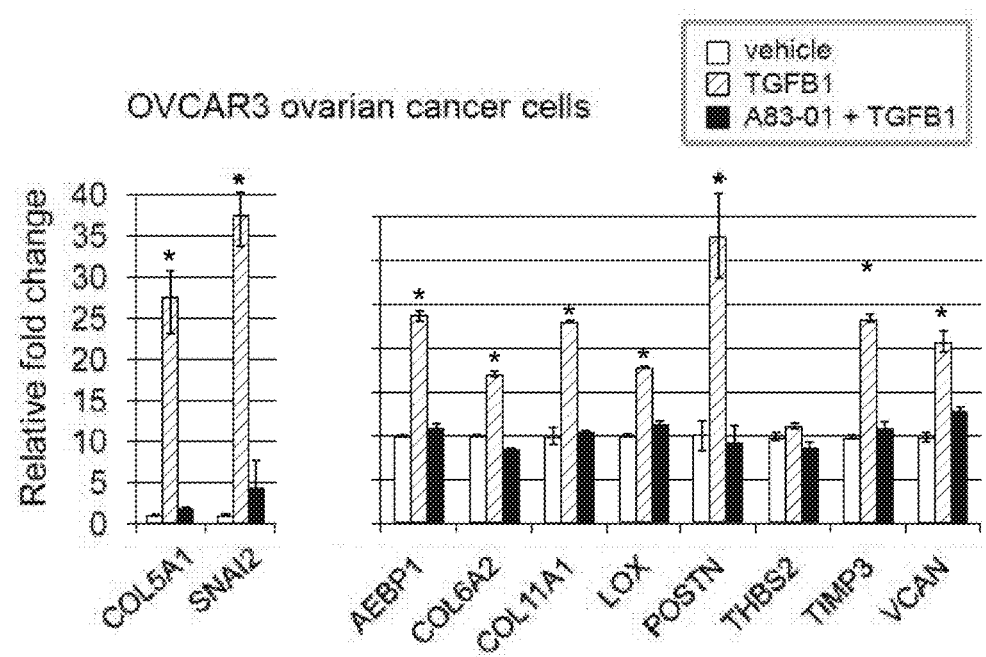

Importantly, The Inventors included the ovarian stromal cell line since many of our poor outcome genes are thought to be expressed in stromal cells. Most of the 10 genes were found to be induced by TGFβ1 in both ovarian stromal and cancer cell lines (FIG. 13C). To further validate that this induction was mediated by TGFβ1 signaling, the Inventors measured expression of the 10 genes in cells pre-treated with the TGFβ1 receptor inhibitor A83-01 before adding TGFβ1. The Inventors found that the TGFβ1-induced expression of the 10 genes was abrogated by A83-01 (FIG. 13C).

Example 22

Enrichment of the 10-Gene OCFS in Metastatic Ovarian Cancer

Figure 14A:
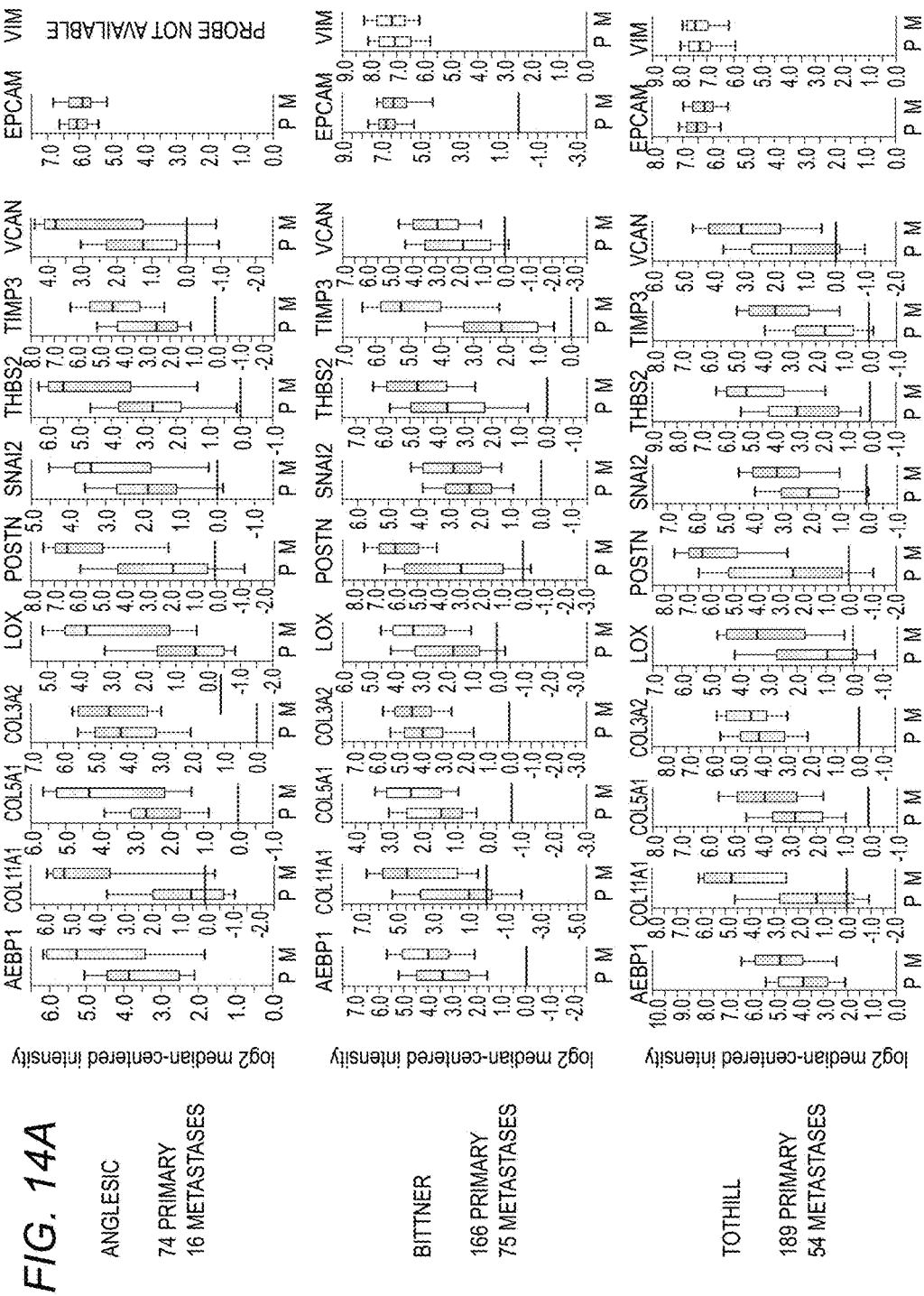

To identify the underlying biological mechanism that could explain the observed association of poor survival with high expression of the collagen-remodeling OCFS genes, the Inventors evaluated the expression of the 10 signature genes in primary and metastatic serous in ovarian tumors in three Oncomine datasets that contained primary ovarian tumors (P) and metastatic tumors (M): Anglesio (P=74, M=16), Bittner (P=166, M=75), and Tothill (P=189, M=54). Markedly higher expression levels of the 10 genes were observed in the metastatic tumors in all three datasets (FIG. 14A). The minimal difference in the expression of the epithelial marker, EPCAM, and the stromal marker, vimentin, in primary and metastatic tumors (FIG. 14A) indicates that the epithelium-to-stroma ratio is not significantly different between samples.

Figure 21:
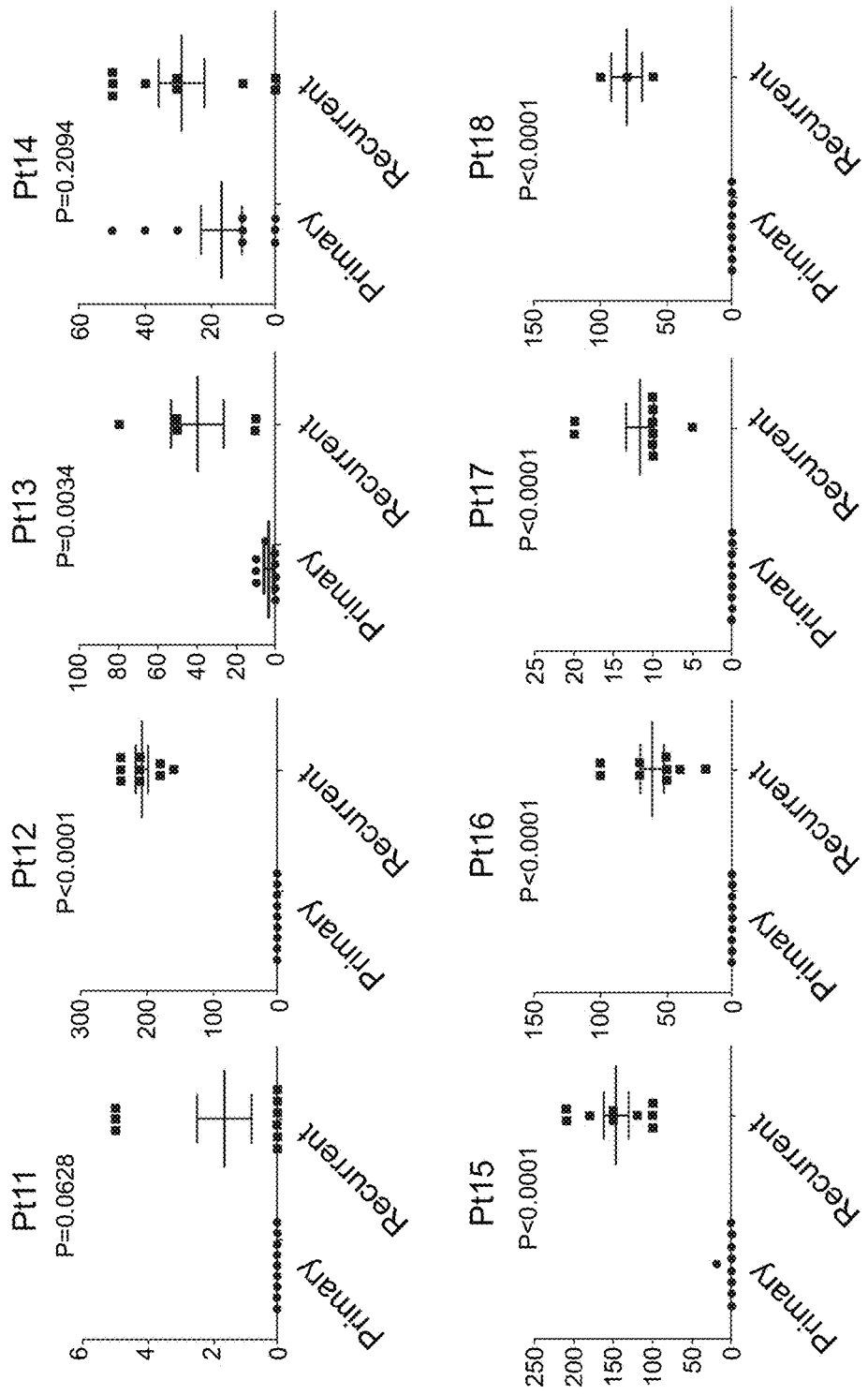
FIG. 21. Increase in COL11A1 expression in recurrent tumors in comparison to primary ovarian tumors. Quantification of the COL11A1 in situ hybridization signal in matched pairs of primary ovarian cancer and recurrent/persistent metastasis from eight patients. H score=% positive stromal cells×intensity (0, 1+, 2+, 3+) under 10× objective. Each point represents the H score in a single field. Nine intratumoral fields were scored in each sample except for two samples in which fewer fields were scored due to minimal amount of tumor tissue. Data are presented as the mean+/−SEM.

Further validation that the OCFS genes are enriched during ovarian cancer progression by using another method of mRNA detection (qPCR) in an independent patient cohort that included 8 normal ovaries, 30 primary serous ovarian tumors, and 29 metastatic serous ovarian tumors from the Women's Cancer Program Biorepository (FIG. 21). Next, the Inventors conducted an unbiased global identification of genes that are differentially expressed between primary tumors and metastases using nine matched pairs of primary ovarian tumors and omental metastases (GSE30587 dataset). The top 20 gene probes that exhibited increased expression in metastases are ranked according to statistical significance in FIG. 3B. This analysis showed a marked overlap between our poor prognosis signature genes and genes that are enriched in metastases (FIG. 14B). One of our signature genes, COL11A1, was identified as the most statistically significant differentially expressed gene in the nine matched pairs of primary and metastatic tumor samples (FIG. 14B). FIG. 14C shows COL11A1 mRNA expression values in matched pairs of primary ovarian tumors and omental metastases in the nine matched tumor pairs.

Example 23

Enrichment of COL11A1 During Ovarian Cancer Disease Progression

To test whether COL11A1 is a marker of tumor progression, the Inventors relied on in situ hybridization in 10 patients with "triplet" samples (primary ovarian cancer, concurrent metastasis, and recurrent/persistent metastasis) and eight additional patients with matched primary ovarian cancer and recurrent/persistent metastatic tumor.

Figure 15A:
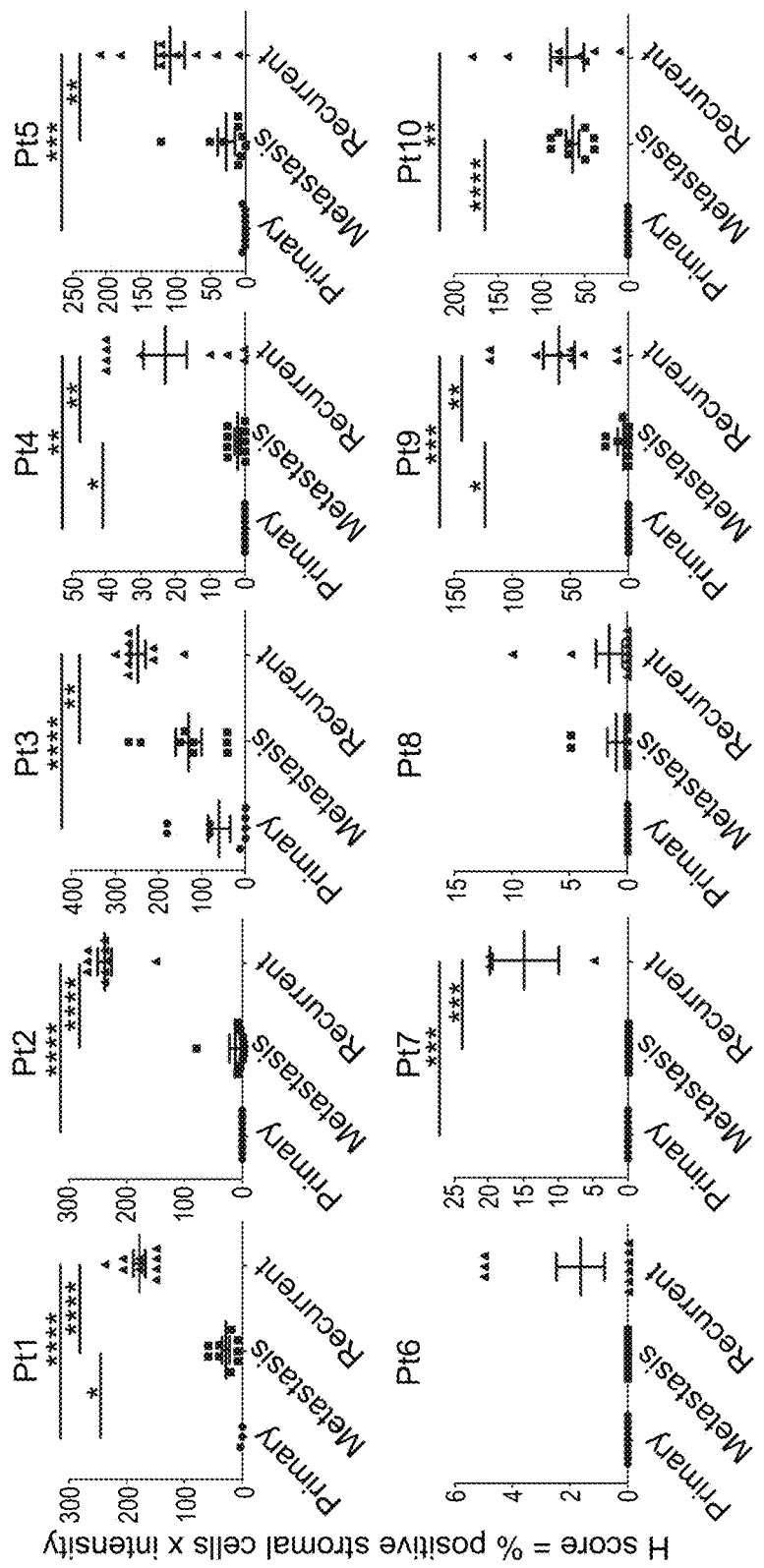
Figure 15D:
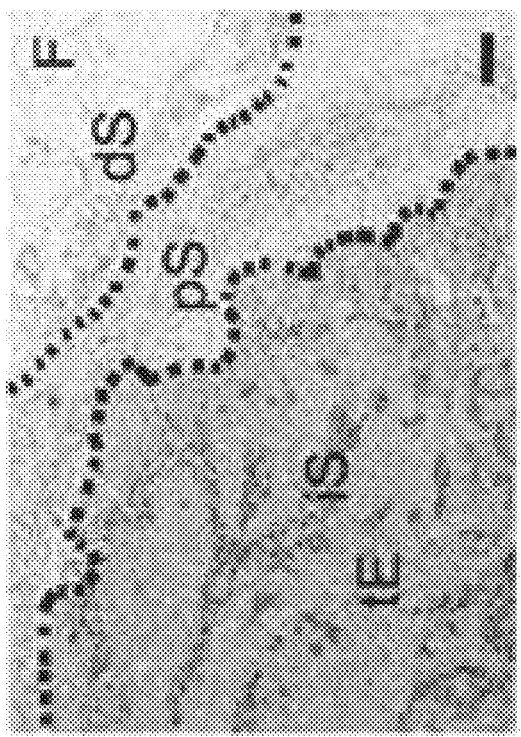
Figure 15C:
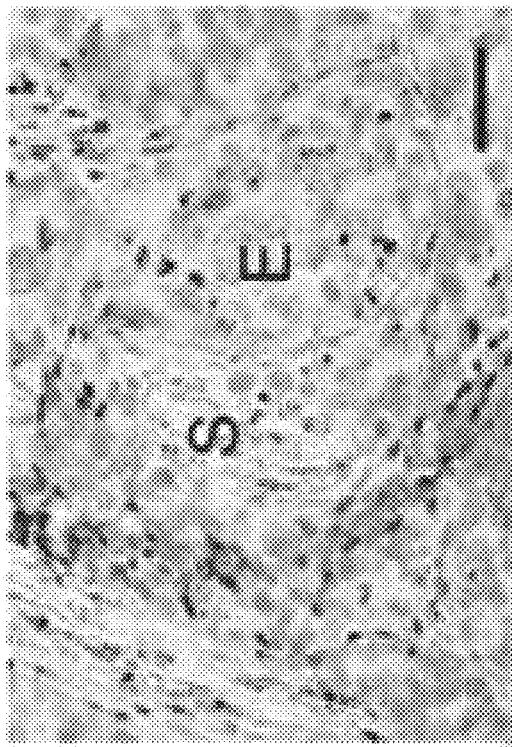
Figure 22:
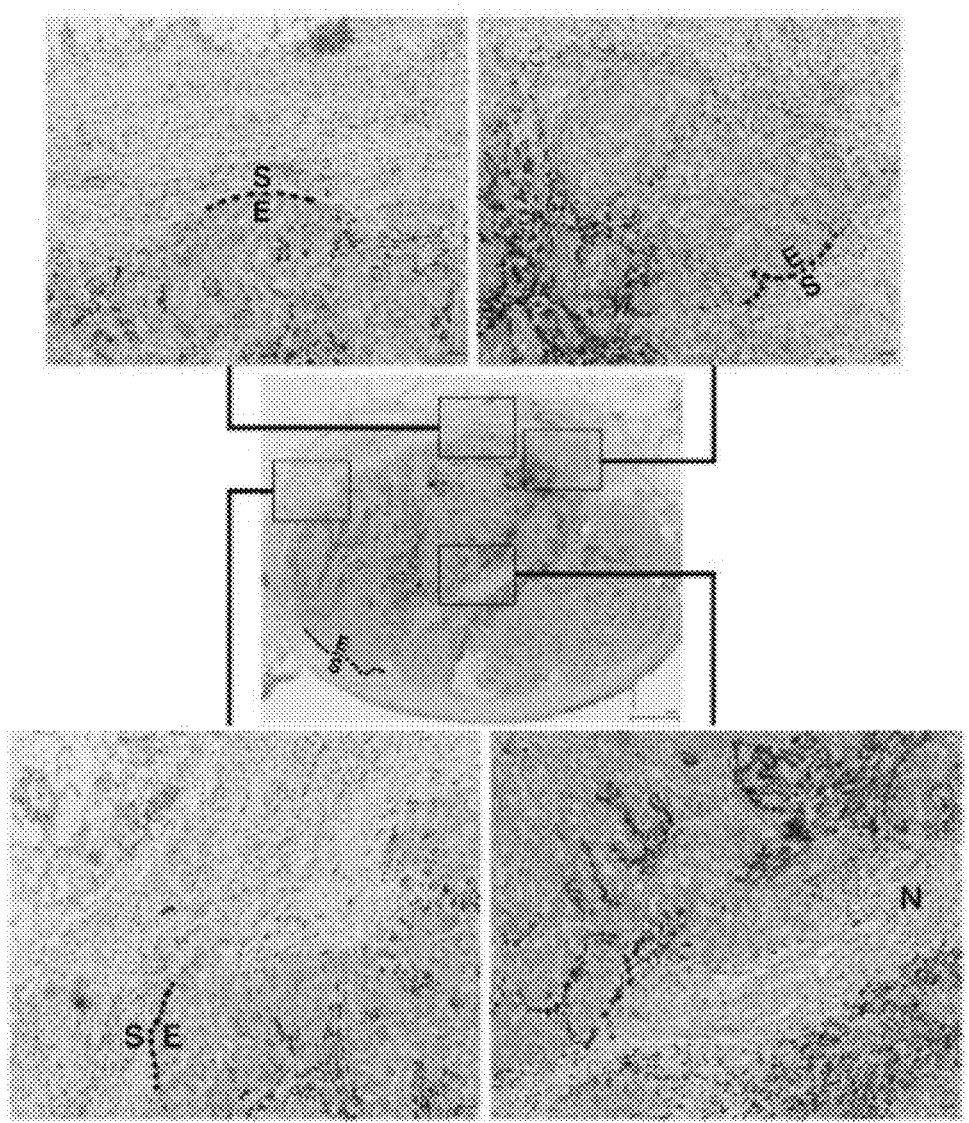
FIG. 22. Confinement of COL11A1 expression to intra- and peri-tumoral stroma. Representative low magnification image of COL11A1 in situ hybridization in a metastatic tumor nodule. Four different fields of the tumor nodule are shown at a higher magnification. Dotted lines demarcate tumor epithelium (E) and peritumoral stroma (S). N denotes a necrotic area. The counter stain is hematoxylin. Size bars, 1 mm (center image) and 100 μm (peripheral images).

Importantly, in each of the 18 patients, COL11A1 expression increased in the recurrent/persistent metastasis compared to the matched primary ovarian tumor (FIG. 15A, B and FIG. 21). In the 10 patients with "triplet" samples, COL11A1 exhibited the lowest levels in primary ovarian cancer samples, medium levels in concurrent metastases, and highest levels in recurrent/persistent metastases (FIG. 15A). Representative in situ hybridization images for Patient 1 are shown in FIG. 15B. To correlate RNA and protein expression, serial sections from primary ovary, concurrent metastatic, and recurrent/persistent metastatic tumors were stained for the COL11A1 protein using immunohistochemistry. The COL11A1 protein levels and pattern of expression in these serial sections were consistent with COL11A1 RNA levels and pattern of expression (FIG. 15B); however, in situ hybridization provided a higher-resolution signal at a cellular level. COL11A1 expression was predominantly confined to stromal cells although rare clusters of positive epithelial cells were observed in some tumors (FIG. 15C). Interestingly, COL11A1 was specifically expressed in the intra/peritumoral stromal cells while stromal cells>1 mm from the epithelial tumor cells were always negative (FIG. 15D and FIG. 22).

Example 24

Attenuation of Tumor Progression Upon COL11A1 Knockdown

Figure 16A:
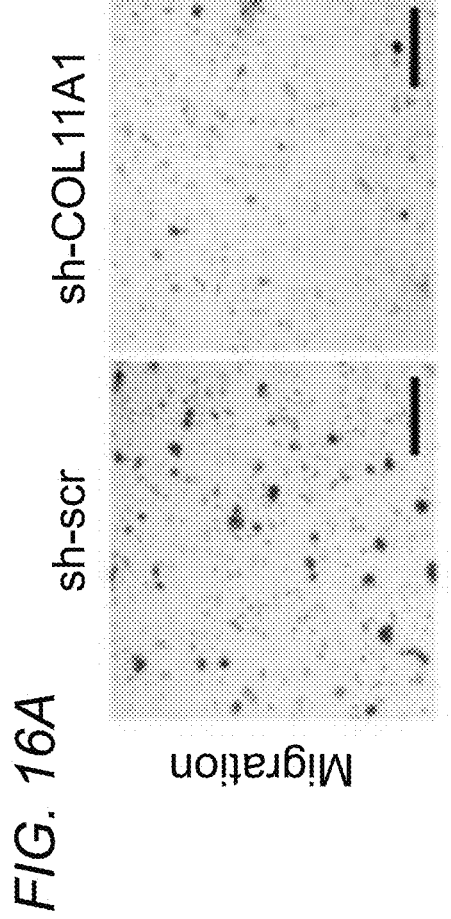
Figure 16B:
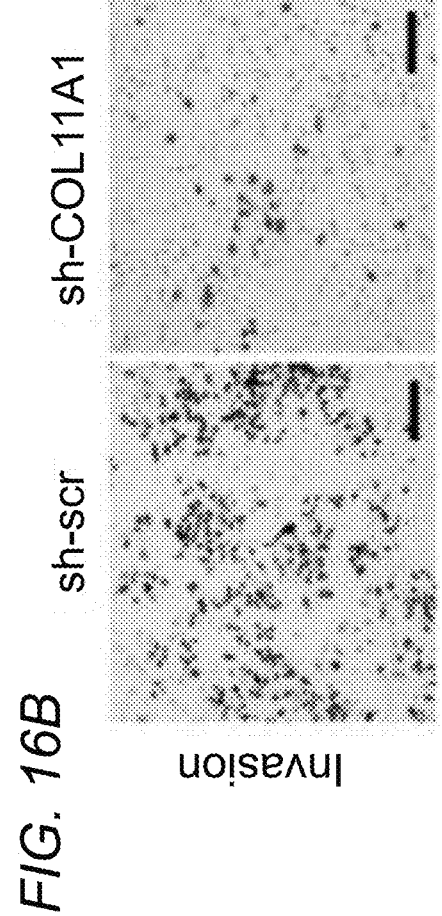
Figure 23A:
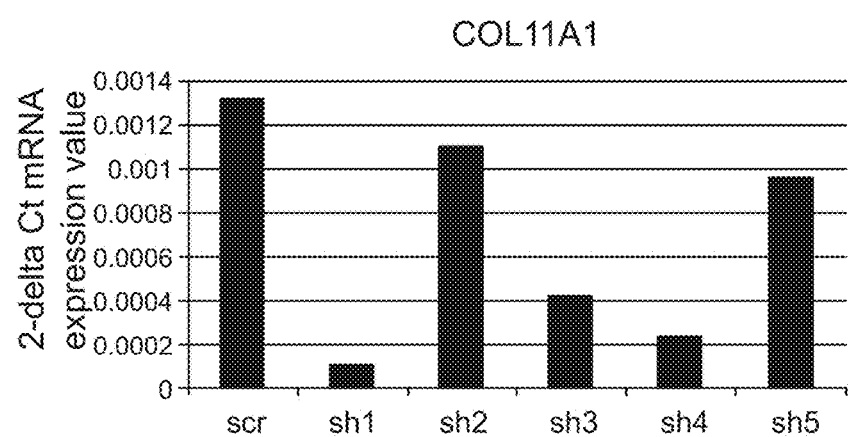
FIG. 23(A) to FIG. 23(C). Knockdown of COL11A1 in the A2780 ovarian cancer cell line. (A) Real-time PCR of COL11A1 in A2780 cells transduced with scrambled control shRNA (sh-scr) and A2780 cells transduced with five different shRNAs targeting COL11A1 (sh1-sh5). (B) Arrows point to primary ovarian tumors. Circles point to metastatic tumor nodules. Top genes enriched in metastatic vs. primary tumors. (C) Western blot analysis of COL11A1 protein expression. The membrane was exposed for different lengths of time to visualize the molecular marker and the COL11A1 band. GAPDH was used as a loading control. Thirty micrograms of cell lysates were loaded onto a mini-PROTEAN TGX gradient gel (4-20%). Protein was transferred to a 0.2 μm PVDF nitrocellulose membrane, which was incubated in blocking buffer for 1 hour and then incubated with primary antibodies against COL11A1 (Abcam ab64883; 1:500 dilution) and GAPDH (Fitzgerald 10R-G109A; 1:5000 dilution) for 1 hour at room temperature. Membranes were incubated with secondary antibodies (goat anti-rabbit IRDye 800 for COL11A1 and goat anti-mouse IRDye 680 for GAPDH; 1:5000 dilution) for 1 hour at room temperature. The signal was analyzed by the Li-Cor Odyssey system.
Figure 23B:
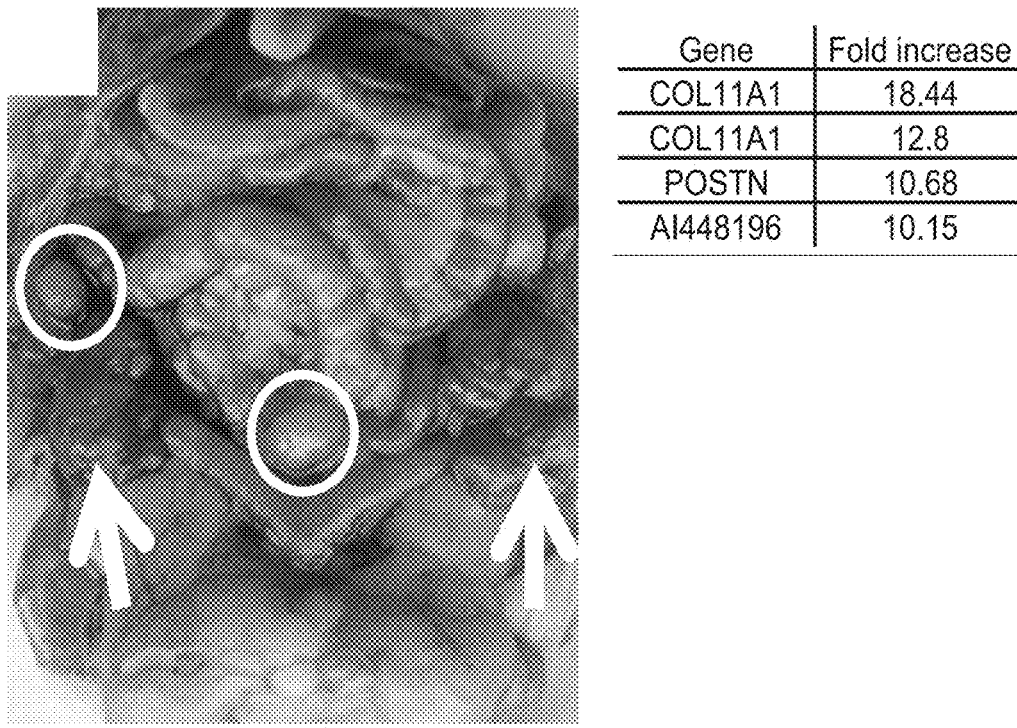
Figure 23C:
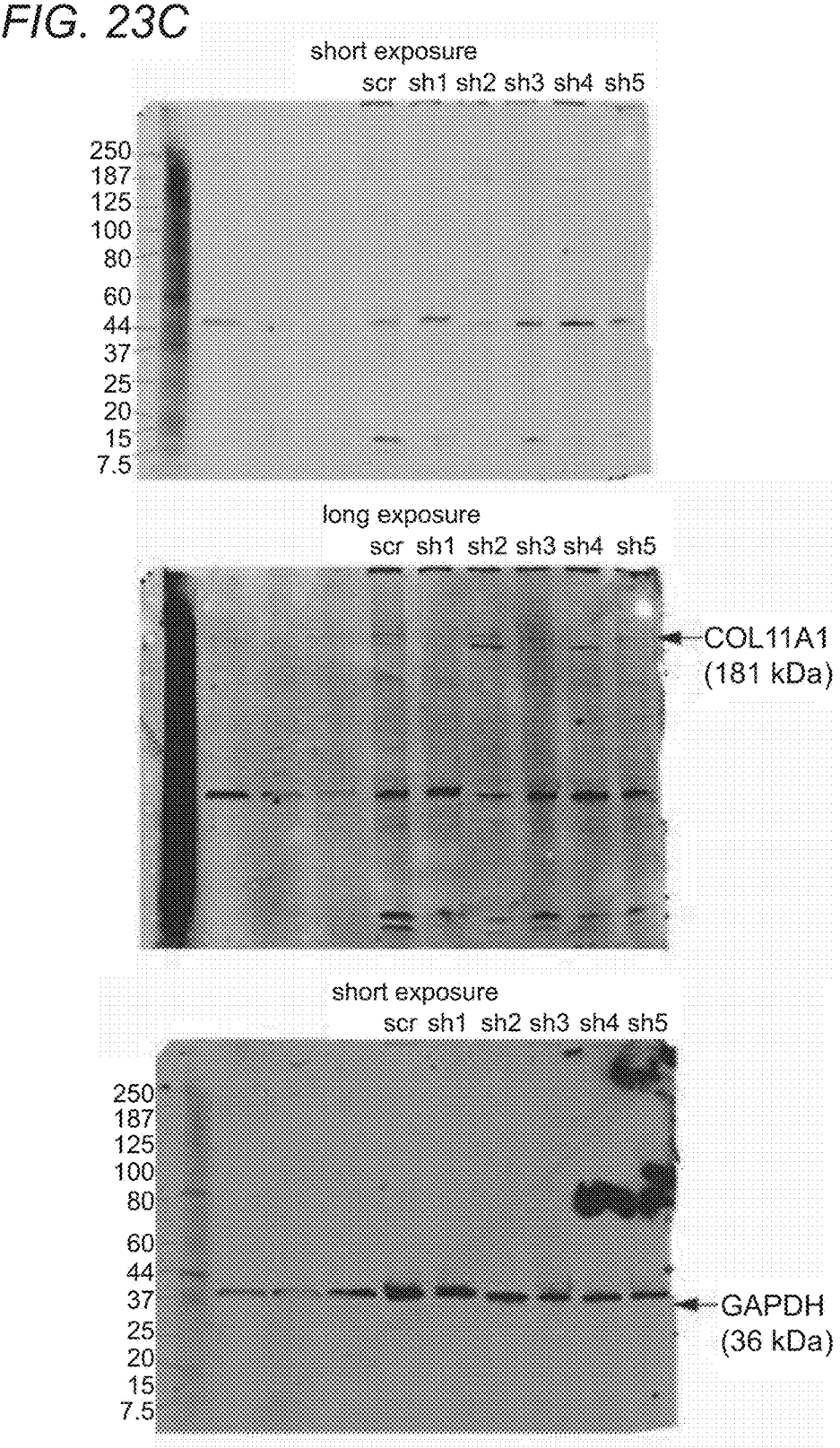

To determine whether COL11A1 has a functional role in tumor progression, a mouse tumor xenograft model with A2780 human ovarian cancer cells was used. Despite their epithelial morphology, these cells exhibit a mesenchymal-like expression profile, including low levels of E-cadherin and high levels of N-cadherin proteins (Ruby Huang, Cancer Science Institute of Singapore, personal communication). A2780 cells have relatively high levels of endogenous COL11A1 and thus may represent the small subset of COL11A1-expressing epithelial tumor cells that the Inventors observed in patient tumors (FIG. 15C). COL11A1 expression in A2780 cells was silenced using shRNA lentiviral particles. Effective silencing of COL11A1 was confirmed by real-time PCR and Western blotting (FIG. 23). COL11A1 knockdown resulted in decreased cell migration and invasion (FIG. 16A,B). To assess the effect of COL11A1 on tumor progression in vivo, the Inventors intraperitoneally injected nude mice with 107 sh-scr A2780 cells or sh-COL11A1 A2780 cells. The experiment was first conducted with 5 mice per group (FIG. 16C) and then replicated with 10 mice per group (FIG. 16D). In both sets of experiments, tumor growth was significantly reduced in mice injected with sh-COL11A1 A2780 cells compared to the mice injected with sh-scr A2780 cells (FIG. 16C,D).

Example 25

Ovarian Cancer Gene Signatures and Biological Mechanisms

Expression profile data have been used extensively in efforts to develop gene signatures that relate to clinical outcomes in ovarian cancer. A key advantage of the 10-gene OCFS signature is that gene selections as based on overlap among three individual signatures of poor outcome, each of which had been derived using entirely different patient populations and statistical methods for microarray analyses. Thus, this signature should be independent of technical variations associated with microarray analyses and should be associated with poor survival in diverse patient populations. Indeed, these 10 genes are highly enriched in patient subgroups with the worst clinical outcome in published datasets, including the discovery and validation datasets used in this study. For example, among patient subgroups identified in the original ovarian TCGA study, our 10 signature genes exhibit the highest expression in the mesenchymal subgroup, which has the worst survival in that dataset. Furthermore, genes involved in 'cell adhesion', 'TGFβ binding', and 'epithelial mesenchymal transition' were significantly upregulated in subtype 2, similar to our observation. In the study by Tothill et al., the OCFS 10 genes are most highly enriched in the C1 subtype, which has the worst survival in that dataset.

The OCFS 10-gene signature is robust in its ability to predict poor survival as demonstrated in two large validation datasets consisting of 260 ovarian cancer patient samples and 1,058 pooled ovarian cancer patient samples. Interestingly, individual genes or groups of genes from the OCFS 10-gene signature, including COL11A1, POSTN, SNAI2, THBS2 and TIMP3, have also been associated with poor survival in other solid tumors including breast, colorectal, lung, oral, and head and neck carcinomas as well as melanoma, suggesting that expression of this signature is not specific to ovarian cancer but might characterize aggressive behavior across cancer types.

Another major strength of the OCFS 10-gene signature is its clear biological relevance to cancer progression. Previously identified gene signatures in ovarian cancer consist of genes that are involved in many diverse biological processes, making it difficult to assess their biological relevance or functional role in cancer progression. All 10 of the OCFS signature genes are present in the 351-gene signature that was identified as upregulated in invasive ductal carcinoma (IDC) when compared to noninvasive ductal carcinoma in situ (DCIS), supporting the important role of these genes in early local invasion. The Inventors further showed that the 10 signature in genes are highly enriched in metastases and that knockdown of one of these genes, COL11A1, results in reduced cell migration, invasion, and tumor progression, suggesting that collagen remodeling could be important in ovarian cancer progression and metastasis. The higher expression of 10 genes in metastasis does not appear to be due to a higher stroma-to-tumor ratio in metastatic tumors for several reasons.

First, tumor samples from the TCGA dataset were selected to have >70% tumor cells. Second, the Inventors did not observe different expression levels of the epithelial marker, EPCAM, and the stromal marker, vimentin, in metastatic tumors compared to primary tumors (FIG. 14A), indicating that the stroma-to-tumor ratio is not significantly different between samples of primary tumors and metastases. Third, in situ hybridization results showed that regardless of the overall amount of stroma in tumor sections, COL11A1 expression was confined to intra-/peri-tumoral stromal cells and rare foci of tumor epithelial cells, while stromal cells that were >1 mm from epithelial tumor cells were completely negative (FIG. 15B-D). This indicates that COL11A1 is a specific marker of carcinoma-associated fibroblasts (CAFs) and possibly cancer cells that are undergoing EMT. The in situ hybridization analysis of COL11A1 in matched triplets of primary ovarian cancer, concurrent metastasis, and recurrent/persistent metastasis, demonstrated a marked increase in COL11A1 during cancer progression in all patients (FIG. 15A), indicating that COL11A1 could serve as a marker of cancer progression.

Example 26

Activated Stroma in Ovarian Cancer

Collagen-rich stroma is thought to maintain tissue architecture and, under normal conditions, serve as a barrier to epithelial cell migration. However, when modified by cancer cells, collagen-rich stroma can promote tumor progression. Enhanced collagen deposition and cross-linking has been shown to increase breast cancer risk. Increased levels of LOX, an enzyme responsible for collagen cross-link formation, result in increased collagen stiffness. POSTN also promotes collagen cross-linking by interacting with BMP-1 to enhance the proteolytic activity of LOX, which results in the reorganization of loose connective tissue into linear tracks of fibers that promote chemotaxis of tumor cells). Furthermore, increased collagen deposition and remodeling increases interstitial pressure, thereby severely compromising the efficacy of drug delivery. Of particular interest, an increase in collagen expression and remodeling has been associated with cisplatin resistance in ovarian cancer, suggesting that cisplatin resistance might be one of the factors contributing to poor survival.

Finally, the clinically-relevant strength of the OCFS 10-gene signature is that it can be not only used as a biomarker to identify patients with poor outcome but also as a guide to individualize their therapy. In fact, several of the OCFS 10 signature genes have been validated as promising therapeutic targets in mouse models. POSTN, an extracellular matrix protein that is highly expressed in late-stage ovarian cancer, is thought to play a role in metastatic colonization by forming a niche for cancer stem cells. Treatment with a POSTN-neutralizing antibody led to a significant decrease in ovarian tumor growth and metastasis in a mouse model. Similarly, inhibiting LOX by treatment with β-aminopropionitrile, neutralizing antibodies, or RNA interference inhibited tumor metastasis in xenograft and transgenic mouse models.

The COL11A1 knockdown result suggests that targeting collagen might be an effective approach to preventing ovarian cancer progression and metastasis. A recent study of collagen mimetic peptides (CMPs), 2-3 kDa small peptides that bind to type I collagen, showed that they can specifically bind to tumors with high matrix metalloproteinase (MMP) activity in xenograft models. This is a promising approach to treating tumors associated with excessive collagen remodeling and high MMP activity. Furthermore, the Inventors showed that collagen-remodeling genes are regulated by TGFβ1, suggesting that targeting TGFβ1 signaling might be an efficient way to impede metastatic progression. High TGFβ1 signaling activity was reported in patients with metastatic ovarian cancer and the antibody against TGFβ was shown to be effective in suppressing metastasis in a preclinical model of ovarian cancer. Currently, there are several TGFβ1 inhibitors in phase I/II clinical trials. It will be important to test the effectiveness of these agents as inhibitors of ovarian cancer progression and metastasis as single agents or in combination with chemotherapy.

Example 27

Genes in the OCFS 10-Gene Signature Provide Clinically-Applicable Assays

Figure 8B:
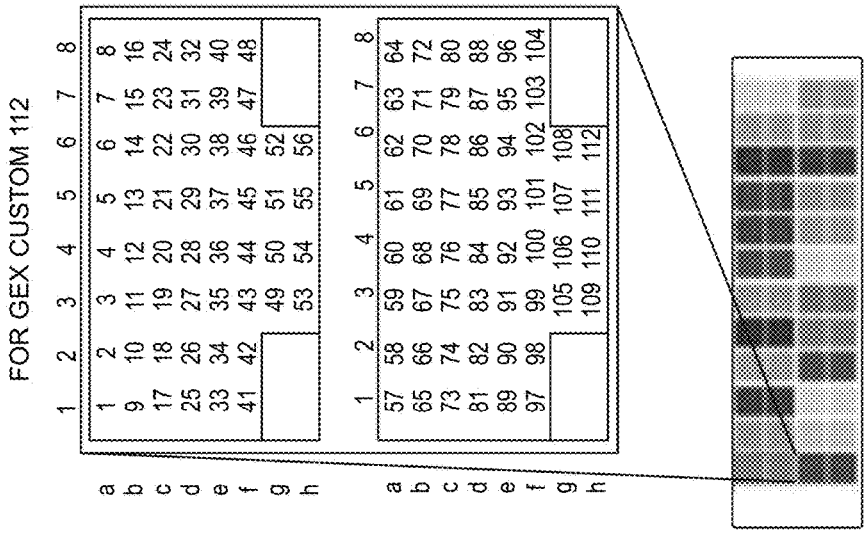
FIG. 8(A) to FIG. 8(B). Clinical applications for ovarian cancer signatures. (A) Ovarian cancer diagnostic triage map. A gene signature will impact clinical practice by enabling physicians to identify patients who are unlikely to benefit from standard treatment and triage in them to clinical trials or individualized therapy. (B) TaqMan® OpenArray® Real-Time PCR design for the quantification of transcripts derived from ovarian cancer samples. Each signature gene will be represented in quadruplicates with duplicate probes at different physical positions on the array.
Figure 8A:
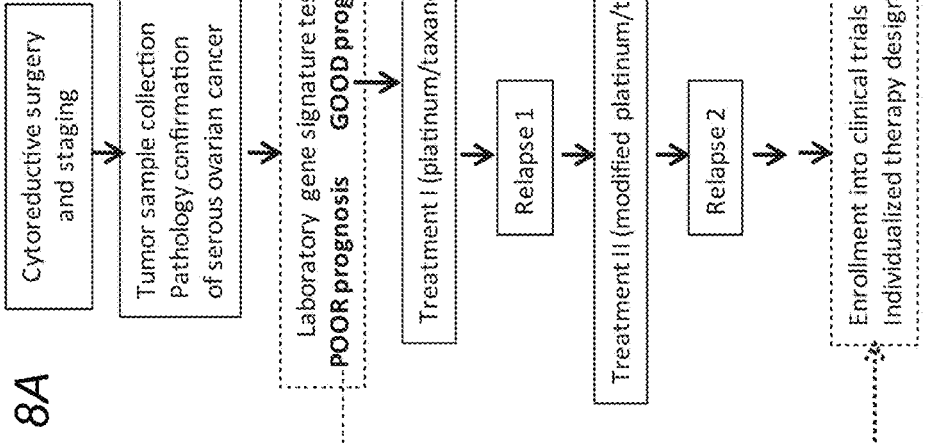
Figure 9E:
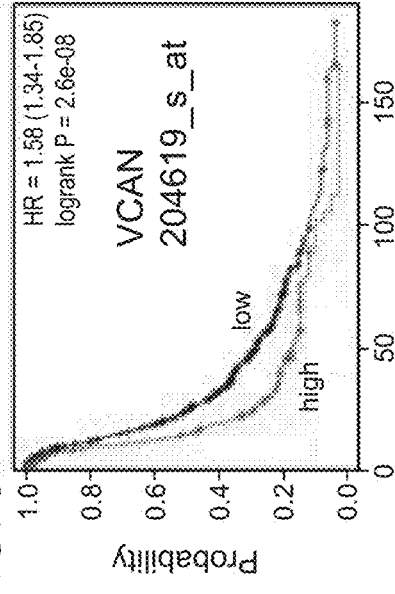
Figure 9F:
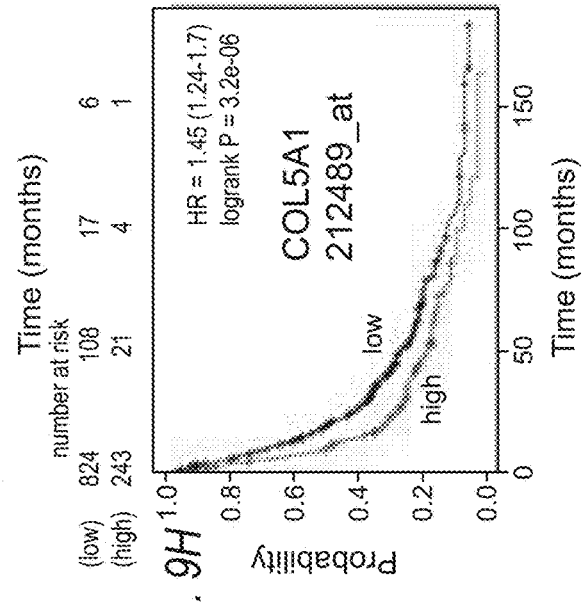
Figure 9G:
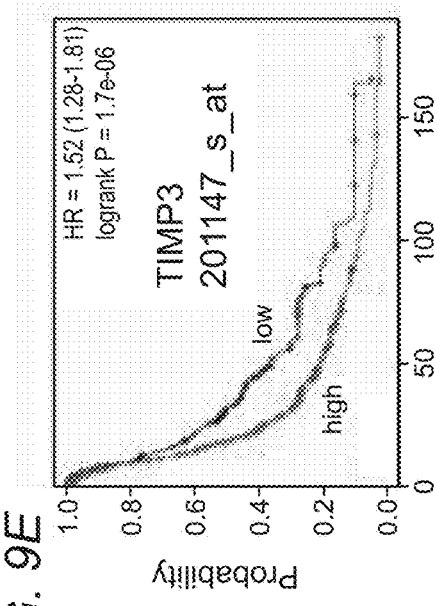
Figure 9H:
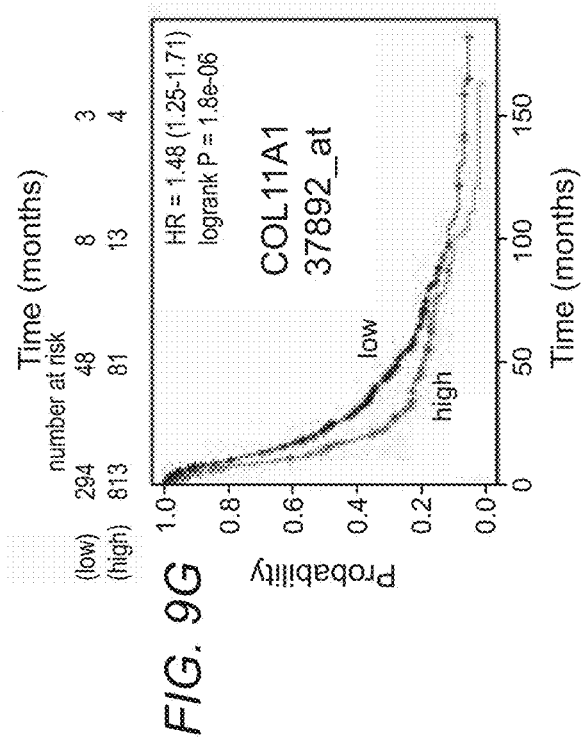
Figure 9J:
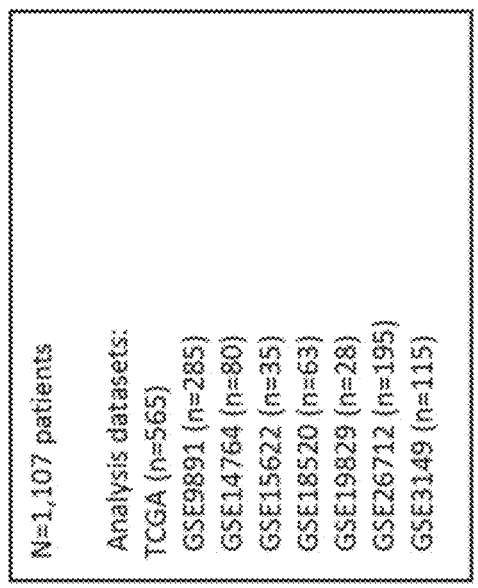
Figure 9I:
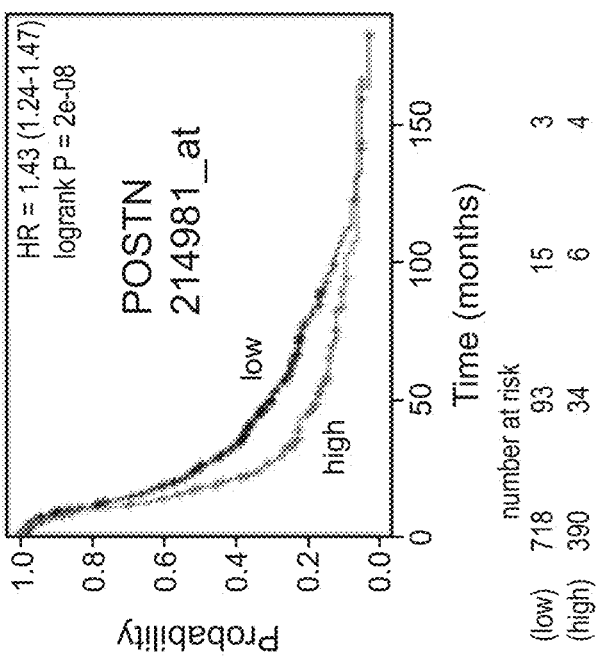

The described OCFS 10-gene signature assay will effectively enhance physicians' abilities to identify patients with a high likelihood of recurrence. FIG. 8A shows the triage map of current clinical practice and the point of care at which our gene signature test will be of clinical value.

A Nanostring assay can be developed for the detection and quantification of the gene signature transcripts. This system is favored for accurate detection of transcripts in paraffin samples without relying on cDNA synthesis or PCR amplification. Assay development paraffin blocks from patients linked to a detailed correlative database with clinical variables, including recurrences. Cox regression of the log hazard ratio on a covariate with a standard deviation of 1.5 based on a sample of 100 observations achieves 85%, and 95%, power at a 0.05 significance level to detect a regression coefficient (log hazard ratio) equal to 0.2 and 0.25 respectively. Sample size can adjusted for an anticipated event rate of 80%.

This prediction power will probably be larger than estimated since the model is constructed with a panel of gene signatures instead of a single covariate. After normalization, the expression of the signature genes will be correlated with outcomes. Risk prediction models with known parameters will be validated with this clinical assay. Model performance can be assess with (1) calibration measures to study the agreement between the observed outcome frequencies and predicted probabilities, (2) discrimination (classification) measures to distinguish subjects with different outcomes at each time cutoff point, and (3) prediction accuracy.

Model calibration will be studied with a calibration curve in which observed frequencies are plotted against predicted probabilities. Ideally, if the observed frequencies and predicted probabilities agree over the whole range of probabilities, the plot will show a 45 degree line with an intercept of 0 and slope of 1. Therefore, Chi-square distribution with 2 degrees of freedom will be used to test the null hypothesis that the intercept is 0 and the slope is 1. Additionally, one can also use the Hosmer-Lemeshow (H-L) goodness-of-fit test for calibration validation. Both equal sizes and equal prediction-intervals will be used to group the patients into subgroups. Especially for the Cox regression based risk model, one can categorize patients into subgroups based on their distribution of relative risk with the Kaplan-Meier method and calculate the goodness-of-fit for calibration validation. One constructs a ROC curve to compare the performance of candidate models by varying the cutoff points of combined risk scores. Standard performance measures such as AUC (c-statistics), partial AUC within a certain specificity range, and F-measure will be computed to evaluate the prediction ability of the risk models given a cutoff time. The Global AUC summary (GAUCS) will also be used to estimate the performance of Cox regression based risk models.

Example 28

Identify the Cellular Context of the Poor-Prognosis Signature Genes

As described, the OCFS 10-gene signature is enriched in metastatic ovarian cancer. To identify the underlying biological mechanism that could explain the observed association of poor survival with high expression of the signature genes, the Inventors evaluated the expression levels of the 10-gene signature in FIG. 12A in primary and metastatic serous ovarian tumors. In the GSE12172 dataset, which includes 74 high-grade serous primary ovarian tumors and 16 unpaired metastatic tumors, higher expression levels of the 10 genes were observed in the metastatic tumors. This observation was further validated using qPCR in an independent patient cohort that included 8 normal, 30 primary, and 29 unpaired metastatic serous ovarian cancer samples from our biorepository. Most of the OCFS 10 signature genes were not expressed in normal ovaries, but their expression was enriched in primary tumors and even further enriched in metastases. Importantly, this indicates that during tumor progression, the cell population expressing the signature genes is enriched or the process resulting in the expression of the signature genes is intensified.

Further, the signature genes are expressed in both MSCs and CSCs. To identify a specific cell type that is characterized by the presence of the signature, the Inventors searched the tissue/cell-specific transcripts in the TranscriptoNet database, which consists of >500 normal tissues and cell types that were isolated from >50 different organs by microdissection (i.e. epithelial cell of the endometrium) or by FACS using specific cell markers (i.e. 27 distinct blood cell types). Since the signature genes are highly co-regulated, the presence or absence of the signature was immediately apparent. Remarkably, the signature was present in only 3 normal cell types: undifferentiated pre-adipocytes (but not differentiated pre-adipocytes) from visceral, subcutaneous and omental fat; cardiomyocytes; and bone marrow MSCs. The common denominator to the 3 cell types is that they are all MSCs. In the entire database, there was no epithelial cell type with significant expression of the signature genes. However, in studies of ovarian CSCs, the Inventors observed enrichment of the gene signature in the ALDH+/CD133+ CSC subpopulation of an epithelial A2780 ovarian cancer cell line, while others have shown enrichment of the signature genes in cisplatin-resistant A2780 cells, supporting the hypothesis that the signature genes are expressed in a specialized subpopulation of malignant cancer cells. Taking all of these pieces of data into account, there are 3 possible mechanisms accounting for the overlap between OCSC, OCDS, and OCFS signatures: 1) as derived from epithelial cancer cells that de-differentiate into CSCs as derived from MSCs that are actively recruited to the tumor from fat and/or bone marrow or from local fibroblasts that de-differentiate into MSC 2) as derived process-specific mechanism, such as any cell undergoing de-differentiation or trans-differentiation into CSCs or MSCs will express the signature genes. These various scenarios accounting for poor outcomes associated with the signature as related to ovarian cancers with a higher proportion of CSCs are more aggressive and chemoresistant. In addition, a high proportion of desmoplastic stroma in ovarian carcinoma is associated with worse prognosis, and poor differentiation and EMT are associated with ovarian cancer aggressiveness.

Example 29

Cell-of-Origin for Signature Genes

To identify the cell-of-origin for one of the signature genes, one can focus on COL11A1 as this gene is not expressed in most normal tissues but its expression is highly elevated in most cancer types in comparison to their respective normal tissue. In situ hybridization for COL11A1 in 8 primary and 8 matched metastatic tumors (5 synchronous and 3 metachronous recurrent metastases) indicates that in both the primary and metastatic tumors, the majority of the signal was detected in a subset of stromal cells while the epithelial cells expressed low or undetectable levels of COL11A1. The ratio of COL11A1-positive to COL11A1-negative cells also increased in metastatic vs. primary tumors. Thus, metastatic tumors contained more COL11A1-expressing cells, although it is unclear if these cells were recruited to the tumor or represented resident cells that converted into a COL11A1-expressing phenotype.

Because most of the COL11A1 signal are detected in cells with stromal morphology, the intuitive conclusion is that COL11A1 is expressed in the stromal, rather than the epithelial, component of the tumor, however, the Inventors cannot exclude the possibility that the stromal cells are derived from epithelial cells through EMT. One can observe that COL11A1 is expressed in stromal cells in close proximity (<1 mm) to malignant epithelial cells while distant stromal cells and stromal cells encapsulating the tumor were negative, which is consistent with the idea that the COL11A1-expressing stromal cells are derived locally rather than recruited from distant sites. Interestingly, in several tumors, the Inventors observed areas in which both epithelial and stromal cells were positive for COL11A1 (FIG. 15). This may represent EMT although this would be difficult to prove as there are no effective markers of EMT in situ.

In conclusion, in situ hybridization in human samples alone cannot mechanisms for signature generation outlined above. A helpful determination the cell-of-origin, can rely on a cell tracking system, such as labeled human cancer cell lines as a source of malignant cancer cells and a mouse host as a source of stromal cells. A previously generated a mouse model by the Inventors in which defined genetic alterations can be introduced into ovarian surface epithelial cells can be applied for such studies. When such cells are implanted under the ovarian bursa, they give rise to primary ovarian tumors as well as metastatic nodules embedded into the peritoneal serosal surfaces, such as the peritoneal wall, intestinal lining, and omentum (FIG. 23B). Expression profiling revealed that many of the signature genes were enriched in the mouse metastatic tumors, with COL11A1 and POSTN showing the highest fold increase in metastatic vs. primary ovarian tumors (FIG. 23B). This is significant because COL11A1 and POSTN are among the genes that exhibit the highest fold increase in human metastatic vs. primary tumors, indicating that a process similar to human ovarian cancer metastatic progression occurs in the mouse model. As a result, this mouse model can be used to study the cellular context of the signature genes.

Example 30

Cell-of-Origin for Signature Genes

The cell-of-origin for the signature transcripts may not be obvious as the majority of the signature genes encode secreted extracellular matrix proteins. Research groups who have identified similar collagen-remodeling gene sets as predictors of poor outcome in breast cancer have attempted to determine their cell-of-origin using laser capture of tumor epithelial and stromal cells but have reached contradictory conclusions.

As gene signatures such as the OCSC, OCDS, and OCFS signatures can be associated with poor outcome in multiple tumor types, including breast, colon, and lung cancer, and multiple metastatic locations, including local invasion in breast cancer and metastatic dissemination to various intraperitoneal organs in ovarian cancer, one can conclude that such signature may not be cancer type-specific nor metastasis site-specific. Such signatures can be either specific to a certain cell type that is present in diverse tumor types (i.e. recruited macrophages or MSCs) or to a common biological process that occurs in diverse cell types (i.e. de-differentiation of cancer cells into CSCs or trans-differentiation of fibroblasts into myofibroblasts or MSCs). To accurately define the therapeutic target, it is important to identify the cellular context of the poor-prognosis signature gene expression.

One hypothesis is that he signature genes are expressed in a specific cell type derived from either malignant cancer cells or host stromal cells. This can be determined using labeled cells of human and mouse origin in a mouse model of metastatic ovarian cancer progression.

Given the potential cell-of-origin questions raised above, a key question is whether various signatures are derived from malignant cancer cells or host stromal cells. Many of the genes in the signature are known inducers of EMT and their expression in cancer cells may make these cells indistinguishable from non-tumor mesenchymal cells. One can use human OVCAR3 cells because of the low endogenous expression of the signature genes, which can be induced by recombinant TGFB1 (FIG. 25). Red fluorescence protein (RFP)-labeled OVCAR3 cells will be compacted using a hanging-drop technique and implanted under the ovarian bursa of nude mice. When the mice develop carcinomatosis, primary ovarian tumors and metastatic tumors will be harvested for 1) fluorescence activated cell sorting (FACS), 2) immunofluorescence (IF), and 3) qPCR. The ratio of RFP+ and RFP− cells in primary and metastatic tumors will be determined by IF and FACS. IF with antibodies against COL11A1 (provided by OncoMatrix as DMTX invaScan kit for detection of invasive tumors [98]) and POSTN (BioVendor, RD172045100) will be used to determine whether COL11A1 and POSTN are expressed in RFP+ or RFP− cells. qPCR analysis will be used to determine the mRNA levels of COL11A1 and POSTN in RFP+ and RFP− cells of the primary and metastatic tumors. In addition to RFP labeling, human- and mouse-specific PCR primers will provide a second layer of assurance that the signature genes are derived from human or mouse cells.

Levels of COL11A1 and POSTN can be elevated in human and mouse metastatic vs. primary tumors. If the signature originates from human cancer cells, enrichment in the relative number of RFP+ cells expressing COL11A1 and POSTN in IF analysis and/or an increase of COL11A1 and POSTN expression levels (with human but not mouse PCR primers) in metastatic vs. primary RFP+ cells would be observed. If the signature originates from mouse host cells, enrichment in the relative number of RFP− cells expressing COL11A1 and POSTN by IF and/or an increase of COL11A1 and POSTN in metastatic vs. primary RFP-cells by qPCR (with mouse but not human primers) would be observed. If COL11A1 and POSTN are elevated in both human RFP+ and mouse RFP− fractions, it is suggested that both human cancer cells and mouse nonmalignant cells upregulate the expression of COL11A1 and POSTN during the process of metastasis.

Example 31

Signature Enrichment in CSC Populations

It has been shown that cancer cells can generate CSCs through EMT. Patient outcome and drug resistance have also been linked to the properties of CSCs. Thus, it is possible that the signature is enriched in patients with poor prognosis because their tumors contain more CSCs.

As it is shown that many of the signature genes are enriched in the CSC population of A2780 cells, the Inventors further confirmed that COL11A1 and POSTN are among the top upregulated genes in OVCAR3 cell spheroids, which are enriched for CSCs. To determine whether COL11A1 and POSTN are specifically overexpressed in the CSC population in OVCAR3 xenografts, one can isolate RFP+/ALDH1+ and RFP+/ALDH− tumor cells and compare expression of COL11A1 and POSTN in the two cell populations by qPCR and IF.

Based on the enrichment of COL11A1 and POSTN in OVCAR3 spheroids, one can anticipate enrichment of these genes in the RFP+/ALDH1+ tumor cell population. Analysis via qRT-PCR of additional signature genes or unbiased expression profiling of CSCs and non-CSCs in primary and metastatic tumors to better characterize these tumor populations. RFP+ selection will assure that the tumor cell populations are of human origin and not derived from the mouse cells.

Example 32

Signature Enrichment in Bone Marrow, Fat, or Other Tissue Sources

Further, signatures as arising from carcinoma-associated stroma may be of bone marrow origin or adipose tissue. Bone marrow from male C57BL6 mice expressing GFP under the ubiquitin promoter mice can be isolated and transplanted into lethally-irradiated female C57BL6 mice expressing RFP under the chicken albumin promoter. Successful engraftment can be determined after 4 weeks by >95% GFP expression in the peripheral blood and bone marrow (and death of control mice without bone marrow transplants). The GFP-bone marrow-engrafted mice can be orthotopically implanted with syngeneic C57BL6 p53−/−; HA-myc; H-ras mouse ovarian cancer cells, which the Inventors recently generated and tested in mice.

Primary and metastatic tumors typically form 4-5 weeks after implantation of hanging drop-compacted cells into female C57BL6 mice. The primary and metastatic tumors are then isolated and analyzed by FACS for the proportion of the cancer cells (HA+), recruited non-bone marrow cells (RFP+), and recruited bone marrow cells (GFP+). Based on the literature in other tumor models, one anticipates that the contribution of cells to the metastatic tumors will be ~70% HA+, ~20% RFP+ and ~10% GFP+. Levels of COL11A1 and POSTN will be determined in each cell fraction by qPCR and IF. Similar experiments will be conducted with adipose tissue implants from ubiquitin-GFP C57BL6 mice into chicken albumin-RFP C57BL6 mice. In this case, one can take the endogenous adipose (RFP+) tissue into account.

Figure 24:
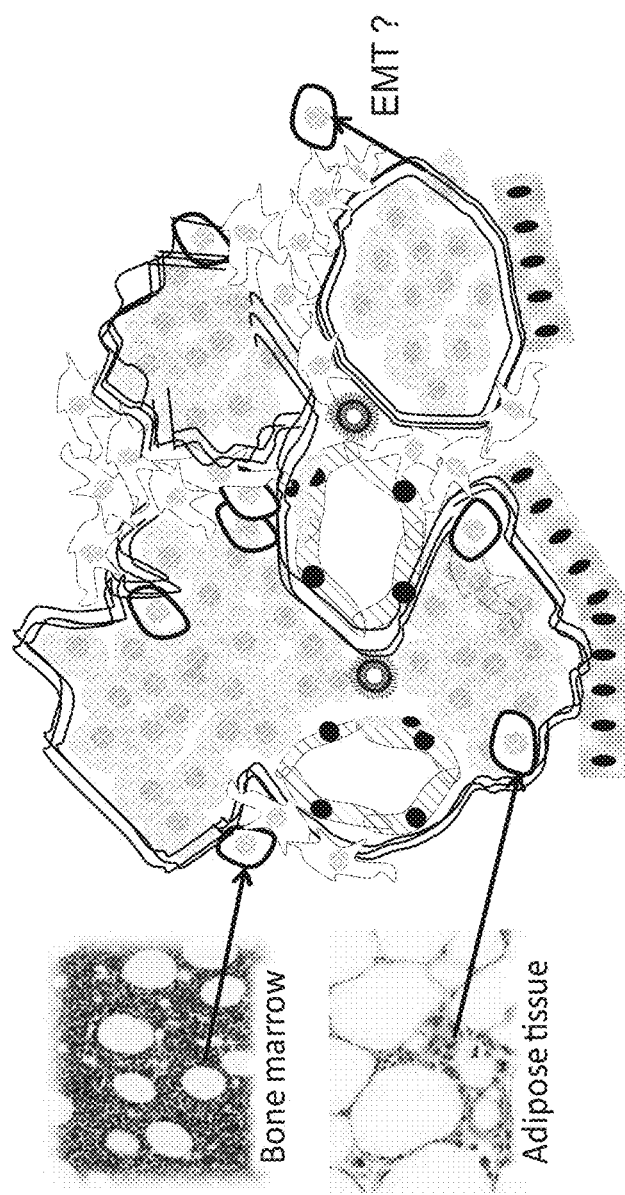
FIG. 24. Graphic overview of various cellular actor responsible for ovarian cancer signature generation.

Using the described approach, expression of COL11A1 and POSTN in metastatic tumors in the GFP+ cells indicates the bone marrow/adipose tissue origin of the signature while increased expression in the RFP+ cells will indicate that the signature originates in mouse cells other than the bone marrow/adipose tissue (FIG. 24). An increase in both GFP+ and RFP+ cell populations indicates that both bone marrow/adipose tissue- and non-bone marrow/adipose tissue-derived cells contribute to the signature gene expression. If the signature genes are solely derived from non-cancer cells, there will be no increase in the signature genes in HA+ cells.

Example 33

Effectiveness of Targeting of the Gene Signature Network

Current chemotherapeutic agents have been largely selected for their ability to destroy rapidly dividing cancer cells rather than the tumor infrastructure that protects the rare specialized cells that drive tumor recurrence and chemoresistance. This might explain why tumor regression does not necessarily translate into increased patient survival. The poor prognosis signature genes that the Inventors identified belong to a molecular network that is required to maintain the structure of the tumor. A better understanding of the components of this underlying structure that drives ovarian cancer progression could reveal the vulnerabilities of the tumor and thus have a major impact on the development of improved therapies for advanced ovarian cancer. Such pre-clinical studies are an important step towards clinical trials in patients with ovarian cancer.

Based on the described results, the Inventors have successfully targeted COL11A1 for reduction of tumor metastasis. One common feature of the signature genes is their extracellular matrix localization and involvement in collagen remodeling, suggesting that collagen remodeling might be a common biological process that contributes to cancer progression and poor overall survival. To test this hypothesis, the Inventors selected COL11A1 because this gene is highly expressed in most solid tumors but, importantly, not expressed in most normal tissues. COL11A1 expression was silenced using shRNA in the A2780 human ovarian cancer cell line, which has high levels of endogenous COL11A1. Knockdown of COL11A1 did not affect cell proliferation (FIG. 25A), however, it resulted in significantly decreased cell migration and invasion in vitro (FIG. 25B). To assess the effect of COL11A1 on tumor progression in vivo, the Inventors injected nude mice with scrambled shRNA (sh-scr) A2780 cells or COL11A1-specific shRNA (sh-COL11A1) A2780 cells. After 14 days, the mice injected with sh-scr A2780 cells developed large disseminated tumors while the mice with sh-COL11A1 A2780 cells developed small focal tumors (FIG. 25C, D). This result suggests that targeting collagen might be an effective approach to preventing ovarian cancer invasion and metastasis.

Example 34

Signature Genes Appear to be Regulated by TGFβ1 Signaling

TGFβ plays a crucial role in almost every aspect of tumor progression and metastasis. In ovarian cancer, increased TGFβ1 signaling activity was reported in metastatic ovarian tumors in comparison to matched primary ovarian tumors and the antibody against TGFβ was shown to be effective in suppressing metastasis in preclinical models of ovarian cancer. Currently, there are several TGFβ inhibitors in phase I/II clinical trials. It will be important to test the effectiveness of these agents as inhibitors of ovarian cancer progression and metastasis as single agents or in combination with chemotherapy.

Figure 26:
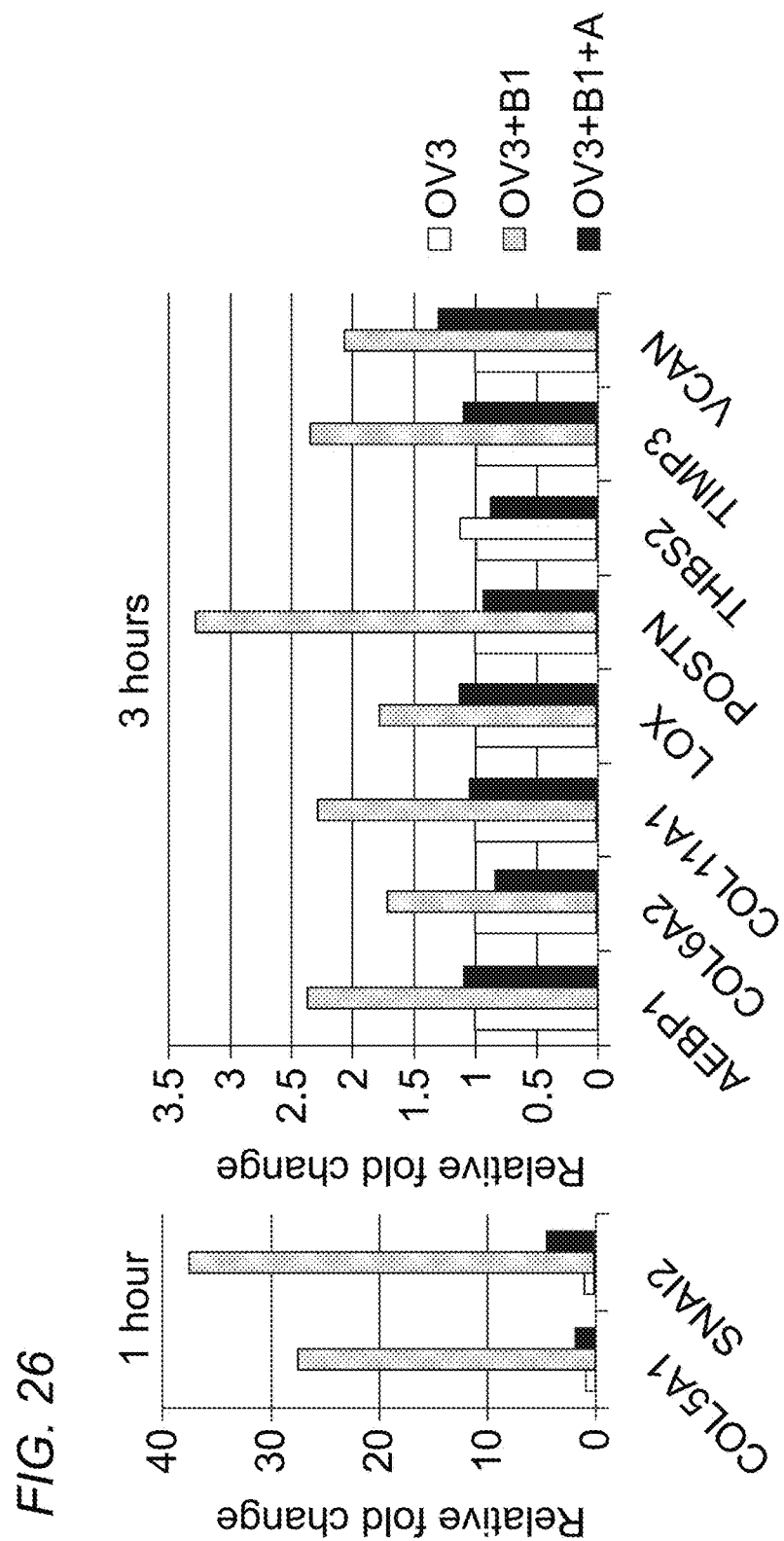
FIG. 26. Induction of the 10 poor outcome signature genes by TGFβ1. OVCAR3 (OV3) cells were treated with 10 ng/ml TGFβ1 (B1) for either 1 hour or 3 hours with (OV3+B1+A) or without (OV3+B1) pre-treatment with the TGFβ inhibitor, A83-01.

To learn more about the possible upstream regulators of the signature genes, the Inventors applied Ingenuity Pathway Analysis to the 61 signature genes in FIG. 12A and identified TGFβ1, TGFβ2, TGFβ3, SMAD3, and SMAD7 as top transcription factors regulating in expression of the signature genes. For validation of the predicted regulation of the signature genes by TGFβ1, the Inventors treated the human ovarian cancer cell line OVCAR3 (exhibits low endogenous levels of the signature genes) with TGFβ1 and measured mRNA expression of the genes before and after TGFβ1 treatment. The 10 OCFS genes showed slightly different induction times in the presence of TGFβ1. Expression of COL5A1 and SNAI2 was markedly induced after 1 hour of treatment with TGFβ1 whereas expression of the remaining 8 genes was induced after 3 hours of treatment with TGFβ1 (FIG. 11). The Inventors then measured expression of the 10 genes in cells pre-treated with the TGFβ1 inhibitor, A83-01, and showed that the TGFβ1 induction was abrogated in cells pre-treated with the inhibitor (FIG. 26), further validating that this induction was truly mediated by TGFβ1 signaling.

One may further evaluate the efficacy of A83-01 (TGFβ inhibitor) and 1D11 (TGFβ neutralizing antibody) in mouse models as described in Aim 2. Since these agents have already been shown to reduce tumor growth in mouse xenografts, special emphasis will be placed on evaluating the effect of TGFβ blockade on cisplatin chemosensitivity and tumor composition, such as the proportion of CSCs and the recruitment of various cell types.

An alternative way to test the role of TGFβ in ovarian cancer progression is to use transgenic mouse models in which TGFβ signaling is completely impaired in stromal cells, such as mice with a conditional knockout of the TGFβ type II receptor. One can have inject the described syngeneic mouse ovarian cancer cells i.p. into Tgfbr2 KO mice. Consistent with the proposed role of TGFβ in ovarian cancer progression, but in contrast to previous observations of a tumor-promoting role for the Tgfbr2 knockout in prostate and breast cancer, preliminary results indicate that growth of ovarian cancer is inhibited upon knockout of the TGFβ type II receptor in mouse stromal cells. Additional experiments can be done to verify this result and determine the effect of the stromal TGFβ type II receptor knockout on the proportion of CSCs and recruitment of stromal cells to the tumor.

Both pro- and anti-tumorigenic activities have been documented for TGFβ signaling in different cancer types, based on the observed increase of TGFβ1 signaling in metastatic ovarian cancer, the suppression of metastasis upon TGFβ1 inhibition in mouse models of ovarian cancer, and our observation that TGFβ induces expression of the signature genes, one anticipates that inhibition of TGFβ signaling by pharmacologic (A83-01), biologic (1D11) or genetic (Tgfbr2 KO mice) means will have a negative effect on the expression of the signature genes with the resultant loss of a nurturing environment for CSCs and an increased chemosensitivity to cisplatin.

Example 35

Targeting Collagen Remodeling Infrastructure as Cancer Therapy

Although under normal physiological conditions collagen-rich stroma maintains tissue architecture and serves as a barrier to epithelial cell migration, it can turn into a collaborator of cancer progression when modified by malignant cancer cells. Specifically, enhanced collagen deposition and cross-linking is associated with mammographic density, which is one of the greatest risk factors for breast cancer. For example, collagen I is enriched and aligned at the stromal border in breast tumors and changes in collagen I organization are associated with poor prognosis in breast cancer. In support of the idea that increased collagen deposition and cross-linking contributes to cancer formation, a rodent model with increased collagen deposition due to altered collagen degradation exhibited increased mammary tumor formation and progression to metastasis. In addition to collagen deposition, increased levels of LOX, an enzyme responsible for collagen cross-link formation, results in increased collagen stiffness. POSTN also promotes collagen cross-linking by interacting with BMP-1 to enhance the proteolytic activity of LOX. This results in the reorganization of loose connective tissue into linear tracks of fibers that serve as highways to promote chemotaxis of tumor cells. Indeed, breast cancer studies using live imaging have demonstrated that cancer cells migrate on collagen fibers in areas enriched in collagen. Collagen stiffness has also been shown to regulate stem cell differentiation and EMT.

Additionally, increased collagen deposition and remodeling increases interstitial pressure, which severely compromises the efficacy of drug delivery. For example, remodeling of the ECM through overexpression of COL6A3 in tumor cells was shown to contribute to cisplatin resistance in ovarian cancer. In contrast, the reduction in collagen stiffness can repress the malignant behavior of mammary epithelial cells and administration of collagenase increased the uptake and distribution of monoclonal antibodies in a mouse model of osteosarcoma. Thus, collagen degradation may be an effective approach to targeting the gene signature network. It remains to be determined whether ECM stiffness in cancer may be restored to normal and how such a restoration may benefit treatment prognosis.

One can test the effectiveness of collagenase in reducing ovarian cancer growth and/or increasing chemosensitivity to cisplatin. The first assessments of efficacy will be done in subcutaneous (s.c.) xenografts of A2780 human ovarian cancer cells (exhibit high expression levels of the signature genes) by direct intratumoral injection of collagenase. Collagenase clostridium histolyticum (XIAFLEX) will be used because this drug has been approved by the FDA for Dupuytren contracture (clinicaltrials.gov; NCT00528606) and is commercially available. Tumors will be disaggregated and analyzed for the presence of CSCs by FACS and immunostaining of tumor sections as described in Aim 2. Depending on the results of the treatment of s.c. tumors, the Inventors will optimize concentration of XIAFLEX for i.p. treatment to facilitate translation to i.p. therapy in ovarian cancer patients.

Another approach to targeting a network of specific genes is through micro RNA (miRNA). The miRNA-29 family, specifically miR-29b, was recently shown to inhibit tumor metastasis by targeting a network of collagen-remodeling genes. One can test the effectiveness of miR-29b in reducing tumor metastasis and/or the proportion of CSCs in our model. While miRNAs have not yet been fully adapted for use in the clinic, significant progress has been made in improving the specificity of delivery. One can also test the effectiveness of siRNA against the collagen-specific chaperone protein gp46 encapsulated in vitamin A-coupled liposomes, which was shown to be effective in resolving fibrosis in preclinical models of liver and pancreatic fibrosis.

Example 36

Development and Validation of an qRT-PCR Assay

The utility of deriving OCSC, OCDS, and OCFS signatures is to enhance physicians' abilities to identify patients with a high likelihood of recurrence, thereby improving therapeutic outcomes. For example, FIG. 8A shows an exemplary triage map of current clinical practice and the point of care at which various OCSC, OCDS, and OCFS signatures provide specific clinical guidance value.

Clinical application of OCSC, OCDS, and OCFS signatures requires development of accurate qRT-PCR (quantitative real-time PCR) based assay, as microarrays are not cost-effective for use in the clinic. A variety of qRT-PCR platforms can be utilized for detection and quantification of OCSC, OCDS, and OCFS transcripts derived from ovarian cancer samples. This includes ABI TaqMan® OpenArray® Real-Time PCR (FIG. 8B). In each instance, it may be highly desirable to design arrays such that custom-selected probes for each gene in the signature are represented in quadruplicates measurements, thereby eliminating outlier measurements and potential false-positive amplifications. A variety of housekeeping genes, such as GUSB, PPIA, TBP, RPLP0, RPL4, 18S, ACTB, and GAPDH, each provide baseline expression transcripts measurements that provide assay normalization. Examples of normalization measurements include delta cycle-threshold measurements.

To test the accuracy and precision of the designed assay, qRT-PCR is performed on 112 patient samples that previously used for microarray analysis in one of the three discovery data sets used for identification of periostin (POSTN)-coexpressing genes. This particular data set includes a correlative clinical database with approximately 300 clinical variables, including patient history, symptoms, treatment, other cancer history, surgeries, recurrences and survival status. RNA will be extracted from both frozen and paraffin-embedded primary ovarian cancer samples and reverse transcribed to obtain cDNA.

After normalization, the expression of various OCSC, OCDS, and OCFS biomarkers are further correlated with clinical outcomes, including progression-free survival (PFS) and overall survival (OS). From Phase 1, the Inventors expect to have approximately 10 genes that are optimized for the prediction of clinical outcomes. The methods described in Phase 1 will be employed to derive a gene signature for each time to event endpoint, PFS and OS. Model validation will be performed using each of the methods described in Phase 2 by randomly splitting the set of 112 patient samples into a ⅔ training set and a ⅓ validation set.

In certain instances, the high levels of statistical robustness may limit the maximum number of genes that are highly correlated with overall survival that overlap when using any of the four statistical methods described in Phase 1 is less than 8. In such instances, one can identify the largest subset of genes whose expressions are available and common to at least three studies and use that particular set for identifying the signature.

Example 37

Personalized Therapeutics

Many of the biomarkers, including COL11A1, LOX, POSTN, THBS2, and VCAN, have been associated with poor prognosis and metastatic progression in various cancer types and some of these genes have been tested as therapeutic targets in pre-clinical models. Other examples include biomarkers COL3A1, DCN, LUM, SPARC, VCAN, COL11A1, COL5A1 and POSTN in FIG. 9 or COL3A1, DCN, LUM, SPARC, TIMP3, and VCAM in FIG. 10. The inventors have validated in pre-clinical models two of the biomarkers, CXCL12 and periostin (POSTN), as suitable targets for ovarian cancer treatment. These results demonstrate that OCSC, OCDS, and OCFS biomarkers are not only predictors of poor survival but also play important roles in tumor progression and thus could be used as therapeutic targets.

To test the effectiveness of targeting individual biomarkers in a mouse model of ovarian cancer, one can identify genes that are significant in ovarian cancer progression, functional assays are necessary. Such assays should identify if the candidate genes are sufficient and required for tumor maintenance and progression and, thus, could be used for targeted therapy. One can functionally characterize the contribution of selected genes to ovarian cancer pathogenesis using a genetically relevant mouse model. Also, one can test inhibitors and small molecules specific for candidate signature network genes for their effectiveness to reduce cancer progression and increase chemosensitivity to cisplatin.

Example 38

OCSC-Focused Therapeutics

For example, the enrichment of OCSCs has been reported as correlated with increased epithelial-mesenchymal transition (EMT), and small molecules inhibiting EMT provides a mechanism for selective targeting. Curiously, it is presently unknown if tumor formation is driven by: 1) recruitment of mesenchymal stem cells (MSCs) to the tumor from bone marrow or fat, or if 2) cancer cells induce de-differentiation of stromal cells into MSCs. As the above described OCSC signature suggests aberrant expression of genes involved in epithelial-mesenchymal transitions (EMT) or TGF-beta, it is of further interest to understand the role of stromal cells, MSCs in tumor formation, and the interrelation with appearance and generation of OCSC populations. Improved understanding of these processes could allow selective targeting of these pathways. In different examples, compounds targeting EMT function include salinomycin, etoposide, abamectin, nigericin, or metformin.

In other examples, a similar approach may rely on antibodies, nucleic acids, peptides and/or proteins, or other biologics to severely defect OCSC function. For example, small interfering RNA (siRNA) or short-hairpin RNA (shRNA) knockdown of FGF1 and FN1 gene expression transcript could achieve these effects. Another example includes targeting of other adhesion markers, such as L1CAM. In different examples, an OCSC-specific antibody could be applied, which targets antigens that could be uniquely, or highly expressed in OCSCs. Examples include antibodies specific for chemoresistance mediator, ABCC5, or surface markers, CD24, CD44, CD117, CD133 or ALDH.

Example 39

Collagenase-Based Therapeutics

As another example, one can test the effectiveness of collagenase in a mouse model of ovarian cancer. Although under normal physiological conditions, collagen-rich stroma maintains tissue architecture and serves as a barrier to epithelial cell migration, it can turn into a collaborator of cancer progression when modified by malignant cancer cells. Specifically, enhanced collagen deposition and cross-linking is associated with mammographic density, which is one of the greatest risk factors for breast cancer. For example, it is suggested that collagen deposition contributes to cancer formation, as an animal model with increased collagen deposition due to altered collagen degradation exhibit increased mammary tumor formation and progression to metastasis. In addition, it has been reported that collagen deposition, increased levels of LOX, an enzyme responsible for collagen cross-link formation, results in increased collagen stiffness. Signature gene, POSTN, also promotes collagen cross-linking by interacting with BMP-1 to enhance the proteolytic activity of LOX. This results in the reorganization of loose connective tissue into linear tracks of fibers that serve as highways to promote chemotaxis of tumor cells. Indeed, breast cancer studies using live imaging have demonstrated that cancer cells migrate on collagen fibers in areas enriched in collagen. Collagen stiffness has also been shown to regulate stem cell differentiation, although the molecular mechanisms of how collagen composition regulates decisions between stem cell expansion and differentiation are not well understood. Furthermore, increased collagen deposition and remodeling increases interstitial pressure, which severely compromises the efficacy of drug delivery. In contrast, the reduction in collagen stiffness can repress the malignant behavior of mammary epithelial cells, and administration of collagenase increased the uptake and distribution of monoclonal antibodies in a mouse model of osteosarcoma. Thus, at least theoretically, collagen degradation by may be an effective approach to targeting the gene signature network. Therefore, one can test the effectiveness of collagenase in reducing ovarian cancer growth and/or increasing sensitivity to chemotherapy. Collagenase clostridium histolyticum (XIAFLEX) can be used for intraperitoneal injections because this drug has been approved by the FDA for Dupuytren contracture (clinicaltrials.gov; NCT00528606) and is commercially available.

One expects that inhibition of individual biomarkers will be effective in reducing tumor growth and/or increasing sensitivity to cisplatin. If the main mechanism by which the biomarkers contribute to tumor progression is collagen deposition and cross-linking, loosening the collagen matrix with collagenase may be the most effective way to inhibit the entire network of biomarkers.

Example 39b

TGF-β-Related Therapeutics

Blockade of TGF-β and its signaling pathway provides multiple therapeutic There are many TGF-β signaling antagonist agents under development at both the pre-clinical and clinical stages. Some major classes of TGF-β inhibitors include ligand traps, antisense oligonucleotides (ASO), small molecule receptor kinase inhibitors, and peptide aptamers. Ligand traps serve as a sink for the excess TGF-β produced by tumor cells and fibroblasts during cancer progression, which increases with aggressiveness and tumor stage. Ligand traps can also include anti-ligand neutralizing antibodies and soluble decoy receptor proteins that incorporate the ectodomains from either TβRII or βRIII/betaglycan protein. Neutralizing antibodies have been raised against individual ligands or may be designed to block all three isomers. One example includes a pan-neutralizing anti-mouse TGF-β monoclonal antibody, 1D11. Examples of decoy receptor proteins include recombinant Fc-fusion proteins containing the soluble ectodomain of either TβRII (TβRII-Fc) or the type III receptor, betaglycan. ASOs can also be used to reduce the bioavailability of active TGF-β ligands in the local tumor microenvironment by blocking TGF-β synthesis. ASOs are single-stranded polynucleotide molecules, 13-25 nucleotide in length, that hybridize to complementary RNA, inhibiting mRNA function, and preventing protein synthesis through accelerated mRNA degradation by RNase H. One example includes AP12009 (Trabedersen).

Another therapeutic strategy is to block TβRI activity through the use of small molecule receptor kinase inhibitors that act via ATP-competitive inhibition of the kinase catalytic activity of the receptor. Examples include small molecule inhibitor of TβRI, SB-431542, TβRI/ALK5 kinase inhibitor, Ki26894, TβRI inhibitor SD-208, dual inhibitor of TβRI/II, LY2109761, or inhibitors selective for the kinase domain of the type 1 TGF-β receptor, LY2157299. Alternatively, other therapeutics targeting related pathways such as EGFR (erlotinib), ABL/PDGFR/KIT (imatinib), and VEGFR/RAF/PDGFR (sorafenib), may be used in combination with a TGF-beta related therapeutics.

Lastly, targeting intracellular TGF-β signaling molecules, such as Smads, is possible with the use of peptide aptamers, although this is the least explored therapeutic strategy. Aptamers are small peptide molecules containing a target-binding and a scaffolding domain that stabilize and interfere with the function of the target. Aptamers may therefore be designed specifically against Smad2 versus Smad3, and against multimeric transcriptional complexes containing Smads and other transcription factors, transcriptional co-activators, or co-repressors. The Trx-SARA aptamer is and has been reported to reduce the levels of Smad2/3.

Example 40

Figure 27:
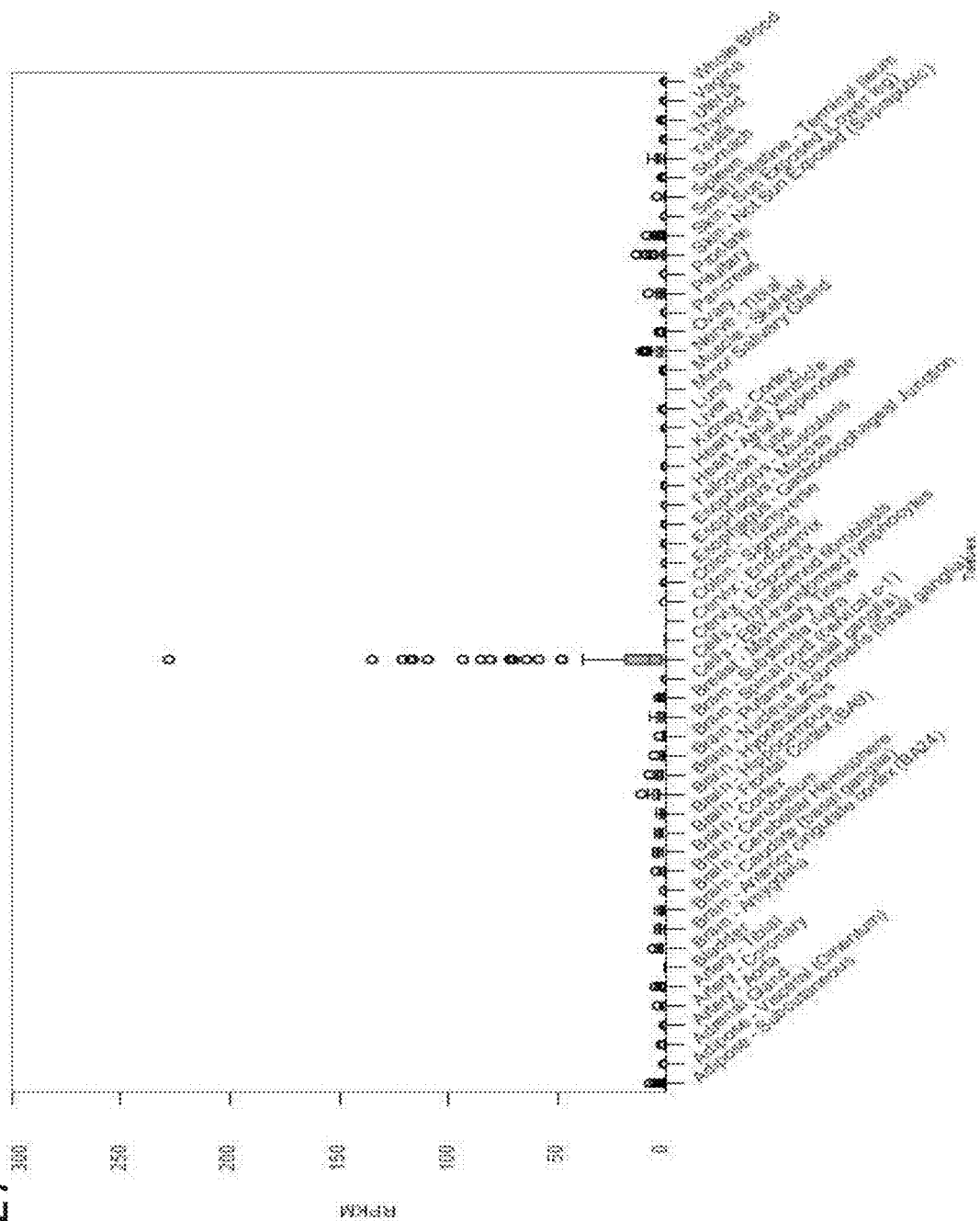
FIG. 27. Expression of COL11A1 mRNA in normal tissues and transformed cell lines. Profiling of various adult human tissues revealed that, with the exception of bone cartilage, negligible levels of COL11A1 mRNA are expressed in most tissues that have been profiled according to the Genotype Tissue-expression (GTEXx) portal.
Figure 28A:
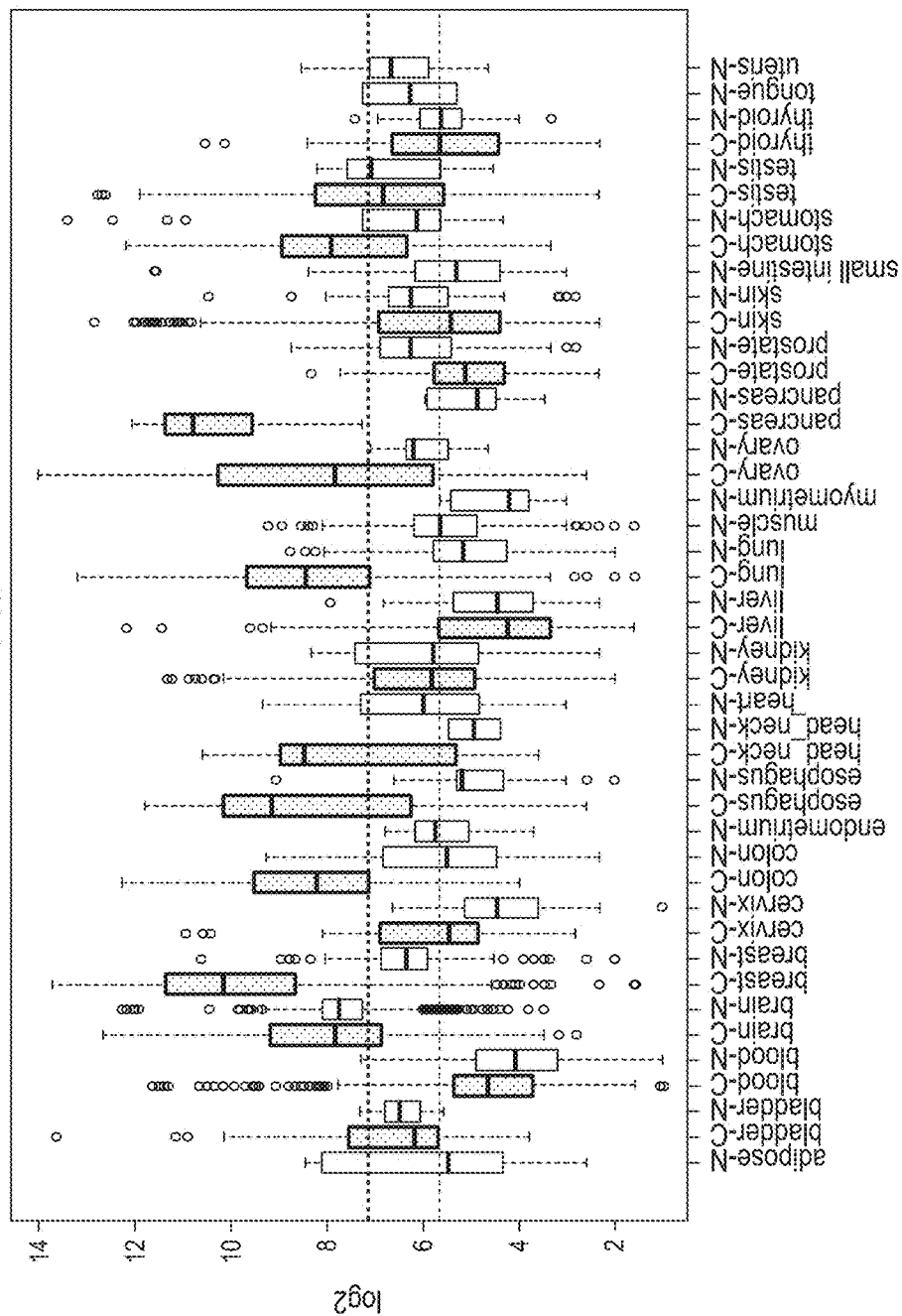
FIG. 28(A) to FIG. 28(B). Differential expression of COL11A1 between normal tissues and cancer. (A) Visualization of COL11A1 expression in normal tissues and corresponding cancers in Gene Expression across Normal and Tumor tissue (GENT). The y axis shows mRNA levels. Green color indicates normal tissue while red color indicates cancer. (B) Oncomine analysis of TCGA datasets. COL11A1 probe: NM_080629_1_6174.
Figure 28:
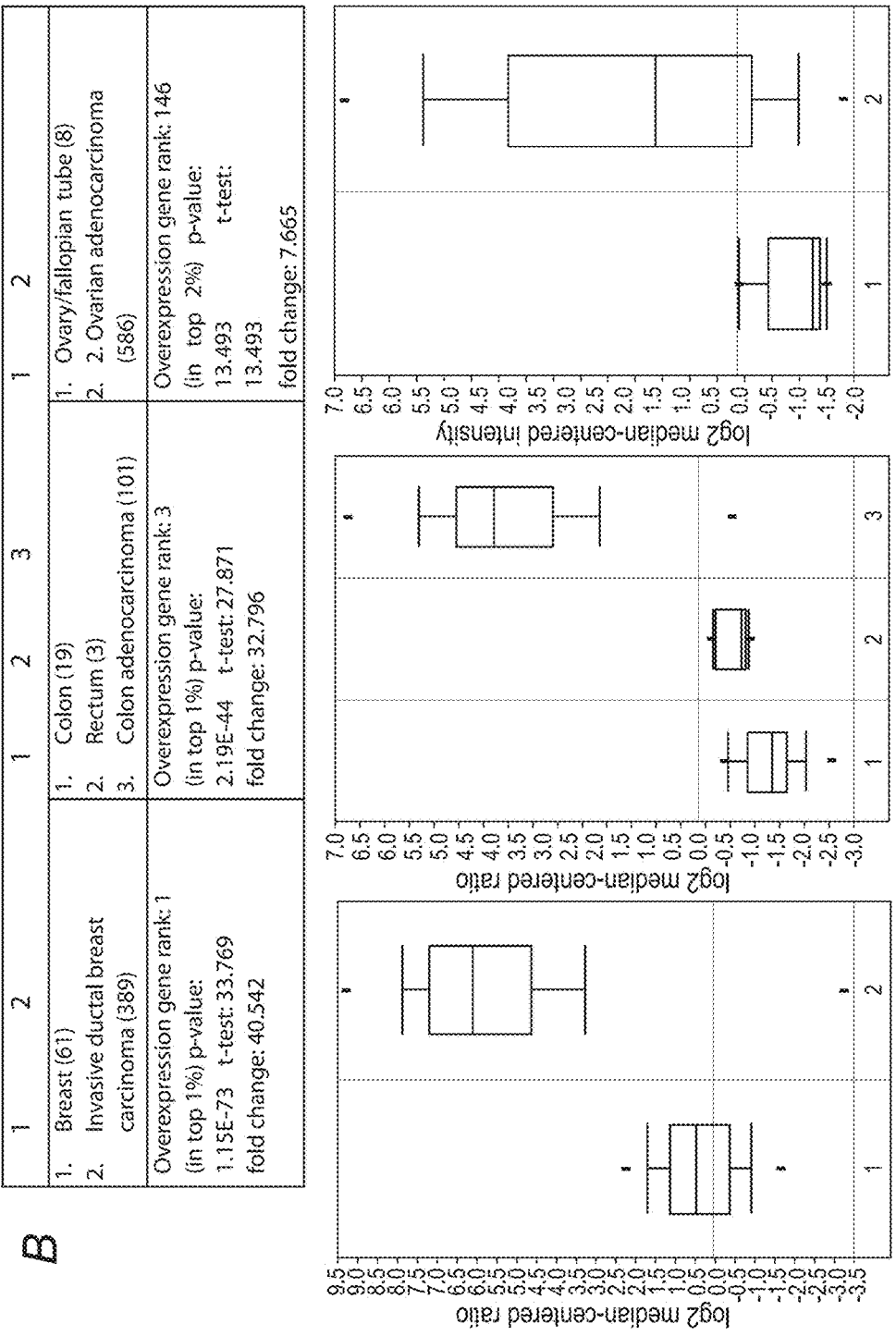

COL11A1 is Among the Most Differentially Expressed Genes Between Cancers and their Corresponding Normal Tissues The COL11A1 gene encodes the pro-alpha1 (XI) chain, which is one of the three chains that make type XI collagen. Profiling of various adult human tissues revealed that, with the exception of bone cartilage, negligible levels of COL11A1 mRNA are expressed in most tissues that have been profiled (FIG. 27). However, increased levels of COL11A1 have been observed in transformed fibroblasts (FIG. 27), indicating that oncogenic transformation may lead to aberrant expression of COL11A1. Indeed, expression of COL11A1 mRNA is elevated in most cancers in comparison to their corresponding normal tissues (FIG. 28A). In many cancers, COL11A1 is ranked among the most statistically significant differentially expressed genes between cancer and its corresponding normal tissue. For example, in colon, breast, and ovarian cancer TCGA datasets, COL11A1 mRNA ranks as the number one, three and 146 most differentially expressed gene, respectively (FIG. 28B).

Example 41

COL11A1 is an Indicator of Cancer Progression, Therapy Resistance and Cancer Recurrence Expression profile studies in multiple cancers types have identified COL11A1 as a differentially expressed gene during cancer progression. For example, in breast cancer, we searched for top 10 most statistically significant differentially expressed probes between invasive ductal carcinoma (IDC) and ductal carcinoma in situ (DCIS) in four large public microarray datasets that used different microarray platforms and probes for COL11A1. In all four studies, COL11A1 probes ranked among the top most significant differentially expressed transcripts between IDC and DCIS (Table 9). We find that in other cancers, COL11A1 expression is increased during different stages of cancer progression, such as transformation (adenoma vs. normal colon; ductal adenocarcinoma vs. chronic pancreatitis; malignant vs. premalignant stomach cancer), local invasion (invasive ductal carcinoma (IDC) vs. ductal carcinoma in situ in breast cancer (DCIS); muscle-invasive vs. noninvasive bladder transitional cell carcinoma), metastasis (primary vs. metastatic melanoma; primary vs. metastatic ovarian cancer), and recurrence (metastatic vs. recurrent ovarian carcinoma) (Table 10). COL11A1 has also been previously identified among expression array signature genes associated with resistance to neoadjuvant therapy in breast cancer, time to recurrence in glioblastoma and time to recurrence and overall survival in ovarian carcinoma (Table 10).

type (FIG. 29A), which was previously shown to be associated with the poorest survival among the four molecular subtypes.

In the Tothill dataset, 259 serous and endometrioid ovarian carcinomas have been clustered based on their expression profiles into six distinct molecular subtypes (C1-C6) (20). The C1 subtype was originally identified based on expression of a distinct set of genes with known roles in extracellular matrix remodeling and invasion. Our Oncom-

TABLE 9

COL11A1 probes ranked among the top most significant differentially expressed transcripts between IDC and DCIS

| Vargas | | Schuetz | | Sgroi | | Lee | |
|---|---|---|---|---|---|---|---|
| ILMN_2392803 | COL11A1 | 229271_x_at | COL11A1 | g393318_3p_a_at | POSTN | 37892_at | COL11A1 |
| ILMN_1769388 | GJB2 | | | 4876385_3p_at | COL11A1 | 32306_g_at | COL1A2 |
| | | 37892_at | COL11A1 | | | | |
| ILMN_1789507 | COL11A1 | | | g4502946_3p_a_at | COL1A2 | | |
| | | 204320_at | COL11A1 | | | 38420_at | COL5A2 |
| ILMN_1752843 | GRM4 | 215446_s_at | LOX | g10946502_3p_a_at | SFRP2 | 39945_at | FAP |
| ILMN_2163873 | FNDC1 | 213764_s_at | MFAP5 | g4505046_3p_a_at | LUM | 32307_s_at | COL1A2 |
| ILMN_1773079 | COL3A1 | 227140_at | INHBA | g8923132_3p_at | ASPN | 658_at | THBS2 |
| ILMN_1731446 | COL11A1 | 226237_at | COL8A1 | Hs.297909.0.S1_3p_s_at | COL3A1 | 34778_at | LRRC15 |
| ILMN 1672776 | COL10A1 | 229479_at | nd | Hs.179729.0.S1_3p_a_at | COL10A1 | | |
| | | | | | | 32488_at | COL3A1 |
| ILMN_1737943 | nd | 217428_s_at | COL10A1 | Hs.28792.0.S1_3p_at | nd | 659_g_at | THBS2 |
| ILMN_1729212 | GRM8 | 222288_at | nd | Hs.111779.1.S1_3p_at | SPARC | 38077_at | COL6A3 |

TABLE 10

COL11A1 in Various Cancers

| COL11A1 | Cancer type | Comparison | Method of detection |
|---|---|---|---|
| Diagnostic marker | Ovary | Primary, metastatic, and recurrent tumors | Expression array, in situ hybridization |
| | Breast | Invasive ductal carcinoma (IDC) vs. ductal carcinoma in situ (DCIS) | Expression array |
| | Stomach | Malignant vs. premalignant | Expression array and qPCR |
| | Bladder | Muscle-invasive vs. noninvasive transitional cell carcinoma | Expression array meta analysis |
| | Pancreas | Ductal adenocarcinoma vs. chronic pancreatitis | Expression array, qPCR and immunohistochemistry |
| | Colon | Adenoma vs. normal colon | RT-PCR |
| | Melanoma | Primary vs. metastatic | Expression array, immunofluorescence |
| Prognostic marker | Breast | Resistance to neoadjuvant chemotherapy | Expression array |
| | Glioblastoma | Time to recurrence | Expression array meta analysis |
| | Ovary | Time to recurrence and overall survival | Expression array, qPCR, in situ hybridization |

Example 42

High Levels of COL11A1 Indicate an Aggressive Molecular Subtype of Cancer

Figure 29:
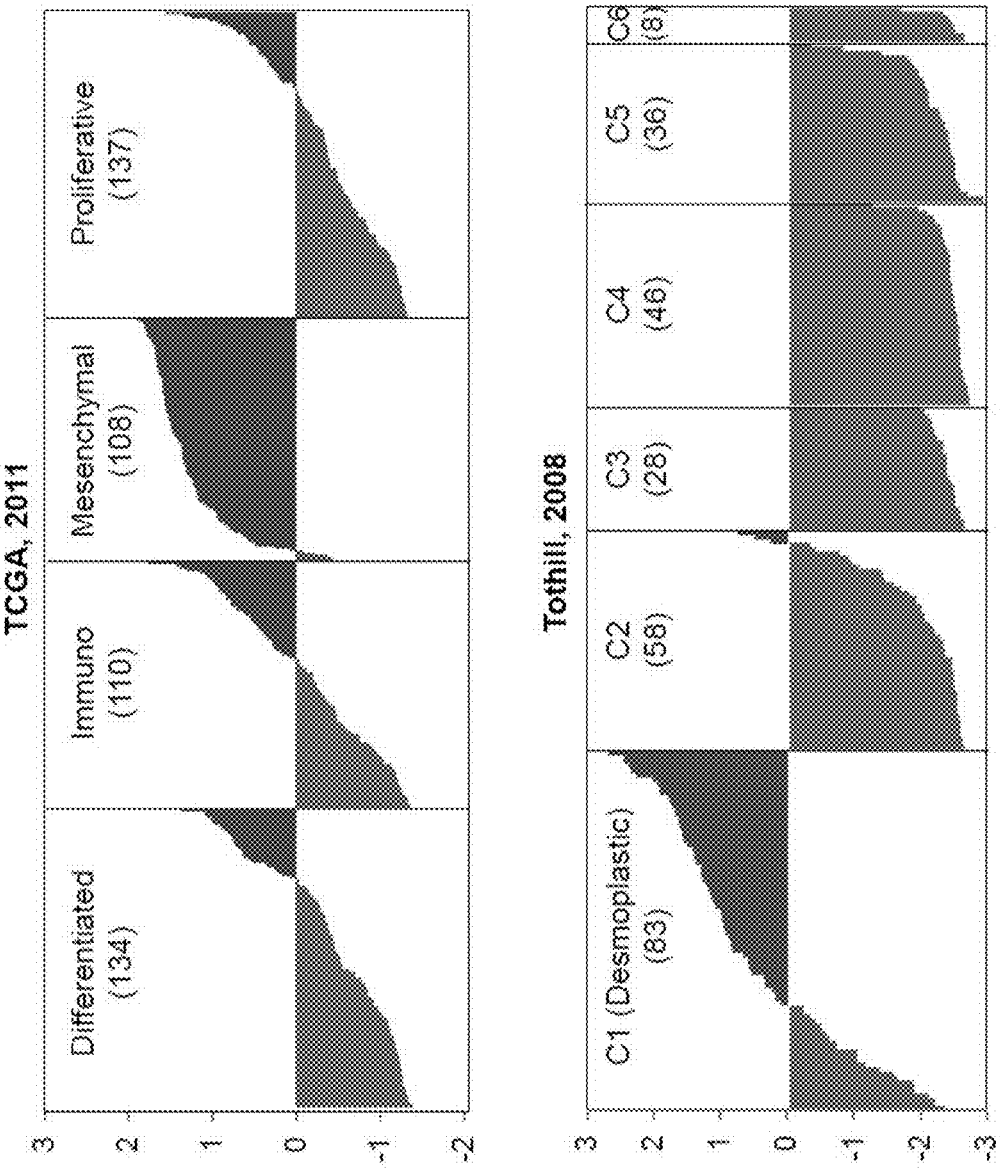
FIG. 29(A) to FIG. 29(B). High expression levels of COL11A1 are associated with Desmoplastic/Mesenchymal molecular subtype of high grade serous ovarian carcinoma. A diagram of COL11A1 mRNA distribution in (A) 489 serous ovarian carcinomas in the TCGA dataset grouped into four distinct molecular subtypes and (B) 259 ovarian serous and endometrioid ovarian carcinomas in the Tothill dataset grouped into six distinct molecular subtypes; The x axis shows individual tumors that are merged into a continuous plot (the number of tumor samples in each subtype is indicated in parentheses).

To determine if high levels of COL11A1 are associated with a specific molecular subtype of invasive ovarian carcinoma, we used two large datasets in which ovarian cancers have been divided into molecular subtypes based on distinct expression profiles. In the ovarian TCGA dataset, 489 patients with serous ovarian carcinoma have been clustered into four molecular subtypes: differentiated, immunoreactive, mesenchymal and proliferative. We show that high levels of COL11A1 predominate in the mesenchymal subine analysis shows that high levels of COL11A1 predominate in the C1 subtype (FIG. 29B). The C1 subtype is associated with the poorest survival among the six subtypes and is characterized by extensive desmoplasia.

Example 43

COL11A1 is a Biomarker of Reactive Tumor Stroma

Since reactive tumor stroma has a prominent role in most aspects of tumor progression its accurate detection and quantification would allow for significant improvements in diagnosis, prognosis and targeted therapy. However, it has been challenging to identify biomarkers of reactive stroma that are not expressed in normal tissues or benign pathological conditions. Currently, there are no effective methods to separate reactive stroma from nonreactive stroma. Therapeutic methods that target both types of stroma are counterproductive and result in significant toxicity due to the death of normal stroma. Therefore, it is of utmost importance to distinguish these two stromal types and develop biomarkers for qualitative and quantitative detection of reactive stroma.

Upon activation, cancer-associated stromal cells exhibit phenotypic changes that partially overlap with myofibroblastic changes during wound healing and fibrosis, including secretion of specific extracellular matrix (ECM) components, cytokines and growth factors. As a result, it is difficult to distinguish biomarkers of cancer-promoting pathology from biomarkers of benign pathologies, such as wound healing, inflammation and fibrosis. Several markers have been used to differentiate between reactive and nonreactive tumor stroma, including α-smooth muscle actin (αSMA), fibroblast activation protein (FAP), podoplanin, palladin, tenascin-C, platelet-derived growth factor receptor (PDGFRα/β), and NG2 chondroitin sulfate proteoglycan. The significant shortcoming of all of these markers is their frequent expression in non-tumor related stroma, such as inflammatory fibroblasts, myofibroblasts, pericytes, and mesenchymal stem cells. For example, targeting FAP-positive stroma successfully diminishes tumor growth in experimental models, confirming the key role of reactive stroma in cancer progression and demonstrating its effectiveness as a therapeutic target. However, depletion of FAP-positive stroma was shown to also induce severe toxicities due to the expression of FAP in the mesenchymal cells of normal bone marrow, muscle and adipose tissue. Similarly, depletion of αSMA-positive stroma in a pancreatic cancer model led to increased tumor aggressiveness and diminished survival. These studies highlight the need for a better understanding of the molecular characteristics of the reactive tumor stroma in order to develop more precise and less toxic targeted therapies and reliable biomarkers for diagnosis and prognosis.

Figure 30:
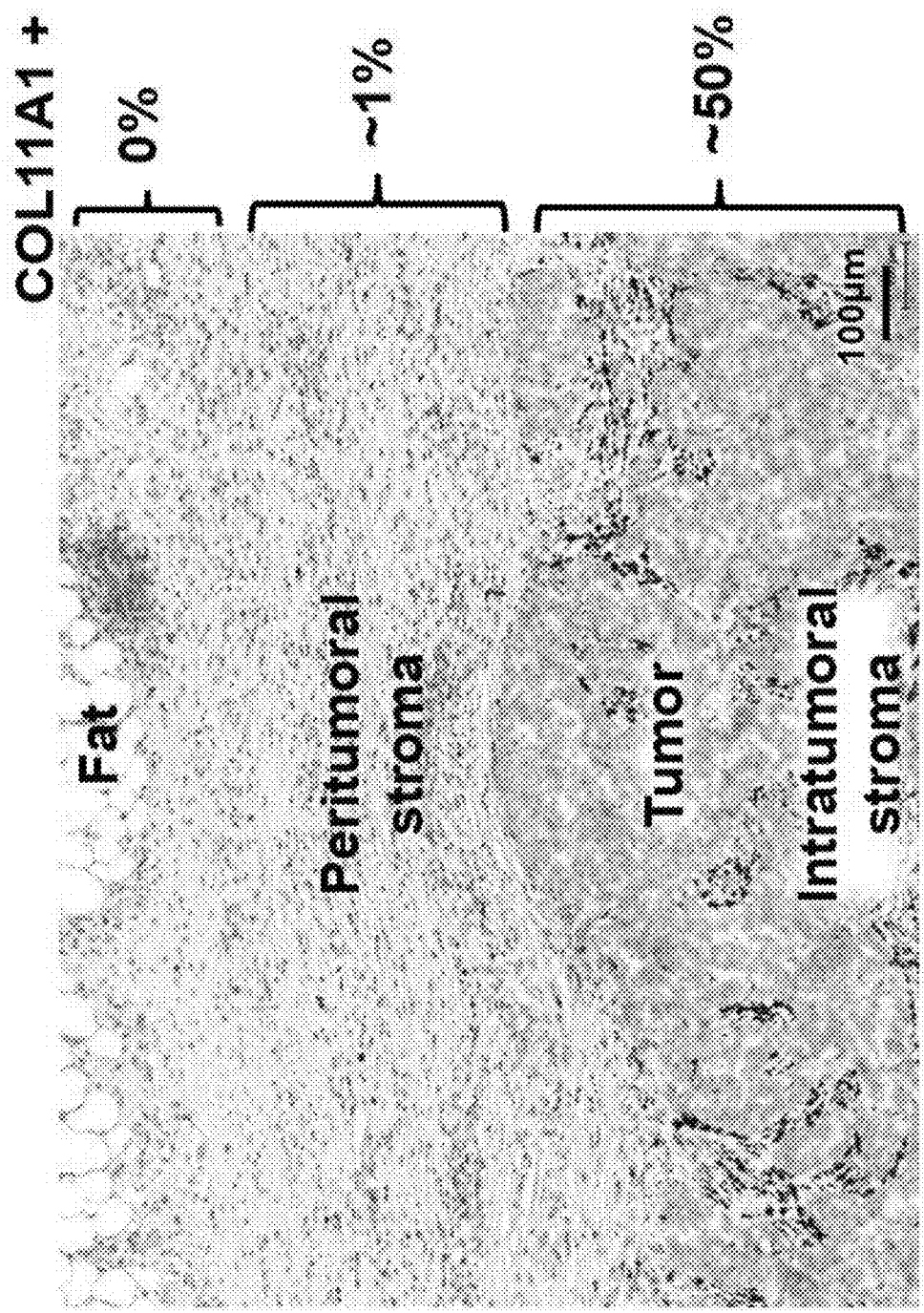
FIG. 30. Expression of COL11A1 in reactive tumor stroma. COL11A1 detection by in situ hybridization shows a distribution of COL11A1 positive cells in different parts of the tumor. Estimated percent of COL11A1-positive stromal cells is shown on the right.

Our searches of various databases indicate that COL11A1 is highly enriched during cancer progression but is not enriched in benign pathologies, such as wound healing, inflammation and fibrosis (refs and tables below). We found that COL11A1 mRNA and pro-protein were focally expressed in a subset of intra/peri-tumoral stromal cells that were positive for various markers of activated stromal myofibroblasts (data not shown). Strikingly, necrotic cells and any cells>1 mm in distance from the epithelial tumor were always negative (data not shown) indicating that COL11A1 expression is highly dependent on cues received from neighboring malignant cells (FIG. 30).

Example 44

A Consistent Set of Genes is Coexpressed with COL11A1 in Different Cancer Types

To better understand the biology of the tumors with high levels of COL11A1, we identified genes that most closely correlate with expression of COL11A1 in TCGA datasets representing 12 different cancer types. Spearman's rank correlations between COL11A1 and coexpressed genes for each cancer type were calculated. The genes were then ranked based on the average correlation of each gene across the 12 cancer types. The top 196 highly correlated genes were selected based on the average correlation of greater than 0.4). In addition, COL11A1 co-expressed genes were ranked based on the average of absolute values of the correlations. 206 most anti-correlated genes across the 12 cancer types were selected based on the mean absolute correlation of less than 0.05. In each cancer type, the top 10% most correlated and the top 10% most anti-correlated genes are highlighted in pink. Notably, COL11A1 correlated genes with high average correlation score also tend to be among the top 10% highest scored genes in each cancer type, i.e. COL3A1 is among the top 10% highest scored genes in 11 of 12 cancer types. This pattern was not observed among anticorrelated genes. This result indicates a remarkable conservation of the COL11A1 correlated, but not anti-correlated, gene signature in different cancer types. It is possible that a specific biological process characterized by the expression of this set of genes is shared across tumor types. Another possibility is that a specific cell type characterized by the expression of these genes is universally recruited to tumors of different types.

Figure 31:
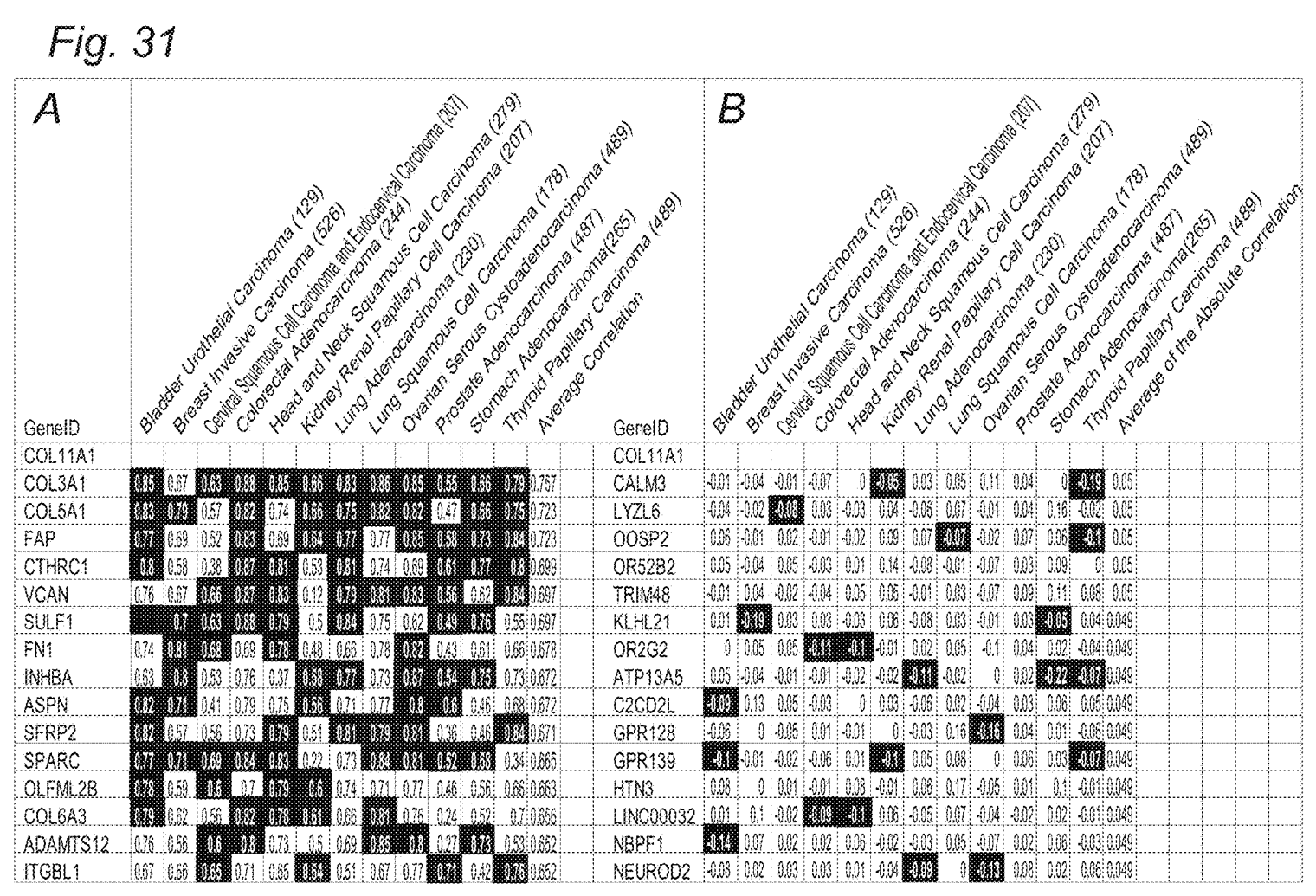

It is shown that genes highly correlated with COL11A1 (average Spearman correlation>0.4) in TCGA datasets representing 12 different cancer types (FIG. 31(A)). The top 10% most correlated genes for each cancer type are highlighted in pink. Genes highly anti-correlated with COL11A1 (average of the absolute Spearman correlation<0.5) in TCGA datasets representing 12 different cancer types (FIG. 31(B)). The top 10% most anti-correlated genes for each cancer type are highlighted in pink color.

This result indicates a remarkable conservation of the COL11A1 correlated, but not anti-correlated, gene signature in different cancer types. It is possible that a specific biological process characterized by the expression of this set of genes is shared across tumor types. Another possibility is that a specific cell type characterized by the expression of these genes is universally recruited to tumors of different types. We can deduce the possible identity of this biological process or cell type by looking for enrichment of the COL11A1 correlated gene signature in previously identified gene signatures of various cell types and biological and molecular processes.

Figure 32:
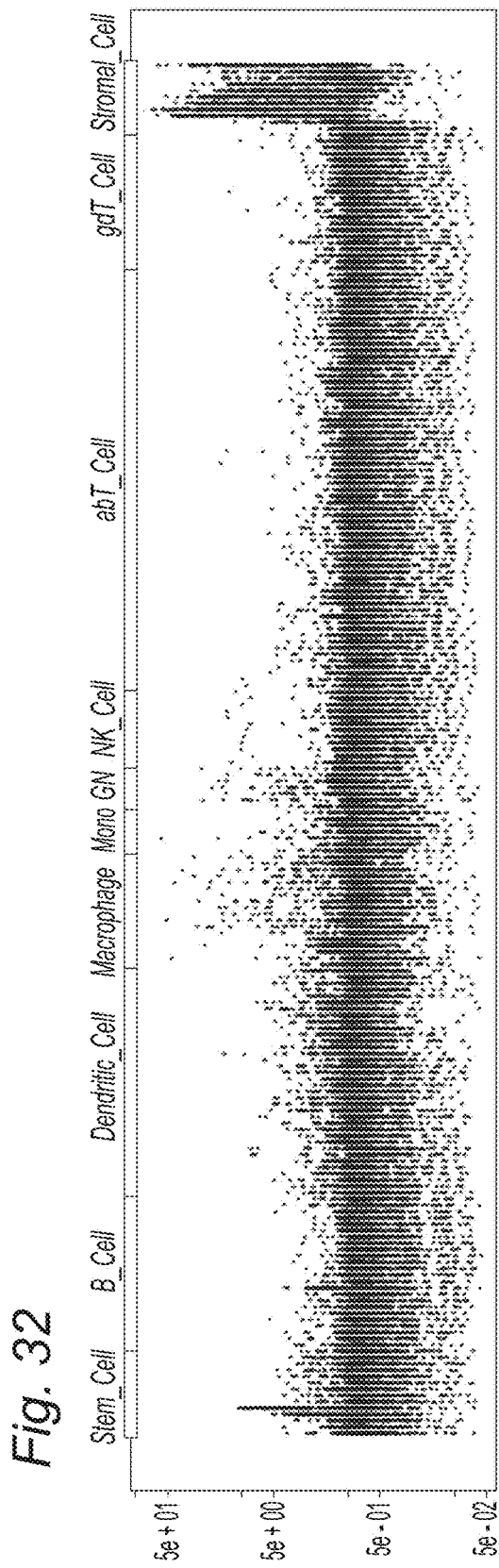
FIG. 32. COL11A1 correlated genes presence in in specific cell types of the immune system. Using the Immunological Genome Project in which expression profiles of XX mouse cell types of myeloid and lymphoid origin isolated by FACS with different combinations of lineage and differentiation markers. We show that COL11A1 correlated genes are primarily enriched in stromal cells (such as skin fibroblast) but not in various myeloid lineages. While the majority of COL11A1 correlated genes are expressed in stromal cells, a subset of genes, including COL11A1 are not expressed in normal stromal cells.

To identify if COL11A1 correlated genes are present in specific cell types of the immune system, we used the Immunological Genome Project in which expression profiles of XX mouse cell types of myeloid and lymphoid origin isolated by FACS with different combinations of lineage and differentiation markers. We show that COL11A1 correlated genes are primarily enriched in stromal cells (such as skin fibroblast) but not in various myeloid lineages (FIG. 32). While the majority of COL11A1 correlated genes are expressed in stromal cells, a subset of genes (red rectangle in FIG. 32), including COL11A1 are not expressed in normal stromal cells.

Example 45

COL11A1 Increases the Percentage of Ovarian Cancer Stem Cells (CSCs)

Figure 33:
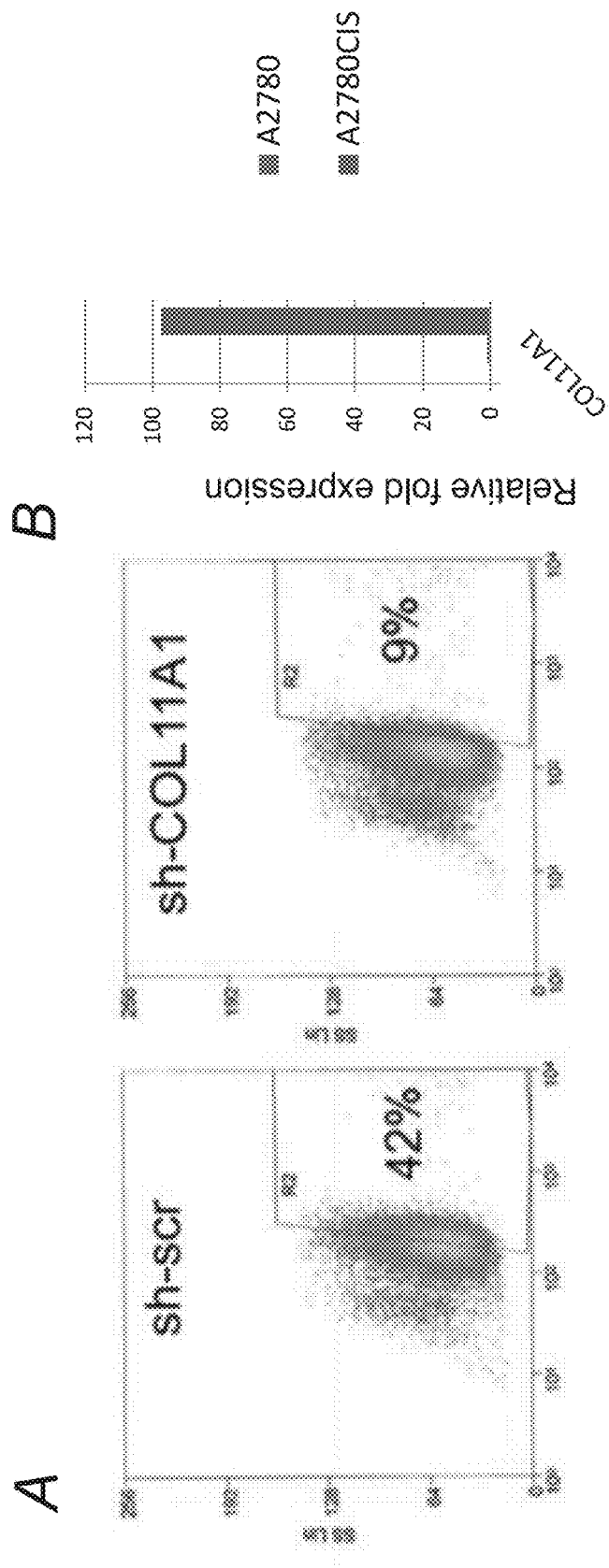
FIG. 33(A) to FIG. 33(C). COL11A1 knockdown experiments. (A) Knockdown of Col11A1 decreases the percentage of cancer stem cells (B) Relative expression following knockdown (C) ALDH expression in the control (scr) and COL11A1 knock-down A2780 cis-R cells (sh1).
Figure 33:
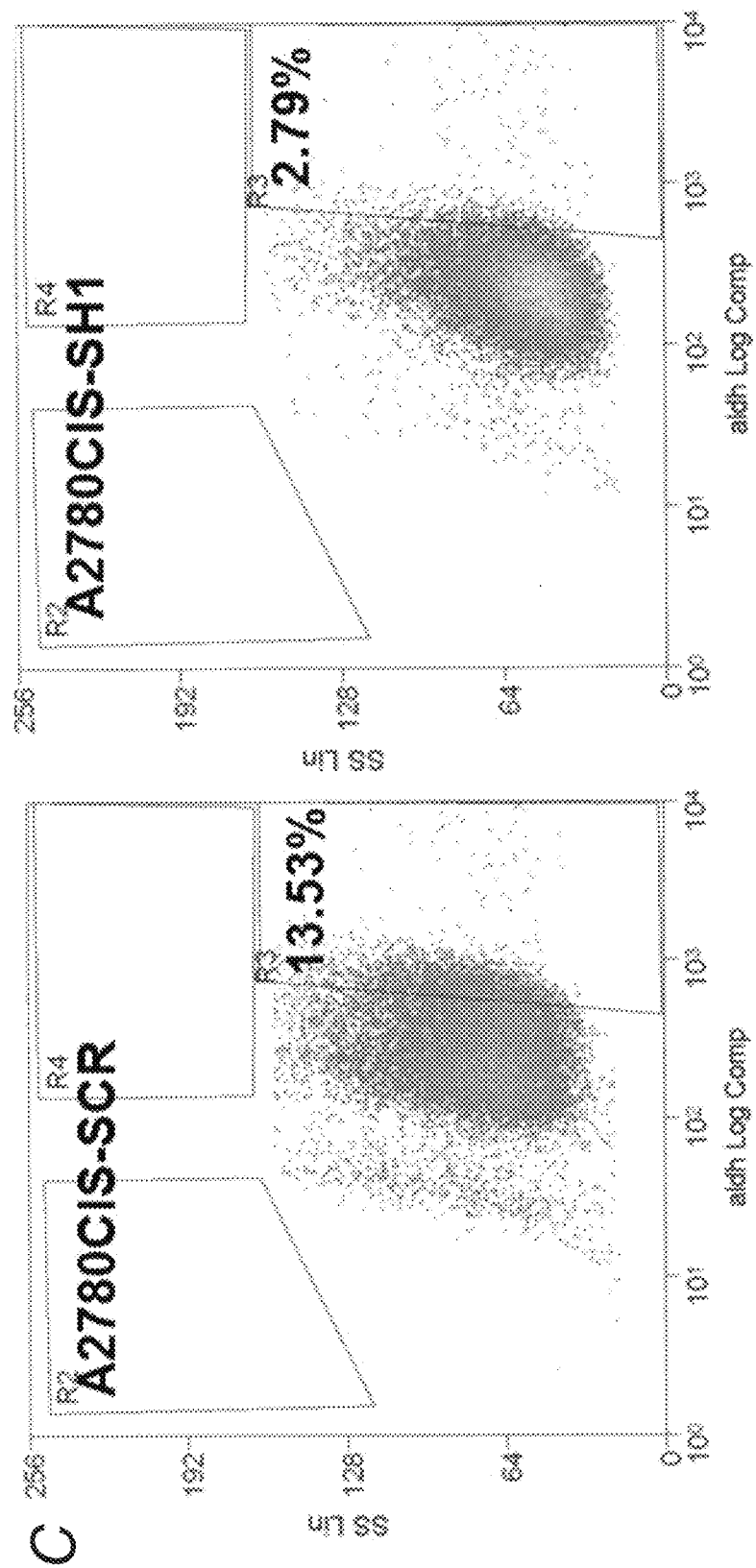

In order to determine the role of COL11A1 in ovarian CSCs, we first knocked down COL11A1 in the A2780 cis-R (SIGMA) cancer cell line, which expresses high endogenous levels of COL11A1. We then measured the expression of aldehyde dehydrogenase (ALDH) in two groups (scrambled, COL11A1 knockdown) using the ALDEFLUOR kit. High ALDH expression is known to be a marker for ovarian CSCs. Our data showed that COL11A1 knockdown led to a significant decrease in the ALDH$^{high}$ population in A2780 cis-R cancer cells (13.53% to 2.79%; FIG. 33), suggesting a role for COL11A1 in CSC survival.

Figure 34:
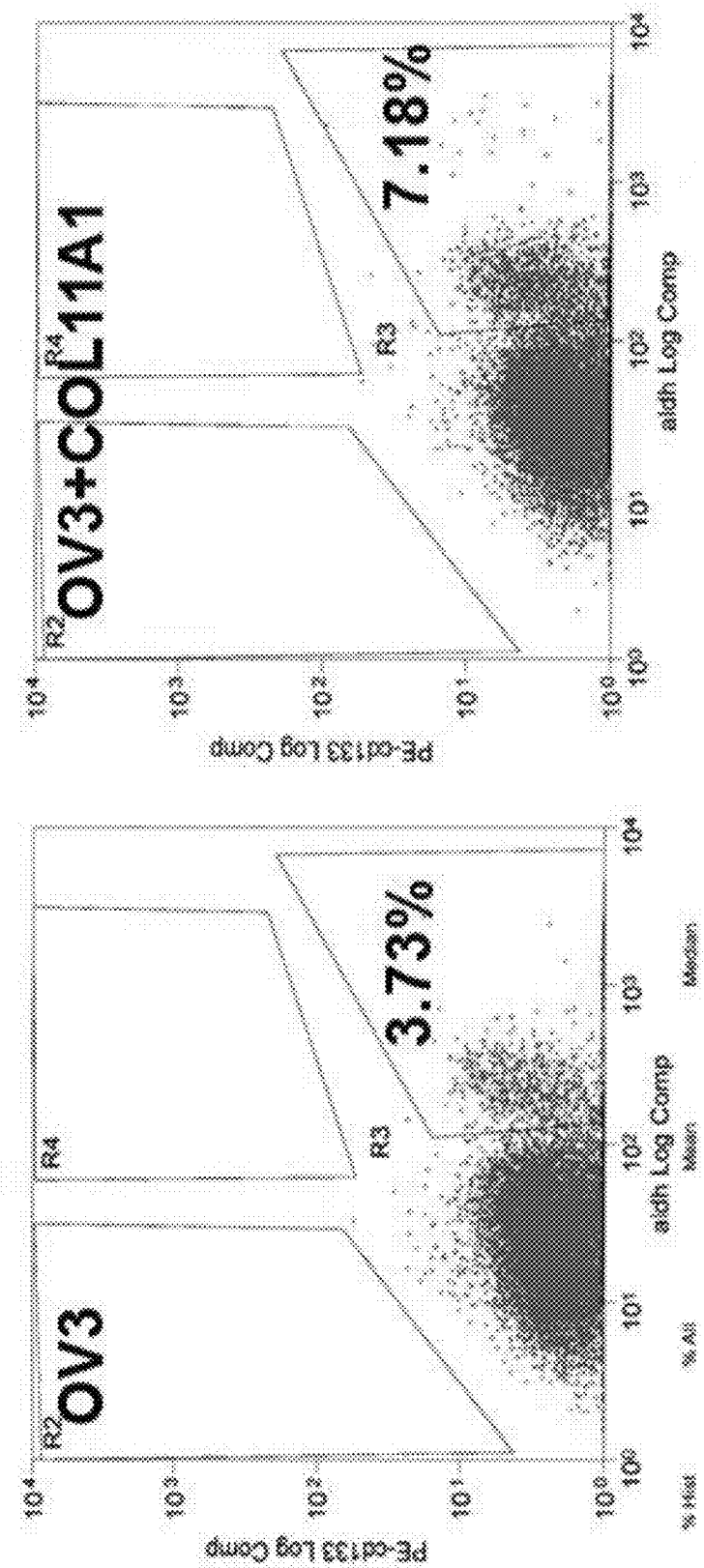
FIG. 34. ALDH expression in OVCAR3 cells before and after treatment with recombinant COL11A1.

Next, we examined if COL11A1 can increase the ALDH$^{high}$ population in human ovarian OVCAR3 cancer cells, which normally express low levels of COL11A1. OVCAR3 cells were cultured in media supplemented with 500 ng/ml human recombinant COL11A1 (a.a. 36-511; Labome) for 48 hours and the percentage of ALDH$^{high}$ cells was measured. The percentage of ALDH$^{high}$ ovarian CSCs increased when cancer cells were treated with recombinant COL11A1 (3.73% to 7.18%; FIG. 34).

Example 46

COL11A1 Confers Cisplatin Resistance in Cancer Cells

Figure 35:
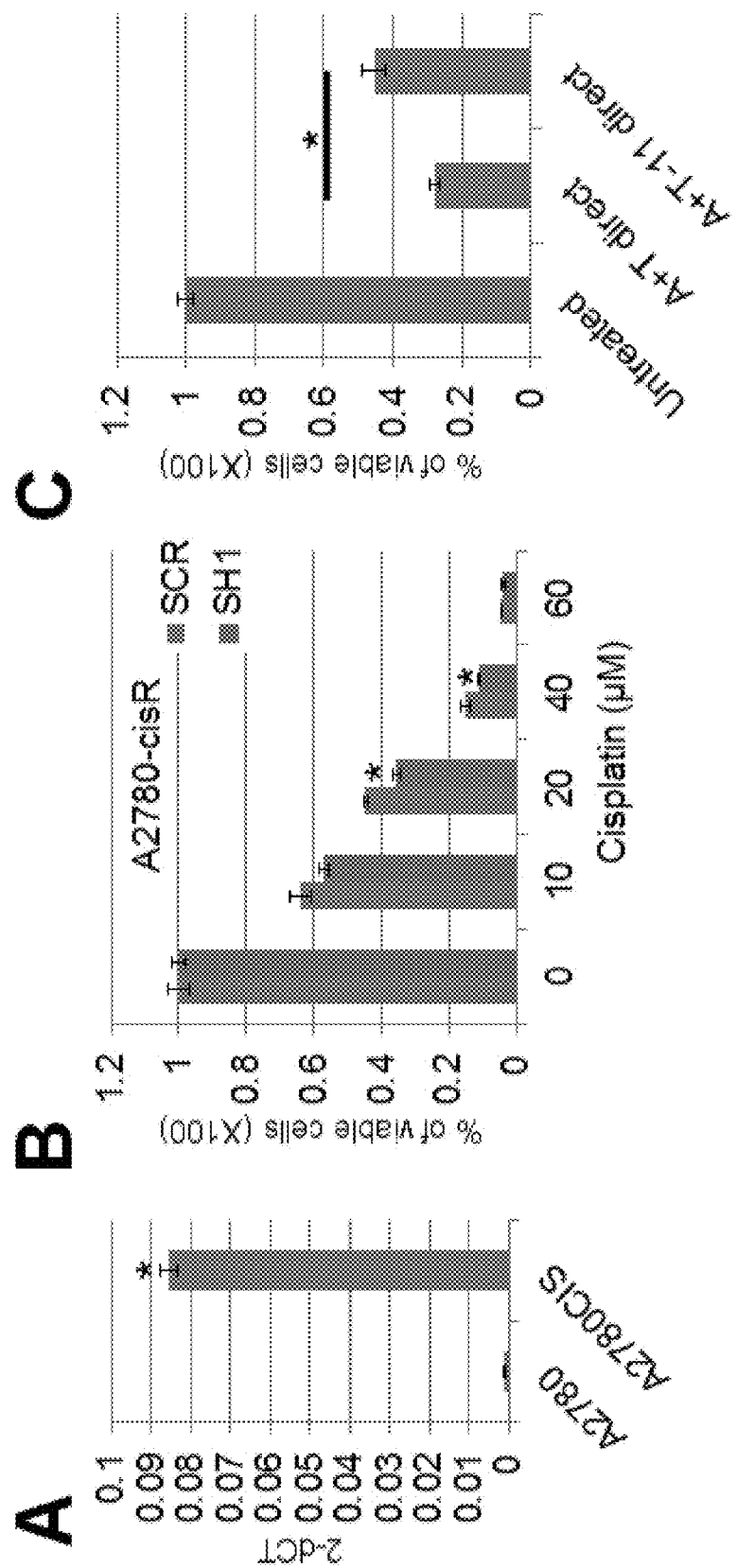
FIG. 35(A) to FIG. 35(C). (A) COL11A1 mRNA expression in parental and cisplatin-resistant A2780 cells. (B) Cell viability after cisplatin treatment in control (scr) and COL11A1 knock-down (sh1) cells. (C) Cell viability after 4 Um cisplatin treatment. A=A2780 cancer cells; T=TRS3 fibroblast cells, T-11=COL11A1-overexpressing TRS3 fibroblast cells. *, p<0.05

We observed that cisplatin resistant cell line A2780 cis-R expresses almost 100-fold higher levels of COL11A1 in comparison to the parental cisplatin sensitive cell line A2780 (FIG. 35A). To determine if COL11A1 plays a role in cisplatin resistance, we knocked down COL11A1 in A2780 cis-R cancer cells, treated them with various concentrations of cisplatin for 72 hours, and measured cell viability using the CellTiterGlo luminescent cell viability assay. A2780 cis-R cells with COL11A1 knockdown (SH1) had a decreased cell survival after cisplatin treatment (20 and 40 μM) than A2780 cis-R cells with intact COL11A1 (SCR) (FIG. 35B).

Next, we asked whether COL11A1 expression in stromal cells can confer cisplatin resistance in adjacent epithelial cells. We cultured GFP-labeled human ovarian cancer cells (A2780, OVCAR3) on a monolayer of human fibroblasts (control and COL11A1-overexpressing) for 48 hours, isolated GFP-positive cancer cells by flow cytometry, treated them with cisplatin for 72 hours, and measured cell viability. Our results showed that A2780 cancer cells became more resistant to cisplatin after co-culture with COL11A1-overexpressing fibroblasts (FIG. 35C). Collectively, our data suggest that high expression of COL11A1 is associated with cisplatin resistance.

Example 47

ADAM12 is a Prognostic Factor Associated with an Aggressive Molecular Subtype of High Grade Serous Ovarian Carcinoma ADAM metallopeptidase domain 12 (ADAM12) is a promising biomarker because of its low expression in normal tissues and high expression in a variety of human cancers. However, ADAM12 levels in ovarian cancer have not been well characterized. We previously identified ADAM12 as one of the signature genes associated with poor survival in high grade serous ovarian carcinoma (HGSOC). Here we sought to determine if high levels of the ADAM12 protein and/or mRNA are associated with clinical variables in HGSOC. We show that high protein levels of ADAM12 in banked preoperative sera are associated with shorter progressionfree and overall survival. Tumor levels of ADAM12 mRNA were also associated with shorter progression-free and overall survival as well as with lymphatic and vascular invasion, and residual tumor volume following cytoreductive surgery. The majority of genes co-expressed with ADAM12 in HGSOC were TGFβ signaling targets that function in collagen remodeling and cellmatrix adhesion. In tumor sections, the ADAM12 protein and mRNA were expressed in epithelial cancer cells and surrounding stromal cells. In vitro data showed that ADAM12 mRNA levels can be increased by TGFβ signaling and direct contact between epithelial and stromal cells. High tumor levels of ADAM12 mRNA were characteristic of the mesenchymal/desmoplastic molecular subtype of HGSOC, which is known to have the poorest prognosis. Thus, ADAM12 may be a useful biomarker of aggressive ovarian cancer for which standard treatment is not effective.

Elevated ADAM12 is a prognostic factor associated with adverse clinical outcomes in high grade serous ovarian carcinoma. ADAM12 is highly expressed in tumor epithelial cells and adjacent stromal cells and is associated with the mesenchymal/desmoplastic molecular subtype of ovarian cancer.

Example 48

ADAM12 Encodes a Member of the ADAM (a Disintegrin and Metalloprotease) Protein Family In humans, two isoforms of ADAM12 (also known as meltrin-α) exist as a result of alternative mRNA splicing: a long transmembrane form (ADAM12-L) and a truncated secreted form lacking the transmembrane and cytoplasmic domains (ADAM12-S). Both ADAM12-L and ADAM12-S are proteolytically processed, and the mature forms translocate to the plasma membrane and extracellular space, respectively, to assume their proteolytic function.

Multiple studies have demonstrated that increased levels of ADAM12 correlate with tumor progression but it is unknown if ADAM12 is an actual perpetrator in tumor progression. In mouse models of breast and prostate cancers, tumor growth and metastasis were diminished in ADAM12-/- mice in comparison to wild type littermates, indicating that ADAM12 may be required for tumor progression. Overexpression studies also support the role of ADAM12 in tumor progression and provide mechanistic insight into the relevance of its adhesion and proteolytic functions.

ADAM12 has attracted attention as a biomarker because of its restricted expression in normal tissues and considerable activation in various disease processes. Aside from high expression in the human placenta and transient expression during embryonic morphogenesis of muscle and bone postnatal ADAM12 expression in healthy and non-injured organs is low. However, levels of ADAM12 are elevated in diseases accompanied by fibrosis. Further, increased levels of ADAM12 have been reported in human cancers including cancers of the breast, liver, head and neck, stomach, bladder, prostate, lung, brain and bone.

ADAM12 has not been examined as a potential biomarker in ovarian cancer. However, ADAM12 was identified in an unbiased screen as one of the transmembrane proteins expressed in ovarian tumor vasculature but not the vasculature of normal ovaries. In the same study, it was noted that expression of ADAM12 was highly variable among ovarian cancers, with high expression in some samples and minimal expression in others, suggesting that ADAM12 might serve as a biomarker in ovarian cancer. We previously identified gene signatures associated with poor survival in HGSOC. Since ADAM12 was among the signature genes, we hypothesize that high levels of ADAM12 are associated with adverse outcome in HGSOC.

Example 49

Validation Methods

Patient Samples.

Studies involving human specimens were approved by the Cedars-Sinai Medical Center Institutional Review Board (IRB). All patients signed an IRB-approved consent for biobanking, clinical data extraction, and molecular analysis. Banked frozen preoperative sera were obtained from the Women's Cancer Program Bioepository and prepared for analysis as described in our previous publications. All patients in this study had advanced stage (FIGO III or IV), high grade (2 or 3) serous ovarian carcinoma. Patients with other malignancies, borderline ovarian tumors, and ovarian tumors of non-epithelial histology were excluded. All patients underwent initial surgical exploration with the intent of optimal cytoreduction (defined as residual disease less than 1 cm) and were treated with at least six cycles of platinum-based chemotherapy. Patients who received intra-peritoneal chemotherapy or underwent neoadjuvant chemotherapy were excluded. Immunohistochemical staining and in situ hybridization were performed on formalin-fixed paraffin-embedded tumors surgically removed from patients and obtained from the Pathology Department archives.

ELISA Assay.

A solid phase ELISA was performed using the Quantikine human ADAM12 ELISA kit (R&D Systems) following the manufacturer's instructions. Briefly, 100 µl of Assay Diluent was added to each well of the 96-well plate pre-coated with a monoclonal antibody specific for human ADAM12. Fifty microliters of ADAM12 standard (0~100 ng/ml) or patient sera were added to each well and incubated for 2 hours at room temperature on a horizontal orbital microplate shaker (500 rpm). The liquids were carefully discarded and the wells were washed four times with 400 µl of the Wash Buffer. 200 µl of ADAM12 Conjugate, an enzyme-linked monoclonal antibody specific for human ADAM12, was added to each well and incubated for 2 hours at room temperature on the shaker. After washing four times with the Wash Buffer, 200 µl of Substrate Solution was added to each well and incubated for 30 minutes at room temperature. The color development was stopped by adding 50 µl of Stop Solution to each well and the optical density at 450 nm was measured by a microplate reader. ADAM12 concentration (ng/ml) in patient sera was calculated by a formula obtained from the ADAM12 standard curve.

Immunohistochemical Staining and In Situ Hybridization.

Immunohistochemical detection of ADAM12 was performed using the Vectastatin Elite ABC kit with rabbit IgG (Vector Laboratories) following the manufacturer's instructions. Formalin-fixed, paraffin-embedded tissue sections were de-paraffinized and rehydrated in a series of xylene and diluted alcohol. Antigen retrieval was performed by boiling the slides in the Antigen Unmasking Solution (Vector Laboratories). Endogenous peroxidase was inactivated by a 30-minute incubation in 0.3% $H_2O_2$ solution in methanol. After blocking with goat serum, a polyclonal ADAM12 Prestige Antibody (Sigma-Aldrich) was incubated at 1:150 dilution for 30 minutes at room temperature. Slides were washed and incubated with the biotinylated rabbit IgG for 30 minutes at room temperature. After washing, the slides were incubated with the ABC reagent for 30 minutes at room temperature, then incubated in the ImmPACT DAB (Vector Laboratories) for 8 minutes, counterstained with Harris hematoxylin (Sigma-Aldrich), dehydrated, and mounted with Permount (Fisher Scientific). ADAM12 in situ hybridization was performed using RNAscope 2.0 FFPE Assay (Advanced Cell Diagnostics, Inc.) as described in Cheon et al., 2014 (31). Slides were examined using the Olympus BX43 upright microscope (Olympus).

Cell Culture.

The OVCAR3 ovarian cancer cell line was obtained from Dennis Slamon (University of California, Los Angeles) and its authenticity was confirmed by Laragen using the short tandem repeat (STR) method. The TRS3 normal ovarian stroma cell line was generated as previously described (31). The OVCAR3 cells and TRS3 cells were cultured in Dulbecco's Modified Eagle Medium (DMEM; Corning) and a 1:1 mixture of MCDB 105 (Sigma) and 199 (GIBCO) media, respectively, supplemented with 10% FBS and 1% penicillin-streptomycin. OVCAR3 cells were co-cultured for 48 hours with TRS3 cells using Millicell 6-well inserts with 0.4 µm PET membrane (Merck Millipore). Alternatively, GFP-labeled OVCAR3 cells were cultured on a monolayer of TRS3 cells for 48 hours and GFP+ cells were sorted using the BD FACSAria™ III cell sorter (BD Biosciences) by the Cedars-Sinai Medical Center (CSMC) flow cytometry core staff. For TGFβ1 treatment, 105 cells were plated in six-well plates, serum-starved overnight, then incubated with 10 ng/mL TGFβ1 (Sigma) for 48 hours before harvesting.

RNA Isolation and Quantitative Real-Time PCR Analysis.

Total RNA was extracted using the RNeasy mini kit (Qiagen) and was reverse-transcribed to cDNA using the QuantiTect Reverse Transcription Kit (Qiagen). A total of 50 ng of cDNA was mixed with primers and iQ SYBR Green Supermix (Bio Rad) in a 96-well plate format. For primers, the $RT^2$ qPCR Primer Assay for Human ADAM12 (Qiagen; PPH07647A) and the ribosomal protein L32 (RPL32; internal control) (Forward: 5'ACAAAGCACATGCTGCCCA-GTG-3' (SEQ ID NO: 1); Reverse: 5'-TTCCACGATG-GCTTTGCGGTTC-3' (SEQ ID NO: 2)) were used. The qRT-PCR reaction was performed using an iCycler thermo cycler (Bio Rad) and the data were analyzed by the 2-ΔCT method. Samples were in duplicate and the experiment was repeated twice.

Statistical Methods.

Abstracted data from medical charts included age, stage, grade, status of cytoreductive surgery, and time to recurrence and death. For statistical considerations, we defined an elevated ADAM12 level as greater than 1.0 ng/ml. Differences in clinical and histopathologic factors between patients with high and low serum ADAM12 were examined with Chi-squared and Fisher's exact test. The Cox regression analysis was performed to assess the significance of potential prognostic factors. Patient survival was analyzed with Kaplan-Meier curves. A p value of less than 0.05 was considered statistically significant.

Analyses of Public Databases.

R2 (http://hgserver1.amc.nl/) was used to statistically analyze and graph data from public microarray datasets. The Kaplan-Meier online plotter tool (http://kmplot.com/analysis/) was used to generate survival curves by combining ADAM12 mRNA data from serous ovarian cancer patients from 13 public ovarian cancer datasets (Supplementary Table I). cBioPortal (http://www.cbioportal.org/) was used to identify ADAM12 correlated transcripts in the ovarian cancer TCGA dataset. DAVID (http://david.abcc.ncifcrf-.gov/) and Ingenuity Pathway Analysis were used for functional annotation of the transcripts and identification of upstream regulators, respectively.

Example 50

Figure 36:
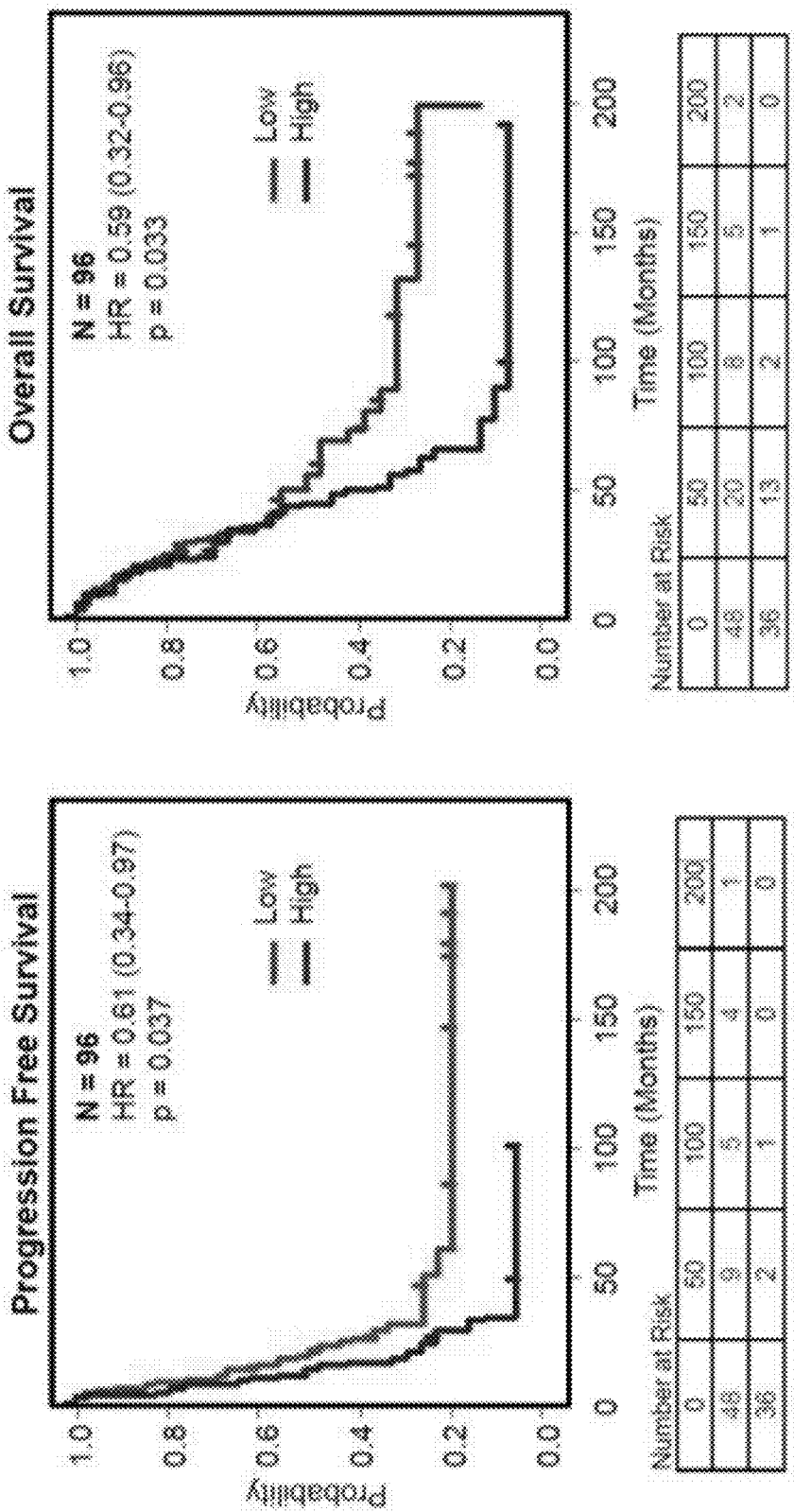
FIG. 36(A) to FIG. 36(D). Kaplan-Meier survival curves in serous ovarian carcinoma patients with low and high levels of ADAM12. (A) Survival curves in HGSOC patients with low (<1 ng/ml) and high (>1 ng/ml) preoperative serum levels of ADAM12. (B) Survival curves in serous ovarian cancer patients with low and high expression levels of ADAM12 mRNA (202952_s_at) from 13 combined public ovarian cancer datasets in the Kaplan-Meier Plotter Database. Comparison of ADAM12 expression levels and clinicopathological parameters in the ovarian cancer TCGA dataset, including (C) lymphatic and venous invasion and (D) size. The graphs and statistical data were generated using R2 Genomics Analysis and Visualization Platform. The x axis shows individual groups where the number of patients in each group is indicated in parentheses. The y axis represents a relative value of ADAM12 mRNA (202952_s_at) expression.
Figure 36:
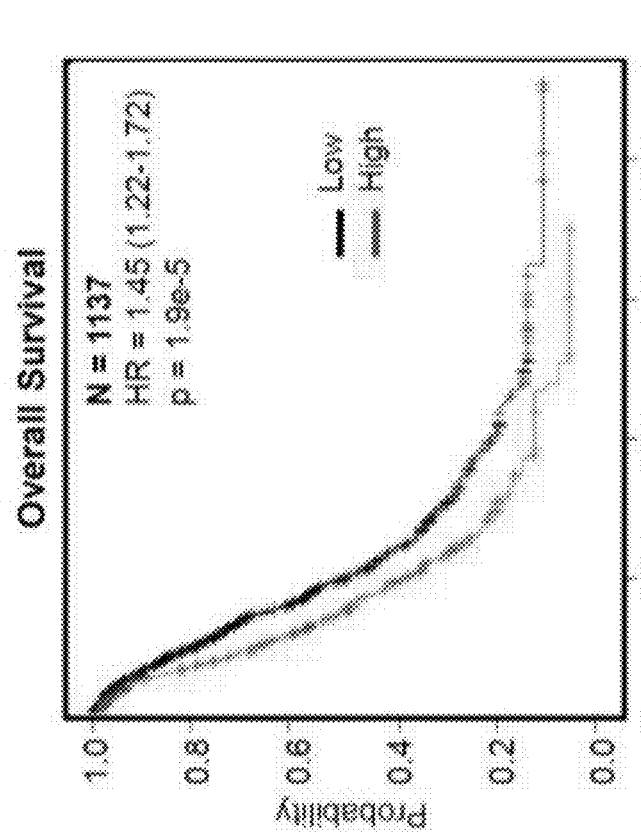
Figure 36:
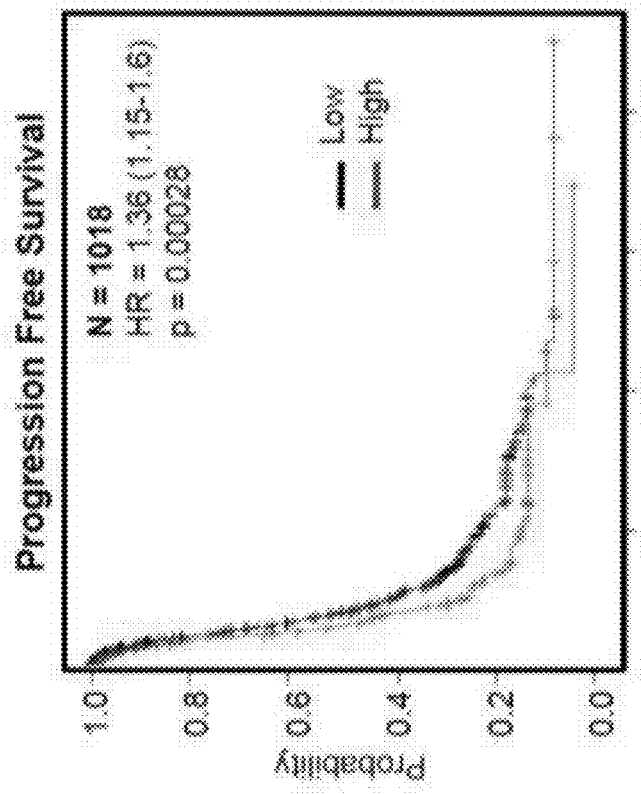
Figure 36:
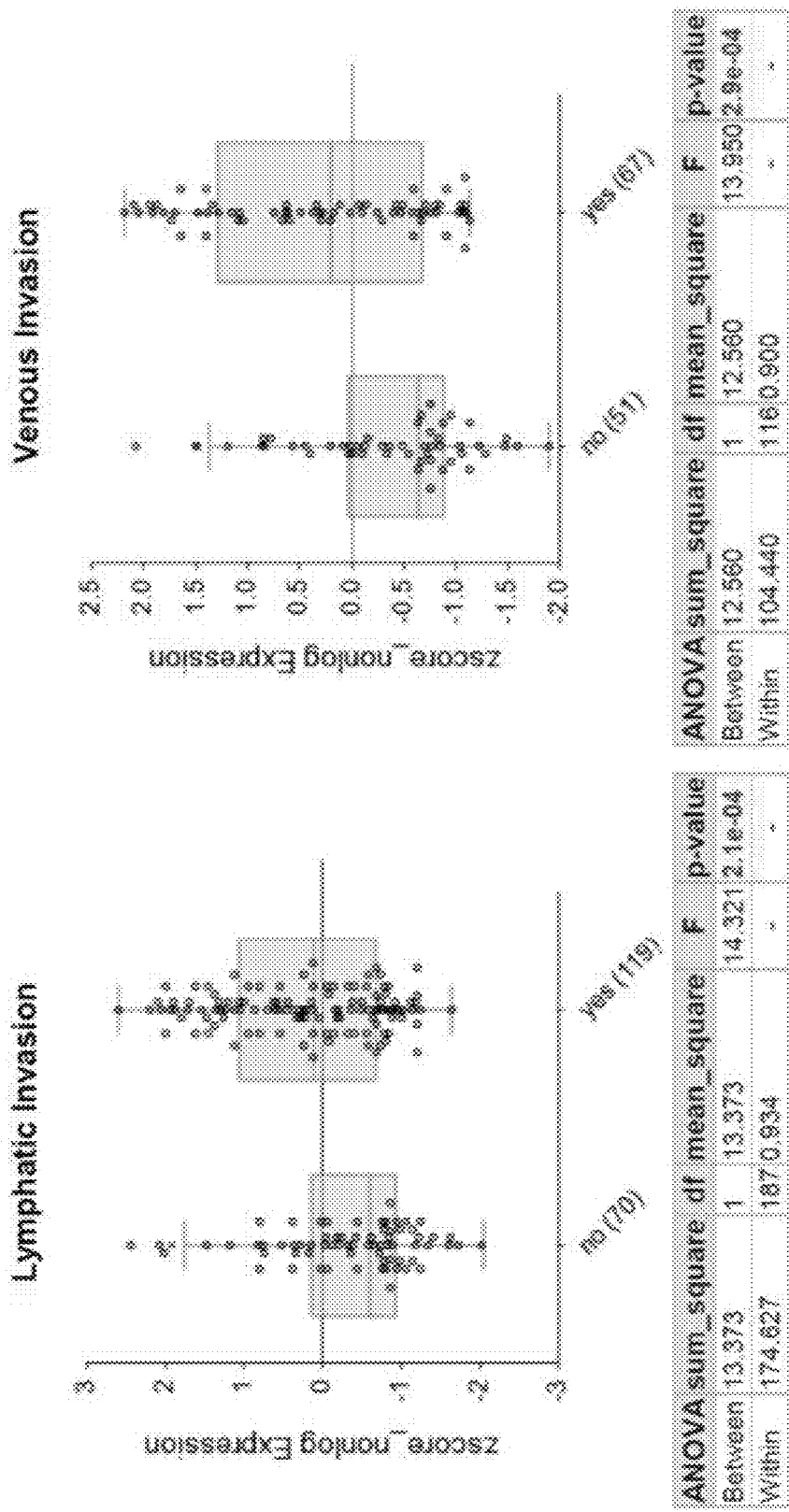
Figure 36:
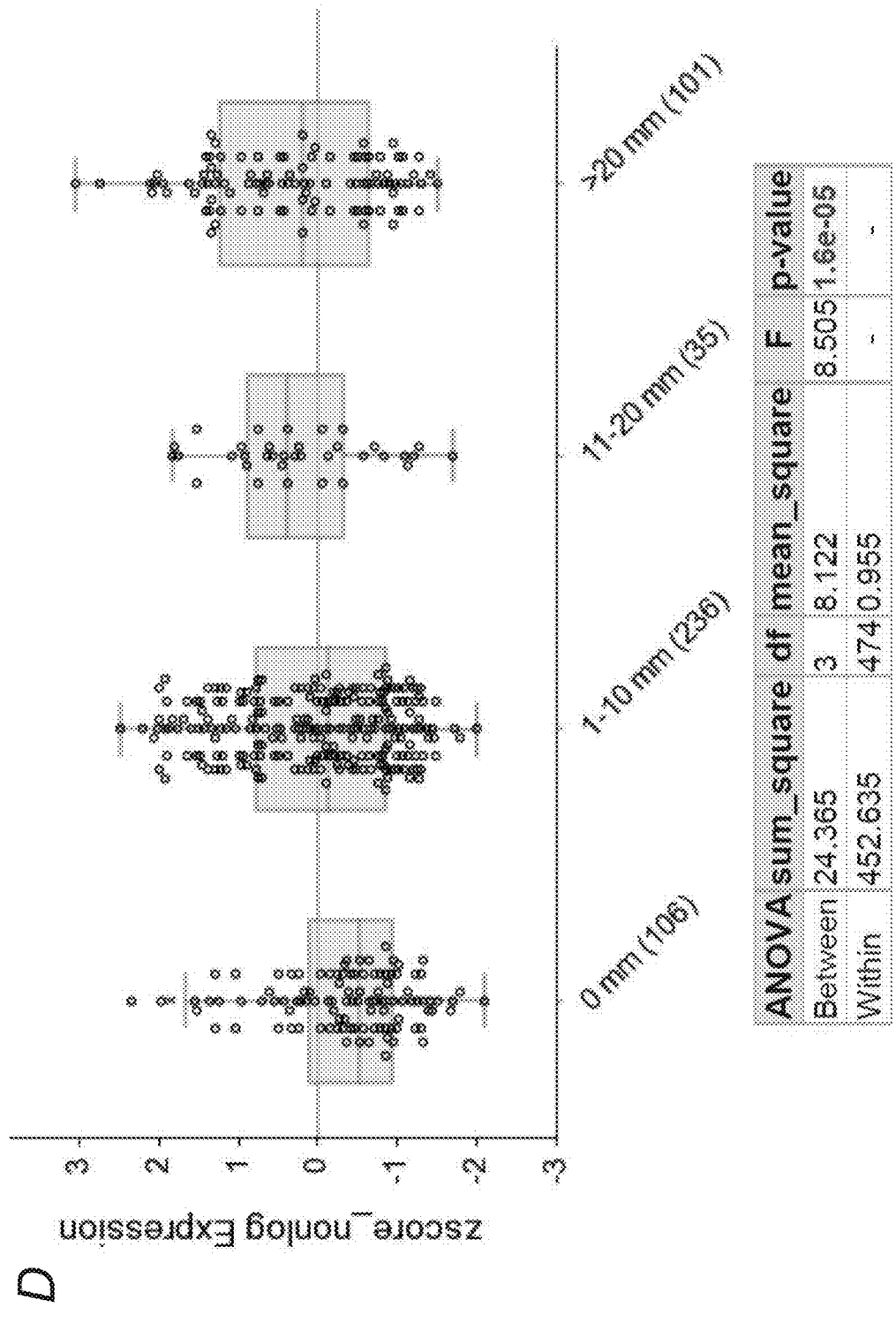

High Serum Protein Levels of ADAM12 are Associated with Poor Survival in Patients with HGSOC Eighty four patients with HGSOC met the criteria for inclusion in the study. All patients underwent initial surgical cytoreduction followed by adjuvant chemotherapy. The majority of patients had grade 3, stage III disease and were optimally resected (residual disease less than 1 cm). ADAM12 levels in banked preoperative sera were determined by ELISA. In order to determine if serum ADAM12 levels correlate with clinical outcome, we used Kaplan-Meier analyses for both time to first recurrence and time to death. Women with low serum ADAM12 levels had a longer median progression-free survival than those with high ADAM12 levels (21 months vs. 14 months, p=0.037) (FIG. 36A). Similarly, women with low ADAM12 levels had a longer median overall disease-specific survival than those with high ADAM12 levels (57 months vs. 45 months, p=0.033) (FIG. 36A). The significance of ADAM12 as an independent prognostic factor was evaluated by Cox regression analysis. ADAM12 levels retained statistical significance (p.=0.02, risk ratio 1.36, confidence intervals 1.06-1.75) after controlling for age, stage (III or IV), grade (2 or 3) and cytoreduction status (optimal or suboptimal).

Example 51

ADAM12 mRNA Levels are Associated with Poor Patient Survival, Increased Tumor Invasion and Decreased Success in Surgical Cytoreduction The existence of multiple expression profile datasets for ovarian cancer facilitated the correlative analysis of ADAM12 mRNA levels with clinical parameters in a large number of patients. High levels of ADAM12 mRNA were associated with poor progression-free and overall survival in a cohort of serous ovarian cancer patients that integrated data from 13 different datasets (FIG. 36B). To determine whether levels of ADAM12 correlate with various clinical parameters, we used the ovarian cancer TCGA dataset. ADAM12 mRNA levels correlated with lymphatic invasion, venous invasion and size of residual tumor after cytoreductive surgery (FIG. 36(C)-FIG. 36(D)) while there was no statistically significant correlation with tumor stage, tumor grade, patient age at diagnosis, performance status, race, or ethnicity (data not shown).

Example 52

ADAM12 mRNA Levels are Associated with the Mesenchymal/Desmoplastic Molecular Subtype of Ovarian Carcinoma Since high serum and mRNA levels of ADAM12 were associated with worse clinical outcomes, we hypothesized that tumors in HGSOC patients with high levels of ADAM12 would exhibit aggressive biology, including increased invasion, suboptimal cytoreduction and poor survival. To determine if high levels of ADAM12 were associated with a specific molecular subtype of HGSOC, we used the ovarian cancer TCGA dataset from 489 patients with HGSOC. Based on expression profiles, the cancer samples in this dataset have been clustered into four molecular subtypes: differentiated, immunoreactive, mesenchymal and proliferative. Strikingly, almost all tumors of the mesenchymal subtype had elevated levels of ADAM12. Similarly in the Tothill dataset, 259 serous and endometrioid ovarian carcinomas have been clustered based on their expression profile into 6 distinct molecular subtypes (C1-C6). The C1 subtype has been characterized by a reactive stroma gene expression signature and was shown to be enriched in tumors with extensive desmoplasia. Almost all tumors in the C1 subtype exhibited elevated levels of ADAM12.

Example 53

ADAM12 is Expressed in Epithelial Cancer Cells and Surrounding Stromal Cells and can be Induced by Epithelial-Stromal Interaction and TGFβ Signaling To better understand the biology of the tumors with high levels of ADAM12, we identified gene transcripts that most closely correlate with expression of ADAM12 in the ovarian cancer TCGA dataset. The majority of the ADAM12-correlated genes were matricellular and extracellular matrix proteins, such as collagens and collagen-remodeling enzymes, which we previously identified as part of a gene signature of poor survival in HGSOC. Gene Ontology (GO) analysis showed that ADAM12-correlated genes are primarily involved in collagen remodeling, tissue development and cell adhesion.

Figure 37:
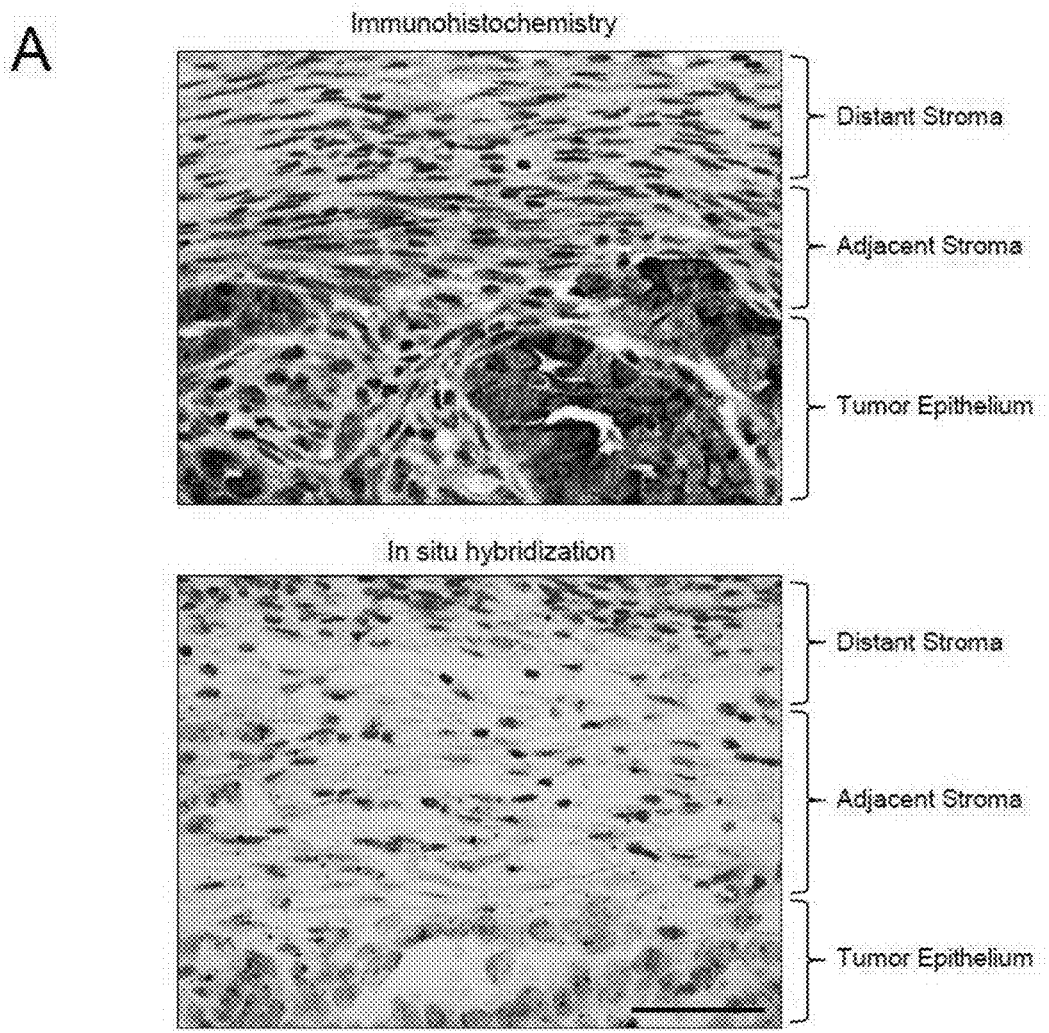
FIG. 37(A) to FIG. 37(C). ADAM12 expression in epithelial and stromal cells in patient tumors and different culture conditions. (A) Representative localization of ADAM12 protein (immunohistochemistry; brown staining) and mRNA (in situ hybridization; brown dots) in ovarian tumor sections from HGSOC patients. Size bar for both photographs=50 µm. (B) and (C) Quantitative real-time PCR of the ADAM12 mRNA in the TRS3 ovarian stromal cell line and OVCAR3 ovarian cancer cell line alone or in co-culture in the presence or absence of 10 ng/ml of recombinant $TGF_\beta 1$. TRS3 stromal cells and GFP-labelled OVCAR3 cancer cells were co-cultured using an insert (insert) or in direct contact (direct) for 48 hours and sorted by FACS before RNA isolation. The top cell line on the x axis represents the cell line from which RNA was isolated. The y axis indicates $2^{-\Delta Ct}$ value. Data indicates mean+/− SEM.
Figure 37:
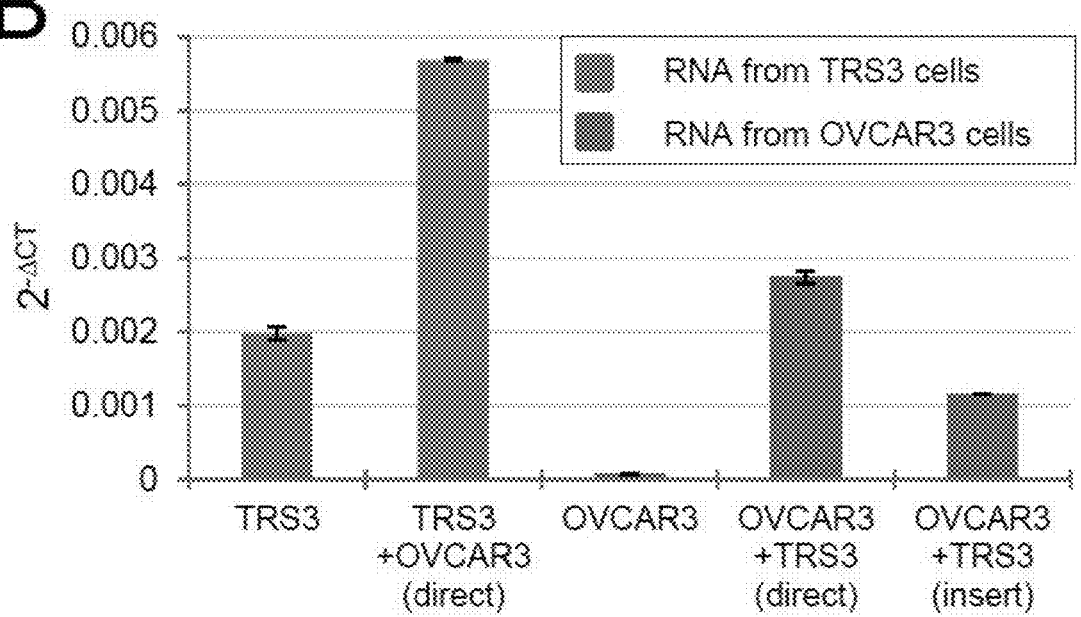
Figure 37:
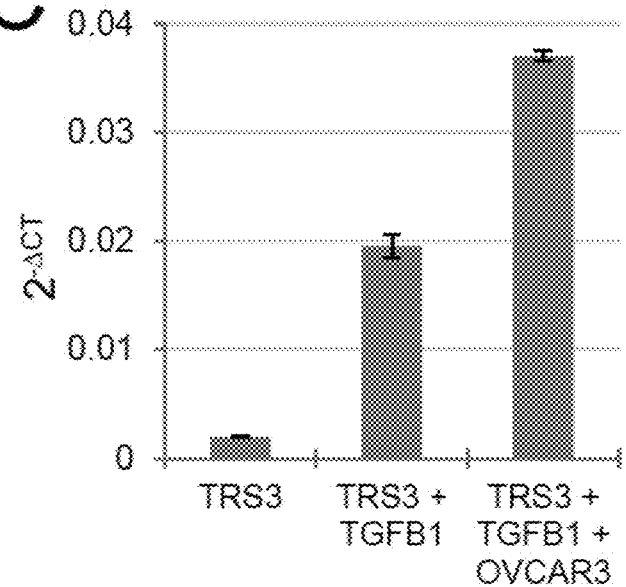
Figure 38:
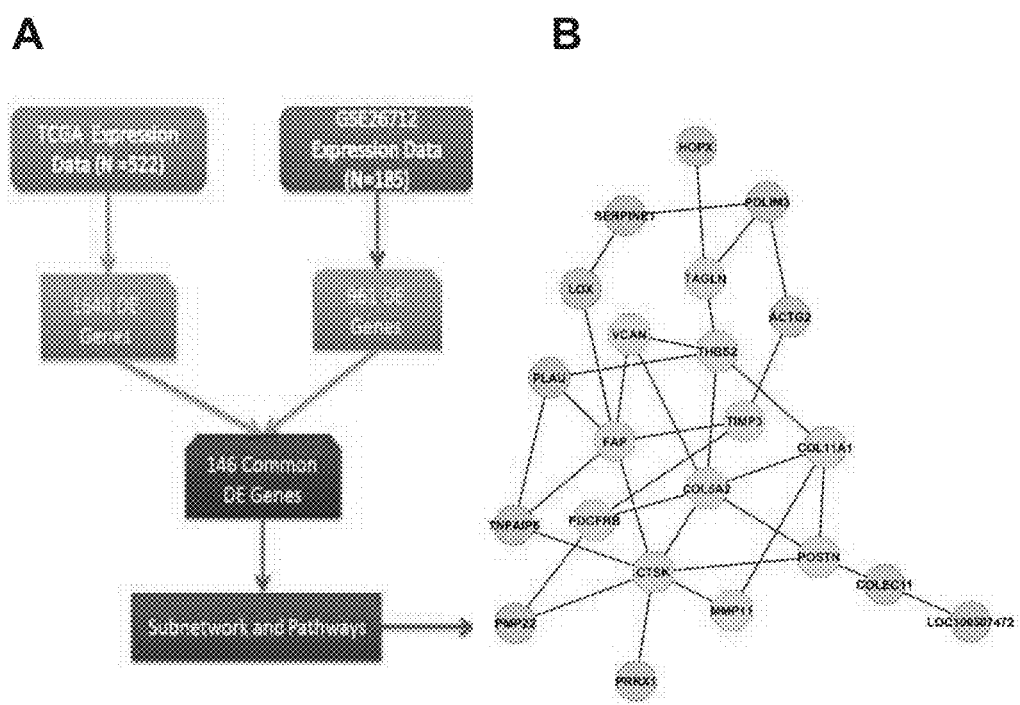
FIG. 38(A) to FIG. 38(D). Derivation and validation of the suboptimal cytoreduction gene signature. (A) Normalized data from ovarian TCGA (n=522) and GSE26712 (n=185) datasets were screened for differentially expressed (DE) genes between patients with residual disease and patients with no residual disease, p<0.05. Common DE genes were used to build networks and pathways. (B) Selected biomarkers with both differentially expressed genes and differentiated networks. The core genes are highlighted in yellow and the four genes selected by logistic regression and forward selection are in red font. (C) External validation of the network genes in the third dataset, GSE9891 (n=248). (D) Sensitivity and specificity of the gene signatures in the validation dataset.
Figure 38:
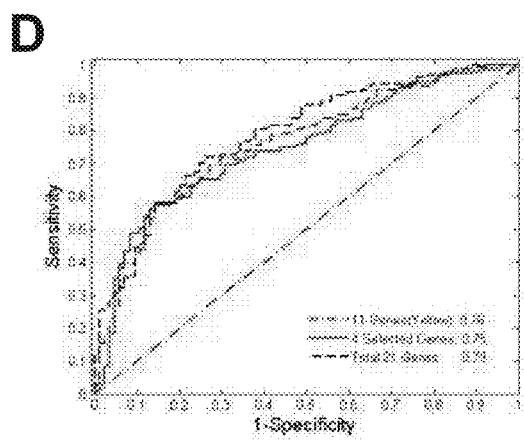

To evaluate the cellular localization of ADAM12 in tumors, an ADAM12-specific polyclonal antibody and an ADAM12-specific probe were used to perform immunohistochemical staining and in situ hybridization on tumor sections from several of our patients with HGSOC. ADAM12 protein and mRNA were detected in tumor epithelial cells and adjacent stromal cells but not in distant (>1 mm) stromal cells (FIG. 37A). To determine if ADAM12 expression is activated by contact between stromal and epithelial cells, SV40 large T antigen-transformed stromal cells from a normal ovary (TRS3 cells) were co-cultured with the epithelial ovarian cancer cell line, OVCAR3. Expression levels of ADAM12 mRNA were 28fold higher in TRS3 stromal cells than in epithelial OVCAR3 cells (FIG. 38B). ADAM12 levels in TRS3 stromal cells were further increased upon direct co-culture with epithelial OVCAR3 cells.

Similarly, ADAM12 levels in OVCAR3 cells increased 39-fold upon direct co-culture with TRS3 stromal cells compared to an only 16-fold increase when the two cell types were cocultured but separated by a membrane insert (FIG. 37B). Ingenuity Pathway Analysis revealed that many of the ADAM12-correlated genes are downstream targets of TGFβ(data not shown), indicating that ADAM12 may be regulated by TGFβ signaling. Consistent with this idea, ADAM12 levels in TRS3 cells increased approximately 10-fold in the presence of recombinant TGFβ1 and were further increased by direct co-culture with OVCAR3 cells (FIG. 37C).

Example 54

Discussion

Several cancer studies have demonstrated the potential utility of ADAM12 as a diagnostic and prognostic marker. For example, Western blot analysis showed elevated levels of ADAM12 in urine from patients with breast cancer compared with healthy control subjects. In addition to detecting the presence of breast cancer, the urine levels of the ADAM12 protein also correlated with tumor stage and progressively increased from patients with in situ carcinoma to locally invasive cancer to metastatic disease. Similarly, urine protein levels of ADAM12 were significantly increased in patients with bladder cancer compared to healthy controls. In the breast cancer study and bladder cancer study, the levels of ADAM12 mRNA and protein increased as a function of cancer stage, with the highest levels found in the largest invasive tumors. In the small number of bladder cancer patients studied, urine protein levels of ADAM12 decreased following tumor resection and increased again upon tumor recurrence, providing further support for the diagnostic utility of ADAM12.

In the current study, we identified significant differences in progression-free and overall survival between women with high and low serum ADAM12 levels in a cohort of patients with stage III/IV HGSOC. Multivariable analyses identified serum ADAM12 as an independent prognostic factor for survival. The presence of lymphovascular invasion is an important predictor of poor survival in ovarian cancer. We showed that ADAM12 mRNA levels correlate with lymphatic and vascular invasion in the ovarian cancer TCGA dataset, supporting the hypothesis that tumors with high levels of ADAM12 are biologically aggressive. Another important predictor of survival is the extent of residual disease after primary cytoreductive surgery. We showed that tumor ADAM12 mRNA levels correlate with the extent of residual disease in the ovarian cancer TCGA dataset, suggesting that ADAM12 may be a biomarker of unresectable ovarian cancer. However, such a biomarker would be useful only if it can stratify patients preoperatively. In cases where the extent of ovarian cancer precludes optimal resection, efforts are made to reduce tumor burden with neoadjuvant chemotherapy prior to interval cytoreductive surgery. Currently, there is no clinical biomarker that can be applied preoperatively to predict when optimal or suboptimal cytoreduction can be surgically accomplished. Since the majority of patients in our cohort were optimally cytoreduced, we were unable to assess the ability of preoperative serum levels of ADAM12 to predict suboptimal cytoreduction. Considering the correlation of tumor ADAM12 mRNA with residual tumor volume and the correlation of preoperative serum ADAM12 protein with poor survival, a study that directly correlates serum ADAM12 with residual disease is warranted. An effective serum biomarker of suboptimal cytoreduction would impact the management of ovarian cancer patients as they could be spared a suboptimal surgical procedure and directly triaged to neoadjuvant chemotherapy.

Outcome predictors based on a molecular subtype rather than surgical staging have been successfully applied in breast cancer where gene signatures are used to predict metastasis and recurrence and to identify patients who are more likely to respond to a specific therapy. In breast cancer, it has been shown that ADAM12 is predominantly up-regulated in claudin-low tumors, an aggressive subtype that exhibits molecular signatures of breast tumor-initiating cells and cells undergoing EMT. In the ovarian cancer TCGA dataset and the Tothill dataset, we observed that high levels of ADAM12 were associated with the mesenchymal and the C1/desmoplastic subtype, respectively. Notably, these subtypes have been associated with the poorest survival when compared to other molecular subtypes in each dataset. A common characteristic of both the mesenchymal and C1/desmoplastic molecular subtypes is extensive desmoplasia. Consistent with this phenotype, the genes co-expressed with ADAM12 in HGSOC are known to be involved in collagen remodeling, tissue organization and cell adhesion. The mechanisms by which desmoplasia contributes to poor survival is still unclear. Possible mechanisms include the presence of a nurturing environment for cancer stem cells, formation of linear collagen tracks for efficient cancer cell migration and invasion, and increased interstitial pressure that thwarts drug delivery. For effective and durable remission, desmoplastic tumors may require different treatment approaches that target both cancer and stromal cells. Thus, in addition to serving as a predictor of poor prognosis, ADAM12 may be a biomarker for an aggressive molecular subtype of ovarian cancer that requires aggressive treatment with current cytotoxic therapy and/or experimental therapies that target stromal cells.

An important aspect of understanding the biomarker potential of ADAM12 in malignancy involves identification of the cells that produce and secrete ADAM12. In a variety of cell culture systems, ADAM12 expression both regulates, and can be induced by, TGFβ signaling). The source of ADAM12 expression within tumor tissue has been debated. Strong expression has been reported in malignant epithelial cells, stromal cells, or both depending upon the cancer type and/or animal model studied. In a mouse model of prostate cancer where expression of SV40 large T-antigen is regulated by the prostate specific probasin promoter, in situ hybridization demonstrated expression of ADAM12 in a subpopulation of stromal cells adjacent to prostate tumor glands. The ADAM12-positive stromal cells were morphologically different from adjacent spindle-shaped fibroblasts and were positive for both $_\alpha$-SMA and SV40 large T-antigen, indicating that they had undergone an epithelial to mesenchymal transition (EMT). Given the role of ADAM12 in myoblast fusion and in the formation of trophoblast syncytia, stromal cells in the prostate that express both markers could have arisen by cell fusion. In ovarian cancer, we detected the ADAM12 mRNA and protein in tumor epithelial cells and adjacent stromal cells. In human tumor sections, it is impossible to track cells to determine if the ADAM12-positive stromal cells were derived from epithelial cells via EMT or cell fusion. Our in vitro co-culture data support the hypothesis that ADAM12 mRNA is induced in both cell types upon direct contact. If this hypothesis is validated in other systems that effectively mimic the microenvironment in cancer, increased ADAM12 levels could be a useful readout for active epithelial-stromal signaling in cancer.

Example 55

Gene Signature that Predicts Residual Disease after Cytoreductive Surgery in Ovarian Cancer In high grade serous ovarian carcinoma (HGSOC), there is an unmet need for a reliable pre-operative predictor of residual disease after cytoreductive surgery (suboptimal cytoreduction), which would assist physicians in triaging which patients should undergo primary debulking surgery (PDS) and which should be treated with neoaduvant chemotherapy (NAC). Outcome predictors based on gene signatures have been successfully applied in breast cancer where gene signatures are not only used to predict metastasis and recurrence but also identify patients who are more likely to respond to a specific therapy.

HGSOC typically presents with metastatic tumor nodules spread throughout the peritoneum. In the U.S., standard primary treatment for HGSOC is surgical cytoreduction followed by chemotherapy. However, in some patients, the aggressive biology of the disease prevents optimal surgical cytoreduction. It has been shown that suboptimal cytoreduction is associated with poor survival. In such cases, it is preferable to forego PDS and to reduce the tumor burden with NAC followed by interval cytoreductione surgery. At present, there is no clinically-applicable biomarker that can predict suboptimal cytoreduction. If such a biomarker existed, patients could be spared an ineffective surgical procedure and be directly triaged to NAC. Several preoperative biomarkers of suboptimal cytoreduction have been evaluated, including computed tomography and serum CA-125 but did not achieve sufficient specificity and/or sensitivity to be used in clinical decision-making.

Example 56

Gene Signature for Triaging Patients

Figure 39:
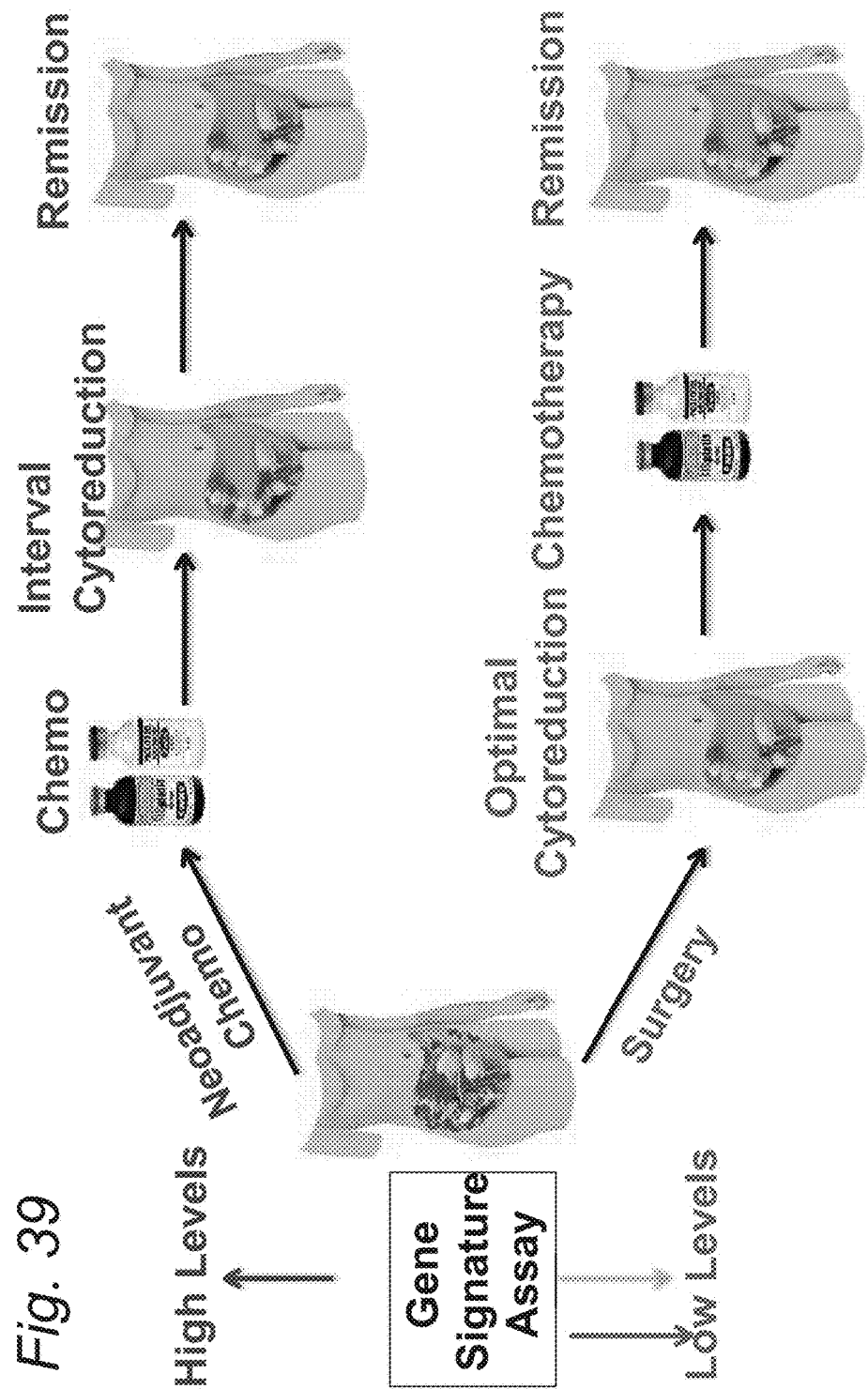
FIG. 39. Use of genetic signature in triaging patients. For example, high gene signature expression level may suggest treatment of neoadjuvant therapy followed by interval cytoreduction, as opposed to a low gene signature expression suggesting standard clinical therapy attempting optimal cytoreduction followed by chemotherapy.

A preoperative image-guided tumor biopsy qPCR expression assay would identify patients who are unlikely to benefit from PDS. Such a test would spare them an ineffective and frequently morbid surgical procedure and facilitate timely initiation of NAC or inclusion into future clinical trials targeting specific pathways that are responsible for the aggressive biology of unresectable disease. As described, standard clinical approach for the treatment of advanced-stage ovarian cancer is upfront cytoreductive surgery followed by a combination of platinum-based and taxane-based chemotherapy. The extent of residual disease following upfront cytoreductive surgery correlates with objective response to adjuvant chemotherapy, rate of pathological complete response at subsequent assessment operations, and progression-free survival and overall survival. As described, it is suggested that optimal cytoreduction as R0 (no macroscopic residual tumour remains), given the robust prognostic value, lower prevalence, and unambiguous assignment associated with this approach after surgery. Importantly, a personalized surgical approach is desirable to enable rational decision-making with regard to the timing of surgery in combination with chemotherapy. Specifically, identification of one or more biomarker to classify patient status is needed that may help physicians decide which patients should undergo surgery and which should be treated with chemotherapy first. In particular this is because standard primary treatment for ovarian cancer is surgery followed by chemotherapy motivated by the rationale that surgery as the primary treatment is to remove as much tumor as possible. Yet, if tumor nodules have invaded vital organs, surgeons may not be able to remove them without compromising the patient's life and leaving tumor nodules larger than 1 cm (defined as suboptimal debulking) is associated with reduced chemosensitivity and poor survival. Currently, if the tumor cannot be effectively removed by surgery, the patient is first treated with chemotherapy to partially shrink the tumor and then by surgery, but difficulty is compounded by the fact that surgeons cannot predict whether surgery will be effective or not and the effect in individual patients is highly divergent depending on the biology of their disease. As such, a biomarker is needed that may help physicians decide which patients should undergo surgery and which should be treated with chemotherapy first As shown, the Inventors have identified a gene signature that predicts suboptimal cytoreduction in HGSOC patients. Using statistical approaches, we constructed gene networks/pathways associated with residual disease in two large datasets: ovarian TCGA and GSE26712 (FIG. 38A). The network consisting of 22 genes (FIG. 38B) was then validated in a third dataset GSE9891. 21 out of 22 genes validated with small p values (FIG. 38C). With the goal of narrowing down the number of informative genes, we tested in the validation dataset the sensitivity and specificity of the entire 22-gene network, the 11-gene core network (yellow), and a combination of four selected genes, COL11A1, TIMP3, FAP, and VCAN (FIG. 38D). The four genes were chosen with logistic regression and forward selection. It is suggested that, for example, elevated expression of one or more of these 4, 11, or 22 genes could provide a triage test to establish neoadjuvant chemotherapy followed by interval cytoreduction is appropriate for an individual patient as opposed to the standard clinical approach of "optimal" cytoreduction followed by chemotherapy (FIG. 39).

Figure 40:
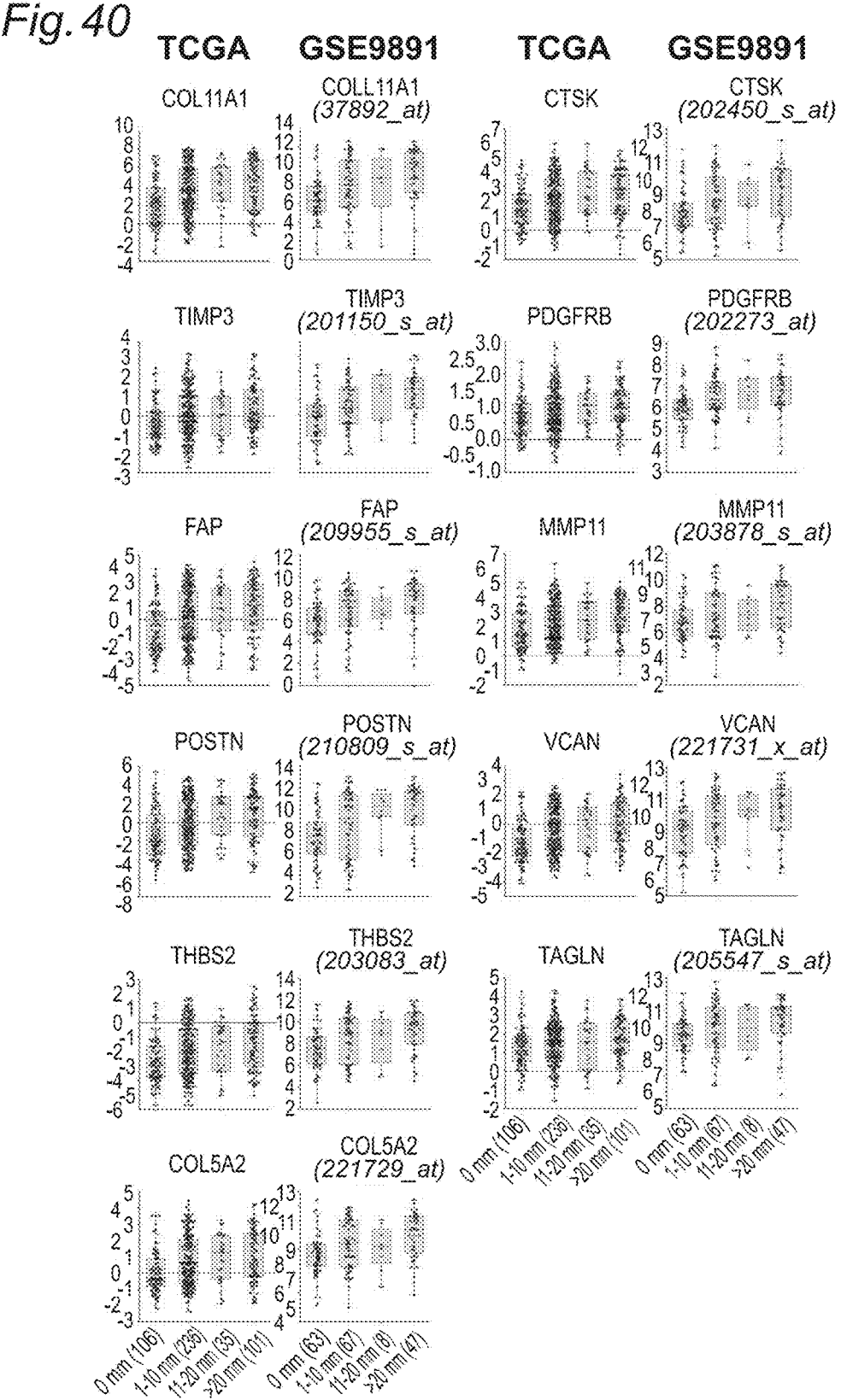
FIG. 40. Expression levels of the '11 cytoreduction signature genes' correlate with the amount of residual disease. Expression levels of the 11 core genes are plotted according to the amount of residual disease in the TCGA and GSE9891 datasets. For most of the genes, expression levels are directly proportional to the amount of residual disease. The X axis shows non-transformed expression levels in the TCGA dataset and log 2 expression levels in the GSE9891 dataset. The y axis shows samples grouped by the amount of residual disease. The number of samples in each group is indicated in parentheses.

In addition to dividing patients to those with no residual disease and with residual disease, the TCGA and GSE9891 datasets stratify patients by the amount of residual disease as 0 mm, 1-10 mm, 11-20 mm, and >20 mm. For each of the 11 genes in the core network (yellow), we tested whether their levels increase with the increased amount of residual disease the TCGA and GSE9891 datasets (FIG. 40).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of ovarian cancer cells, ovarian cancer stem cells (OCSCs) and OCSC candidates, method of detecting biomarkers, prognostic and/or diagnostic panels that include OCSC, OCDS, and OCFS biomarkers and the techniques used to manufacture or express OCSC, OCDS, and OCFS biomarkers, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of determining the presence or absence of a high level of expression of 10 genes in a human individual with serous ovarian cancer, comprising:
   obtaining a biological sample from the human individual with serous ovarian cancer, and
   detecting the presence or absence of a high level of expression in the human individual with serous ovarian cancer, relative to a normal baseline standard from human individuals, for 10 genes wherein the 10 genes consist of AEBP1, COL11A1, COL5A1, COL6A2, LOX, POSTN, SNAI2, THBS2, TIMP3, and VCAN, and wherein the detecting comprises measuring the expression level of the 10 genes using quantitative real-time PCR.

2. The method of claim 1, further comprising administering treatment to the individual with serous ovarian cancer.

3. The method of claim 2, wherein the treatment comprises primary debulking surgery (PDS) followed by chemotherapy and/or neoadjuvant chemotherapy followed by interval cytoreduction.

4. The method of claim 3, wherein chemotherapy is selected from the group consisting of paclitaxel, cisplatin, carboplatin and combinations thereof.

5. The method of claim 1, wherein the biological sample comprises ovarian cyst fluid, urine, or serum.

6. The method of claim 1, wherein the biological sample comprises a tumor biopsy sample.

* * * * *